(12) United States Patent
Thunuguntla et al.

(10) Patent No.: US 9,006,454 B2
(45) Date of Patent: Apr. 14, 2015

(54) DIHYDROOROTATE DEHYDROGENASE INHIBITORS

(75) Inventors: Siva Sanjeeva Rao Thunuguntla, Hyderabad (IN); Hosahalli Subramanya, Bangalore (IN); Satish Reddy Kunnam, Borenarasapur (IN); Sekhar Reddy Sanivaru Vijay, Pulivendula (IN); Chakrapani Bingi, Bhongir (IN); Raviraj Kusanur, Hangal (IN); Matthias Schwarz, Gland (CH); Michael Arlt, Alsbach (DE)

(73) Assignee: Merck Serono S.A., Coinsins (CH)

( * ) Notice: Subject to any disclaimer, the term of this patent is extended or adjusted under 35 U.S.C. 154(b) by 638 days.

(21) Appl. No.: 13/262,640

(22) PCT Filed: Mar. 26, 2010

(86) PCT No.: PCT/EP2010/054034
§ 371 (c)(1),
(2), (4) Date: Oct. 2, 2011

(87) PCT Pub. No.: WO2010/115736
PCT Pub. Date: Oct. 14, 2010

(65) Prior Publication Data
US 2012/0028959 A1 Feb. 2, 2012

Related U.S. Application Data

(60) Provisional application No. 61/178,156, filed on May 14, 2009.

(30) Foreign Application Priority Data

Apr. 2, 2009 (IN) .............................. 696/DEL/2009
May 18, 2009 (EP) ..................................... 09160526

(51) Int. Cl.
| | | |
|---|---|---|
| *C07D 235/18* | (2006.01) |
| *C07D 403/10* | (2006.01) |
| *C07D 403/12* | (2006.01) |
| *C07D 401/10* | (2006.01) |
| *C07D 401/12* | (2006.01) |
| *A61K 31/4184* | (2006.01) |
| *C07D 209/08* | (2006.01) |
| *C07D 401/04* | (2006.01) |
| *C07D 403/04* | (2006.01) |
| *C07D 409/10* | (2006.01) |
| *C07D 413/10* | (2006.01) |
| *C07D 417/10* | (2006.01) |
| *C07D 471/04* | (2006.01) |

(52) U.S. Cl.
CPC ............ *C07D 209/08* (2013.01); *C07D 235/18* (2013.01); *C07D 401/04* (2013.01); *C07D 401/10* (2013.01); *C07D 403/04* (2013.01); *C07D 409/10* (2013.01); *C07D 413/10* (2013.01); *C07D 417/10* (2013.01); *C07D 471/04* (2013.01)

(58) Field of Classification Search
USPC ...................................................... 548/310.7
See application file for complete search history.

(56) References Cited

U.S. PATENT DOCUMENTS

| | | | | |
|---|---|---|---|---|
| 4,769,384 | A | * | 9/1988 | Kise et al. ...................... 514/394 |
| 5,494,911 | A | | 2/1996 | Bartlett et al. |
| 5,532,259 | A | | 7/1996 | Bartlett et al. |
| 5,814,651 | A | * | 9/1998 | Duplantier et al. ........... 514/394 |
| 6,251,686 | B1 | | 6/2001 | Studer et al. |
| 6,841,561 | B1 | | 1/2005 | Tan et al. |
| 7,781,596 | B1 | | 8/2010 | Lubisch et al. |
| 8,648,201 | B2 | * | 2/2014 | Calderini et al. .......... 546/273.4 |

FOREIGN PATENT DOCUMENTS

| | | | |
|---|---|---|---|
| CA | 2349227 | C * | 5/2000 |
| EP | 0527736 | | 4/1997 |
| EP | 1391457 | | 2/2004 |
| JP | H05506425 | | 9/1993 |
| JP | 11322700 | | 11/1999 |
| JP | 11343285 | | 12/1999 |

(Continued)

OTHER PUBLICATIONS

Denny et al., CA 112:55716, 1990.*
Huang et al., Bioorganic & Medicinal Chemistry, 14(17), (2006), pp. 6106-6119.*
Denny et al., Journal of Medicinal Chemistry, (1990), 33(2), pp. 814-819.*
PubChem CID 17861155, created Dec. 4, 2007.*
PubChem CID 21689703, created Dec. 5, 2007.*

(Continued)

*Primary Examiner* — Laura L. Stockton
(74) *Attorney, Agent, or Firm* — Akerman LLP; Peter A. Chiabotti

(57) ABSTRACT

The invention relates to compounds of formula (I) wherein $R^1, R^2, X^1, X^2, Y, R^a, R^b$, Q have the meanings given in claim 1. The compounds are useful e.g. in the treatment of autoimmune disorders, such as multiple sclerosis and also in the treatment of cancer disorders.

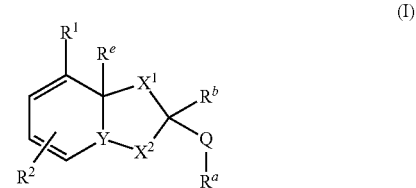

(I)

5 Claims, No Drawings

(56) References Cited

FOREIGN PATENT DOCUMENTS

| WO | 91/17748 | 11/1991 |
| WO | 01/02369 | 1/2001 |
| WO | 2004/035549 | 4/2004 |
| WO | 2005/009941 | 2/2005 |
| WO | 2005/020899 | 3/2005 |
| WO | 2006/009734 | 1/2006 |
| WO | 2006/039718 | 4/2006 |
| WO | WO-2006/080821 A1 * | 8/2006 |
| WO | 2006/130673 | 12/2006 |
| WO | 2008/073451 | 6/2008 |

OTHER PUBLICATIONS

Greene et al., Biochem Pharmacol, 50:861-867 (1995).
Davis et al., FASEB J, 10(6) : 1270-1273 (1996).
Kensler et al., Design of Enzyme Inhibitors as Drugs (1989), pp. 379-401.
Cody et al., Am. J. Clin. Oncol. 16, 526-528 (1993).
Andreson et al., Cancer Commun.,1 (6):381-387 (1989).
Chen et al., Cancer Res., 46(10):5014-5019 (Oct. 1986).
Pizzorno et al., Cancer Res., 52:1660-1665 (Apr. 1, 1992).
Marcinkeviciene et al., Biochem Pharmacol., 60, 339 (2000).
Haque, et al., J. Med. Chem., 45, 4669-4678 (2002).
Heikkila et al., J Med Chem. 50: 186-191 (2007).
Heikkila et al., Bioorg Med Chem Lett. 16: 88-92 (2006).
Gustafson et al., Curr. Genet., 30, 159-165 (1996).
Kovarik et al., Expert Opin. Emerg. Drugs, 8, 47-62 (2003).
Allison, Transplantation Proc., 25(3) Suppl. 2, 8-18 (1993).
Makowka, Immunolog Rev.,136, 51-70 (1993).
Davis et al., FASEB J, 10(6) :Abst C23 (1996).
Milenkovic et al., Exp Hematol, 23: Abst 121 (1995).
Styren et al., Beneficial effects of Teriflunomide in experimental allergic encephalomyelitis. 34th Annu Meet Soc Neurosci; (Oct. 23-27, San Diego) Abst 344.5 (2004).
Li et al., Multiple Scler, 10(Suppl. 2) : Abst P685 (2004).
Suzuki, et al., Chem. Pharm. Bull., vol. 51, 1170-1173 (2003).
Yashuhara et al., J. Chem. Soc, Perkin Trans. 1, 529-534 (1999).
Higuchi, "Pro-drugs as Novel Delivery Systems", vol. 14 of the A.C.S. Symposium Series, American Chemical Society (1975).
Roche, "Bioreversible Carriers in Drug Design: Theory and Application", edited by, Pergamon Press: New York, pp. 14-21 (1987).
Int. J. Pharm. 115, 61-67 (1995).
Kocienski, "Protecting Groups", Georg Thieme Verlag Stuttgart, New York (1994), Table of contents.
Greene et al., "Protective Groups in Organic Synthesis", Wiley Interscience, 3rd Edition (1999).
Pharmaceutical Research, 3(6), 318 (1986).
Synthetic communication 34(21), 3909-3914 (2004).
Chemical Communications, Cambridge, United Kingdom, (5), 564-565 (2004).
J. Med Chem 47(2), 335-374 (2004).
Journal of the Chemical Society, Perkin Transactions 2: Physical Organic Chemistry (1972-1999), (1 ), 35-7 (1984).
Tetrahedron Letters, 64(35), 8164-8168 (2008).
Tetrahedron Letters, 46(34), 5751-5754 (2005).
Tetrahedron letters 42(38), 6683-6686 (2001).
Tetrahedron letter, 46(24), 4255-4259 (2005).
Tetrahedron letter 45(29), 5661-5663 (2004).
Obshchei Khimii, 30, 2693-2698 (1960).
Synlett, (6), 829-831 (2000).
Synlett, (2), 221-224 (2008).
Bioorganic and medicinal chemistry letters 15(5), 1529-1534 (2005).
Bioorganic and medicinal chemistry letters 17(16), 4419-4427 (2007).
Bioorganic and medicinal chemistry letters 15(3), 631-634 (2005).
Ulrich et al., Eur. J. Biochem. 268, 1861-1868 (2001).
Roehm, et al., "An improved colorimetric assay for cell proliferation and viability utilizing the tetrazolium salt," XTT. J. Immunol. Methods 142:257-265 (1991).

* cited by examiner

DIHYDROOROTATE DEHYDROGENASE INHIBITORS

CROSS-REFERENCE TO RELATED APPLICATIONS

This application claims the benefit of International Application No. PCT/EP2010,054034, filed Mar. 26, 2010, which claims priority to Indian Patent Application No. 696/DEL/2009, filed Apr. 2, 2009; U.S. Provisional Application No. 61/178,156, filed May 14, 2009; and European Application No. 09160526.1, filed May 18, 2009.

FIELD OF THE INVENTION

The present invention relates to Dihydroorotate Dehydrogenase inhibitors, their use as medicament and their use for treating multiple sclerosis and other diseases such as inflammatory disorders, rheumatoid arthritis and cancer.

In particular, the invention relates to compounds of formula I:

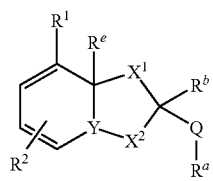

Wherein $R^1$ denotes COOH, COOA, COA, $CF_3$, acyl, cyano, Het, tetrazoyl, sulfonyl, or if Q is —C≡C— or Hetarylene, or if Q is a tetrasubstituted Arylene, $R^1$ also denotes $CON(R^3)_2$ or CONHA.

$R^2$ denotes H, Hal, A, O-A, Ar;

$R^a$ denotes Ar, Het, O-Het, NH-Het, O—Ar, —O—$(CH_2)_m$-Het, —NH—$(CH_2)_m$-Het, NH—Ar, $S(O)_2Ar$, $S(O)Ar$, —S—Ar, $OCF_3$, Y denotes $CR^f$ or N $X^1$, $X^2$ denote each independently of one another $CR^cR^d$, $NR^c$, $NR^d$, and when Y denote $CR^f$, also O or S, provided that one of $X^1$ and $X^2$ is $CR^cR^d$ or $NR^c$;

$R^b$ and $R^c$ together represent a chemical bond;

$R^f$ and $R^e$ together represent a chemical bond, when Y is $CR^f$ $R^e$ and $R^c$, in the definition of $X^1$, together represent a chemical bond when Y is N, and $R^b$ and $R^c$, in the definition of $X^2$, together represent a chemical bond;

$R^d$ denotes H, A, —$(CH_2)_m$—COOH;

Q denotes a group —C≡C—, Arylene, Hetarylene, or the group

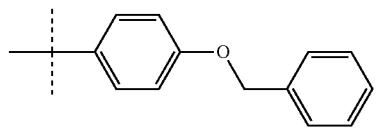

Hal denotes F, Cl, Br or I;

A is a branched or linear alkyl having 1 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O, or S and/or by —CH═CH— or —C≡C— groups, or denotes cycloalkyl or cycloalkylalkylen having 3-7 ring C atoms;

Ar denotes a monocyclic or bicyclic, saturated, unsaturated or aromatic carbocyclic ring having 6 to 14 carbon atoms which may be unsubstituted or substituted by a group selected from $(R^4)_n$ and/or $(R^5)_n$;

Het denotes a monocyclic or bicyclic, saturated, unsaturated or aromatic heterocyclic ring having 1 to 4 N, O and/or S atoms which may which may be unsubstituted or substituted by a group selected from $(R^4)_n$ and/or $(R^5)_n$;

Arylene denotes a divalent monocyclic or bicyclic, saturated, unsaturated or aromatic carbocyclic ring having 6 to 14 carbon atoms which may be unsubstituted or substituted by a group selected from $(R^4)_n$ and/or $(R^5)_n$;

Hetarylene denotes a divalent monocyclic or bicyclic, saturated, unsaturated or aromatic heterocyclic ring having 1 to 4 N, O and/or S atoms which may which may be unsubstituted or substituted by a group selected from $(R^4)_n$ and/or $(R^5)_n$;

$R^3$ is H or alkyl;

$R^4$ and $R^5$ are each independently selected from Hal, hydroxy, alkoxy, carboxy, carboxy-alkyl, perfluoro-alkyl, perfluoro-alkyloxy, acyl, alkylsulfonyl, sulfonyl, cyano, nitro, amino, amido, alkyl optionally substituted by a carboxy, or Het-alkyl optionally substituted by an acyl, alkylsulfonyl, —$O(CH_2)_n$Ar, —$O(CH_2)_n$Het, —$(CH_2)_m$Het, OA, —$NHCO(CH_2)_m$Ar, NHCO—$(CH_2)_m$Het, CONHA, or alkyl;

n denotes 0, 1, 2, 3, 4, 5;

and m denotes 0, 1, 2, 3, 4, 5, 6;

and pharmaceutically acceptable derivatives, solvates, tautomers, salts and stereoisomers thereof, including mixtures thereof in all ratios.

Formula I also includes all tautomeric forms. Preferred tautomeric forms are represented by the following formulae for example wherein $X^1$ and $X^2$ are $NR^c$ or $NR^d$, $R^d$ is H, $R^b$ and $R^c$ form a bond and $R^1$ is COOH, $R^2$, Q, $R^a$ are as defined above, Y is $CR^f$ wherein $R^f$ is as defined above:

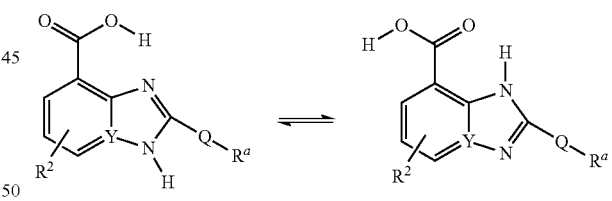

More particularly, the invention relates to the use of compounds of formula I and pharmaceutically acceptable derivatives, solvates, tautomers, salts and stereoiso-mers thereof, including mixtures thereof in all ratios as a medicament, especially for treating multiple sclerosis and other diseases such as inflammatory disorders, rheumatoid arthritis and cancer.

BACKGROUND OF THE INVENTION

The compounds of formula I and related formulae preferably are inhibitors of dihydroorotate dehydrogenase (DHODH or DHOD). DHODH is a protein which catalyzes the fourth step in de novo pyrimidine nucleotide pathway. (Greene et al. Biochem Pharmacol 1995, 50:861-7; Davis J. P et al. FASEB J 1996, 10(6): Abst C23). It catalyses the only oxidation/reduction reaction in that pathway which is the step of converting DHO (dihydroorotate) to orotate with the aid of flavin cofactor and an electron acceptor.

Inhibitors of dihydroorotate dehydrogenase have found wider application as chemotherapeutic agents. Initially explored as anticancer drugs (Kensler et al. 1989 in: Design of Enzyme Inhibitors as Drugs; Sandler, M., and Smith, H. J. Eds., pp 379-401 Oxford Univ Press, Oxford England; Cody et al. Am. J. Clin. Oncol. 16, 526-528 (1993)). As an example for DHODH inhibitors, the quinoline derivative Brequinar (6-Fluoro-2-(2'-fluoro[1,1'-biphenyl]-4-yl)-3-methyl-4-quinolinecarboxylic Acid) exhibits an anticancer activity towards L1210 murine leukemia. (Andreson L W. Et al. Cancer Commun. 1989; 1(6):381-7; Chen S F. et al. Cancer Res. 1986 October; 46(10):5014-9.). It has also been shown that Brequinar potentiates 5-fluorouracil antitumor activity in a murine model colon 38 tumor by tissue-specific modulation of uridine nucleotide pools. (G Pizzorno et al. Cancer Res. 1992 Apr. 1; 52:1660-5.)

DHODH inhibitors have also been suggested as antibiotics, especially against *Helicobacter Pylori* (Marcinkeviciene et al. Biochem Pharmacol. 2000, 60, 339; Haque, T. S. et al., J. Med. Chem. 2002, 45, 4669-4678), useful for treating *Plasmodium falciparum* related diseases (Heikkila, T. et al. J Med. Chem. 50: 186-91 (2007); Heikkila, T. et al. Bioorg Med Chem. Lett. 16: 88-92 (2006)), and as antifungal agents (Gustafson, G. et al. Curr. Genet. 1996, 30, 159).

DHODH inhibitors can also be useful for the treatment of viral mediated diseases (see U.S. Pat. No. 6,841,561).

Furthermore, inhibition of DHODH is a promising target for treating transplant rejection, rheumatoid arthritis, psoriasis as well as autoimmune diseases (Kovarik, J. M. et al. Expert Opin. Emerg. Drugs 2003, 8, 47.; Allison, A. C. Transplantation Proc. (1993) 25(3) Suppl. 2, 8-18); Makowka, L., Immunolog Rev. (1993) 136, 51-70; Davis J. P et al. Biochemistry 1996, 35:1270-3.).

Leflunomide, a well known DHODH inhibitor is a synthetic, low-molecular weight drug of the isoxazole class (see EP0527736, JP 1993506425, JP 1999322700, JP 1999343285, U.S. Pat. No. 5,494,911, U.S. Pat. No. 5,532,259, WO19991017748). This drug is currently marketed and used in the treatment of Rheumatoid arthritis and is also under evaluation for use in the treatment of inflammatory bowel disease and chronic allograft rejection.

In vivo, Leflunomide is quickly transformed in its active metabolite Teriflunomide that exerts its anti-inflammatory, antiproliferative and immunosuppressive effects via mechanisms that are not completely understood. Teriflunomide is not only a potential inhibitor of protein tyrosine kinase in vivo but a 100-1,000-fold greater inhibitor of DHODH (Davis J. P et al. FASEB J 1996, 10(6):Abst C23; Davis J. P et al. Biochemistry 1996, 35:1270-3.).

Another study examined the activity of Teriflunomide on the proliferation of spleen colony-forming units (CFU) and shows that Teriflunomide in a dose-dependently manner inhibited CFU cycling (Milenkovic, P. et al. Exp Hematol 1995, 23: Abst 121.). The effects of Teriflunomide on the behavioral consequences of experimental allergic encephalomyelitis (EAE) were assessed in female Lewis rats to determine the drug's potential utility in multiple sclerosis. Oral treatment with Teriflunomide at 3 and 10 mg/kg or with dexamethasone at 1 mg/kg began 10 days after inoculation with guinea pig spinal cord and Freund's adjuvant, when clonal expansion of inflammatory and immune cells had already occurred. Both compounds caused a significant delay in the onset of disease and in symptom severity (Styren, S. D. et al. Beneficial effects of Teriflunomide in experimental allergic encephalomyelitis. 34th Annu Meet Soc Neurosci (October 23-27, San Diego) 2004, Abst 344.5.).

Teriflunomide was tested in a phase II study in 179 patients with multiple sclerosis with relapses. Once-daily oral treatment with this drug (7 and 14 mg) for 369 weeks led to a reduced number of unique active lesions as compared to placebo. (Li, D. K. B. et al. Multiple Scler 2004, 10(Suppl. 2): Abst P685.)

An increasing number of patients affected by autoimmune and related diseases require new drugs that can treat such diseases. There is still a crucial need for immunosuppressive agents that are further useful in a wide variety of autoimmune and chronic inflammatory diseases, including systemic lupus erythematosus, chronic rheumatoid arthritis, multiple sclerosis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma. They are also useful as part of chemotherapeutic regimens for the treatment of cancers, lymphomas and leukemias, alone or in combination with classic antitumoral compounds well known by the one skilled in the art.

DETAILED DESCRIPTION OF THE PREFERRED EMBODIMENTS

A primary objective of the present invention is to provide novel compounds of formula I and related formulae which are inhibitors of dihydroorotate dehydrogenase. In particular, the invention refers to novel compounds, which inhibits DHODH, to a process for their manufacture and pharmaceutical compositions containing them, and to their use for the treatment and prevention in diseases, in particular their use in diseases where there is an advantage in inhibiting DHODH. The compounds of formula I and related formulae may be useful for treating and/or preventing, but not restricted to, autoimmune and chronic inflammatory diseases, including systemic lupus erythematosus, chronic rheumatoid arthritis, multiple sclerosis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma. The compounds of formula I and related formulae can be also useful as part of chemotherapeutic regimens for the treatment of cancers, lymphomas and leukemias alone or in combination with classic antitumoral compounds well known by the one skilled in the art.

More particularly, the present invention relates to compounds of formula I and related formulae for the treatment of multiple sclerosis and related diseases, rheumatoid arthritis and transplant rejection.

The inventions further relates to the use of compounds according to formula I and related formulae in combination with immunomodulating agents such as Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy) ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate melphalan; meprednisone; mercaptopurine; methylprednisolone; methylprednisolone acetate; methylprednisolone hemisuccinate; misoprostol; muromonab-cd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA41g, or other adhesion molecule inhibitors, e.g. mAbs or low molecular weight inhibitors including Selectin antagonists and VLA-4 antagonists. A preferred composition is comprising a compound of formula I and Cyclosporin A, FK506, rapamycin, 40-(2-hydroxy)ethyl-rapamycin or Fingolimod.;

The dihydroorotate dehydrogenase inhibitors according to formula I and related formulae may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below:

aq (aqueous), h (hour), g (gram), L (liter), mg (milligram), MHz (Megahertz), µM (micormolar) min. (minute), mm (millimeter), mmol (millimole), mM (millimolar), m.p. (melting point), eq (equivalent), mL (milliliter), µL (microliter), ACN or MeCN (acetonitrile), BINAP (2,2'-bis(disphenylphosphino)-1,1'-binaphthalene, BOC (tert-butoxy-carbonyl), CBZ (carbobenzoxy), CDCl3 (deuterated chloroform), CD3OD (deuterated methanol), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-d6 (deuterated dimethylsulfoxide), EDC (1-(3-dimethyl-amino-propyl)-3-ethylcarbodiimide), ESI (Electrospray ionization), EtOAc (ethyl acetate), Et2O (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K2CO3 (potassium carbonate), LC (Liquid Chromatography), MeOH (methanol), MgSO4 (magnesium sulfate), MS (mass spectrometry), MTBE (Methyl tert-butyl ether), Mtr. (4-Methoxy-2,3,6-trimethylbenzensulfonyl), MW (microwave), NaHCO3 (sodium bicarbonate), NaBH4 (sodium borohydride), NMM (N-methyl morpholine), NMR (Nuclear Magnetic Resonance), PPA (polyphosphoric acid), POA (phenoxyacetate), PyBOP® (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Depending on the nature of $X^1$, $X^2$, $R^a$, $R^b$, $R^c$, $R^d$, $R^e$, $R^1$, $R^2$, Y, and Q, different synthetic strategies may be selected for the synthesis of compounds of formula I and related formulae. In the process illustrated in the following schemes, $X^1$, $X^2$, $R^a$, $R^b$, $R^c$, $R^d$, $R^e$, $R^1$, $R^2$, Y and Q are as above defined in the description.

In general, the dihidroorotate dehydrogenase inhibitors according to formula I and related formulae of this invention may be prepared from readily available starting materials. If such starting materials are not commercially available they may be prepared by standard synthetic techniques. The following general methods and procedures described hereinafter in the examples may be employed to prepare compounds of formula I and related formulae.

The process for the preparation of compounds of formula I and related formulae, wherein $X^1$, $X^2$, $R^a$, $R^b$, $R^c$, $R^d$, $R^e$, $R^1$, $R^2$, Y and Q are as defined above, and as outlined in the following schemes, is also object of the invention.

In Scheme 1, coupling of aryl-1,2 diamine of formula (A) with an acid of formula (B) is achieved in the presence of a coupling agent such as HATU or from the corresponding acid chloride (prepared from acid of formula B with a chorinating reagent such as thionyl chloride or oxalyl chloride) in a solvent such as DMF to form a compound of formula (C). Compound (C) will undergo cyclization for example in AcOH under reflux to give the corresponding compound of formula I, wherein $X^1$ and $X^2$ are $NR^c$, $NR^d$ and $R^b$ and $R^c$ together represent a chemical bond, and wherein Y is $CR^f$, $R^f$ and $R^e$ together represent a bond, according to scheme 1;

Scheme 1

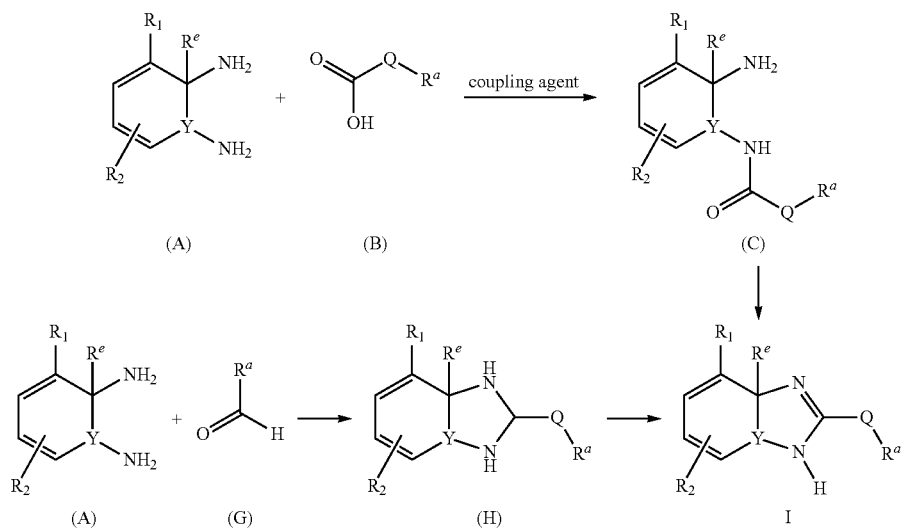

An alternative route for compounds of formula (I), wherein $X^1$ and $X^2$ are $NR^c$, $NR^d$, wherein Y is $CR^f$, $R^f$ and $R^e$ together form a bond, and wherein $R^b$ and $R^c$ together represent a chemical bond and wherein Q represents a single bond, involves the reaction of aryl-1,2 diamine of formula (A) with an aldehyde of formula (G) to form the intermediate (H) which can undergo oxydation in the presence an oxydative reagent such as oxygen to form compounds of formula (I).

In case of formula I wherein $X^1$ is O and $X^2$ is $NR^c$ and $R^b$ and $R^c$ together represent a chemical bond, Y is $CR^f$, $R^f$ and $R^e$ together form a bond, the 2-Amino-Phenol derivatives (D) will react with the acyl-chloride (B') derived from the corresponding acid (B), in a solvent such as DCM in the presence of a base such as TEA. Compound (J) will undergo cyclization for example in the presence of PPA in an appropriate solvent to give the corresponding compound of formula I wherein $X^1$ is O and $X^2$ is $NR^d$ according to scheme 2.

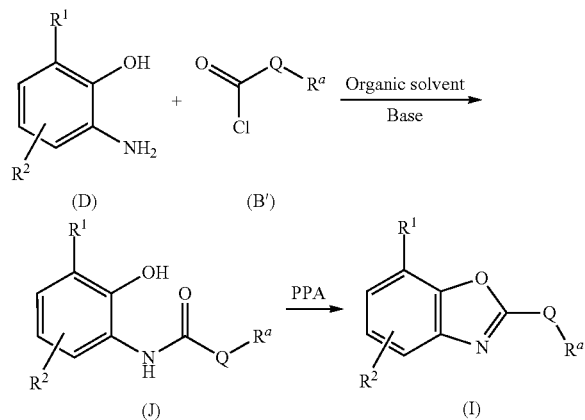

In case of formula I wherein $X^1$ is $NR^d$ and $X^2$ is $CR^cR^d$ and $R^b$ and $R^c$ together represent a chemical bond, Y is $CR^f$, $R^f$ and $R^e$ together form a bond, the iodoaniline (E) will react with ethynyl derivatives (F) in the presence of a CuI, a palladium catalyst such as $PdCl_2(PPh_3)_2$, a polar solvent such as THF and a suitable base to give the corresponding compound of formula I wherein $X^1$ is $NR^d$ and $X^2$ is CH according to scheme 3.

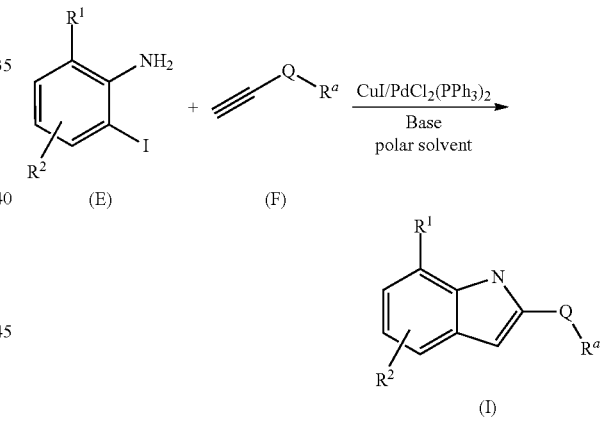

Alternative reaction conditions can be used as described in Naoyuki Suzuki, et al. *Chem. Pharm. Bull.*, Vol. 51, 1170-1173 (2003), or Yashuhara et al. *J. Chem. Soc., Perkin Trans.* 1, 1999, 529-534.

If the above set out general synthetic methods are not applicable for the obtention of compounds of formula I and related formulae, suitable methods of preparation known by a person skilled in the art should be used.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine, lysine, arginine, and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

According to a further general process, compounds of formula I and related formulae, (A), (B), (B'), (C), (D), (E) (F), (G) and (J) can be converted to alternative compounds of formula I and related formulae, employing suitable interconversion techniques well known by a person skilled in the art.

In general, the synthesis pathways for any individual compound of formula I and related formulae will depend on the specific substitutents of each molecule and upon the ready availability of intermediates necessary; again such factors being appreciated by those of ordinary skill in the art.

Compounds of this invention can be isolated in association with solvent molecules by crystallization from evaporation of an appropriate solvent. The pharmaceutically acceptable acid addition salts of the compounds of formula I and related formulae, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula I and related formulae, which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula I and related formulae can furthermore be obtained by liberating compounds of the formula I from one of their functional derivatives by treatment with a solvolysing or hydrogenolysing agent.

Preferred starting materials for the solvolysis or hydrogenolysis are those which conform to the formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula I, but carry a —COOR" group, in which R" denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I and related formulae are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using LiOH, NaOH or KOH in water, water/THF, water/THF/ethanol or water/dioxane, at temperatures between 0 and 100° C.

Free amino groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as dichloromethane or THF and/or in the presence of a base, such as triethylamine or pyridine, at temperatures between −60° C. and +30° C.

Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoro-methylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The formula I and related formulae also encompasses the optically active forms (stereo-isomers), the enantiomers, the racemates, tautomers, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds. Preferably "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A. C. S. Symposium Series, American Chemical Society (1975). Examples of esters useful as prodrugs for compounds containing carboxyl groups can be found on pages 14-21 of "Bioreversible Carriers in Drug Design: Theory and Application", edited by E. B. Roche, Pergamon Press: New York (1987). It is intended that these references, and any others cited throughout this specification, are incorporated herein by reference.

These also include biodegradable polymer derivatives of the compounds according to the invention, as described, for example, in Int. J. Pharm. 115, 61-67 (1995).

The formula I and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Very particularly, preferred embodiments of formula I are the compounds of formula II, III:

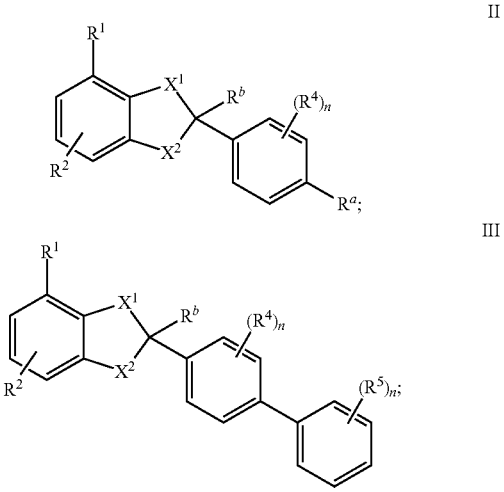

wherein $X^1$, $X^2$, $R^b$, $R^1$, $R^2$, $R^4$, $R^5$, n are as defined above. Formula II and formula III, wherein $R^1$ is COOH, are especially preferred.

Preference is given to the compounds of the present invention selected from the following group I1 to I192:

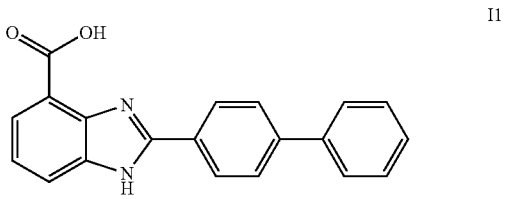

-continued
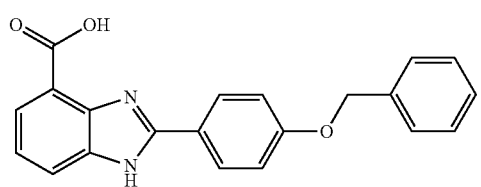
I2
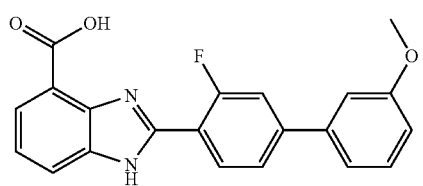
I3
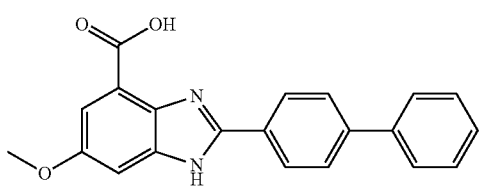
I4
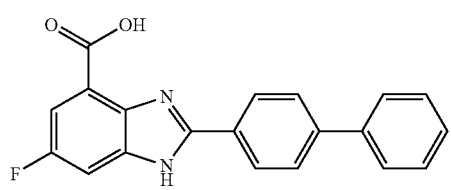
I5
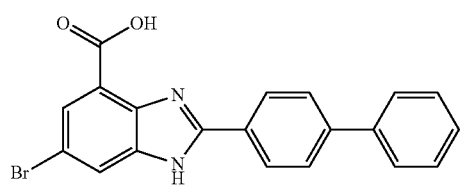
I6
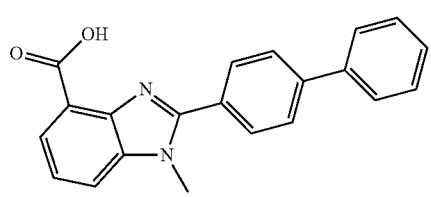
I7
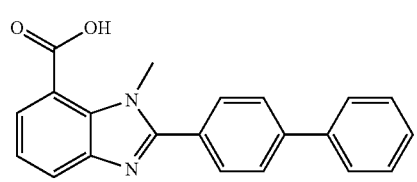
I8
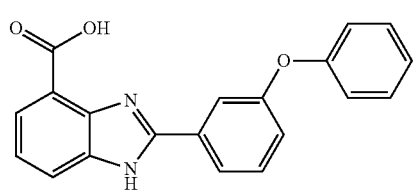
I9
-continued
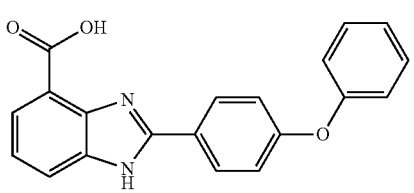
I10
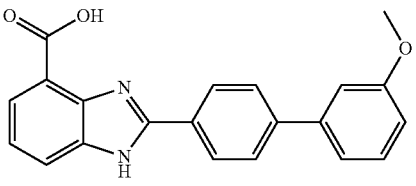
I11
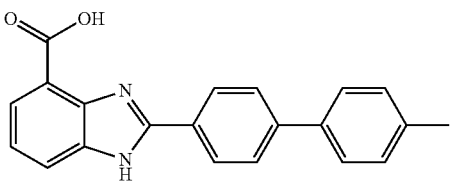
I12
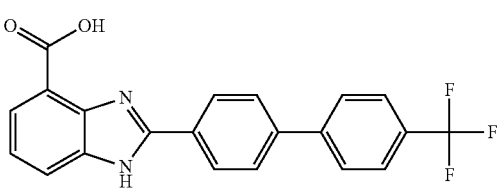
I13
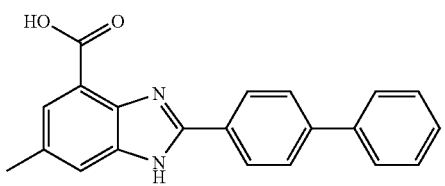
I14
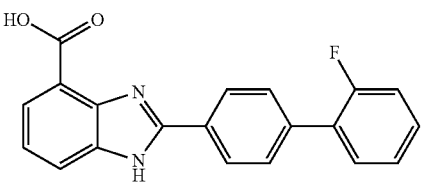
I15
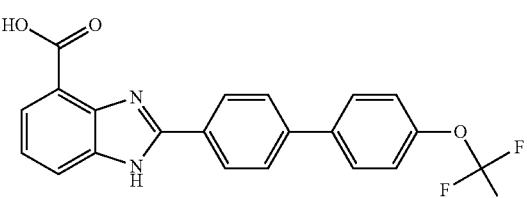
I16
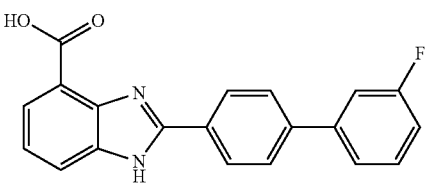
I17

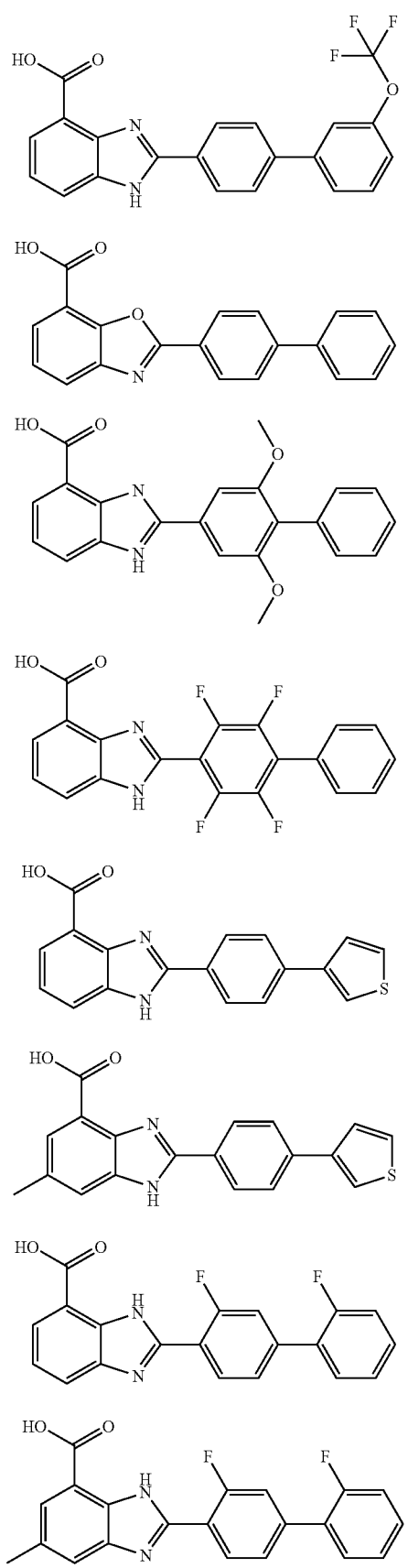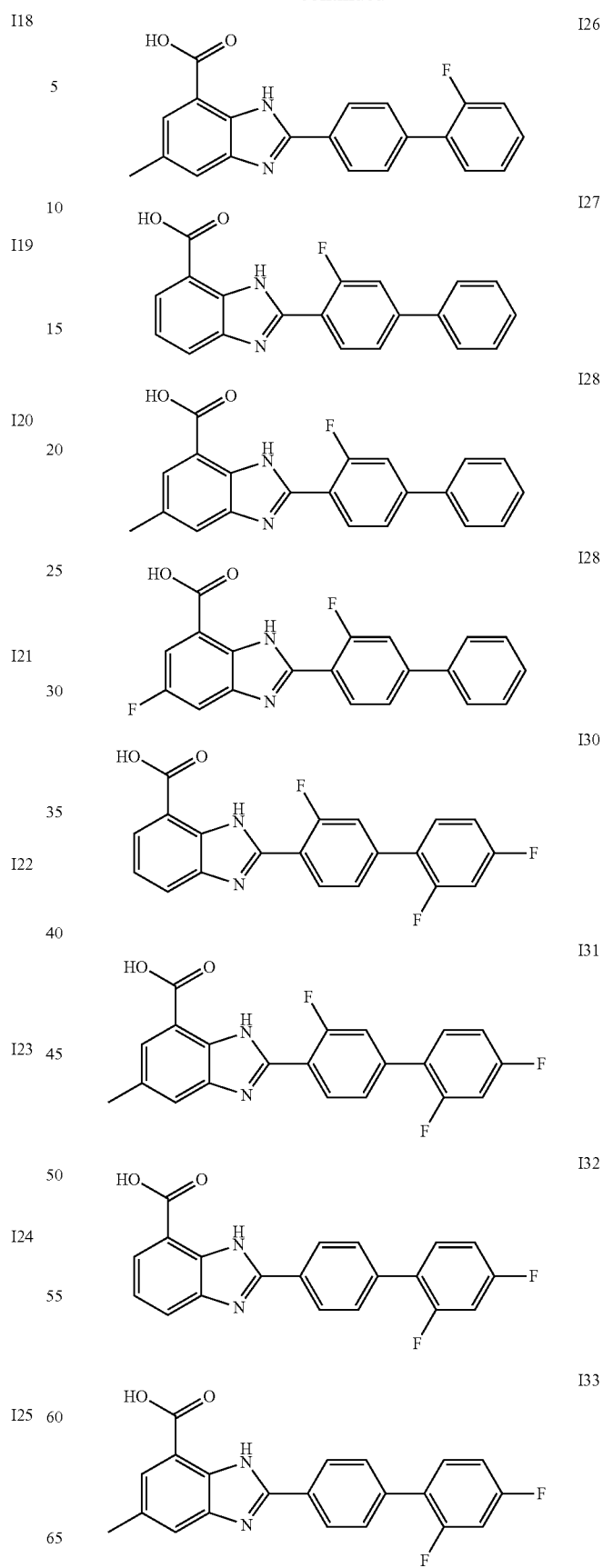

-continued

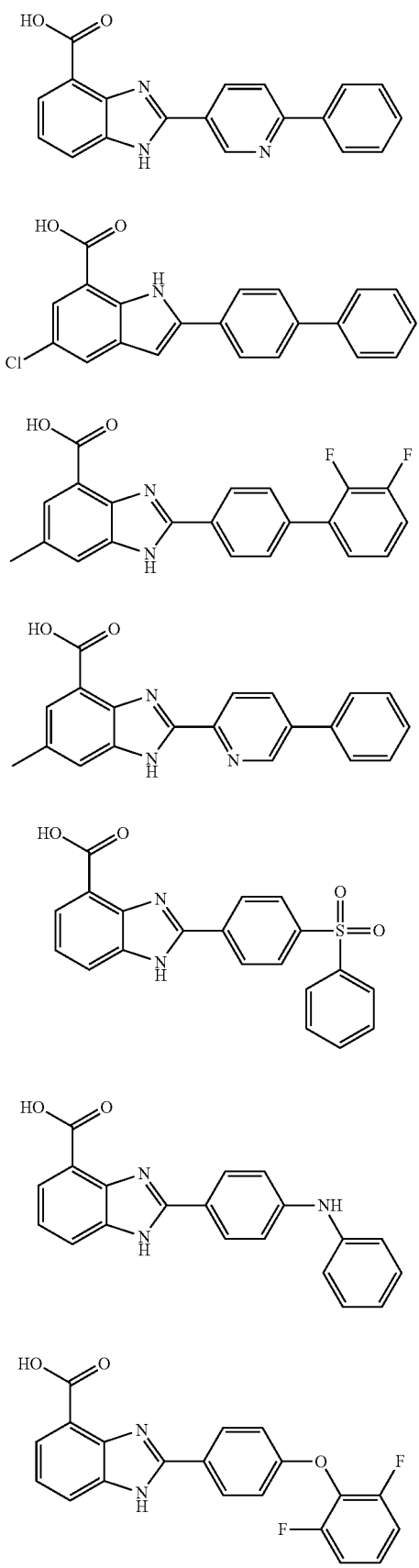
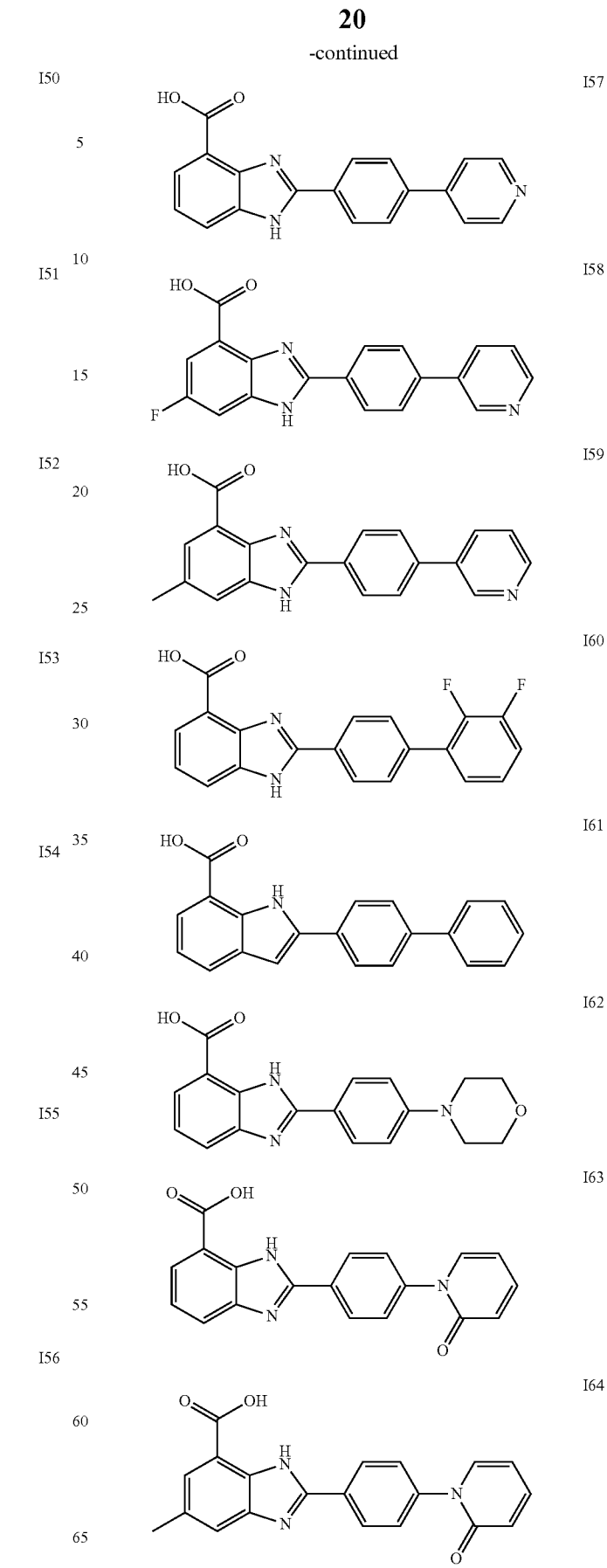

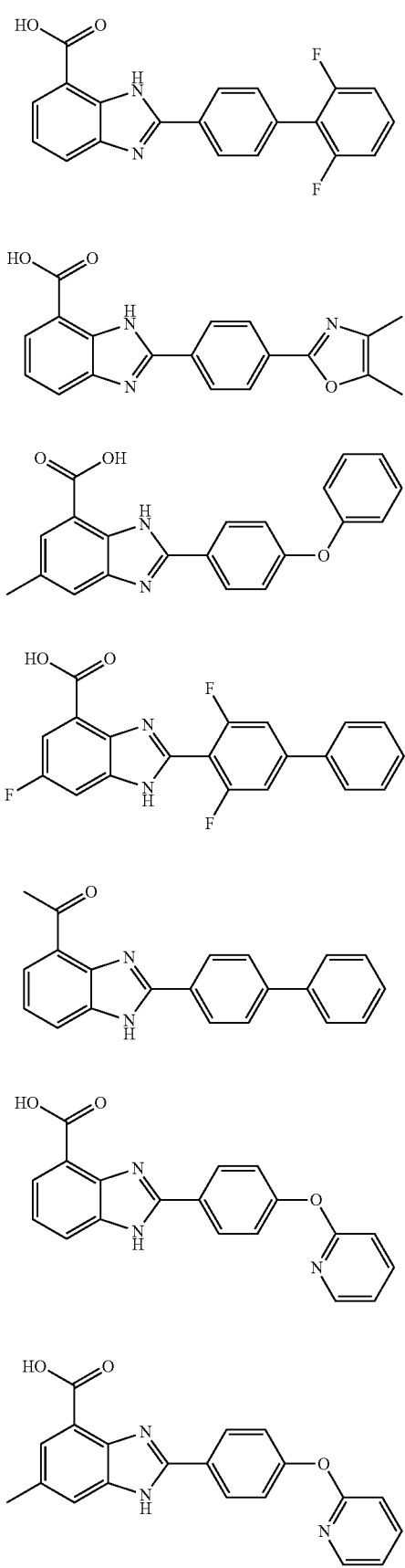
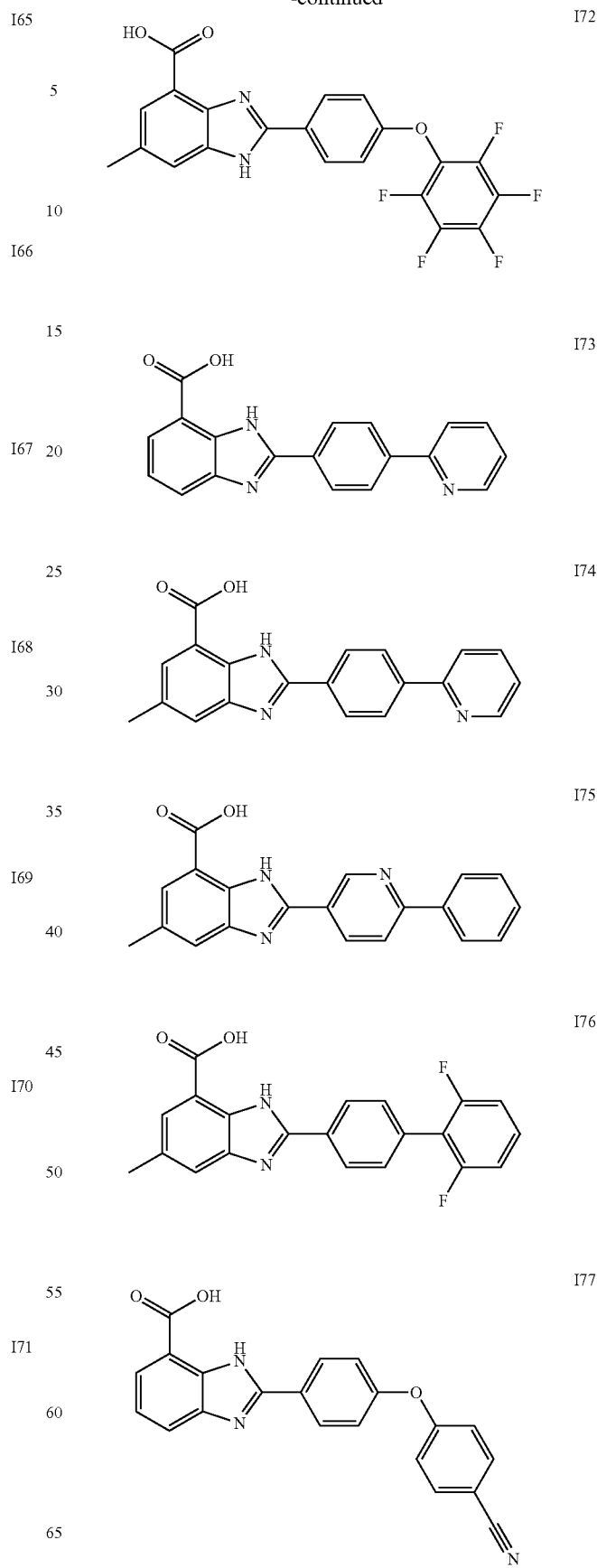

I78
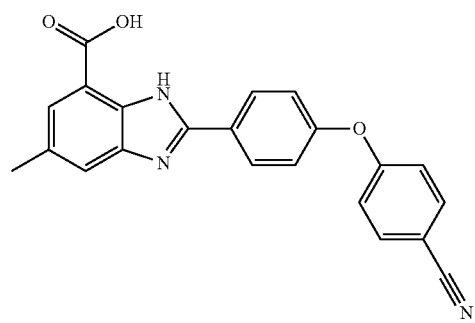
I79
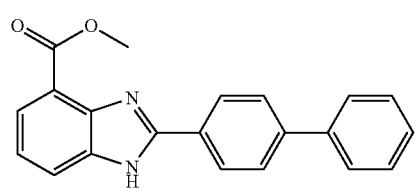
I80
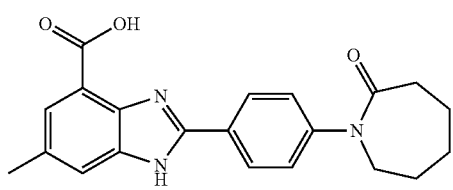
I81
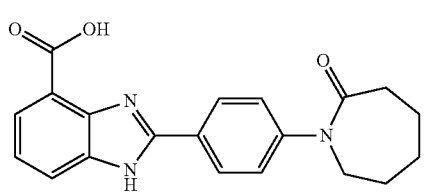
I82
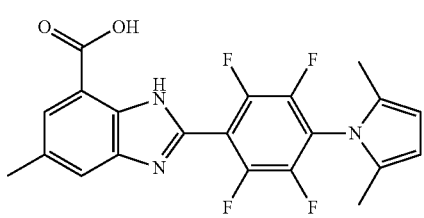
I83
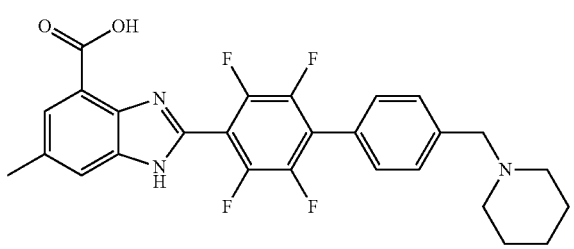
I84
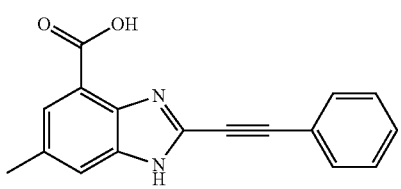
I85
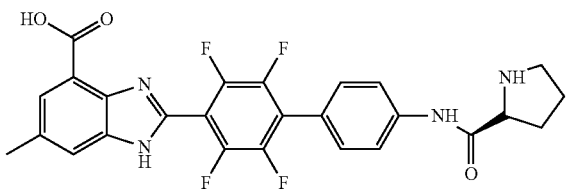
I86
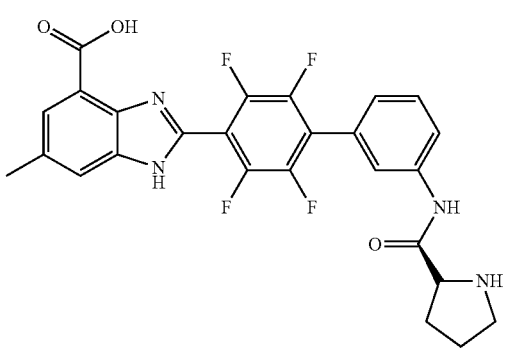
I87
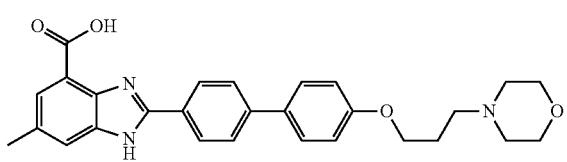
I88
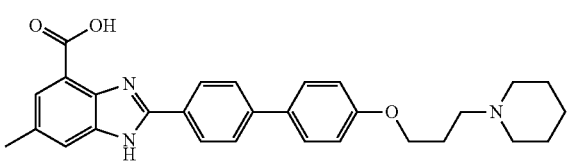
I89
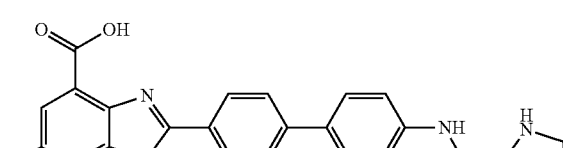
I90
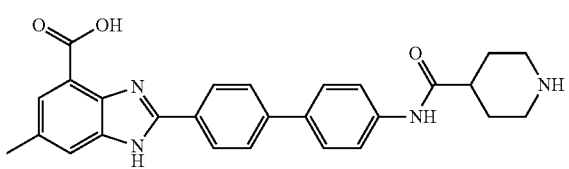
I91
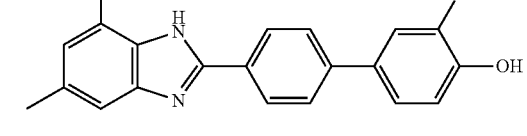

I92 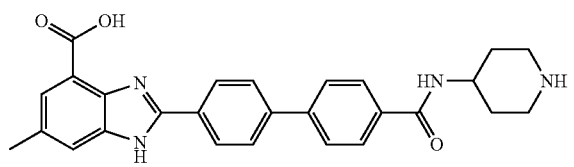
I93 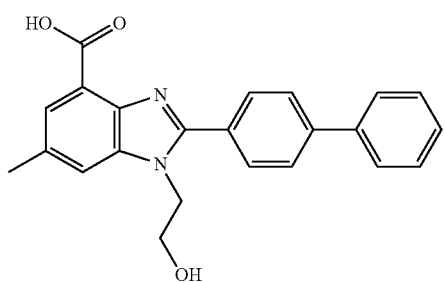
I94 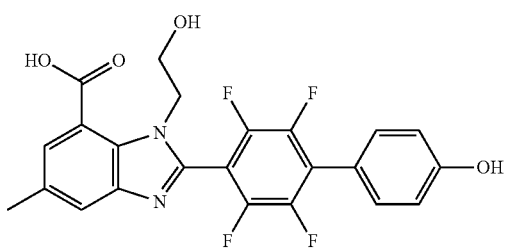
I95 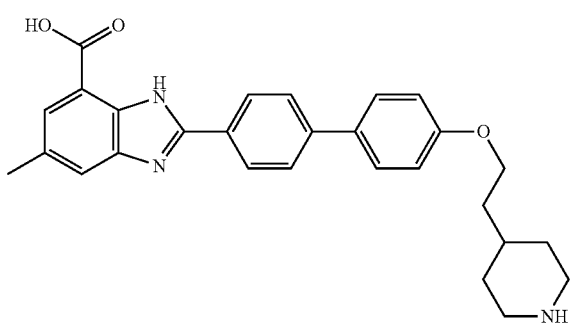
I96 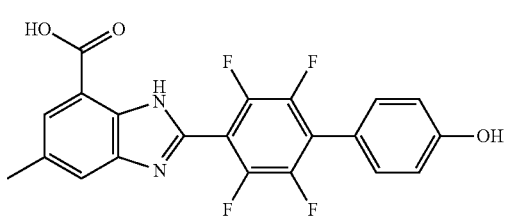
I97 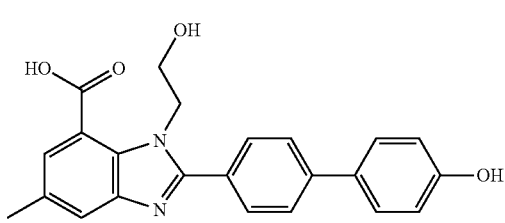
I98 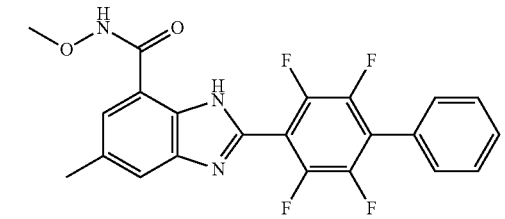
I99 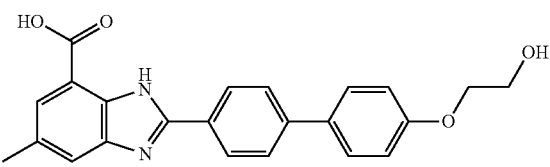
I100 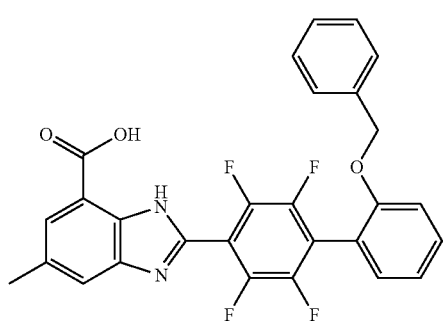
I101 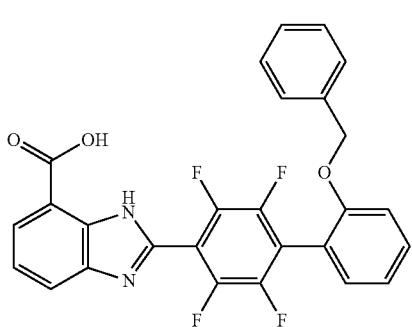
I102 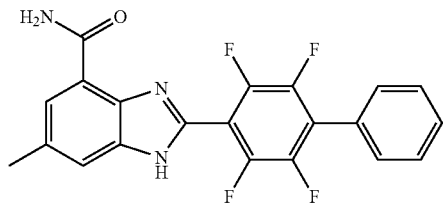
I103 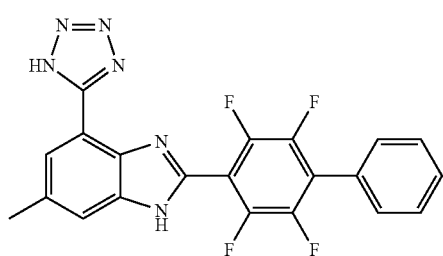

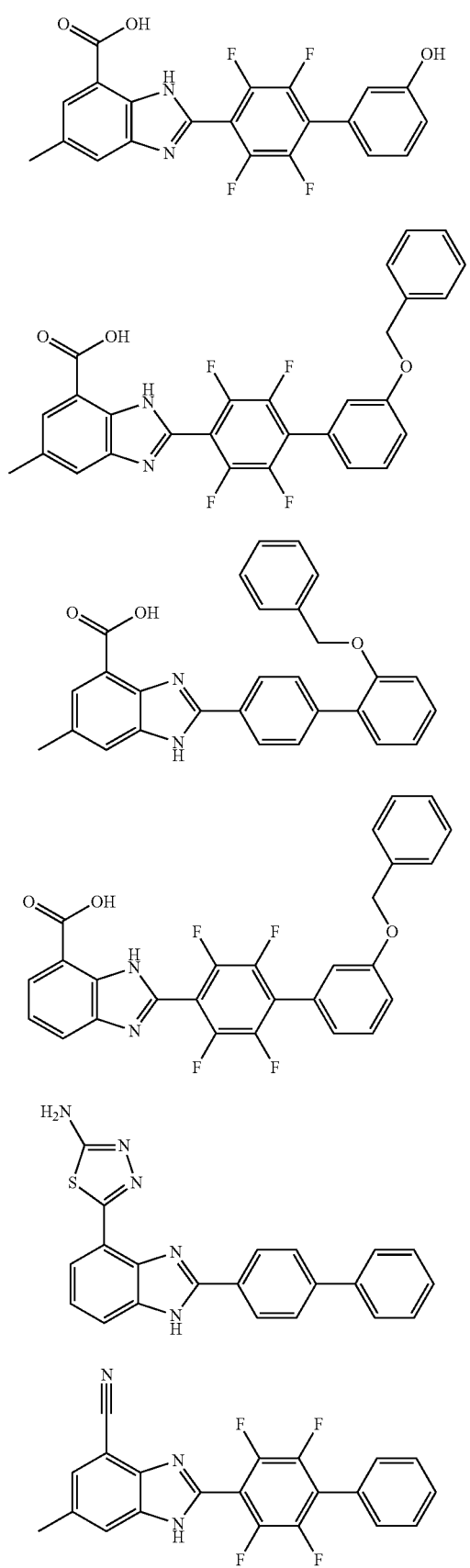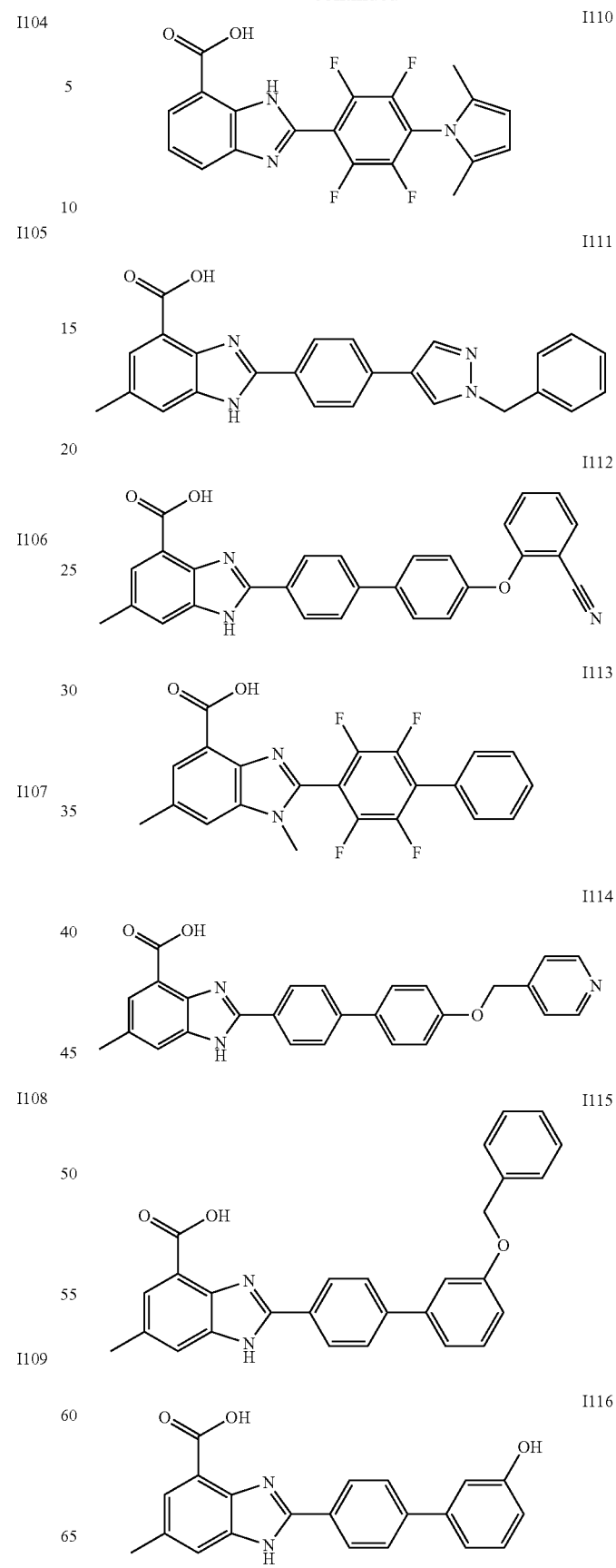

-continued

I117
I118
I119
I120
I121
I122
I123
I124
I125
I126
I127
I128
I129
I130

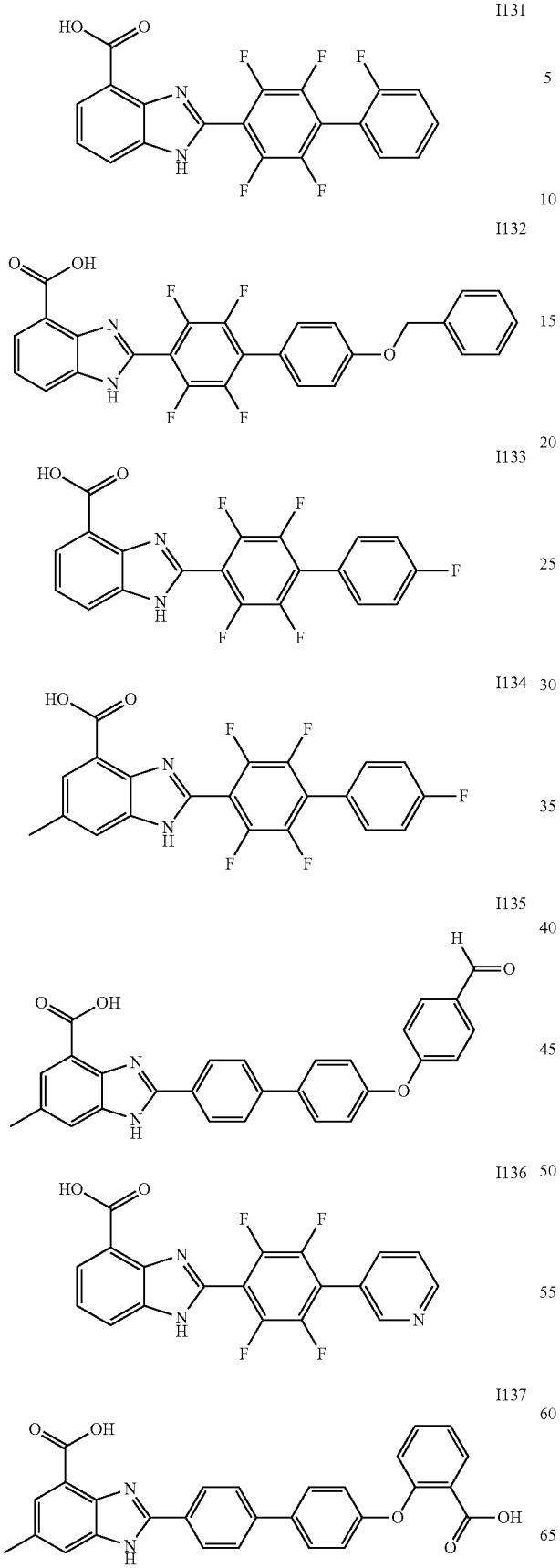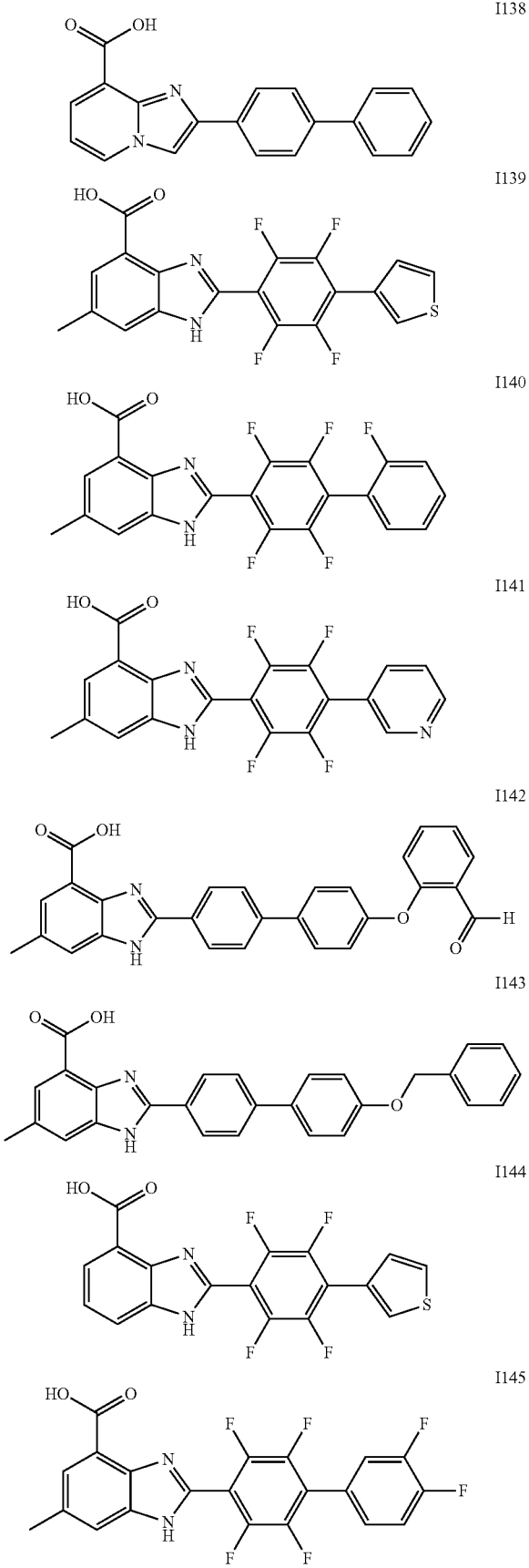

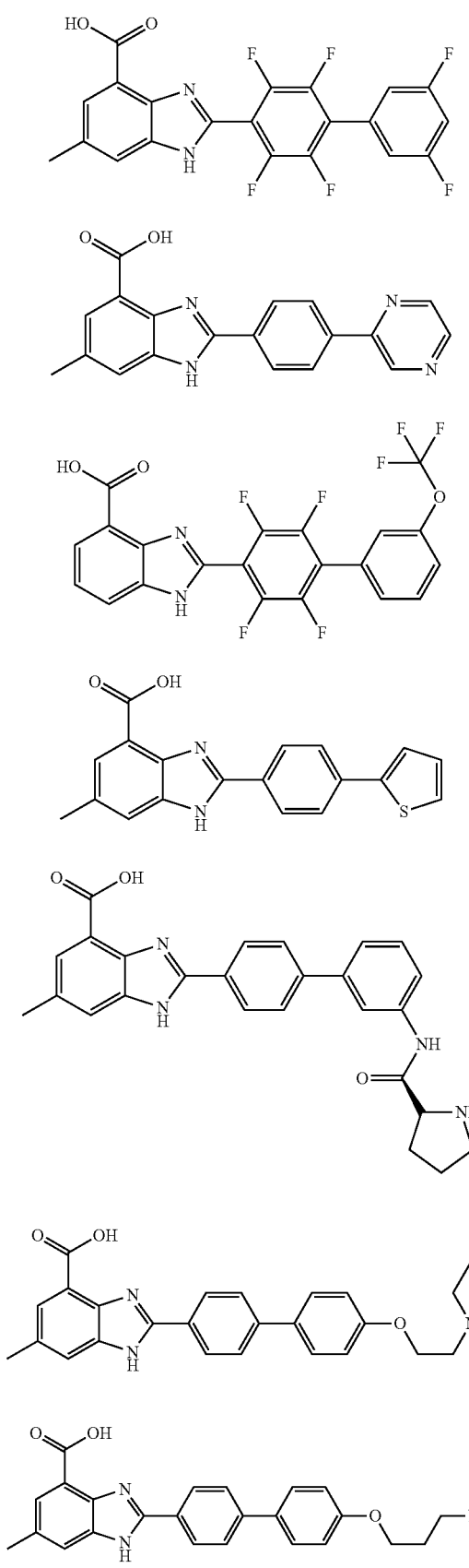
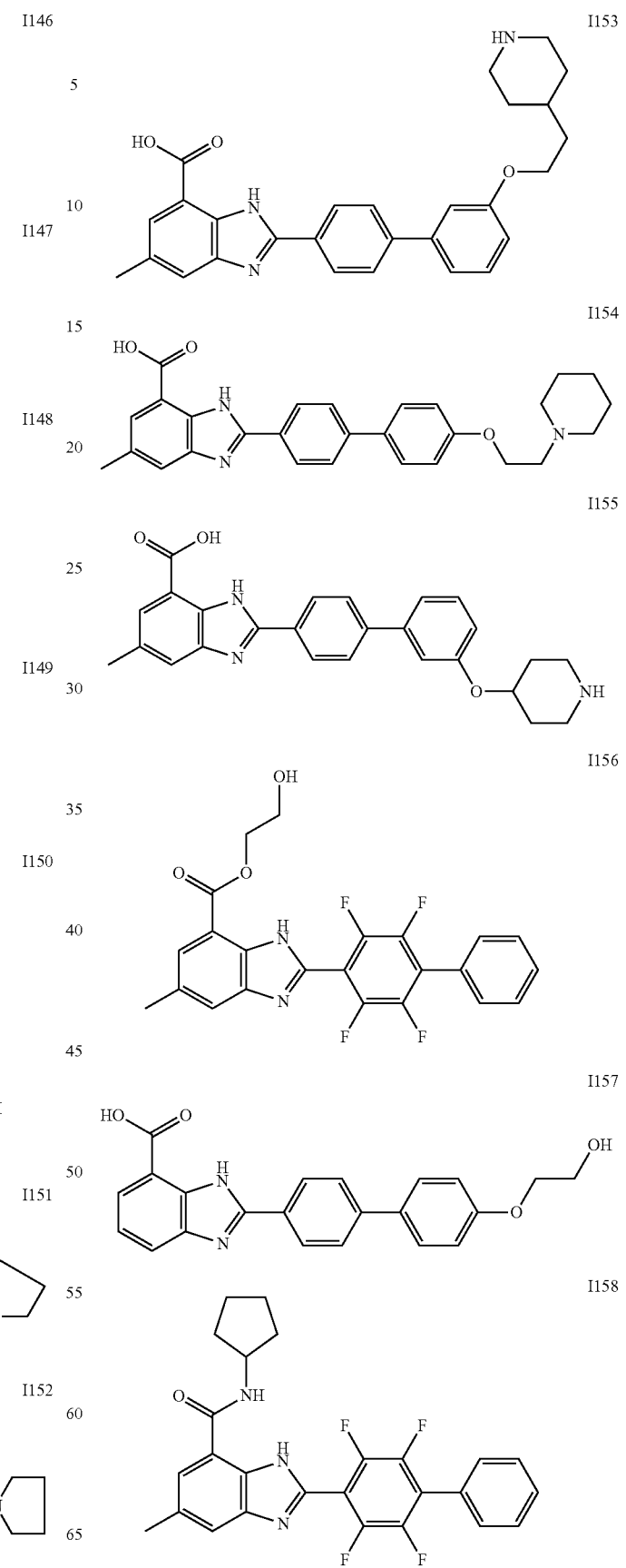

-continued

I159, I160, I161, I162, I163, I164, I165, I166, I167, I168, I169, I170, I171

I172 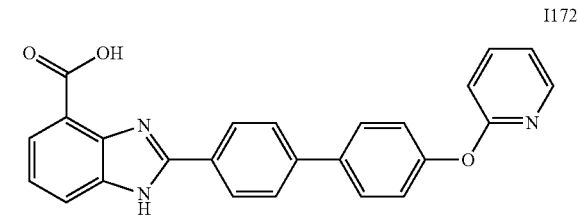
I173 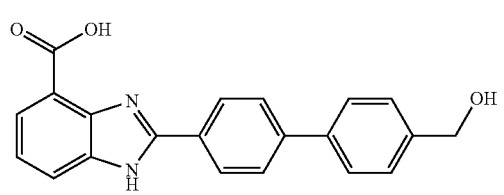
I174 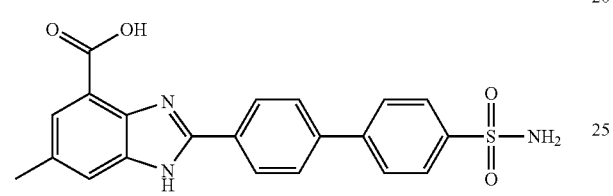
I175 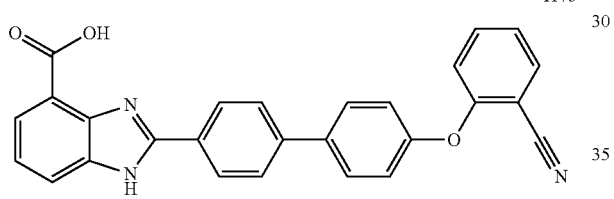
I176 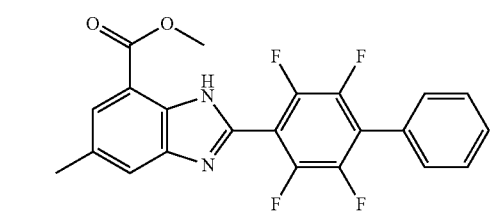
I177 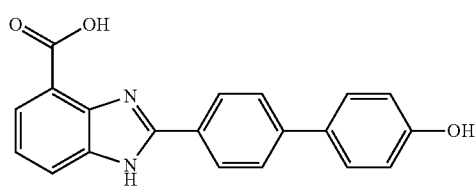
I178 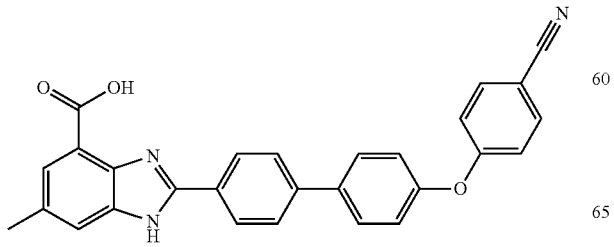
I179 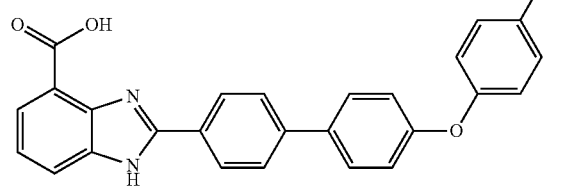
I180 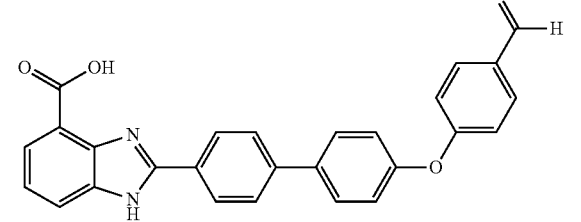
I181 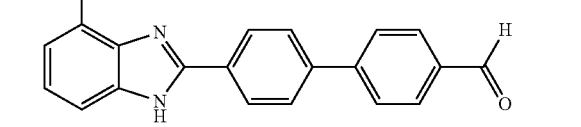
I182 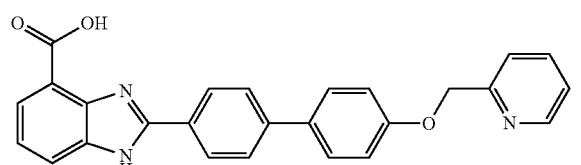
I183 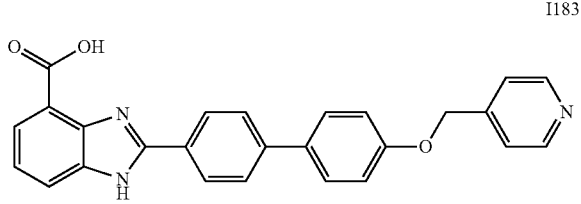
I184 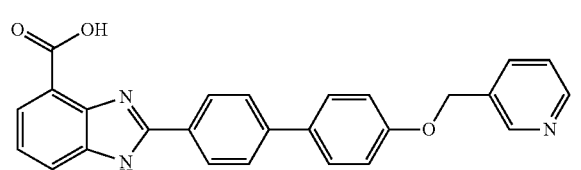
I185

-continued

I186

I187

I188

I189

I190

I191

I192 and pharmaceutically acceptable derivatives, solvates, tautomers, salts and stereoisomers thereof, including mixtures thereof in all ratios.

Alternatively, the present invention provides compounds of Formula (I) wherein $R^1$ is CONHA, $R^a$ is A or —O—$(CH_2)_m$—Ar, Q is a single bond, wherein A denotes a branched or linear alkyl having 1 to 12 C-atoms, wherein one or more, preferably 1 to 7H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by —CH=CH— or —C≡C— groups, or denotes cycloalkyl or cycloalkylalkylen having 3-7 ring C atoms;

Above and below, all radicals, such as $X^1$, $X^2$, Q, $R^1$, $R^2$, $R^3$, $R^4$, $R^5$, $R^a$, $R^b$, $R^c$, $R^d$, $R^e$, A, Het, Ar, have the meaning indicated under the formula I, unless expressly stated otherwise.

Generally, compounds of formula I are the more preferred, the more preferred substituents they carry.

$X^1$ preferably denotes $NR^c$, $NR^d$, or O, especially $NR^c$.

$X^2$ preferably denotes $NR^c$, $NR^d$ or $CR^cR^d$.

In a preferred embodiment, one of $X^1$ or $X^2$ denotes $NR^c$ or $NR^d$

In another preferred embodiment, both $X^1$ and $X^2$ denote $NR^c$ or $NR^d$ $R^1$ preferably denotes COOH, COOalkyl, A, COOA, COA, Het, CONHA, cyano, acyl, $R^1$ most preferably denotes one of the following groups:

COOH, COOMe, COO(CH$_2$)$_2$OH, COO(CH$_2$)$_2$OR$^3$, CN, COMe, CONH$_2$, CONHOMe, CF$_3$, wherein $R^3$ is as defined above.

$R^2$ preferably denotes H, A, alkyl, Hal, O-alkyl, O-A, especially H, Me, OMe, F, Cl or Br.

$R^d$ preferably denotes H, A or alkyl, especially H.

$R^a$ preferably denotes Ar, Het, O—Ar, O-Het, especially Ar or Het.

$R^a$ more preferably denotes phenyl, pyridinyl, oxazolyl, thienyl, benzothiazolyl.

$R^a$ very most preferably denotes phenyl, pyridinyl, or pyrrole.

$R^a$ most preferably denotes one of the following groups:

-continued
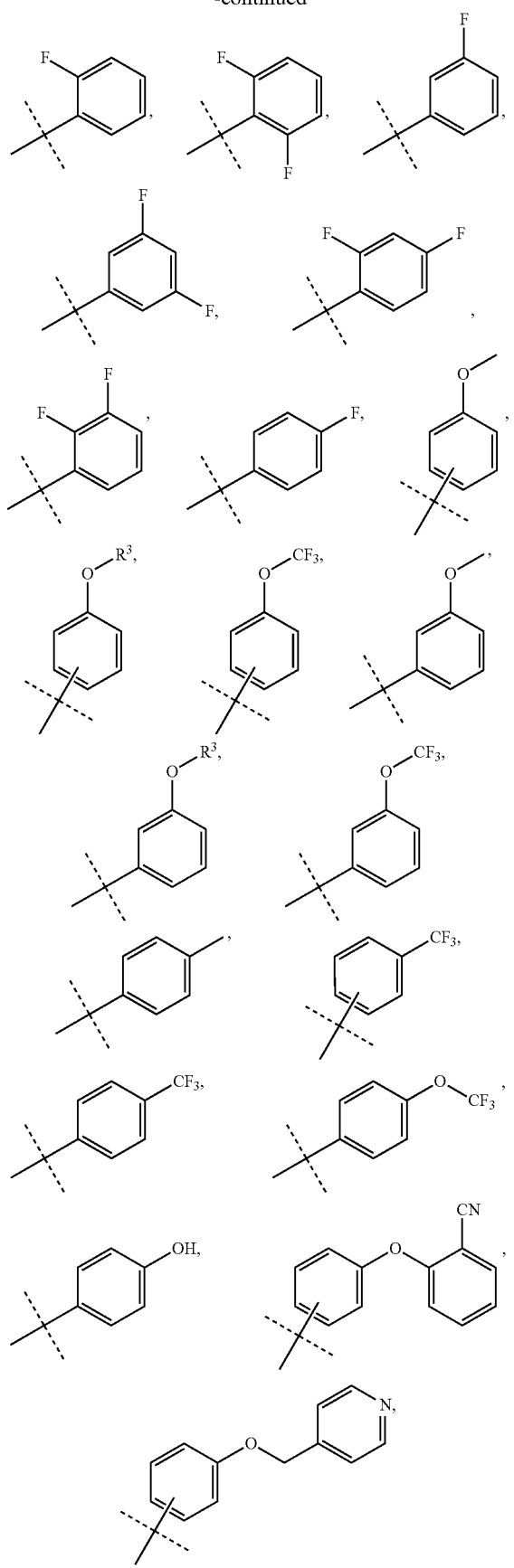
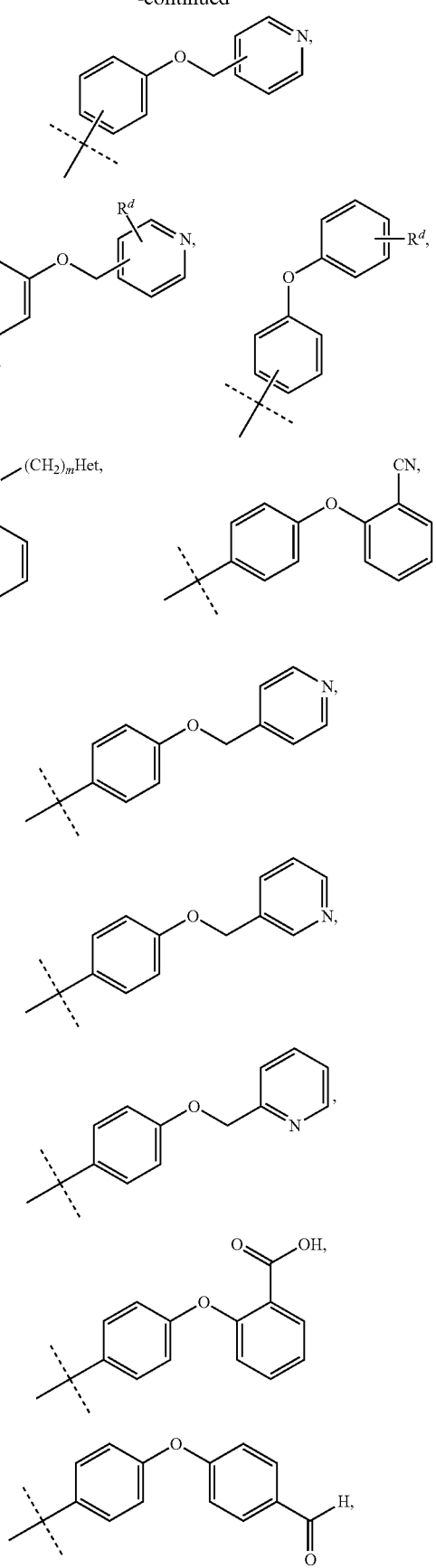

-continued
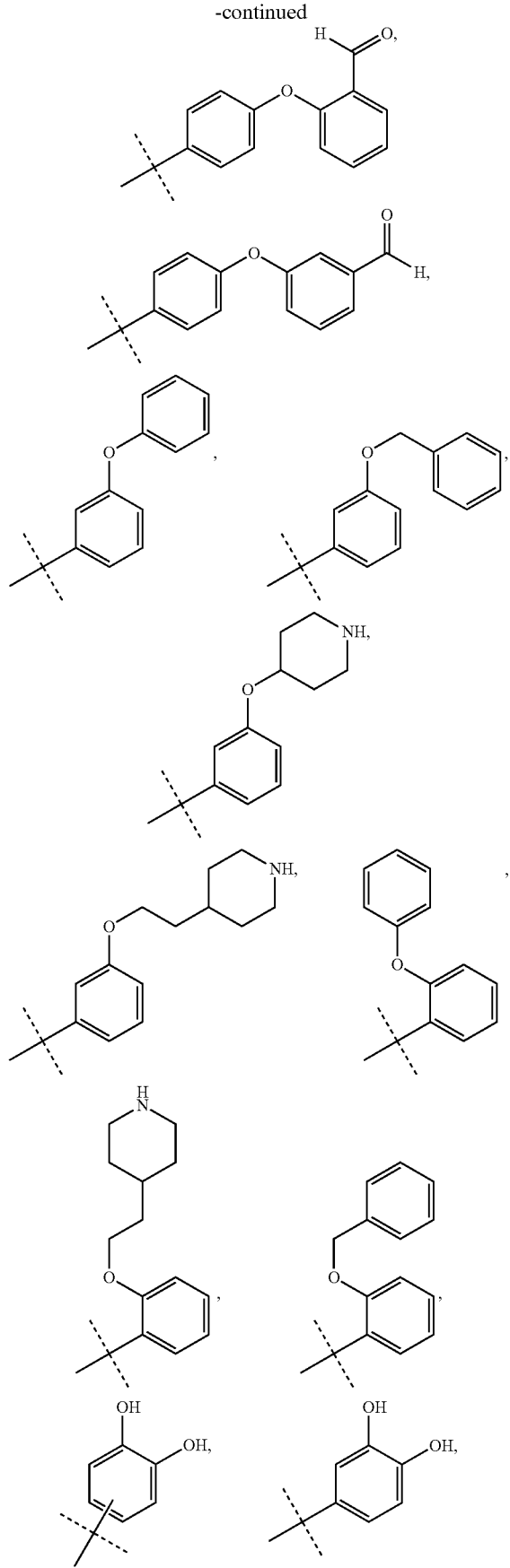
-continued
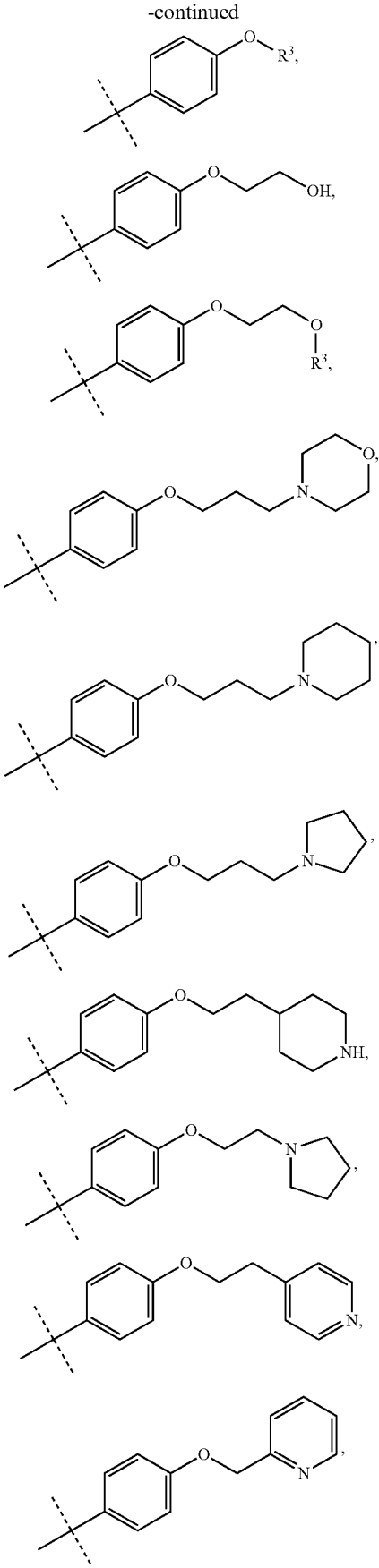

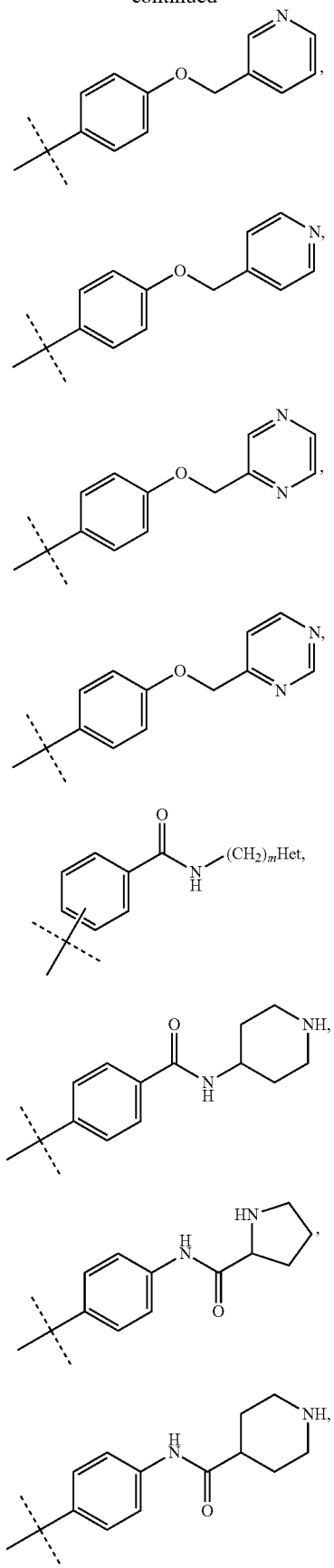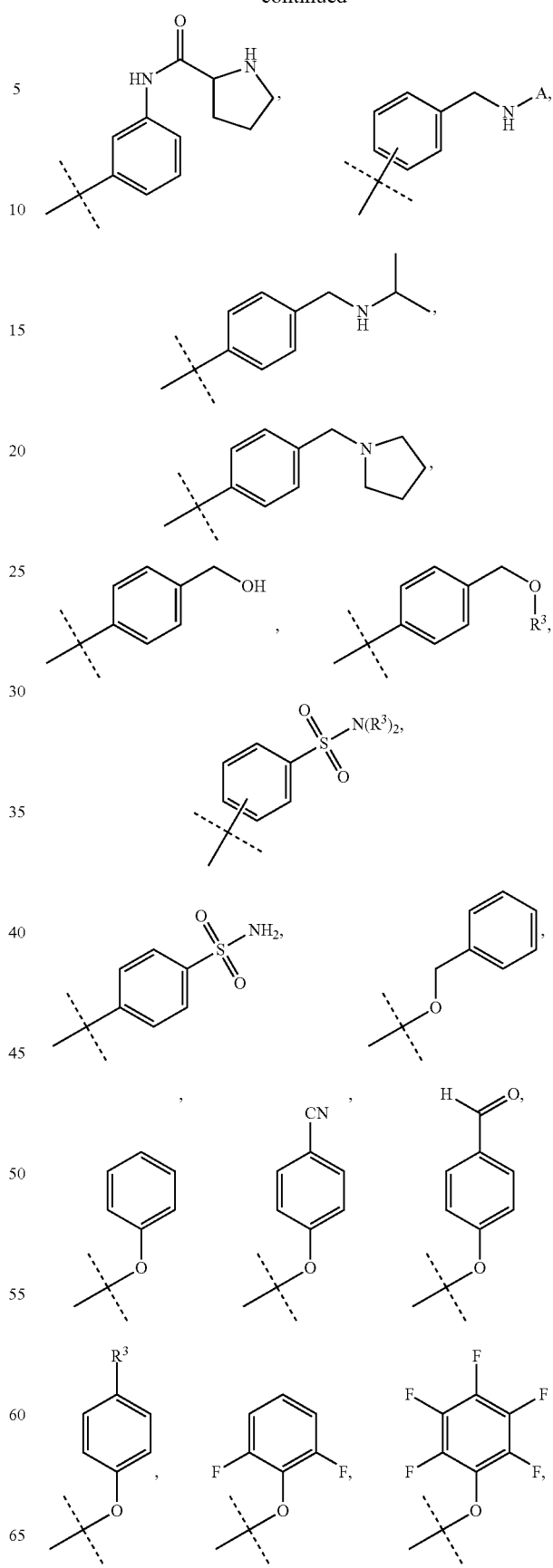

47

-continued

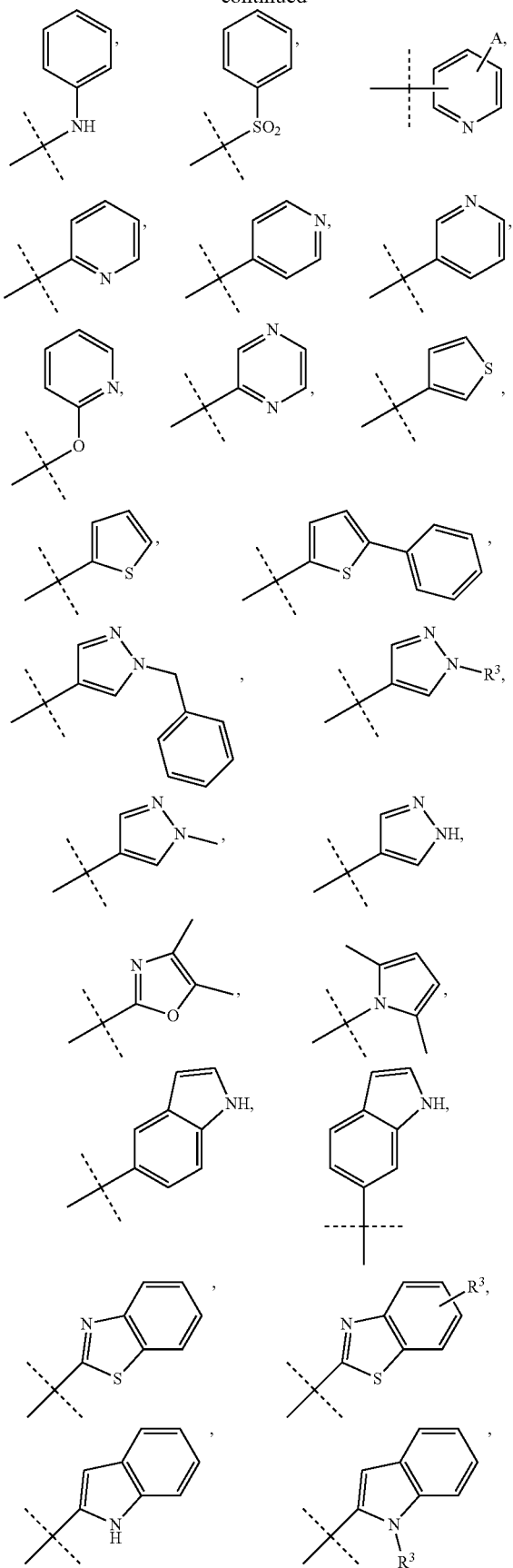

48

-continued

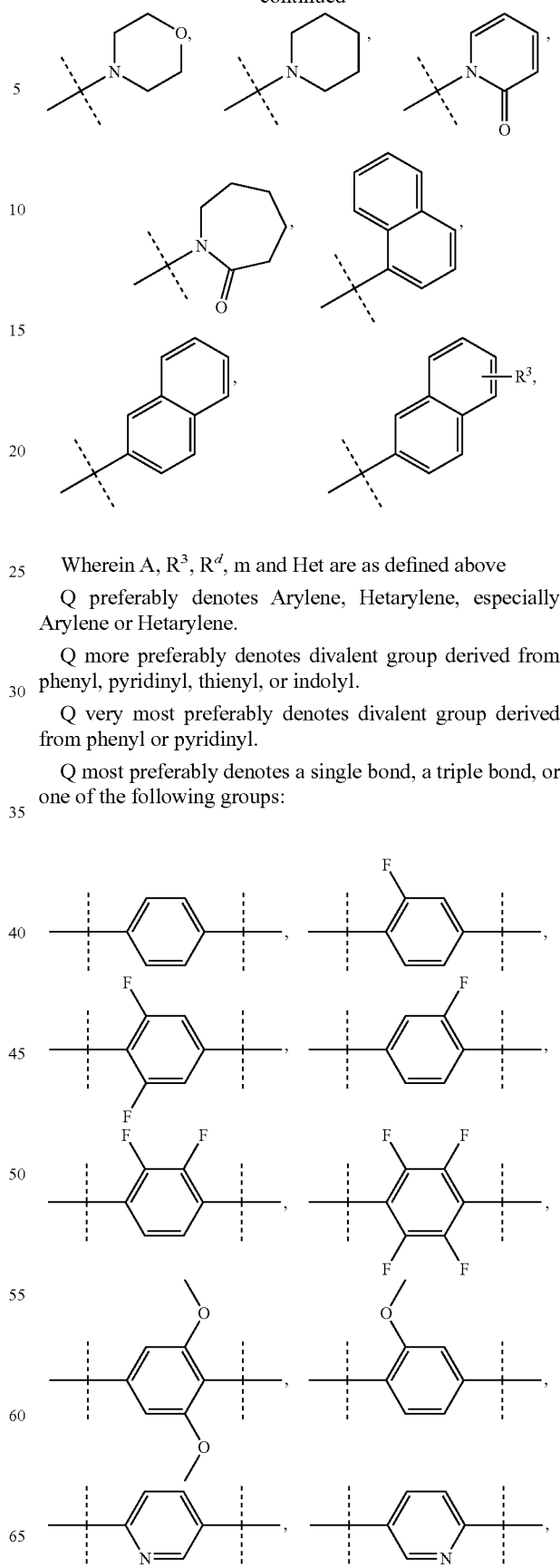

Wherein A, $R^3$, $R^d$, m and Het are as defined above

Q preferably denotes Arylene, Hetarylene, especially Arylene or Hetarylene.

Q more preferably denotes divalent group derived from phenyl, pyridinyl, thienyl, or indolyl.

Q very most preferably denotes divalent group derived from phenyl or pyridinyl.

Q most preferably denotes a single bond, a triple bond, or one of the following groups:

-continued

The group A very particularly preferably denotes alkyl having 1, 2, 3, 4, 5 or 6 carbon atoms.

Alkyl preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl, pentafluoroethyl or 1,1,1-trifluoroethyl.

Cycloalkyl preferably denotes cyclopropyl, cyclobutyl, cyclopentyl, cyclohexyl or cycloheptyl.

Cycloalkylalkylene preferably denotes cyclopropylmethylene, cyclobutylmethylene, cyclopentylmethylene, cyclohexylmethylene or cycloheptylmethylene.

Alkylene is preferably methylene, ethylene, propylene, butylene, pentylene or hexylene, furthermore branched alkylene.

Perfluoroalkyl preferably denotes $CF_3$.

Hal denotes Cl, Br, I, F and preferably F or Br.

Alkoxy is branched or linear and preferably denotes a group —O—$(CH_2)_n$—$CH_3$. Most preferablyalkoxy is Methoxy or Ethoxy.

Carboxy denotes a group —COOH.

Carboxyalkyl denotes an ester group, preferably an alkyl ester, such as COOMe or COOEt.

Sulfonyl denotes a group —$SO_2$—OH, —$SO_2$—$NH_2$, —$SO_2$NHA.

Alkylsulfonyl denotes a group —$SO_2$-alkyl, preferably Methylsulfonyl or Ethylsulfonyl.

Acyl denotes a group —C(O)R, wherein R can be A, Ar, Het as defined above. Preferably Acyl denotes acetyl (—C(O)$CH_3$).

Amino denotes the group —NRR''' where each R, R''' is independently hydrogen or alkyl or Ar or Het or A or Het-alkyl or Ar-alkyl, and where R and R''', together with the nitrogen atom to which they are attached, can optionally form a 3-8-membered Het ring.

Amido refers to the group —C(O)NRR''' where each R, R''' is independently hydrogen or alkyl or Ar or Het or A or Het-alkyl or Ar-alkyl, and where R and R''', together with the nitrogen atom to which they are attached, can optionally form a 3-8-membered Het ring.

Ar preferably denotes phenyl, which may be unsubstituted or monosubstituted, disubstituted or trisubstituted by a substitutent selected from $R^4$ and/or $R^5$;

Ar very particularly preferably denotes one of the following groups:

wherein $R^4$ and $R^5$ are as defined above.

More particularly, Ar is one of the following groups:

wherein $R^4$, $R^5$ is as defined above and preferably, wherein $R^4$ is Hal and $R^5$ is Hal, alkyl, O-alkyl or H.

Most preferably, Ar is unsubstituted or

Arylene is preferably a divalent group derived from Ar and more preferably denotes phenyl, which may be unsubstituted or monosubstituted, disubstituted or trisubstituted by a substitutent selected from $R^4$ and/or $R^5$;

Arylene very particularly denotes one of the following groups:

wherein $R^4$ and $R^5$ are as defined above.

More particularly, Arylene is one of the following groups:

wherein $R^4$, $R^5$ is as defined above and preferably, wherein $R^4$ is Hal and $R^5$ is Hal, alkyl, O-alkyl or H.

Het preferably denotes a monocyclic or bicyclic, saturated, unsaturated or aromatic heterocyclic ring having 1 to 3 N, O and/or S atoms which may which may be unsubstituted or substituted by a group selected from $(R^4)_n$ and/or $(R^5)_n$;

Het more preferably denotes a monocyclic or bicyclic, saturated, unsaturated or aromatic heterocyclic ring having 1 to 3 N, O and/or S atoms which may which may be unsubstituted or substituted by a group selected from $(R^4)_n$ and/or $(R^5)_n$;

Het is preferably a 6 to 14 membered ring system and denotes, not withstanding further substitutions, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, indazolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxane-6-yl, 2,1,3-benzothiadiazol-4- or -5-yl or 2,1,3-benzoxadiazol-5-yl.

The heterocyclic radicals may also be partially or fully hydrogenated. Het can thus also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)-phenyl or also 3,4-dihydro-2H-1,5-benzodioxepin-6- or -7-yl, furthermore preferably 2,3-dihydrobenzofuranyl or 2,3-dihydro-2-oxofuranyl.

Het very particularly denotes one of the following groups:

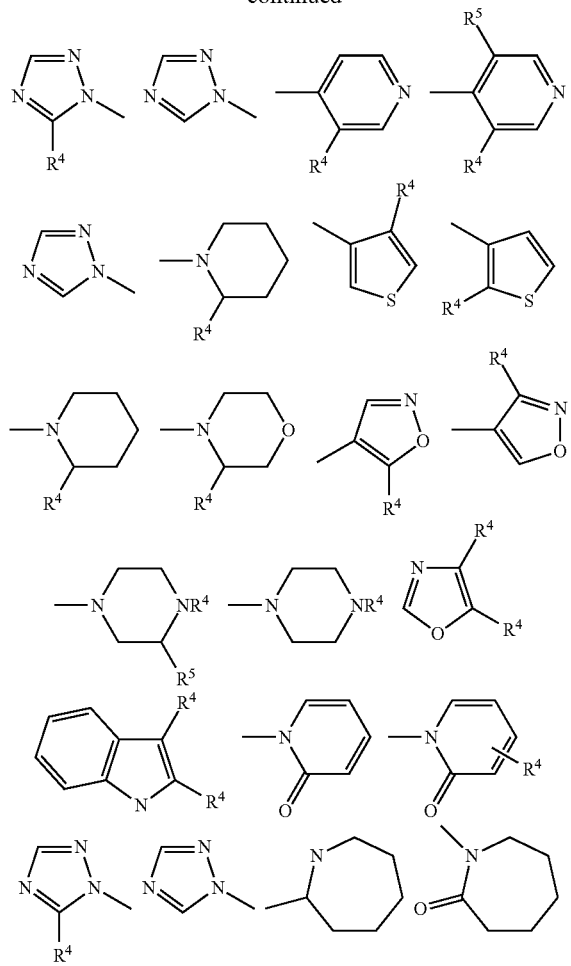

Hetarylene is preferably derived from the group Het as defined above and is most preferably

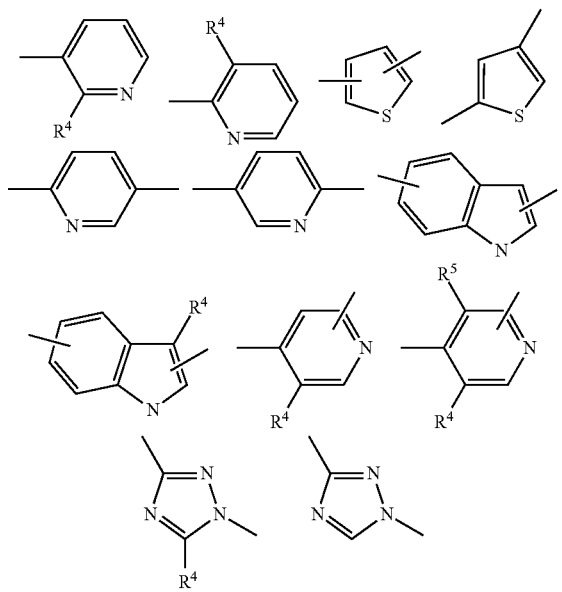

Wherein $R^4$ and $R^5$ are as defined above.

In another specific embodiment, the invention provides compounds of formula I wherein $R^1$ denotes COOH, COOalkyl, $CF_3$, acyl, cyano, preferably COOH;

In another specific embodiment, the invention provides compounds of formula I wherein $R^1$ denotes COOH, COOMe, $CF_3$, acetyl, cyano;

In another specific embodiment, the invention provides compounds of formula I wherein $R^1$ denotes COOH, COOalkyl, $CF_3$, acyl, cyano; $R^2$ denotes H, Hal, alkyl, O-alkyl;

In another specific embodiment, the invention provides compounds of formula I wherein $R^1$ denotes COOH, COOMe, $CF_3$, acetyl, cyano; $R^2$ denotes H, F, Cl or Br, Me, OMe;

In another specific embodiment, the invention provides compounds of formula I wherein $R^1$ denotes COOH, COOalkyl, $CF_3$, acyl, cyano; $R^2$ denotes H, Hal, alkyl, O-alkyl; $X^1$ and $X^2$ are as define above;

In another specific embodiment, the invention provides compounds of formula I wherein $R^1$ denotes COOH, COOMe, $CF_3$, acetyl, cyano; $R^2$ denotes H, F, Cl or Br, Me, OMe; $X^1$ and $X^2$ are as define above;

In another specific embodiment, the invention provides compounds of formula I wherein $R^1$ denotes COOH, COOalkyl, $CF_3$, acyl, cyano; $R^2$ denotes H, Hal, alkyl, O-alkyl; $X^1$ and $X^2$ are as define above; $R^d$ is H or alkyl;

In another specific embodiment, the invention provides compounds of formula I wherein $R^1$ denotes COOH, COOMe, $CF_3$, acetyl, cyano; $R^2$ denotes H, F, Cl or Br, Me, OMe; $X^1$ and $X^2$ are as define above; $R^d$ is H or Me;

In another specific embodiment, the invention provides compounds of formula I wherein $R^1$ denotes COOH, COOalkyl, $CF_3$, acyl, cyano; $R^2$ denotes H, Hal, alkyl, O-alkyl; $X^1$ and $X^2$ are as define above; $R^d$ is H or alkyl; Q denotes Arylene, Hetarylene;

In another specific embodiment, the invention provides compounds of formula I wherein $R^1$ denotes COOH, COOMe, $CF_3$, acetyl, cyano; $R^2$ denotes H, F, Cl or Br, Me, OMe; $X^1$ and $X^2$ are as define above; $R^d$ is H or Me; Q denotes Arylene, Hetarylene;

In another specific embodiment, the invention provides compounds of formula I wherein $R^1$ denotes COOH, COOalkyl, $CF_3$, acyl, cyano; $R^2$ denotes H, Hal, alkyl, O-alkyl; $X^1$ and $X^2$ are as define above; $R^d$ is H or alkyl; Q denotes Arylene, Hetarylene In another specific embodiment, the invention provides compounds of formula I wherein $R^1$ denotes COOH, COOMe, $CF_3$, acetyl, cyano; $R^2$ denotes H, F, Cl or Br, Me, OMe; $X^1$ and $X^2$ are as define above; $R^d$ is H or Me; Q denotes Arylene, Hetarylene;

In another specific embodiment, the invention provides compounds of formula I wherein $R^1$ denotes COOH, COOalkyl, $CF_3$, acyl, cyano; $R^2$ denotes H, Hal, alkyl, O-alkyl; $X^1$ and $X^2$ are as define above; $R^d$ is H or alkyl; Q denotes Arylene, Hetarylene;

In another specific embodiment, the invention provides compounds of formula I wherein $R^1$ denotes COOH, COOMe, $CF_3$, acetyl, cyano; $R^2$ denotes H, F, Cl or Br, Me, OMe; $X^1$ and $X^2$ are as define above; $R^d$ is H or Me; Q denotes Arylene, Hetarylene;

In another specific embodiment, the invention provides compounds of formula I wherein $R^1$ denotes COOH, COOalkyl, $CF_3$, acyl, cyano; $R^2$ denotes H, Hal, alkyl, O-alkyl; $X^1$ and $X^2$ are as define above; $R^d$ is H or alkyl; Q denotes —NH—, NHC(O)—; $R^a$ denotes Ar, O—Ar, O—$(CH_2)_m$—Ar, Het, O-Het, NH—Ar, $SO_2$Ar; m denotes 0, 1, 2;

In another specific embodiment, the invention provides compounds of formula I wherein $R^1$ denotes COOH, COOMe, $CF_3$, acetyl, cyano; $R^2$ denotes H, F, Cl or Br, Me, OMe; $X^1$ and $X^2$ are as define above; $R^d$ is H or Me; Q denotes Arylene, Hetarylene; $R^a$ denotes Ar, O—Ar, O—$(CH_2)_m$—Ar, Het, O-Het, NH—Ar, $SO_2$Ar; m denotes 0, 1, 2;

In another specific embodiment, the invention provides compounds of formula I wherein $R^1$ denotes COOH, COOalkyl, $CF_3$, acyl, cyano; $R^2$ denotes H, Hal, alkyl, O-alkyl; $X^1$ and $X^2$ are as define above; $R^d$ is H or alkyl; Q denotes Arylene, Hetarylene; $R^a$ denotes Ar, O—Ar, O—$(CH_2)_m$—Ar, Het, O-Het, NH—Ar, $SO_2$Ar; m denotes 0, 1, 2;

In another specific embodiment, the invention provides compounds of formula I wherein $R^1$ denotes COOH, COOMe, $CF_3$, acetyl, cyano; $R^2$ denotes H, F, Cl or Br, Me, OMe; $X^1$ and $X^2$ are as define above; $R^d$ is H or Me; Q denotes Arylene, Hetarylene; $R^a$ denotes Ar, O—Ar, O—$(CH_2)_m$—Ar, Het, O-Het, NH—Ar, $SO_2$Ar; m denotes 0, 1, 2;

In another specific embodiment, the invention provides compounds of formula I wherein $R^1$ denotes COOH, COOalkyl, $CF_3$, acyl, cyano; $R^2$ denotes H, Hal, alkyl, O-alkyl; $X^1$ and $X^2$ are as define above d; $R^d$ is H or alkyl; Q denotes —NH—, NHC(O)—; $R^a$ denotes Ar, O— Ar, O—$(CH_2)_m$—Ar, Het, O-Het, NH—Ar, $SO_2$Ar; m denotes 0, 1, 2; wherein Ar is selected from phenyl or naphtyl and Het is selected from pyridinyl, thienyl, indolyl, benzothiazolyl, morpholino, pyridinyl-2-one, oxazolyl, azepan-2-one; wherein Ar and Het as defined are unsubstituted or substituted by a group selected from $(R^4)_n$ and/or $(R^5)_n$; wherein $R^4$ and/or $R^5$ are each independently selected from Hal, alkoxy, perfluoroalkyl, perfluoroalkoxy, alkyl, cyano; n denotes 0, 1, 2, 3, 4, 5;

In another specific embodiment, the invention provides compounds of formula I wherein $R^1$ denotes COOH, COOMe, $CF_3$, acetyl, cyano; $R^2$ denotes H, F, Cl or Br, Me, OMe; $X^1$ and $X^2$ are as define above; $R^d$ is H or Me; Q denotes —NH—, NHC(O)—; $R^a$ denotes Ar, O—Ar, O—$(CH_2)_m$—Ar, Het, O-Het, NH—Ar, $SO_2$Ar; m denotes 0, 1, 2; wherein Ar is selected from Phenyl or Naphtyl and Het is selected from pyridinyl, thienyl, indolyl, benzothiazolyl, morpholino, pyridinyl-2-one, oxazolyl, azepan-2-one; wherein Ar and Het as defined are unsubstituted or substituted by a group selected from $(R^4)_n$ and/or $(R^5)_n$; wherein $R^4$ and/or $R^5$ are each independently selected from F, Cl or Br, OMe, $CF_3$, $OCF_3$, Me, cyano; n denotes 0, 1, 2, 3, 4, 5;

In another specific embodiment, the invention provides compounds of formula I wherein $R^1$ denotes COOH, COOalkyl, $CF_3$, acyl, cyano; $R^2$ denotes H, Hal, alkyl, O-alkyl; $X^1$ and $X^2$ are as define above; $R^d$ is H or alkyl; Q denotes Arylene, Hetarylene; $R^a$ denotes Ar, O—Ar, O—$(CH_2)_m$—Ar, Het, O-Het, NH—Ar, $SO_2$Ar; m denotes 0, 1, 2; wherein Ar is selected from Phenyl or Naphtyl and Het is selected from pyridinyl, thienyl, indolyl, benzothiazolyl, morpholino, pyridinyl-2-one, oxazolyl, azepan-2-one; wherein Ar and Het as defined are unsubstituted or substituted by a group selected from $(R^4)_n$ and/or $(R^5)_n$; wherein $R^4$ and/or $R^5$ are each independently selected from Hal, alkoxy, Perfluoroalkyl, perfluoroalkoxy, alkyl, cyano; n denotes 0, 1, 2, 3, 4, 5;

In another specific embodiment, the invention provides compounds of formula I wherein $R^1$ denotes COOH, COOMe, $CF_3$, acetyl, cyano; $R^2$ denotes H, F, Cl or Br, Me, OMe; $X^1$ and $X^2$ are as define above; $R^d$ is H or Me; Q denotes Arylene, Hetarylene; $R^a$ denotes Ar, O—Ar, O—$(CH_2)_m$—Ar, Het, O-Het, NH—Ar, $SO_2Ar$; m denotes 0, 1, 2; wherein Ar is selected from Phenyl or Naphtyl and Het is selected from pyridinyl, thienyl, indolyl, benzothiazolyl, morpholino, pyridinyl-2-one, oxazolyl, azepan-2-one; wherein Ar and Het as defined are unsubstituted or substituted by a group selected from $(R^4)_n$ and/or $(R)_n$; wherein $R^4$ and/or $R^5$ are each independently selected from F, Cl or Br, OMe, $CF_3$, $OCF_3$, Me, cyano; n denotes 0, 1, 2, 3, 4, 5;

In a very specific embodiment the invention provides compounds of formula II

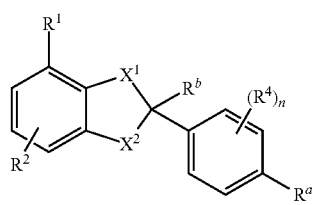

II wherein $R^1$, $R^2$, $X^1$, $X^2$, $R^a$, $R^b$, $R^4$ and n are as defined in formula I, and pharmaceutically acceptable derivatives, solvates, tautomers, salts and stereoisomers thereof, including mixtures thereof in all ratios;

In a very specific preferred embodiment the invention provides compounds of formula IIa

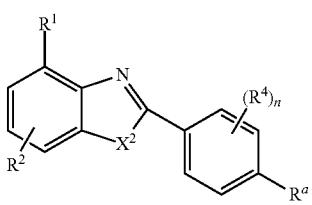

IIa wherein $R^1$, $R^2$, $X^2$, $R^a$, $R^4$ are as described in formula II and pharmaceutically acceptable derivatives, solvates, tautomers, salts and stereoisomers thereof, including mixtures thereof in all ratios;

In a very specific preferred embodiment the invention provides compounds of formula IIb

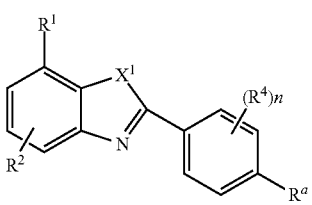

IIb

Wherein $R^1$, $R^2$, $X^1$, $R^a$, $R^4$ are as described in formula II and pharmaceutically acceptable derivatives, solvates, tautomers, salts and stereoisomers thereof, including mixtures thereof in all ratios;

In a very specific embodiment the invention provides compounds of formula III

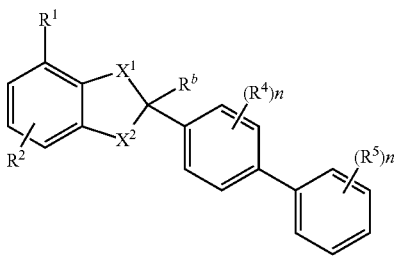

III wherein $R^1$, $R^2$, $X^1$, $X^2$, $R^a$, $R^b$, $R^4$, $R^5$ and n are as defined in formula I, and pharmaceutically acceptable derivatives, solvates, tautomers, salts and stereoisomers thereof, including mixtures thereof in all ratios;

In a very specific embodiment the invention provides compounds of formula IIIa

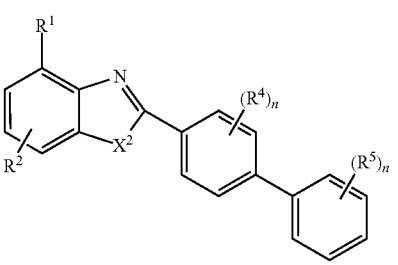

IIIa wherein $R^1$, $R^2$, $X^2$, $R^4$, $R^5$, n are as described in formula III and pharmaceutically acceptable derivatives, solvates, tautomers, salts and stereoisomers thereof, including mixtures thereof in all ratios;

In a very specific embodiment the invention provides compounds of formula IIIb

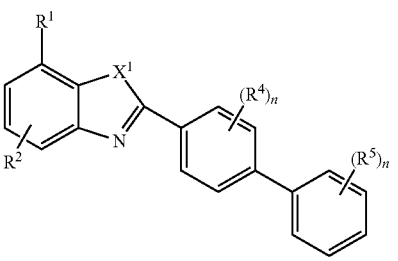

IIIb wherein $R^1$, $R^2$, $X^1$, $R^4$, $R^5$, m are as described in formula III and pharmaceutically acceptable derivatives, solvates, tautomers, salts and stereoisomers thereof, including mixtures thereof in all ratios;

The compounds of the formula I, II, IIa, IIb, III, IIIa, IIIb and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3$^{rd}$ Edition 1999.

Use can also be made here of variants which are known per se, but are not mentioned here in greater detail.

If desired, the starting materials can also be formed in situ so that they are not isolated from the reaction mixture, but instead are immediately converted further into the compounds of the formula I.

The starting compounds for the preparation of compounds of formula I are generally known. If they are novel, they can, however, be prepared by methods known per se.

The reactions are preferably carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Accordingly, the invention relates, in particular, to the use of compounds of the formula I, II, IIa, IIb, III, IIIa, IIIb as defined above, wherein $X^1$, $X^2$, $R^1$, $R^2$, $R^3$, $R^4$, $R^5$, Q, $R^a$ and $R^b$, $R^c$, $R^d$, Ar, Het and alkyl are as defined above as a medicament.

Accordingly, the invention relates, in particular, to the use of compounds of the formula I, II, IIa, IIb, III, IIIa, IIIb as defined above, wherein $X^1$, $X^2$, $R^1$, $R^2$, $R^3$, $R^4$, $R^5$, Q, $R^a$ and $R^b$, $R^c$, $R^d$, Ar, Het and alkyl are as defined above for the preparation of pharmaceutical formulation for the prevention and/or the treatment of multiple sclerosis and related disorders.

The said compounds of the formula I, II, IIa, IIb, III, IIIa, IIIb can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I, II, IIa, IIb, III, IIIa, IIIb contains an acidic center, such as a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example sodium- or potassium methoxide and sodium or potassiumpropoxide, alkalihydrides, such as sodium- or potassiumhydride; and various organic bases, such as piperidine, diethanolamine and N-methyl-glutamine, benzathine, choline, diethanolamine, ethylenediamine, meglumine, benethamine, diethylamine, piperazine and tromethamine. The aluminium salts of the compounds of the formula I, II, IIa, IIb, III, IIIa, IIIb are likewise included. In the case of certain compounds of the formula I and related formulae, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzene-sulfonate, and other organic acids and corresponding salts thereof, such as acetate, trifluoro-acetate, tartrate, maleate, succinate, citrate, benzoate, salicylate, ascorbate and the like. Accordingly, pharmaceutically acceptable acid-addition salts of the compounds of the formula I and related formulae include the following: acetate, adipate, alginate, arginate, aspartate, benzoate, benzene-sulfonate (besylate), bisulfate, bisulfite, bromide, butyrate, camphorate, camphor-sulfonate, caprylate, chloride, chlorobenzoate, citrate, cyclo-pentane-propionate, digluconate, dihydrogen-phosphate, dinitrobenzoate, dodecyl-sulfate, ethanesulfonate, fumarate, galacterate (from mucic acid), galacturonate, glucoheptanoate, gluconate, glutamate, glycerophosphate, hemi-succinate, hemisulfate, heptanoate, hexanoate, hippurate, hydro-chloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula I, II, IIa, IIb, III, IIIa, IIIb include aluminium, ammonium, calcium, copper, iron(III), iron(II), lithium, magnesium, manganese(III), manganese(II), potassium, sodium and zink salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethyl-amine, 2-diethyl-aminoethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropyl-amine and tris(hydroxy-methyl)-methylamine (tromethamine), but this is not intended to represent a restriction.

Compounds of the formula I, II, IIa, IIb, III, IIIa, IIIb of the present invention which contain basic nitrogen-containing groups can be quaternised using agents such as ($C_1$-$C_4$)-alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, do-decyl, lauryl, myristyl and stearyl chloride, bromide and iodide; and aryl-($C_1$-$C_4$)alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula I, II, IIa, IIb, III, IIIa, IIIb are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula I, II, IIa, IIb, III, IIIa, IIIb are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula I, II, IIa, IIb, III, IIIa, IIIb contains more than one group which is capable of forming pharmaceutically acceptable salts of this type, the formula I also encompasses multiple salts. Typical multiple salts include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I, II, IIa, IIb, III, IIIa, IIIb in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula I, II, IIa, IIb, III, IIIa, IIIb can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula I, II, IIa, IIb, III, IIIa, IIIb in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function or in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonabcd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA41g, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod. These further medicaments, such as interferon beta, may be administered concomitantly or sequentially, e.g. by subcutaneous, intramuscular or oral routes.

The invention furthermore relates to the use of compounds of formula I, II, IIa, IIb, III, IIIa, IIIb in combination with at least one further medicament active ingredient, preferably medicaments used in the treatment of cancer wherein said antitumoral compounds are selected from those well know by the one skilled in the related art.

These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I, II, IIa, IIb, III, IIIa, IIIb and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I, II, IIa, IIb, III, IIIa, IIIb and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

In one aspect, the present invention provides the use of compounds according to formula (I) and related formulae, wherein $R^1$ denotes COOH, COOA, COA, CONHA, CON$(R^3)_2$, $CF_3$, acyl, cyano, Het, tetrazoyl, sulfonyl,; $R^2$ denotes H, Hal, A, O-alkyl, Ar; $R^a$ denotes H, A, Ar, Het, O-Het, NH-Het, O—Ar, —O—$(CH_2)_m$—Ar, —O—$(CH_2)_m$-Het, —NH—$(CH_2)_m$-Het, NH—Ar, $S(O)_2$Ar, $S(O)$Ar, —S—Ar, $OCF_3$,; Q denotes a single bond, a group —C≡C—, Arylene or Hetarylene and pharmaceutically acceptable derivatives, solvates, tautomers, salts and stereoisomers thereof, including mixtures thereof in all ratios as a medicament.

In a second aspect, the present invention relates the use of compounds according to formula (I) and related formulae, and pharmaceutically usable derivatives, salts, tautomers, solvates and stereoisomers thereof, including mixtures thereof in all ratios, for the preparation of a medicament for the treatment and/or prophylaxis of diseases in which the inhibition, activation, regulation, and/or modulation of dihydroorotate dehydrogenase plays a role.

In a third aspect, the present invention relates to the use of compounds according to formula (I) and related formulae, and pharmaceutically usable derivatives, salts, tautomers, solvates and stereoisomers thereof, including mixtures thereof in all ratios, for the preparation of a medicament for the treatment and/or prophylaxis of a dihydroorotate dehydrogenase associated disorder.

In a fourth aspect, the present invention relates to the use of compounds according to formula (I) and related formulae, wherein the dihydroorotate dehydrogenase associated disorder is an autoimmune disorder or condition associated with an overactive immune response.

In a fifth aspect, the present invention related to the use of compounds according to formula (I) and related formulae, and pharmaceutically usable derivatives, salts, tautomers, solvates and stereoisomers thereof, including mixtures thereof in all ratios, for the preparation of a medicament for the treatment and/or prophylaxis of an immunoregulatory abnormality.

In a sixth aspect, the present invention relates to the use according to the fifth aspect, wherein the immunoregulatory abnormality is an autoimmune or chronic inflammatory disease selected from the group consisting of: systemic lupus erythematosis, chronic rheumatoid arthritis, type I diabetes mellitus, inflammatory bowel disease, biliary cirrhosis, uveitis, multiple sclerosis, amyotrophic lateral sclerosis (ALS), Crohn's disease, ulcerative colitis, bullous pemphigoid, sarcoidosis, psoriasis, autoimmune myositis, Wegener's granulomatosis, ichthyosis, Graves ophthalmopathy and asthma.

In a seventh aspect, the present invention relates to the use according to the sixth aspect, wherein the immunoregulatory abnormality is bone marrow or organ transplant rejection or graft-versus-host disease.

In a height aspect, the present invention relates to a kit or a set comprising at least one compound of Formula (I), preferably in combination with immunomodulating agents. Alternatively, the kit consists of separate packs of:
(a) an effective amount of a compound of the formula (I) and/or pharmaceutically usable derivatives, solvates and stereoisomers thereof, including mixtures thereof in all ratios, and
(b) an effective amount of a further medicament active ingredient.

A therapeutically effective amount of a compound of the formula I, II, IIa, IIb, III, IIIa, IIIb and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a Dihydroorate dehydrogenase related disorder, comprising administering to said subject an effective amount of a compound of formula I, II, IIa, IIb, III, IIIa, IIIb. The present invention preferably relates to a method, wherein the Dihydroorate dehydrogenase associated disorder is an autoimmune disorder or condition associated with an overactive immune response or cancer. The present invention furthermore relates to a method of treating a subject suffering from an immunerogulatory abnormality, comprising administering to said subject a compound of formula I, II, IIa, IIb, III, IIIa, IIIb in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

Preferred compounds of formula I and related formulae exhibit a $IC_{50}$ for the binding to the Dihydroorotate dehydrogenase of less than about 5 µM, preferably less than about 1 µM and even more preferred less than about 0.010 µM.

Compounds according to formula I and related formulae may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In general, the synthesis pathways for any individual compound of formula I and related formulae will depend on the specific substitutents of each molecule and upon the ready availability of intermediates necessary; again such factors being appreciated by those of ordinary skill in the art.

Compounds of this invention can be isolated in association with solvent molecules by crystallization from evaporation of an appropriate solvent. The pharmaceutically acceptable acid addition salts of the compounds of formula I and related formulae which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula I and related formulae, which contain an acid center, with a suitable base. Both types of salts may be formed or interconverted using ion-exchange resin techniques.

Nomenclature of the compounds of this invention has been determined using ISIS/draw 2.5 SP1 software.

In the following the present invention shall be illustrated by means of some examples, which are not construed to be viewed as limiting the scope of the invention.

EXAMPLES

The commercially available starting materials used in the following experimental description were purchased from Aldrich or Fluka unless otherwise reported. The HPLC, NMR and MS data provided in the examples described below are obtained as followed:

The HPLC Data:

Method A: HPLC columns: Xbridge™ C8 column 50 mm×4.6 mm at a flow of 2 mL/min; 8 min gradient from 0.1% TFA in H$_2$O to 0.07% TFA in ACN.

Method B: HPLC columns: Xbridge™ C8 column 50 mm×4.6 mm at a flow of 1 mL/min; 8 min gradient H$_2$O ammonium acetate (10 μM, pH 9)—ACN from 95:5 to 0:100.

Method C: HPLC columns: ATLANTIS C18 75×4.6 mm 5 U at a flow of 0.8 mL/min; A—0.1% HCOOH B-ACN Method D: HPLC columns: C18 BDS, 50×4.6 mm, SC\307 at a flow of 0.8 mL/min; A—0.1% TFA, B-ACN: Flow—0.8 mL/min.

UV detection (maxplot) for all methods. Mass spectrum data: LC/MS Waters ZMD (ESI); GC/MS: GC Agilent 6890N & MS Agilent 5973.

$^1$H-NMR data: Bruker DPX-300 MHz unless otherwise reported.

The preparative HPLC purifications are performed with HPLC waters Prep LC 4000 System equipped with columns ®PrepMS C18 10 μm, 50×300 mm, unless otherwise reported. All HPLC purifications were performed with a gradient of ACN/H$_2$O or ACN/H$_2$O/TFA (0.1%).

Example 1

2-Biphenyl-4-yl-1H-benzoimidazole-4-carboxylic acid

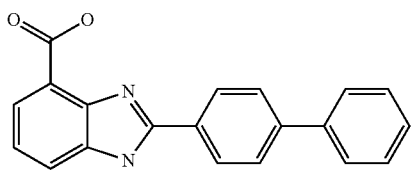

Step 1:
2-Hydroxyimino-N-(2-nitro-phenyl)-acetamide

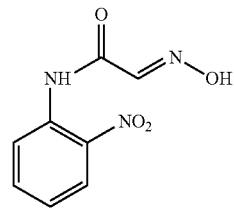 [SMILES: O=C(/C=N/O)Nc1ccccc1[N+](=O)[O-]]

A solution of chloral hydrate (29 g, 175 mmol), hydroxylamine hydrochloride (69.4 g, 1000 mmol) and anhydrous sodium sulphate (21 g, 149 mmol) in water (800 mL) was heated to 65° C. To this a suspension, 2-nitroaniline (20 g, 150 mmol) in 2 molar aqueous HCl (20 mL) was added. This mixture was stirred overnight at the same temperature, then cooled to room temperature. The precipitated product was collected by filtration, washed with water dried in a vacuum oven to give 25 g of the required product as a yellow coloured solid (83%).

$^1$H NMR (300 MHz, DMSO-d$_6$): δ (ppm)=12.62 (s, 1H), 10.94 (s, 1H), 8.29 (d, 1H, J=8.4 Hz), 8.13 (dd, 1H, J=8.4 & 1.2 Hz), 7.77 (m, 1H), 7.62 (s, 1H), 7.36 (m, 1H). HPLC purity: 85%.

Step 2: 7-Nitro-1H-indole-2,3-dione

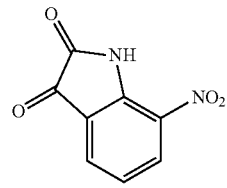 [SMILES: O=C1Nc2c(cccc2[N+](=O)[O-])C1=O]

2-Hydroxyimino-N-(2-nitro-phenyl)-acetamide (15 g, 72 mmol) was carefully added in small portions to a stirred solution of preheated (90° C.) conc. sulphuric acid (45 mL) over a period of 30 min and the resulting mixture was stirred for another 2 h at the same temperature. It was then cooled to room temperature, poured into crushed ice, the precipitated products was collected by filtrations. The collected precipitated products were washed with water and dried in a vacuum oven to get a brick red colour powder.

$^1$H NMR (300 MHz, DMSO-d$_6$): δ (ppm)=11.68 (s, 1H), 8.31 (dd, 1H, J=8.4 & 0.9 Hz), 7.92 (dd, 1H, J=8.4 & 0.9 Hz), 7.25 (m, 1H). HPLC purity: 93%

Step 3: 2-Amino-3-nitro-benzoic acid

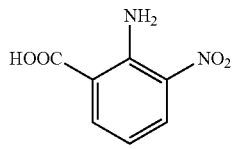 [SMILES: Nc1c(C(=O)O)cccc1[N+](=O)[O-]]

To a ice cold solution of 7-nitro-1H-indole-2,3-dione (9 g, 47 mmol) in 2 M aqueous sodium hydroxide (50 mL), 30% hydrogen peroxide (9 mL) was added drop wise. The mixture was warmed to room temperature and stirred overnight. The mixture was carefully acidified by addition of a saturated citric acid solution. The solid precipitate was collected by filtration, washed with water and dried in a vacuum oven to get 6 g of the required product as a yellow coloured solid (70%).

$^1$H NMR (300 MHz, DMSO-d$_6$): δ (ppm)=8.9 (br.s, 1H), 8.19 (m, 2H), 6.63 (m, 1H). HPLC purity: 98%. LCMC (–ive mode): 93% and m/z: 181.9

Step 4: 2-Amino-3-nitro-benzoic acid methyl ester

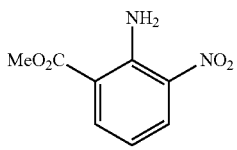 [SMILES: COC(=O)c1cccc([N+](=O)[O-])c1N]

To a solution of 2-amino-3-nitro-benzoic acid (6 g, 33 mmol) in methanol (20 mL), an ethereal solution of diazomethane gas was added until the staring material is completely consumed. The reaction mixture was then evaporated under reduced pressure. The crude solid obtained was purified by flash column chromatography using 5% ethylacetate & hexane as an eluent, to obtain the required product as a yellow coloured solid.

$^1$H NMR (300 MHz, DMSO-d$_6$): δ (ppm)=8.35 (m, 3H), 8.22 (m, 1H), 6.75 (m, 1H), 3.86 (s, 3H). HPLC purity: 99%

Step 5: 2,3-Diamino-benzoic acid methyl ester

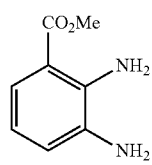 [SMILES: COC(=O)c1cccc(N)c1N]

To a solution of 2-amino-3-nitro-benzoic acid methyl ester (2 g, 10 mmol) in methanol, a suspension of 10% Pd/C (300 mg) in methanol 5 mL was added and hydrogenated with a hydrogen balloon over a period of 8 h. The reaction mixture was filtered and the filtrate was concentrated under reduced pressure to obtain 1.5 g of the required compound as a brown coloured solid (88%).

$^1$H NMR (300 MHz, DMSO-d$_6$): δ (ppm)=7.09 (dd, 1H, J=8.1 & 1.2 Hz), 6.70 (dd, 1H, J=8.1 & 1.2 Hz), 6.3.8 (m, 1H), 6.199 (s, 2H), 4.77 (s, 2H), 3.76 (s, 3H).

Step 6: 2-Amino-3-[(biphenyl-4-carbonyl)-amino]-benzoic acid methyl ester

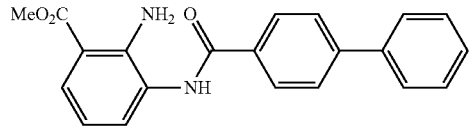 [SMILES: COC(=O)c1cccc(NC(=O)c2ccc(-c3ccccc3)cc2)c1N]

To a stirred solution of 2,3-diamino-benzoic acid methyl ester (200 mg, 1.2 mmol, and biphenyl benzoic acid (238 mg, 1.2 mmol), HATU (1.14 g, 3 mmol) in dry DMF (5 mL) was added diisopropylethyl amine (0.6 mL, 3.6 mmol). The mixture was stirred at ambient temperature overnight and poured into water (50 mL). The precipitated solid was filtered and dried in a vacuum oven to afford the required compound which was used directly for the next step without any purification (300 mg, 72%).

Step 7: 2-Biphenyl-4-yl-1H-benzoimidazole-4-carboxylic acid methyl ester

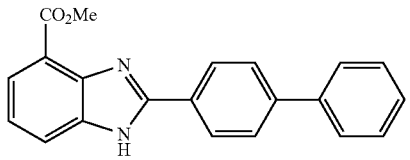

2-Amino-3-[(biphenyl-4-carbonyl)-amino]-benzoic acid methyl ester (300 mg, 0.86 mmol) was dissolved in glacial acetic acid (20 mL) and heated to 130° C. until the reaction was completed which was monitored by TLC (2 to 3 h). After the reaction is completed the solvent was removed and the solid residue was purified over silica gel using chloroform and methanol as an eluent to get the required product 9.

$^1$H NMR (300 MHz, DMSO-d$_6$): δ (ppm)=12.43 (s, 1H), 8.42 (m, 2H), 8.01 (m, 1H), 7.98-7.78 (m, 5H), 7.55-7.33 (m, 4H), 4.00 (s, 3H).

Step 8: 2-Biphenyl-4-yl-1H-benzoimidazole-4-carboxylic acid

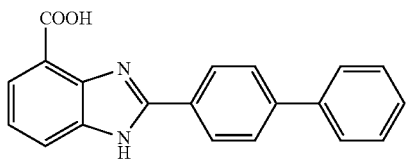 [SMILES: O=C(O)c1cccc2[nH]c(-c3ccc(-c4ccccc4)cc3)nc12]

2-Biphenyl-4-yl-1H-benzoimidazole-4-carboxylic acid methyl ester (180 mg, 0.54 mmol) was taken in THF (20 mL) and was refluxed with 5N NaOH (5 mL) solution for 14 h. It was then cooled to room temperature; THF was removed under reduced pressure to obtain a thick mass. This residue was diluted with water (10 mL) and adjusted pH to 2 with conc. hydrochloric acid. The precipitated solid was filtered, washed with water and dried in a vacuum oven to obtain compound the required compound as a pale yellow solid.

$^1$H NMR (300 MHz, DMSO-$d_6$): δ (ppm)=12.20 (m, 1H) 8.41 (m, 2H) 8.02-7.76 (m, 6H) 7.56 (t, 2H) 7.44-7.34 (m, 2H). HPLC purity: 90.37%.

Example 2

2-(4-Benzyloxy-phenyl)-1H-benzoimidazole-4-carboxylic acid

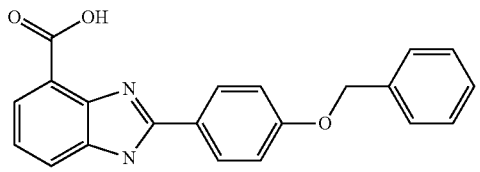 [SMILES: O=C(O)c1cccc2[nH]c(-c3ccc(OCc4ccccc4)cc3)nc12]

Example 2 is obtained as described in example 1 but starting from 4-(benzyloxy)benzoic acid (procured commercially from aldrich).

$^1$H NMR (300 MHz, DMSO-$d_6$): δ (ppm)=8.26 (d, 2H, J=8.7 Hz), 7.94 (dd, 2H, $J_1$=11.4 Hz, $J_2$=11.1 Hz), 7.51-7.35 (m, 6H), 7.26 (d, 2H, J=9 Hz), 5.25 (s, 2H). HPLC purity: 92.44%.

Example 3

2-(3-Fluoro-3'-methoxy-biphenyl-4-yl)-1H-benzoimidazole-4-carboxylic acid

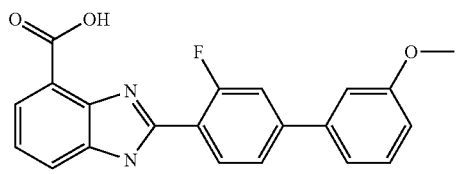 [SMILES: COc1cccc(-c2ccc(-c3nc4c(C(=O)O)cccc4[nH]3)c(F)c2)c1]

Step 1: 3-Fluoro-3'-methoxy-4-methyl-biphenyl

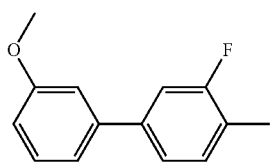 [SMILES: COc1cccc(-c2ccc(C)c(F)c2)c1]

A mixture of toluene (22.7 mL) and water (22.7 mL+7.5 mL) was degassed with nitrogen for 30 min. A mixture of cesium carbonate (3.3 g, 1.04 mmol), 4-bromo-2-fluoro-1-methyl-benzene (1.0 g, 5.2 mmol), 3-methoxyphenylboronic acid (0.8 g, 5.2 mmol) and tetrakis triphenyl phosphene palladium (0.294 g, 0.26 mmol) was added to the above degassed aq. toluene and the resulting mixture was refluxed for 5 h. After the reaction was completed, it was cooled and extracted with ethyl acetate. The combined ethyl acetate layers were dried over sodium sulphate and concentrated. The residue was purified by column chromatography using 10% ethyl acetate in hexane to obtain the title compound (0.85 g, 74%).

$^1$H NMR (300 MHz, CDCl$_3$): δ (ppm)=2.4 (s, 3H), 3.9 (s, 3H), 6.9-7.4 (m, 7H).

Step 2:
4-Bromomethyl-3-fluoro-3'-methoxy-biphenyl

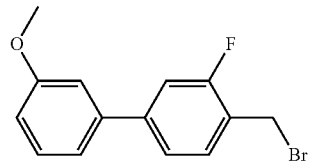 [SMILES: COc1cccc(-c2ccc(CBr)c(F)c2)c1]

To a solution of 3-fluoro-3'-methoxy-4-methyl-bipheny (0.5 g, 1.7 mmol, 1.0 eq) in chloroform (30 mL), was added N-bromo succinimide (0.3 g, 1.7 mmol followed by catalytic amount of dibenzoyl peroxide. The reaction mixture was refluxed by irradiating with a tungsten lamp for 3 hours. After the reaction was completed, it was cooled to room temperature and washed with water. The combined organic layers were dried over anhydrous sodium sulphate and concentrated. The resulting residue was purified by column chromatography using 5% ethyl acetate in hexane to obtain the title compound (0.45 g, 89%).

$^1$H NMR (300 MHz, CDCl$_3$): δ (ppm)=3.9 (s, 3H), 4.6 (s, 2H), 6.9-7.4 (m, 7H)

Step 3:
3-Fluoro-3'-methoxy-biphenyl-4-carbaldehyde

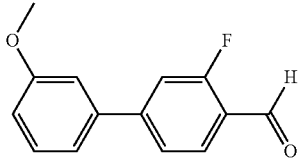 [SMILES: COc1cccc(-c2ccc(C=O)c(F)c2)c1]

To a solution of 4-bromomethyl-3-fluoro-3'-methoxy-biphenyl (0.45 g, 1.5 mmol) in dimethyl sulfoxide (10 mL) was added sodium bicarbonate (1.79 g, 21.3 mmol) and the resulting mixture was then stirred at 100° C. for 2 h. After the reaction was completed, it was cooled to room temperature and quenched with brine solution. The mixture was extracted with diethylether (50 mL×2) and the combined ether layers were washed with water, dried over anhydrous sodium sulphate and concentrated. The resulting residue was purified by column chromatography using 4% ethyl acetate in hexane to obtain the title compound.

$^1$H NMR (300 MHz, CDCl$_3$): δ (ppm)=3.9 (s, 3H), 6.9-7.4 (m, 7H), 10.4 (s, 1H)

Step 4: 2-(3-Fluoro-3'-methoxy-biphenyl-4-yl)-1H-benzoimidazole-4-carboxylic acid

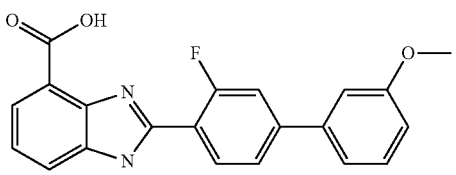 [SMILES: COc1cccc(-c2ccc(-c3nc4c(C(=O)O)cccc4[nH]3)c(F)c2)c1]

A solution of 2,3-diaminobenzoic acid (0.15 g, 0.824 mmol) in methanol (2 mL) was acidified with acetic acid (0.5 mL) To this mixture was added a solution of 3-fluoro-3'-methoxy-biphenyl-4-carbaldehyde (0.2466 g, 1.0695 mmol) in methanol followed by a solution of cupric acetate (0.183 g, 0.919 mmol) in water (4 mL). The resulting mixture was stirred vigorously and heated to 70° C. for 5 minutes and then filtered hot. The precipitate was washed with water and dissolved in ethanol (5 mL) containing 0.5 mL conc. HCl. A solution of sodium sulphide (0.082 g, 1.0512 mmol) in water was added. The reaction mixture was kept acidic by adding 2-3 drops of conc HCl. The reaction mixture was filtered hot to remove copper sulfide. The pH of the solution adjusted to 4 and diluted with water. The precipitate formed was filtered, washed with water and dried. The residue obtained was purified by column chromatography using 5% methanol in dichloromethane to obtain the title compound.

$^1$H NMR (300 MHz, DMSO-d$_6$): δ (ppm)=13.20 (br.s, 1H), 12.00 (br.s, 1H), 8.27 (t, 1H, J=8.1 Hz), 7.98 (d, 1H, J=7.5 Hz), 7.87-7.76 (m, 4H), 7.47-7.35 (m, 4H), 7.02 (d, 1H, J=5.1 Hz), 3.80 (s, 3H). HPLC purity: 86.60%.

Example 4

2-Biphenyl-4-yl-6-methoxy-1H-benzoimidazole-4-carboxylic acid

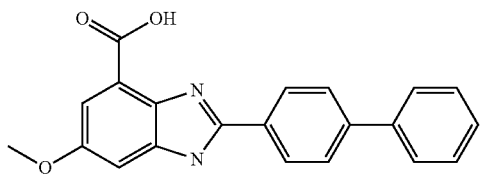 [SMILES: COc1cc(C(=O)O)c2nc(-c3ccc(-c4ccccc4)cc3)[nH]c2c1]

Step 1: 2-Hydroxyimino-N-(4-methoxy-2-nitro-phenyl)-acetamide

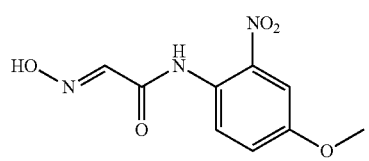 [SMILES: COc1ccc(NC(=O)/C=N/O)c([N+](=O)[O-])c1]

A slurry of 4-methoxy-2-nitro-phenylamine (5 g, 29.7 mmol), chloral hydrate (5.51 g, 33.3 mmol), sodium sulphate (21 g, 148.8 mmol), hydroxylamine hydrochloride (6.6 g, 95.2 mmol) and conc. HCl (5 mL) in water (150 mL) was heated for 2 h. After completion of the reaction, a solid separates out. The reaction mixture was then cooled to room temperature and the solids were filtered, washed with water (2-3 times) and dried under vacuum to obtain the title compound as off white solid (5 g, 70.40%) which was directly used for the next reaction.

Step-2; 5-Methoxy-7-nitro-1H-indole-2,3-dione

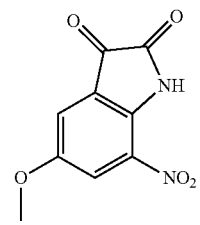 [SMILES: COc1cc2c(c([N+](=O)[O-])c1)NC(=O)C2=O]

2-Hydroxyimino-N-(4-methoxy-2-nitro-phenyl)-acetamide (5 g, 22 mmol) was added portion wise to a hot solution of conc. H$_2$SO$_4$ (20 mL, 4 vol) at 60° C. After completion of the addition, temperature was raised to 80° C. and maintained the same for one hour. After completion of the reaction, the reaction mixture was poured on to the crushed ice and the resulting precipitate separated was filtered, washed with water (2-3 times) and dried under vacuum to obtain the title compound as brick red colored solid which was used directly for the next reaction.

Step 3: 2-Amino-5-methoxy-3-nitro-benzoic acid

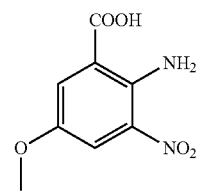

To a slurry of 5-methoxy-7-nitro-1H-indole-2,3-dione (3 g, 13.5 mmol) in aqueous 2N NaOH solution (30 mL), was added an aq. Solution of 33% hydrogen peroxide (3 mL) slowly at 0° C. After completion of the addition, the reaction mixture was stirred at room temperature for 4 h. After completion of the reaction, the reaction mixture was acidified with 2N HCl at 0° C. The resulting precipitate was filtered, washed with water (2-3 times) and dried under vacuum to obtain the title compound as yellow solid which was directly used for the next reaction.

Step 4: 2-Amino-5-methoxy-3-nitro-benzoic acid methyl ester

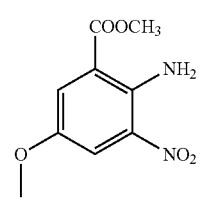 [SMILES: COC(=O)c1cc(OC)cc([N+](=O)[O-])c1N]

To a solution of 2-amino-5-methoxy-3-nitro-benzoic acid (2 g, 9.4 mmol) in methanol (100 mL) was added slowly a saturated ethereal solution of diazomethane gas until the starting material was completely consumed (25 mL). Ether was removed under vacuum and the resulting residue was purified by column chromatography using 5% ethyl acetate in hexane to obtain the title compound as a yellow solid which was used directly for the next reaction.

Step 5: 2,3-Diamino-5-methoxy-benzoic acid methyl ester

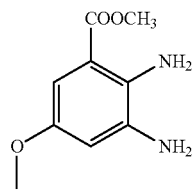

A slurry of 2-amino-5-methoxy-3-nitro-benzoic acid methyl ester (1 g, 4.4 mmol) and 10% Pd/C (0.2 g, 20%) in methanol was hydrogenated with a hydrogen balloon for 6 h. After the reaction was completed, the mixture was filtered through a celite bed and the filtrates were evaporated to dryness. The obtained residue was purified over silica gel column using (30% ethyl acetate/hexane) as eluent to obtain the title compound as off white solid.

$^1$H NMR (300 MHz, DMSO-$d_6$): δ (ppm)=6.56-6.55 (m, 1H), 6.41-6.40 (m, 1H), 6.00-5.80 (bs, 2H), 5.20-4.80 (bs, 2H), 3.76 (s, 3H), 3.69 (s, 3H)

Step 6: 2-Biphenyl-4-yl-6-methoxy-1H-benzoimidazole-4-carboxylic acid

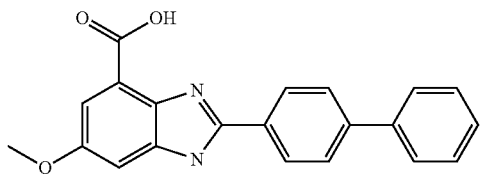 [SMILES: COc1cc(C(=O)O)c2nc(-c3ccc(-c4ccccc4)cc3)[nH]c2c1]

The above title compound is obtained as described in example 1 but starting from methyl 2,3-diamino-5-methoxy-benzoate.

$^1$H NMR (300 MHz, DMSO-$d_6$): δ (ppm)=12.8 (s, 1H), 8.32-8.19 (m, 2H), 7.86 (dd, 2H, $J_1$=8.4 Hz, $J_2$=8.4 Hz), 7.77 (d, 2H, J=7.2 Hz), 7.57-7.40 (m, 3H), 7.21 (d, 1H, J=2.4 Hz), 7.00 (d, 1H, J=2.4 Hz), 6.88-6.81 (m, 1H), 3.8 (s, 3H). HPLC purity: 90.40%.

Example 5

2-Biphenyl-4-yl-6-fluoro-1H-benzoimidazole-4-carboxylic acid

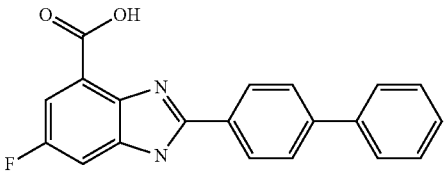 [SMILES: O=C(O)c1cc(F)cc2[nH]c(-c3ccc(-c4ccccc4)cc3)nc12]

Step 1: N-(4-Fluoro-phenyl)-2-hydroxyimino-acetamide

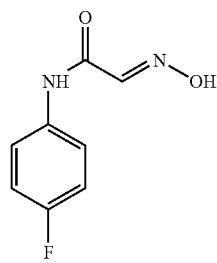

To a slurry of 4-fluoro-phenylamine (5 g, 45.0 mmol) in water (150 mL), was added chloral hydrate (11.28 g, 67.56 mmol), sodium sulphate (31.97 g, 225.2 mmol), hydroxylamine hydrochloride (6.21, 90.0 mmol), conc. HCl (5 mL) and the reaction mixture was heated to 85° C. It was stirred for another 2 h at the same temperature. After completion of the reaction, a solid separated out. The reaction mixture was cooled to room temperature and filtered, washed with water (2-3 times) and dried to obtain the title compound as off white solid.

Step 2: 5-Fluoro-1H-indole-2,3-dione

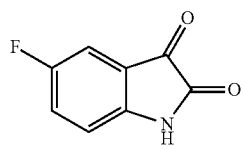

To a hot solution of conc. $H_2SO_4$ (20 mL) at 60° C., (N-(4-Fluoro-phenyl)-2-hydroxyimino-acetamide (5 g, 27.0 mmol) was added portion wise. After completion of the addition, the temperature was increased to 80° C. and maintained for one hour. After completion of the reaction, the reaction mixture was poured on to crushed ice and the resulting precipitate was filtered, washed with water (2-3 times) and dried to obtain the title compound as brick red solid.

Step 3: 5-Fluoro-7-nitro-1H-indole-2,3-dione

To a solution of 5-fluoro-1H-indole-2,3-dione (2.5 g, 15.0 mmol) in conc. $H_2SO_4$ (9 mL) was added very slowly fuming nitric acid (1.5 mL) at −5 to 0° C. The reaction mixture was stirred at the same temperature for one hour. After completion of the reaction, the reaction mixture was poured onto crushed ice and the resulting precipitate was filtered, washed with water (2-3 times) and dried under vacuum to obtain the title compound as yellow solid (3 g, 94.30%) which was used for the next step directly.

Step 4: 2-Amino-5-fluoro-3-nitro-benzoic acid

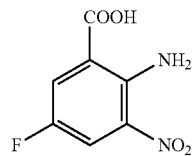

To a slurry of 5-fluoro-7-nitro-1H-indole-2,3-dione (3 g, 14.2 mmol) in aqueous 5N NaOH solution (30 mL) was added slowly an aq. solution of 33% hydrogen peroxide (3 mL) at 0° C. After completion of the addition, the reaction mixture was stirred at room temperature for 4 h. After completion of the reaction, the reaction mixture was acidified with 2N HCl and the resulting precipitate was filtered, washed with water (2-3 times) and dried under vacuum to obtain the title compound as yellow solid (2 g, 70.17%).

Step 5: 2-Amino-5-methoxy-3-nitro-benzoic acid methyl ester

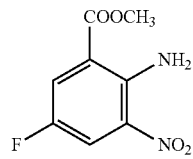 [SMILES: COC(=O)c1cc(F)cc(N)c1N]

To a solution of 2-amino-5-fluoro-3-nitro-benzoic acid (2 g, 0.001 mol) in methanol (100 mL) was added a saturated ethereal solution of diazomethane gas (50 mL) until the starting material was consumed. The reaction mixture was concentrated to dryness and the residue obtained was purified by column chromatography using 5% ethyl acetate in hexane as an eluent to obtain the title compound as yellow solid which was directly used for the next step (1.8 g, 84.11%).

Step 6: 2,3-Diamino-5-fluoro-benzoic acid methyl ester

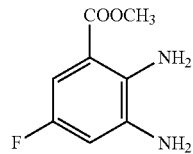

A slurry of 2-amino-5-fluoro-3-nitro-benzoic acid methyl ester (1.8 g, 84.0 mmol) and 10% Pd/C (0.5 g) in methanol (50 mL) was hydrogenated with a hydrogen balloon for 2 h. After completion of the reaction, the reaction mixture was filtered over celite bed, concentrated to dryness. the resulting residue was purified by column chromatography using 30% ethyl acetate in hexane to obtain the title compound as off white solid.

$^1$H NMR (300 MHz, DMSO-d$_6$): δ (ppm)=6.72 (m, 1H), 6.54 (m, 1H), 6.13 (s, 2H) 5.21 (s, 2H), 3.77 (s, 3H)

Step 7: 2-Biphenyl-4-yl-6-fluoro-1H-benzoimidazole-4-carboxylic acid

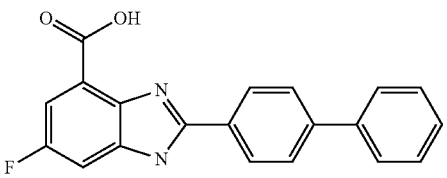

The above title compound was obtained as described in example 1 but starting from methyl 2,3-diamino-5-fluorobenzoate.

$^1$H NMR (300 MHz, DMSO-d$_6$): δ (ppm)=8.43 (d, 2H, J=8.4 Hz), 7.94 (d, 2H, J=8.4 Hz), 7.88 (dd, 1H, J$_1$=8.7 Hz J$_2$=8.4 Hz), 7.81 (d, 2H, J=7.2 Hz), 7.71 (dd, 1H, J$_1$=9.9 Hz, J$_2$=9.9 Hz), 7.53 (t, 2H, J=9 Hz), 7.46 (d, 1H, J=1.8 Hz). HPLC purity: 94.30%.

Example 6

2-Biphenyl-4-yl-6-bromo-1H-benzoimidazole-4-carboxylic acid

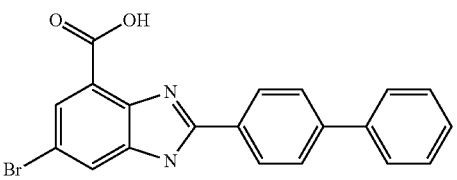

Step 1: N-(4-Bromo-phenyl)-2-hydroxyimino-acetamide

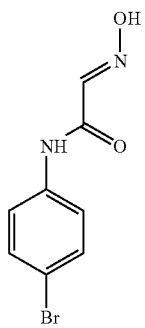 [SMILES: O=C(/C=N/O)Nc1ccc(Br)cc1]

To a slurry of 4-bromo-phenylamine (10 g, 58.13 mmol) in water (200 mL) was added chloral hydrate (11.65 g, 69.76 mmol), sodium sulphate (50 g), hydroxylamine hydrochloride (12.8 g, 186 mmol) and conc. HCl (15 mL). The reaction mixture was then heated to 85° C. and stirred for another 2 h. After completion of the reaction, a solid separated out. The mixture was cooled to room temperature, filtered and washed with water (2-3 times) and dried to obtain the title compound as off white solid (12 g, 84.9%).

Step 2: 5-Bromo-1H-indole-2,3-dione

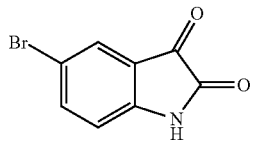

To a hot solution of conc. $H_2SO_4$ (48 mL) at 60° C. was added portion wise (N-(4-bromo-phenyl)-2-hydroxyimino-acetamide (12 g, 41.1 mmol). After completion of the addition, the temperature was increased to 80° C. and maintained for one hour. After completion of the reaction, the reaction mixture was poured on to crushed ice and the resulting precipitate was filtered, washed with water (2-3 times) and dried to obtain the title compound as brick red solid (10 g, 89%).

Step 3: 5-Bromo-7-nitro-1H-indole-2,3-dione

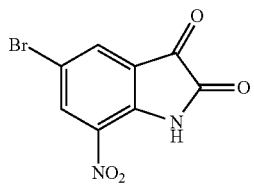

To a solution of 5-bromo-1H-indole-2,3-dione (5 g, 22.1 mmol) in conc. $H_2SO_4$ (22.5 mL) was added fuming nitric acid (1.45 mL) very slowly at −5 to 0° C. The reaction mixture was stirred at the same temperature for one hour. After completion of the reaction, the reaction mixture was poured on to crushed ice and the resulting precipitate was filtered, washed with water (2-3 times) and dried under vacuum to obtain the title compound as yellow solid (5.5 g, 91.8%) which was used for the next step directly.

Step 4: 2-Amino-5-bromo-3-nitro-benzoic acid

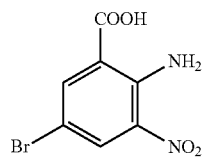 [SMILES: Nc1c(C(=O)O)cc(Br)cc1[N+](=O)[O-]]

To a slurry of 5-bromo-7-nitro-1H-indole-2,3-dione (5.5 g, 20.3 mmol) in aqueous 5N NaOH solution (23.2 mL) was added an aq. solution of 33% hydrogen peroxide solution (4.96 mL) slowly at 0° C. After completion of the addition, the reaction mixture was stirred at room temperature for 4 h. After completion of the reaction, the reaction mixture was acidified with 2N HCl and the solid the resulting precipitate was filtered, washed with water (2-3 times) and dried under vacuum to obtain the title compound as yellow solid (5 g, 94.5%).

Step 5: 2-Amino-5-bromo-3-nitro-benzoic acid methyl ester

To a solution of 2-amino-5-bromo-3-nitro-benzoic acid (5 g, 19.15 mmol) in methanol (100 mL) was added a saturated ethereal solution of diazomethane gas (75 mL) until the starting material was consumed. The reaction mixture was concentrated to dryness and the residue obtained was purified by column chromatography using 5% ethyl acetate in hexane as an eluent to obtain the title compound as yellow solid which was directly used for the next step (5 g, 94.3%).

Step 6: 2,3-Diamino-5-bromo-benzoic acid methyl ester

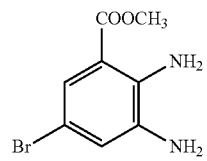 [SMILES: COC(=O)c1cc(Br)cc(N)c1N]

To a solution of 2-amino-5-bromo-3-nitro-benzoic acid methyl ester (5 g, 18.18 mmol) in methanol (15 mL) was added nickel chloride (10.8 g, 45.4 mmol) and was cooled to 0° C. To this cold solution, sodium borohydride (3.45 g, 90 mmol) was added in small portions. After the addition, the reaction mixture was diluted with water, extracted with ethyl acetate. The combined organic layers were dried, concentrated and the resulting residue was purified by column chromatography using 30% ethyl acetate in hexane to obtain the title compound as grey coloured solid.

Step 7: 2-Biphenyl-4-yl-6-bromo-1H-benzoimidazole-4-carboxylic acid

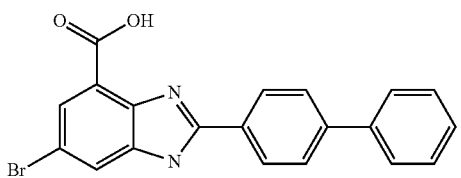

The title compound is obtained as described in example 1 but starting from methyl 2,3-diamino-5-bromobenzoate.

$^1$H NMR (300 MHz, DMSO-d$_6$): δ (ppm)=12.20 (br.s, 1H), 12.4 (br.s, 1H), 8.43 (d, 1H, J=6.3 Hz), 7.95-7.78 (m, 5H), 7.54-7.34 (m, 5H). HPLC purity: 89.69%.

Example 7 & 8

2-Biphenyl-4-yl-1-methyl-1H-benzoimidazole-4-carboxylic acid & 2-Biphenyl-4-yl-3-methyl-3H-benzoimidazole-4-carboxylic acid

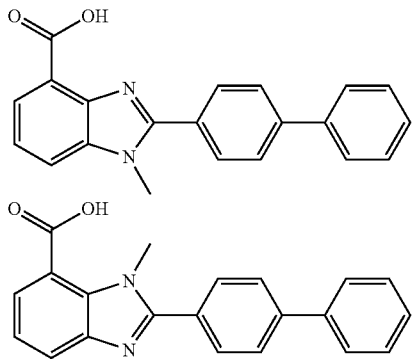

Example 7 and 8 are obtained from example 1 by the following procedure.

To a cold solution of 2-biphenyl-4-yl-1-methyl-1H-benzoimidazole-4-carboxylic acid (400 mg, 1.27 mmol) in dry DMF (20 mL), potassium carbonate (800 mg, 5.79 mmol) and methyl iodide (0.235 mL, 3.77 mmol) were added slowly at 5° C. The reaction mixture was then stirred overnight at room temperature. After the starting material was completely consumed, DMF was removed under vacuum. The resulting residue was directly purified by column chromatography and two compounds were isolated and characterized as methyl esters of 1H- and 3H-isomers. The corresponding carboxylic acids were prepared by hydrolysis with lithium hydroxide (aq. solution of 5 N, 10 mL) at room temperature for 8 h in THF-Water mixture.

Example 7

$^1$H NMR (300 MHz, DMSO-d$_6$): δ (ppm)=8.05 (t, 3H) 7.96-7.86 (m, 3H) 7.82-7.76 (m, 2H), 7.58-7.42 (m, 4H), 4.15 (s, 3H). HPLC purity: 95.09%.

Example 8

$^1$H NMR (300 MHz, DMSO-d$_6$): δ (ppm)=12.40 (br.s, 1H), 7.95 (m, 5H), 7.86-7.72 (m, 3H), 7.60-7.30 (m, 3H), 3.85 (s, 3H). HPLC purity: 97.97%.

Example 9

2-(3-Phenoxy-phenyl)-3H-benzoimidazole-4-carboxylic acid

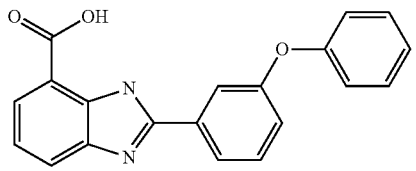 [SMILES: O=C(O)c1cccc2nc(-c3cccc(Oc4ccccc4)c3)[nH]c12]

Example 9 is obtained as described in example 1 but starting from 3-phenoxybenzoic acid (prepared according to the literature method Synthetic communication 34(21), 3909-3914; 2004).

$^1$H NMR (300 MHz, DMSO-d$_6$): δ (ppm)=13.2 (br.s, 1H), 12.45 (br.s, 1H), 8.23 (d, 1H), 8.20 (s, 1H), 7.90 (d, 1H), 7.82 (d, 1H), 7.56 (t, 1H), 7.44 (t, 2H), 7.31 (t, 1H) 7.24-7.08 (m, 4H). HPLC purity: 95.18%.

Example 10

2-(4-Phenoxy-phenyl)-3H-benzoimidazole-4-carboxylic acid

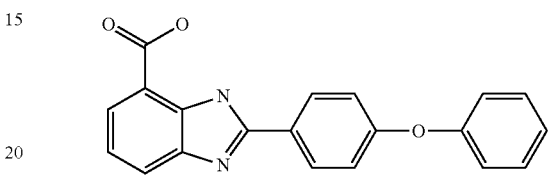

Example 10 is obtained as described in example 1 but starting from 3-phenoxybenzoic acid (procured commercially from aldrich).

$^1$H NMR (300 MHz, DMSO-d$_6$): δ (ppm)=12.20 (br.s, 1H) 8.33 (d, 2H, J=8.3 Hz), 7.88 (d, 1H, J=8.1 Hz), 7.79 (d, 1H, J=7.5 Hz), 7.46 (t, 2H, J=7.5 Hz), 7.30 (t, 1H, J=7.8 Hz), 7.23 (t, 1H, J=7.5 Hz), 7.13 (m, 4H). HPLC purity: 94.79%.

Example 11

2-(3'-Methoxy-biphenyl-4-yl)-3H-benzoimidazole-4-carboxylic acid

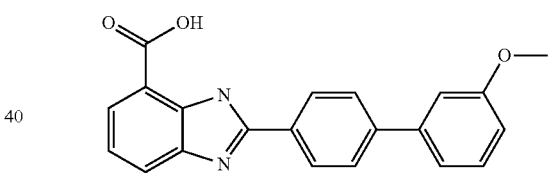

Example 11 is obtained as described in example 1 but starting from 3'-methoxybiphenyl-4-carboxylic acid (prepared according to the literature method Chemical Communications (Cambridge, United Kingdom), (5), 564-565; 2004).

$^1$H NMR (300 MHz, DMSO-d$_6$): δ (ppm)=12.85 (br.s, 1H), 8.27 (d, 2H), 7.89 (d, 2H), 7.72-7.66 (m, 1H), 7.58-7.52 (m, 1H), 7.46-7.20 (m, 5H), 7.25-6.80 (m, 1H), 3.80 (s, 3H). HPLC purity: 90.20%.

Example 12

2-(4'-Methyl-biphenyl-4-yl)-3H-benzoimidazole-4-carboxylic acid

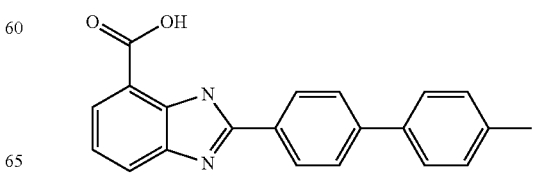

Example 12 is obtained as described in example 1 but starting from 4'-methylbiphenyl-4-carboxylic acid (prepared according to the literature method Tetrahedron 2008, 64(35), 8164-8168).

¹H NMR (300 MHz, DMSO-d₆): δ (ppm)=13.00 (br.s, 1H), 8.25 (d, 2H), 7.85 (d, 2H), 7.67 (d, 3H), 7.33 (d, 2H), 7.24-7.18 (m, 3H), 2.40 (s, 3H). HPLC purity: 96.34%.

Example 13

2-(4'-Trifluoromethyl-biphenyl-4-yl)-3H-benzoimidazole-4-carboxylic acid

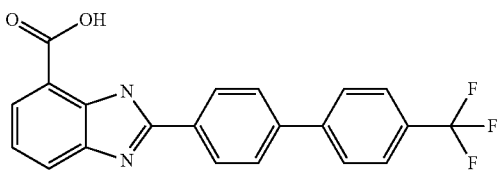 [SMILES: O=C(O)c1cccc2nc(-c3ccc(-c4ccc(C(F)(F)F)cc4)cc3)[nH]c12]

Example 13 is obtained as described in example 1 but starting from 4'-(trifluoromethyl)biphenyl-4-carboxylic acid (prepared according to the literature method Tetrahedron Letters, 46(34), 5751-5754; 2005).

¹H NMR (300 MHz, DMSO-d₆): δ (ppm)=13.20 (br.s, 1H), 8.31 (m, 2H), 7.90 (dd, 4H, J1=16.5 Hz, J2=15.6 Hz), 7.86 (d, 2H, J=8.1 Hz), 7.68-7.58 (m, 2H), 7.30-7.20 (m, 2H). HPLC purity: 91.51%.

Example 14

2-Biphenyl-4-yl-6-methyl-1H-benzoimidazole-4-carboxylic acid

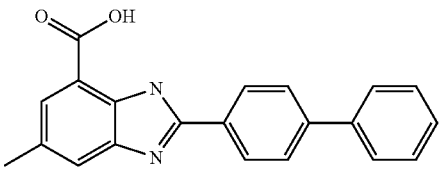 [SMILES: Cc1cc(C(=O)O)c2[nH]c(-c3ccc(-c4ccccc4)cc3)nc2c1]

Step 1: 2-Hydroxyimino-N-p-tolyl-acetamide

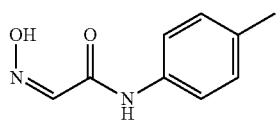

A solution of chloral hydrate (38 g, 0.223 mol), hydroxylamine hydrochloride (41 g, 0.594 mol) and sodium sulphate (40 g, 0.281 mol) in water (800 mL) was heated to 90° C. To this mixture was added a solution of p-toluidine (20 g, 0.1866 mol) in conc. HCl (30 mL) The resulting mixture was stirred for another 2 h. After the reaction is completed, the reaction mixture was cooled to room temperature, the precipitate was filtered and washed with water (100 mL). The solid was dried in a vacuum oven to get the required product as a grey coloured solid.

¹H NMR (300 MHz, DMSO-d₆): δ (ppm)=12.15 (s, 1H), 10.09 (s, 1H), 7.6 (s, 1H). 7.56 (d, 2H, J=8.4), 7.12 (d, 2H, J=8.4), 2.26 (s, 3H).

Step 2: 5-Methyl-1H-indole-2,3-dione

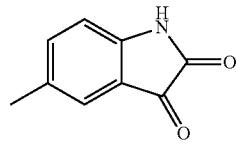

2-Hydroxyimino-N-p-tolyl-acetamide (14 g, 0.0078 mol) was added portion wise to a preheated (60° C.) conc. H₂SO₄ (70 mL) over a period of 30 min. After the addition, the mixture was stirred at the same temperature for another 1 h. The reaction mixture was cooled to room temperature and was poured into crushed ice. The precipitate was collected by filtration and washed with chilled water several times. Finally it was dried in a vacuum oven to get the required product as brick red coloured solid.

¹H NMR (300 MHz, DMSO-d₆): δ (ppm)=10.94 (s, 1H), 7.42 (d, 1H, J=1.2), 7.32 (s, 1H) 6.82 (d, 1H, J=8.1), 2.51 (s, 3H).

Step 3: 5-Methyl-7-nitro-1H-indole-2,3-dione

Fuming nitric acid (10 mL) was added drop wise over a period of 30 min to a solution of 5-methyl-1H-indole-2,3-dione (20 g, 0.124 mol) in conc. H₂SO₄ (80 mL) at −5° C., utes. The reaction mass was stirred for another 5-10 min at the same temperature and was poured into crushed ice. The precipitate was filtered and washed with chilled water several times. Finally it was dried in a vacuum oven to get 6.5 g of the required product as a yellow coloured solid.

¹H NMR (300 MHz, DMSO-d₆): δ (ppm)=11.60 (s, 1H), 8.15 (m, 1H), 7.79 (m, 1H), 2.51 (s, 3H).

Step 4: 2-Amino-5-methyl-3-nitro-benzoic acid

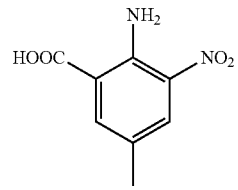

A solution of 5-methyl-7-nitro-1H-indole-2,3-dione (6.5 g, 0.0315 mol) in 2N NaOH (35 mL) was cooled to 20° C. and a 30% aq. solution of H₂O₂ (6.5 mL) was added slowly over a period of 15 min. The reaction mixture was brought to room temperature and stirred for 12 h, then diluted with water (75 mL). The pH was adjusted to 2 with conc. HCl. The formed precipitate was filtered and dried in a vacuum oven to get 5.3 g of the required product as a yellow coloured solid (85%).

$^1$H NMR (300 MHz, DMSO-$d_6$): δ (ppm)=13.4 (br.s, 1H), 8.34 (br.s, 2H), 8.14 (s, 1H), 8.07 (s, 1H), 2.24 (s, 3H).

Step 5: 2-Amino-5-methyl-3-nitro-benzoic acid methyl ester

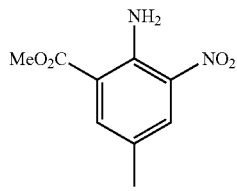

To a solution of 2-amino-5-methyl-3-nitro-benzoic acid (5 g, 24 mmol) in a mixture of methanol & ether (8:2, 50 mL), a freshly generated diazomethane gas collected in ether was added until the reaction completes. The reaction mixture was evaporated under reduced pressure and was purified by flash column chromatography using 5% ethyl acetate in hexane as an eluent to get 4.5 g (83%) of the required product as a yellow coloured solid.

$^1$H NMR (300 MHz, CDCl$_3$): δ (ppm)=8.31 (br.s, 2H), 8.21 (s, 1H), 8.08 (s, 1H), 3.91 (s, 3H,) 2.29 (s, 3H).

Step 6: 2,3-Diamino-5-methyl-benzoic acid methyl ester

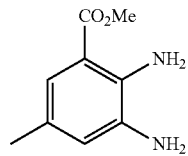

A solution of 2-amino-5-methyl-3-nitro-benzoic acid methyl ester (5.5 g, 26 mmol) in methanol (200 mL) was hydrogenated with hydrogen balloon in presence of 10% Palladium on charcoal (1.5 g) for 12 h. The reaction mixture was filtered and the filtrate was concentrated under reduced pressure to get the required product as a brown coloured solid 4.5 g (95%).

Example 14 is obtained as described in example 1 but starting from 2,3-diamino-5-methyl-benzoic acid methyl ester $^1$H NMR (300 MHz, DMSO-$d_6$): δ (ppm)=8.41 (d, 2H, J=8.1 Hz), 7.97 (d, 2H, J=8.4 Hz), 7.84-7.81 (m, 4H), 7.56-7.51 (m, 2H), 7.46 (s, 1H), 2.54 (s, 3H). HPLC purity: 97.77%.

Example 15

2-(2'-Fluoro-biphenyl-4-yl)-3H-benzoimidazole-4-carboxylic acid

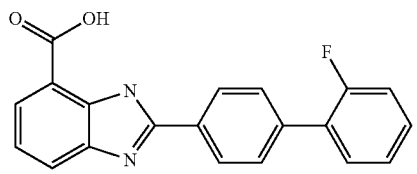 [SMILES: O=C(O)c1cccc2nc(-c3ccc(-c4ccccc4F)cc3)[nH]c12]

Example 15 is obtained as described in example 1 but starting from 2'-fluorobiphenyl-4-carboxylic acid (prepared according to the literature method J Med Chem 47(2), 335-374, 2004).

$^1$H NMR (300 MHz, CD$_3$OD): δ (ppm)=7.45 (d, 2H, J=8.4 Hz), 7.37 (d, 1H, J=7.5 Hz), 7.24 (d, 1H, J=9 Hz), 7.09 (d, 2H, J=7.2 Hz), 6.87-6.77 (m, 2H), 6.67-6.63 (m, 1H), 6.55-6.43 (m, 2H). HPLC purity: 96.85%.

Example 16

2-(4'-Trifluoromethoxy-biphenyl-4-yl)-3H-benzoimidazole-4-carboxylic acid

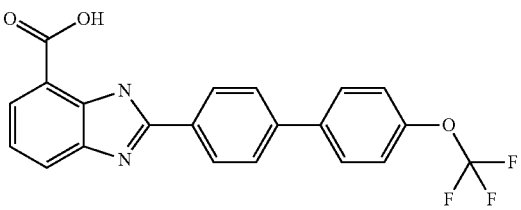 [SMILES: O=C(O)c1cccc2nc(-c3ccc(-c4ccc(OC(F)(F)F)cc4)cc3)[nH]c12]

Example 16 is obtained as described in example 1 but starting from 4'-(trifluoromethoxy)biphenyl-4-carboxylic acid Step 1:
4'-Trifluoromethoxy-biphenyl-4-carbaldehyde

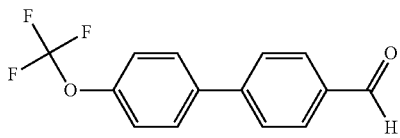 [SMILES: O=Cc1ccc(-c2ccc(OC(F)(F)F)cc2)cc1]

A mixture of toluene (70 mL) and water (10 mL) was degassed with nitrogen for 30 min. A mixture of sodium carbonate (3.2 g, 30.43 mmol), 4-bromobenzaldehyde (2.0 g, 10.6 mmol), 4-trifluoromethoxyphenylboronic acid (2.86 g, 13.95 mmol) and tetrakis triphenyl phosphene palladium(0) (1.0 g, 1.562 mmol) were added to the above degassed water/toluene mixture. The reaction mixture refluxed overnight. After the reaction is completed, the reaction mixture was cooled to room temperature and extracted with ethyl acetate. The combined organic layers were dried over sodium sulphate and concentrated. The resulting residue was purified by column chromatography using 3% ethyl acetate in hexane to obtain the title compound. $^1$H NMR (300 MHz, CDCl$_3$): δ (ppm)=7.2-8.0 (m, 8H), 10.0 (s, 1H).

Step 2: 4'-Trifluoromethoxy-biphenyl-4-carboxylic acid

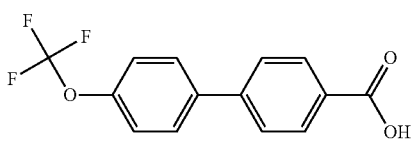 [SMILES: O=C(O)c1ccc(-c2ccc(OC(F)(F)F)cc2)cc1]

To a cold solution of 4'-trifluoromethoxy-biphenyl-4-carbaldehyde (0.9 g, 3.38 mmol) in acetone (10 mL) the Jone's reagent was added slowly at 0° C. drop wise until reaction completes. Acetone was removed completely and the residue was diluted with water, extracted with ethyl acetate and the combined organic layers were washed with water and brine, dried over sodium sulphate and concentrated to obtain the title compound (0.7 g, 77%).

$^1$H NMR (300 MHz, DMSO-d$_6$): δ (ppm)=7.2-8.0 (m, 8H), 13.0 (bs, 1H)

Step 3: 2-(4'-Trifluoromethoxy-biphenyl-4-yl)-3H-benzoimidazole-4-carboxylic acid

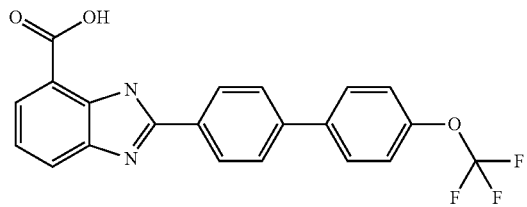 [SMILES: O=C(O)c1cccc2nc(-c3ccc(-c4ccc(OC(F)(F)F)cc4)cc3)[nH]c12]

$^1$H NMR (300 MHz, CD$_3$OD): δ (ppm)=7.48-7.40 (m, 3H), 7.27-7.19 (m, 3H), 7.07 (d, 2H, J=8.7 Hz), 6.92-6.87 (m, 1H), 6.63 (d, 2H, J=8.4 Hz). HPLC purity: 98.94%.

Example 17

2-(3'-Fluoro-biphenyl-4-yl)-3H-benzoimidazole-4-carboxylic acid

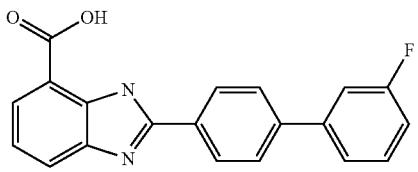 [SMILES: O=C(O)c1cccc2nc(-c3ccc(-c4cccc(F)c4)cc3)[nH]c12]

Example 17 is obtained as described in example 1 but starting from 3'-fluorobiphenyl-4-carboxylic acid (prepared according to the literature method Journal of the Chemical Society, Perkin Transactions 2: Physical Organic Chemistry (1972-1999), (1), 35-7; 1984).

$^1$H NMR (300 MHz, DMSO-d$_6$): δ (ppm)=8.42 (d, 2H, J=8.4 Hz) 7.96-7.87 (m, 3H) 7.68-7.65 (m, 2H) 7.57-7.26 (m, 4H). HPLC purity: 94.48%.

Example 18

2-(3'-Trifluoromethoxy-biphenyl-4-yl)-3H-benzoimidazole-4-carboxylic acid

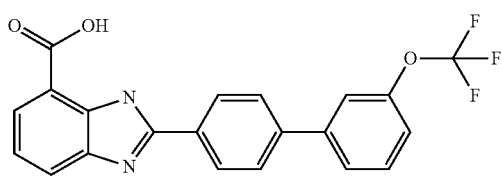 [SMILES: O=C(O)c1cccc2nc(-c3ccc(-c4cccc(OC(F)(F)F)c4)cc3)[nH]c12]

Example 18 is obtained as described in example 1 but starting from 3'-(trifluoromethoxy)biphenyl-4-carboxylic acid.

Step 1: 3'-Trifluoromethoxy-biphenyl-4-carbaldehyde

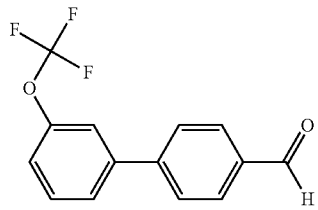 [SMILES: O=Cc1ccc(-c2cccc(OC(F)(F)F)c2)cc1]

A mixture of toluene (35 mL) and water (5 mL) was degassed with nitrogen for 30 minutes. A mixture of sodium carbonate (1.9 g, 18.09 mmol), 4-bromobenzaldehyde (0.7 g, 3.72 mmol), 3-trifluoromethoxyphenylboronic acid (2.86 g, 4.78 mmol) and tetrakis triphenyl phosphene palladium(0) (0.9 g, 0.75 mmol) was added to the above degassed water/toluene mixture. The reaction mixture was refluxed overnight. After the reaction is completed it was cooled to room temperature and extracted with ethyl acetate. The combined organic layers were dried over sodium sulphate and concentrated. The resulting residue was purified by column chromatography using 5% ethyl acetate in hexane to obtain the title compound (0.8 g, 80%).

$^1$H NMR (300 MHz, CDCl3): δ (ppm)=7.2-8.0 (m, 8H), 10.0 (s, 1H)

Step 2: 3'-Trifluoromethoxy-biphenyl-4-carboxylic acid

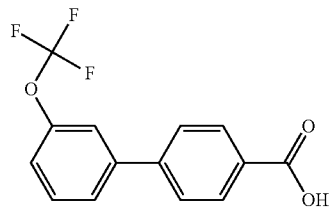 [SMILES: O=C(O)c1ccc(-c2cccc(OC(F)(F)F)c2)cc1]

To a cold solution of 3'-trifluoromethoxy-biphenyl-4-carbaldehyde (0.8 g, 3.0 mmol) in acetone (10 mL) the Jone's reagent was added slowly at 0° C. until reaction completes. Acetone was removed completely and diluted with water. The mixture was extracted with ethyl acetate and the combined organic layers were washed with water and brine, dried over sodium sulphate and concentrated to obtain the title compound (0.7 g, 82%).

$^1$H NMR (300 MHz, CDCl$_3$): δ (ppm)=7.4-8.2 (m, 8H, Ar—H).

Step 3: 2-(3'-Trifluoromethoxy-biphenyl-4-yl)-3H-benzoimidazole-4-carboxylic acid

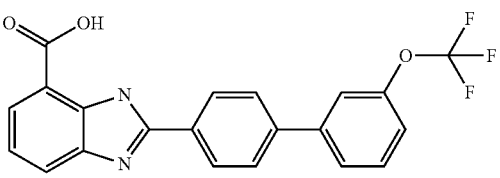 [SMILES: O=C(O)c1cccc2nc(-c3ccc(-c4cccc(OC(F)(F)F)c4)cc3)[nH]c12]

$^1$H NMR (300 MHz, CD$_3$OD): δ (ppm)=7.49-7.44 (m, 3H), 7.30-7.22 (m, 3H), 7.01-6.81 (m, 4H). 6.61-6.57 (m, 1H). HPLC purity: 98.64%.

Example 19

2-Biphenyl-4-yl-benzooxazole-7-carboxylic acid

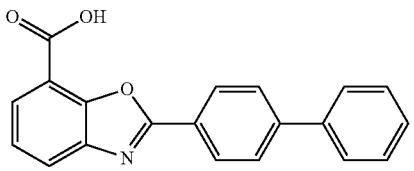

Step 1: Methyl 2-hydroxy-3-nitrobenzoate

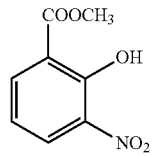

To a ice cold solution of salicylic acid (10 g, 0.072 mol) in methanol (100 mL), was added drop wise SOCl$_2$ (12.8 g, 0.1 mol). After the addition, the mixture was warmed to room temperature and heated to reflux for 12 h. After reaction is completed the reaction mixture was cooled to room temperature and the excess methanol was evaporated under reduced pressure to obtain 9 g of methyl 2-hydroxybenzoate as a white solid. (81%). A solution of methyl 2-hydroxybenzoate (9 g, 0.059 mol) in glacial acetic acid (90 mL) was cooled to 15° C., fuming nitric acid (11.2 mL) was added drop wise. The reaction mixture was warmed to room temperature and stirred for 4 h. When the reaction is completed, the reaction mixture was poured into crushed ice. The precipitate was collected by filtration and washed several times with chilled water, then dried in a vacuum oven to the required product as a yellow coloured solid.

$^1$H NMR (300 MHz, CDCl$_3$): δ (ppm)=12.0 (s, 1H), 8.2-8.1 (m, 2H), 7.01 (t, 1H, J=8.1 Hz) 4.01 (s, 3H).

Step 3: methyl 3-amino-2-hydroxybenzoate

A solution of methyl 2-hydroxy-3-nitrobenzoate (2 g, 0.010 mol) in methanol (30 mL), was hydrogenated with a hydrogen balloon in the presence of 10% palladium on chacoal (600 mg) for 7 h. After the reaction is completed, the reaction mixture was filtered through celite bed and the filtrate was concentrated under reduced pressure to obtain 1.6 g of the above required compound (72%) as a grey coloured solid.

$^1$H NMR (300 MHz, CDCl$_3$): δ (ppm)=10.88 (s, 1H), 6.87 (d, 1H, J=7.5 Hz), 6.72 (d, 1H, J=7.8 Hz), 3.88 (s, 3H).

Step 4:
3-[(Biphenyl-4-carbonyl)-amino]-2-hydroxy-benzoic acid methyl ester

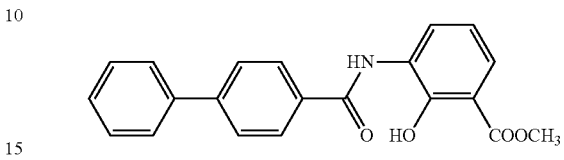

To an ice cold solution of 4-biphenyl benzoic acid (1.5 g, 23 mmol), triethyl amine (6.2 mL, 46 mmol) in THF (50 mL), SOCl$_2$ (5 mL, 46 mmol) was added drop wise and continued stirring for another 3 h at the same temperature. After completion of the reaction, it was concentrated under reduced pressure to get the 4-bipehnyl benzoyl chloride which was used directly for the next reaction.

To an ice cold solution of methyl 3-amino-2-hydroxybenzoate (700 mg, 9.2 mmol) and pyridine (13 mL) in DCM (100 mL) was added slowly a solution of biphenyl benzoyl chloride (2.1 g, 9.7 mmol) in DCM. The reaction mixture was stirred for another 12 h at room temperature and diluted with another 200 mL of DCM and washed with an aq. solution of 2N. HCl followed by water. The combined organic layers were dried over sodium sulphate and concentrated to dryness to get the 350 mg of the required product as a white coloured solid.

$^1$H NMR (300 MHz, CDCl$_3$): δ (ppm)=11.40 (s, 1H), 8.77 (dd, 1H, J=8.1 Hz, J=8.1 Hz), 8.66 (br.s, 1H), 8.00 (m, 2H), 7.77 (m, 2H), 7.66-7.58 (m, 3H), 7.51-7.40 (m, 3H), 6.97 (t, 1H, J=8.1 Hz), 3.99 (s, 3H).

Step 5: 2-Biphenyl-4-yl-benzooxazole-7-carboxylic acid

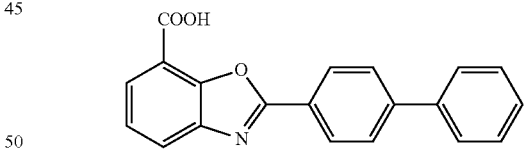

3-[(biphenyl-4-carbonyl)-amino]-2-hydroxy-benzoic acid methyl ester (100 mg, 0.28 mmol) was suspended in PPA (500 mg) and heated at 170° C. for 4 h. The reaction was monitored by TLC. After completion of the reaction, the crude mixture was cooled to room temperature and ice water was added. The pH was adjusted to 5 with an aq. solution of 5N NaOH and was extracted with ethyl acetate (3×50 mL). The combined organic phases were dried over sodium sulphate and concentrated under reduced pressure. The crude mixture was purified by column chromatography to get 35 mg of the required product as a pale pink coloured solid.

$^1$H NMR (300 MHz, CDCl$_3$): δ (ppm)=13.20 (br.s, 1H), 8.30 (d, 2H, J=10.5 Hz) 8.10-7.90 (m, 4H), 7.80 (d, 2H, J=12 Hz), 7.54 (t, 3H, J=10.5 Hz) 7.48-7.44 (m, 1H). HPLC purity: 85.64%.

Example 20

2-(2,6-Dimethoxy-biphenyl-4-yl)-1H-benzoimidazole-4-carboxylic acid

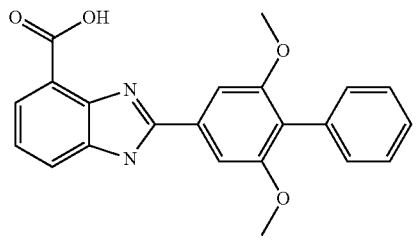 [SMILES: COc1cc(-c2nc3c(C(=O)O)cccc3[nH]2)cc(OC)c1-c1ccccc1]

Example 20 is obtained as described in example 1 but starting from 2,6-dimethoxybiphenyl-4-carboxylic acid.

Step 1; 2,6-Dimethoxy-biphenyl-4-carboxylic acid methyl ester

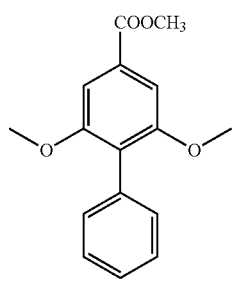

A mixture of toluene (70 mL) and water (10 mL) was degassed with nitrogen for 30 min. A mixture of cesium carbonate (2.3 g, 7.07 mmol), 4-bromo-3,5-dimethoxy methylbenzoate (2.0 g, 7.2 mmol), phenylboronic acid (1.2 g, 9.9 mmol) and tetrakis triphenyl phosphene palladium(0) (1.0 g, 0.8 mmol) was added to the above degassed water/toluene mixture. The reaction mixture was refluxed overnight. After the reaction is completed it was cooled to room temperature and extracted with ethyl acetate. The combined organic layers were dried over sodium sulphate and concentrated. The resulting residue was purified by column chromatography using 8% ethyl acetate in hexane to obtain the title compound.
$^1$H NMR (300 MHz, CDCl3): δ (ppm)=3.8 (s, 6H), 4.0 (s, 3H,), 7.3-7.8 (m, 7H).

Step 2: 2,6-Dimethoxy-biphenyl-4-carboxylic acid

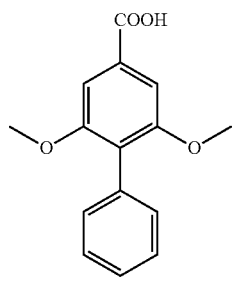

To a solution of 2,6-dimethoxy-biphenyl-4-carboxylic acid methyl ester (0.9 g, 3.3 mmol) in 10% aq. THF, an aq. solution of 5 N NaOH (5 mL) was added and the reaction mixture was refluxed for 5 h. After the reaction is completed, THF was removed completely under the vacuum and acidified with an aq. solution of 50% HCl. The resulting precipitate was filtered and washed thoroughly with water and dried to obtain the title compound (0.6 g, 70.5%).
$^1$H NMR (300 MHz, DMSO-$d_6$): δ (ppm)=3.8 (s, 6H), 7.2-7.6 (m, 7H), 13.0 (bs, 1H).

Step 3: 2-(2,6-Dimethoxy-biphenyl-4-yl)-1H-benzoimidazole-4-carboxylic acid

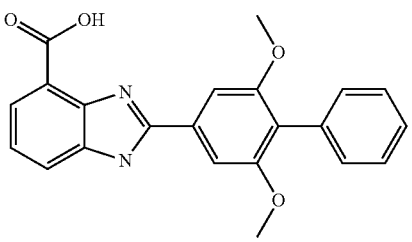

$^1$H NMR (300 MHz, DMSO-$d_6$): δ (ppm)=8.08 (d, 1H, J=7.8 Hz), 8.00 (d, 1H, J=7.5 Hz), 7.80-7.76 (m, 2H), 7.58-7.53 (m, 1H), 7.43-7.26 (m, 5H), 3.84 (s, 6H). HPLC purity: 90.23%.

Example 21

2-(2,3,5,6-Tetrafluoro-biphenyl-4-yl)-1H-benzoimidazole-4-carboxylic acid

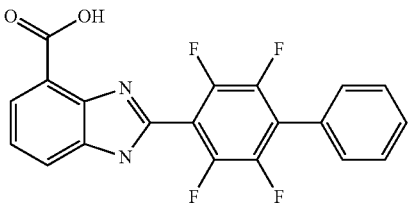 [SMILES: O=C(O)c1cccc2[nH]c(-c3c(F)c(F)c(-c4ccccc4)c(F)c3F)nc12]

Example 21 is obtained as described in example 1 but starting from 2,3,5,6-tetrafluorobiphenyl-4-carboxylic acid Step 1: 4-Bromo-2,3,5,6-tetrafluoro-benzoic acid methyl ester

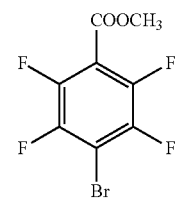 [SMILES: COC(=O)c1c(F)c(F)c(Br)c(F)c1F]

To a solution of 4-bromo-2,3,5,6-tetrafluoro-benzoic acid (20 g, 73.49 mmol) in methanol (20 mL) was added an ethereal solution of diazomethane gas until the starting material is completely consumed. Reaction mixture was then evaporated under reduced pressure. The crude solid obtained was purified by flash column chromatography using 5% ethyl acetate in hexane, to obtain title compound as colorless crystalline solid (18 g, 85%).
$^1$H NMR (300 MHz, CDCl$_3$): δ (ppm)=4.0 (s, 3H)

Step 2: 2,3,5,6-Tetrafluoro-biphenyl-4-carboxylic acid methyl ester

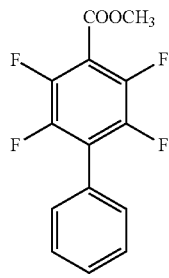 [SMILES: COC(=O)c1c(F)c(F)c(-c2ccccc2)c(F)c1F]

A mixture of toluene (370 mL) and water (70 mL) was degassed with nitrogen for 30 minutes. A mixture of cesium carbonate (102.6 g, 315 mmol), 4-bromo-2,3,5,6-tetrafluoro-benzoic acid methyl ester (30.0 g, 105 mmol), phenyl boronic acid (19.26 g, 157 mmol) and tetrakis triphenyl phosphene palladium(0) (11.5 g, 9.9 mmol) were added to the above degassed water/toluene mixture. The reaction mixture was refluxed overnight. After the reaction is completed, it was cooled to room temperature and extracted with ethyl acetate. The combined organic layers were dried over sodium sulphate and concentrated. The resulting residue was purified by column chromatography using 5% ethyl acetate in hexane to obtain the title compound (26.5 g, 88.6%).

$^1$H NMR (300 MHz, CDCl$_3$): δ (ppm)=4.0 (s, 3H), 7.4-7.6 (m, 5H)

Step 3: 2,3,5,6-Tetrafluoro-biphenyl-4-carboxylic acid

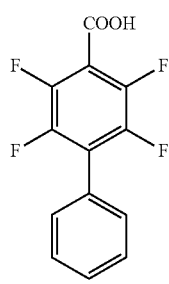 [SMILES: O=C(O)c1c(F)c(F)c(-c2ccccc2)c(F)c1F]

To a solution of 2,3,5,6-tetrafluoro-biphenyl-4-carboxylic acid methyl ester (20 g, 70.4 mmol) in tetrahydrofuran (350 mL) was added an aq. solution of 5 N sodium hydroxide (150 mL). The reaction mixture refluxed with stirring for 4 hours. Progress of the reaction was monitored by TLC. The reaction mixture was then concentrated and the resulting residue was cooled to 10° C. and acidified with an aq. Solution of 50% HCl. The formed precipitate was filtered, washed thoroughly with water and dried to obtain title compound as colorless solid (17 g, 89.4%).

$^1$H NMR (300 MHz, DMSO-D6): δ (ppm)=7.6 (s, 5H).

Step 4: 2-(2,3,5,6-Tetrafluoro-biphenyl-4-yl)-1H-benzoimidazole-4-carboxylic acid

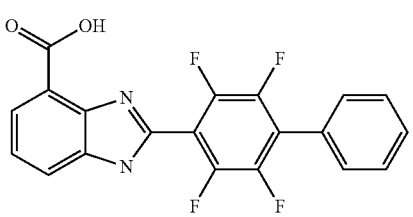 [SMILES: O=C(O)c1cccc2[nH]c(-c3c(F)c(F)c(-c4ccccc4)c(F)c3F)nc12]

$^1$H NMR (300 MHz, DMSO-d$_6$): δ (ppm)=13.2 (br.s, 2H), 8.06 (d, 1H, J=8.1 Hz), 7.95-7.88 (m, 2H), 7.61-7.59 (m, 4H), 7.44-7.39 (m, 1H). HPLC purity: 91.99%

Example 22

2-(4-Thiophen-3-yl-phenyl)-1H-benzoimidazole-4-carboxylic acid

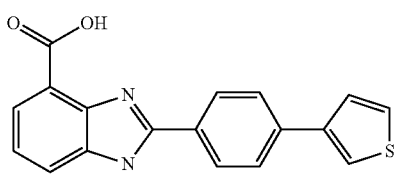 [SMILES: O=C(O)c1cccc2[nH]c(-c3ccc(-c4ccsc4)cc3)nc12]

Example 22 is obtained as described in example 1 but starting from 4-(3-thienyl)benzoic acid (prepared according to the literature method Tetrahedron letters 42(38), 6683-6686; 2001).

$^1$H NMR (300 MHz, DMSO-d$_6$): δ (ppm)=13.6 (br.s, 1H), 12.35 (br.s, 1H), 8.37-7.92 (m, 6H), 7.82 (d, 1H, J=7.5 Hz), 7.69 (s, 2H), 7.33 (m, 1H). HPLC purity: 88.42%.

Example 23

6-Methyl-2-(4-thiophen-3-yl-phenyl)-1H-benzoimidazole-4-carboxylic acid

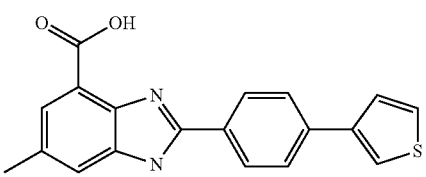 [SMILES: Cc1cc(C(=O)O)c2nc(-c3ccc(-c4ccsc4)cc3)[nH]c2c1]

Example 23 is obtained as described in example 14 but starting from 4-(3-thienyl)benzoic acid.

$^1$H NMR (300 MHz, DMSO-d$_6$): δ (ppm)=12.20 (br.s, 2H), 8.40-8.20 (m, 2H), 8.05-7.89 (m, 3H), 7.71-7.65 (m, 4H), 2.2 (s, 3H). HPLC purity: 87.17%.

Example 24

2-(3,2'-Difluoro-biphenyl-4-yl)-3H-benzoimidazole-4-carboxylic acid

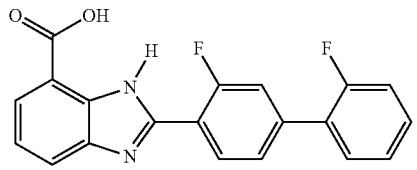 [SMILES: O=C(O)c1cccc2nc(-c3ccc(-c4ccccc4F)cc3F)[nH]c12]

Example 24 is obtained as described in example 1 but starting from 2',3-difluorobiphenyl-4-carboxylic acid (prepared as described in PCT Int Appl. 2005009941 3 Feb. 2005).

$^1$H NMR (300 MHz, DMSO-$d_6$): δ (ppm)=8.27 (t, 1H, J=8.1 Hz), 8.03 (d, 1H, J=8.1 Hz), 7.92 (d, 1H, J=7.5 Hz), 7.68 (dd, 3H, $J_1$=19.8 Hz, $J_2$=16.5 Hz), 7.53-7.36 (m, 4H). HPLC purity: 94.41%.

Example 25

2-(3,2'-Difluoro-biphenyl-4-yl)-6-methyl-3H-benzoimidazole-4-carboxylic acid

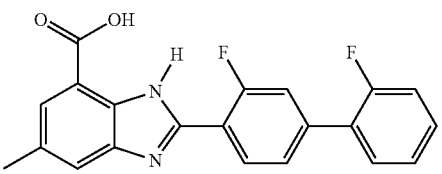 [SMILES: Cc1cc(C(=O)O)c2[nH]c(-c3ccc(-c4ccccc4F)cc3F)nc2c1]

Example 25 is obtained as described in example 14 but starting from 2',3-difluorobiphenyl-4-carboxylic acid.

$^1$H NMR (300 MHz, DMSO-$d_6$): δ (ppm)=11.80 (br.s, 1H), 8.27 (t, 1H, J=8.1 Hz), 7.80 (s, 1H), 7.71-7.61 (m, 4H), 7.55-7.48 (m, 1H), 7.38 (dd, 2H, $J_1$=13.8 Hz, $J_2$=12.9 Hz), 2.09 (s, 3H). HPLC purity: 91.16%.

Example 26

2-(2'-Fluoro-biphenyl-4-yl)-6-methyl-3H-benzoimidazole-4-carboxylic acid

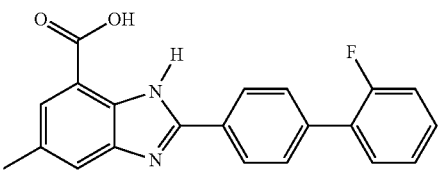 [SMILES: Cc1cc(C(=O)O)c2[nH]c(-c3ccc(-c4ccccc4F)cc3)nc2c1]

Example 26 is obtained as described in example 14 but starting from 2'-fluorobiphenyl-4-carboxylic acid (prepared according to the literature method J Med Chem 47(2), 335-374, 2004).

$^1$H NMR (300 MHz, DMSO-$d_6$): δ (ppm)=8.34 (d, 2H, J=8.7 Hz), 7.69-7.53 (m, 5H), 7.46-7.42 (m, 1H), 7.34 (dd, 2H, $J_1$=12.9 Hz, $J_2$=12.9 Hz), 2.43 (s, 3H). HPLC purity: 92.24%.

Example 27

2-(3-Fluoro-biphenyl-4-yl)-3H-benzoimidazole-4-carboxylic acid

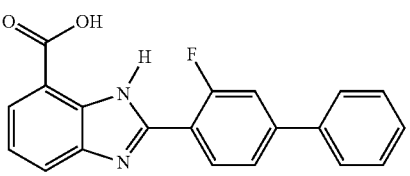 [SMILES: O=C(O)c1cccc2nc(-c3ccc(-c4ccccc4)cc3F)[nH]c12]

Example 27 is obtained as described in example 1 but starting from 3-fluorobiphenyl-4-carboxylic acid (prepared according to the literature method Tetrahedron letter, 46(24), 4255-4259, 2005).

$^1$H NMR (300 MHz, DMSO-$d_6$): δ (ppm)=13.4 (br.s, 1H), 12.20 (br.s, 1H), 8.28 (t, 1H, J=8.1 Hz), 7.99 (d, 1H, J=7.8 Hz), 7.88-7.75 (m, 5H), 7.56-7.35 (m, 4H). HPLC purity: 89.03%.

Example 28

2-(3-Fluoro-biphenyl-4-yl)-6-methyl-3H-benzoimidazole-4-carboxylic acid

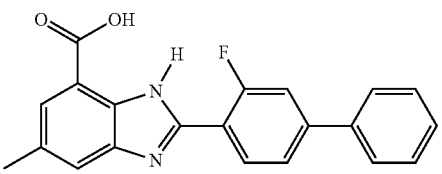 [SMILES: Cc1cc(C(=O)O)c2[nH]c(-c3ccc(-c4ccccc4)cc3F)nc2c1]

Example 28 is obtained as described in example 14 but starting from 3-fluorobiphenyl-4-carboxylic acid.

$^1$H NMR (300 MHz, DMSO-$d_6$): δ (ppm)=12.20 (br.s, 1H), 8.42-8.27 (m, 1H), 7.83-7.25 (m, 4H), 7.54-7.44 (m, 5H), 2.50 (s, 3H). HPLC purity: 93.70%.

Example 29

6-Fluoro-2-(3-fluoro-biphenyl-4-yl)-3H-benzoimidazole-4-carboxylic acid

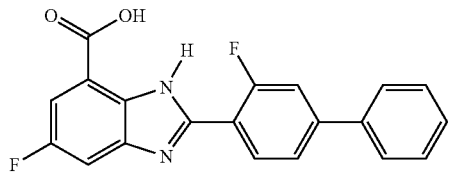 [SMILES: O=C(O)c1cc(F)cc2nc(-c3ccc(-c4ccccc4)cc3F)[nH]c12]

Example 29 is obtained as described in example 5 but starting from 3-fluorobiphenyl-4-carboxylic acid (prepared according to the literature method Tetrahedron letter, 46(24), 4255-4259, 2005).

$^1$H NMR (300 MHz, DMSO-$d_6$): δ (ppm)=13.8 (br.s, 1H), 12.03 (br.s, 1H), 8.23 (t, 1H), 7.84-7.74 (m, 5H), 7.63-7.60 (m, 1H), 7.55-7.43 (m, 3H). HPLC purity: 89.90%.

Example 30

2-(3,2',4'-Trifluoro-biphenyl-4-yl)-3H-benzoimidazole-4-carboxylic acid

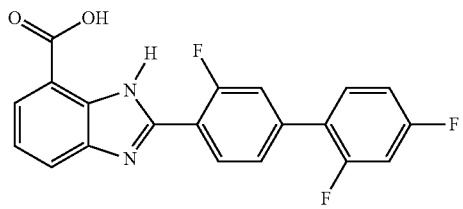 [SMILES: O=C(O)c1cccc2nc(-c3ccc(-c4ccc(F)cc4F)cc3F)[nH]c12]

Example 30 is obtained as described in example 1 but starting from 2',3,4'-trifluorobiphenyl-4-carboxylic acid.

Step 1: 3,2',4'-Trifluoro-biphenyl-4-carboxaldehyde

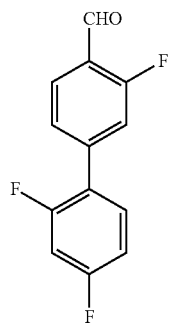 [SMILES: O=Cc1ccc(-c2ccc(F)cc2F)cc1F]

A mixture of toluene (40 mL) and water (10 mL) was degassed with nitrogen for 30 minutes. A mixture of sodium carbonate (1.04 g, 9.8 mmol), 2-fluoro-4-bromobenzaldehyde (1 g, 4.9 mmol), 2,4-difluoro phenylboronic acid (0.78 g, 4.9 mmol) and dichloro bis(diphenylphosphine)ferrocene palladium (II) (0.18 g, 0.2 mmol) was added to the above degassed water/toluene mixture. The reaction mixture was refluxed overnight. After the reaction is completed it was cooled to room temperature and extracted with ethyl acetate. The combined organic layers were dried over sodium sulphate and concentrated. The resulting residue was purified by column chromatography using 2% ethyl acetate in hexane to obtain the title compound.

$^1$H NMR (300 MHz, CDCl$_3$): δ (ppm)=δ 7.0 (m, 2H), 7.5 (m, 3H), 8.0 (t, 1H), 10.5 (s, 1H).

Step 2: 3,2',4'-Trifluoro-biphenyl-4-carboxylic acid

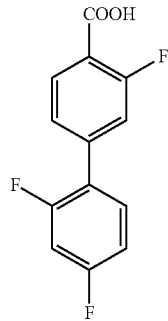 [SMILES: O=C(O)c1ccc(-c2ccc(F)cc2F)cc1F]

To a cold solution of 3,2',4'-trifluoro-biphenyl-4-carboxaldehyde (0.45 g, 1.9 mmol) in acetone (10 mL), the Jone's reagent was added slowly drop wise at 0° C. until the reaction completes. Acetone was removed completely and the reaction mixture was diluted with water, extracted with ethyl acetate and the combined organic layers were washed with water and brine, dried over sodium sulphate and concentrated to get the title compound (0.410 g, 85%)

$^1$H NMR (300 MHz, DMSO-d$_6$): δ (ppm)=7.2 (m, 6H), 13.0 (bs, 1H).

Step 3: 2-(3,2',4'-Trifluoro-biphenyl-4-yl)-3H-benzoimidazole-4-carboxylic acid

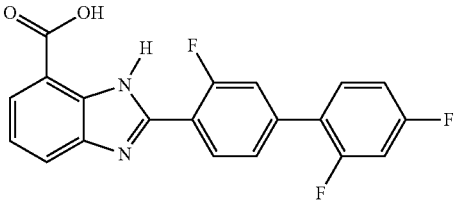 [SMILES: O=C(O)c1cccc2nc(-c3ccc(-c4ccc(F)cc4F)cc3F)[nH]c12]

$^1$H NMR (300 MHz, DMSO-d$_6$): δ (ppm)=8.27 (t, 1H, J=8.2 Hz), 8.01 (d, 1H, J=7.8 Hz), 7.89 (d, 1H, J=7.5 Hz), 7.80-7.59 (m, 3H), 7.49 (d, 1H, J=2.7 Hz), 7.47-7.38 (m, 1H), 7.30-7.24 (m, 1H). HPLC purity: 93.78%.

Example 31

6-Methyl-2-(3,2',4'-trifluoro-biphenyl-4-yl)-3H-benzoimidazole-4-carboxylic acid

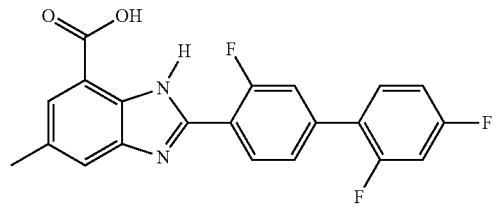 [SMILES: Cc1cc(C(=O)O)c2[nH]c(-c3ccc(-c4ccc(F)cc4F)cc3F)nc2c1]

Example 31 is obtained as described in example 14 but starting from 2',3,4'-trifluorobiphenyl-4-carboxylic acid.

$^1$H NMR (300 MHz, DMSO-d$_6$): δ (ppm)=7.48 (t, 1H, J=8.4 Hz), 7.03 (s, 1H), 6.97 (s, 1H), 6.88-6.75 (m, 3H), 6.35-6.28 (m, 2H), 2.50 (s, 3H). HPLC purity: 90.58%.

Example 32

2-(2',4'-Difluoro-biphenyl-4-yl)-3H-benzoimidazole-4-carboxylic acid

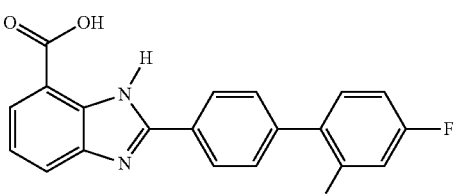

Example 32 is obtained as described in example 1 but starting from 2',4'-difluorobiphenyl-4-carboxylic acid (prepared according to the literature method J Med Chem 47(2), 355-374; 2004).

$^1$H NMR (300 MHz, DMSO-d$_6$): δ (ppm)=8.43 (d, 2H, J=8.4 Hz), 8.03 (dd, 2H, J$_1$=18.6 Hz, J$_2$=18.0 Hz), 7.83-7.69

(m, 3H), 7.55 (t, 1H, J=8.1 Hz), 7.49-7.41 (m, 1H), 7.31-7.24 (m, 1H). HPLC purity: 91.91%.

Example 33

2-(2',4'-Difluoro-biphenyl-4-yl)-6-methyl-3H-benzoimidazole-4-carboxylic acid

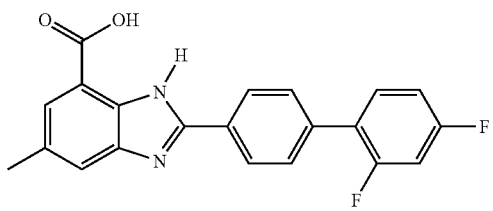 [SMILES: Cc1cc(C(=O)O)c2[nH]c(-c3ccc(-c4ccc(F)cc4F)cc3)nc2c1]

Example 33 is obtained as described in example 14 but starting from 2',4'-difluorobiphenyl-4-carboxylic acid.

$^1$H NMR (300 MHz, CD$_3$OD): δ (ppm)=7.42 (d, 2H, J=8.4 Hz), 7.20 (s, 1H), 7.05-7.02 (m, 3H), 6.83 (dd, 1H, J$_1$=15.6 Hz, J$_2$=15 Hz), 6.37-6.30 (m, 2H), 2.49 (s, 3H). HPLC purity: 90.00%.

Example 34

6-Fluoro-2-(3,2',4'-trifluoro-biphenyl-4-yl)-3H-benzoimidazole-4-carboxylic acid

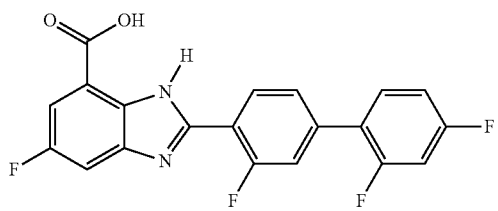 [SMILES: O=C(O)c1cc(F)cc2nc(-c3ccc(-c4ccc(F)cc4F)cc3F)[nH]c12]

Example 34 is obtained as described in example 5 but starting from 2',3,4'-trifluorobiphenyl-4-carboxylic acid.

$^1$H NMR (300 MHz, CD$_3$OD): δ (ppm)=7.47 (t, 2H, J=8.7 Hz), 6.98-6.79 (m, 4H), 6.37-6.30 (m, 2H). HPLC purity: 87.73%.

Example 35

2-Biphenyl-4-yl-6-chloro-3H-benzoimidazole-4-carboxylic acid

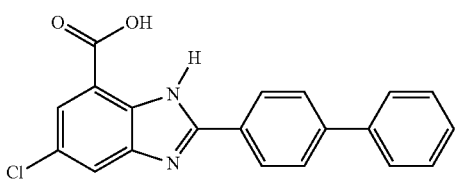

Example 35 is obtained as described in example 1 but starting from methyl 2,3-diamino-5-chlorobenzoate.

Step 1:
N-(4-Chlororo-phenyl)-2-hydroxyimino-acetamide

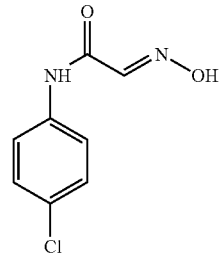 [SMILES: O=C(/C=N/O)Nc1ccc(Cl)cc1]

To a slurry of 4-chloro-phenylamine (5 g, 39.3 mmol) in water (150 mL) was added chloral hydrate (9.86 g, 59.05 mmol), sodium sulphate (27.95 g, 196.8 mmol), hydroxylamine hydrochloride (5.46 g, 78.74 mmol) and conc. HCl (5 mL). The reaction mixture was heated to 85° C. It was stirred for another 2 h at the same temperature. After completion of the reaction, solid separated out. The reaction mixture was cooled to room temperature, filtered, washed with water (2-3 times) and dried to obtain the title compound as off white solid (5.5 g, 71.42%).

Step 2: 5-Chloro-1H-indole-2,3-dione

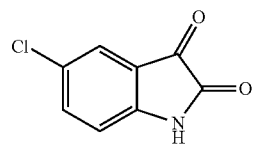

To a hot solution of conc. H$_2$SO$_4$ (20 mL) at 60° C. was added portion wise N-(4-chloro-phenyl)-2-hydroxyimino-acetamide (5.5 g, 27.0 mmol). After the addition, the temperature was increased to 80° C. and maintained for one hour. After completion of the reaction, the reaction mixture was poured on to crushed ice and the resulting precipitated solid was separated, filtered, washed with water (2-3 times) and dried to obtain the title compound as brick red solid.

Step 3; 5-Chloro-7-nitro-1H-indole-2,3-dione

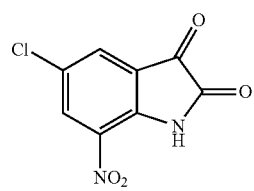

To a solution of 5-chloro-1H-indole-2,3-dione (2.8 g, 15.46 mmol) in conc. H$_2$SO$_4$ (9 mL) was added fuming nitric acid (1.5 mL) very slowly at −5 to 0° C. The reaction mixture was stirred at the same temperature for one hour. After completion of the reaction, the reaction mixture was poured on to crushed ice, and the resulting precipitate was filtered, washed with water (2-3 times) and dried under vacuum to obtain the title compound as yellow solid (3.2 g, 94.11%) which was used for the next step directly.

Step 4: 2-Amino-5-chloro-3-nitro-benzoic acid

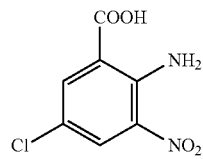 [SMILES: Nc1c(C(=O)O)cc(Cl)cc1[N+](=O)[O-]]

To a slurry of 5-chloro-7-nitro-1H-indole-2,3-dione (3.2 g, 14.15 mmol) in aqueous 5N NaOH solution (30 mL) added an aq. solution of 33% hydrogen peroxide solution (3 mL) slowly at 0° C. After the addition, the reaction mixture was stirred at room temperature for 4 h. After completion of the reaction, the reaction mixture was acidified with an aq. solution of 2N HCl and the resulting precipitated was filtered, washed with water (2-3 times) and dried under vacuum to obtain the title compound as yellow solid (2 g, 70.17%).

Step 6: 2-Amino-5-chloro-3-nitro-benzoic acid methyl ester

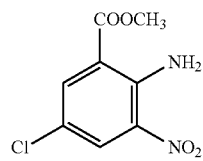

To a solution of 2-amino-5-chloro-3-nitro-benzoic acid (2 g, 1.0 mmol) in methanol (100 mL) was added a saturated ethereal solution of diazomethane gas (50 mL) till all the starting material was consumed. The reaction mixture was concentrated to dryness and the residue obtained was purified by column chromatography using 5% ethyl acetate in hexane as an eluent to obtain the title compound as yellow solid which was directly used for the next step (1.8 g, 84.11%).

Step 6: 2,3-Diamino-5-chloro-benzoic acid methyl ester

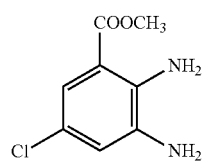 [SMILES: COC(=O)c1cc(Cl)cc(N)c1N]

A slurry of 2-amino-5-chloro-3-nitro-benzoic acid methyl ester (1.8 g, 8.40 mmol) and 10% Pd/C (0.5 g) in methanol (50 mL) was hydrogenated with a hydrogen balloon for 2 h. After completion of reaction, the reaction mixture was filtered over a celite bed and concentrated to dryness. The resulting residue was purified by column chromatography using 30% ethyl acetate in hexane to obtain the title compound as off white solid.

$^1$H NMR (300 MHz, DMSO-d$_6$): δ (ppm)=7.01 (s, 1H), 6.69 (s, 1H), 6.35 (s, 2H) 5.19 (s, 2H), 3.77 (s, 3H)

Step 7: 2-Biphenyl-4-yl-6-chloro-3H-benzoimidazole-4-carboxylic acid

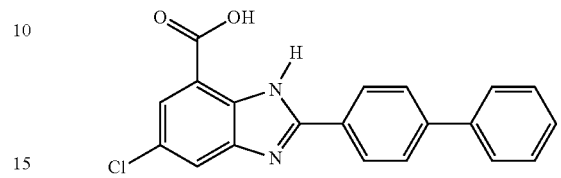

$^1$H NMR (300 MHz, DMSO-d$_6$): δ (ppm)=8.42 (d, 2H, J=8.4 Hz), 8.03 (d, 1H, J=1.8 Hz), 7.89 (d, 2H, J=8.4 Hz), 7.81-7.77 (s, 3H), 7.55-7.40 (m, 3H). HPLC purity: 94.37%.

Example 36

6-Fluoro-2-(1H-indol-5-yl)-3H-benzoimidazole-4-carboxylic acid

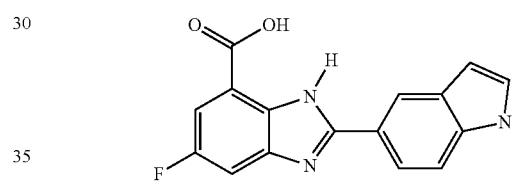

Example 36 is obtained as described in example 5 but starting from 1H-indole-5-carboxylic acid (commercially procured from Aldrich).

$^1$H NMR (300 MHz, DMSO-d$_6$): δ (ppm)=13.4 (br.s, 1H), 12.2 (br.s, 1H), 11.39 (br.s, 1H), 8.58 (s, 1H), 8.31 (s, 2H), 7.88 (d, 1H), 7.71 (d, 1H), 7.54-7.45 (m, 2H). HPLC purity: 87.11%.

Example 37

6-Fluoro-2-(1H-indol-6-yl)-3H-benzoimidazole-4-carboxylic acid

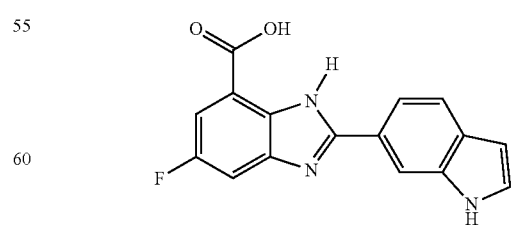

Example 37 is obtained as described in example 5 but starting from 1H-indole-6-carboxylic acid (commercially procured from Aldrich).

$^1$H NMR (300 MHz, DMSO-d$_6$): δ (ppm)=11.8 (br.s, 1H), 11.07 (br.s, 1H), 8.32 (s, 1H), 7.83 (d, 1H, J=8.4 Hz), 7.67-7.60 (m, 2H), 7.51 (s, 1H), 7.37-7.34 (m, 3H). HPLC purity: 88.98%.

Example 38

2-Biphenyl-4-yl-3H-benzoimidazole-4-carbonitrile

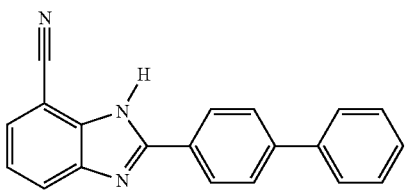 [SMILES: N#Cc1cccc2nc(-c3ccc(-c4ccccc4)cc3)[nH]c12]

Step 1:
2-Biphenyl-4-yl-1H-benzoimidazole-4-carboxylic acid amide

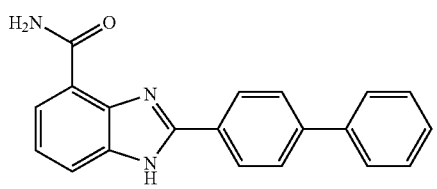 [SMILES: NC(=O)c1cccc2[nH]c(-c3ccc(-c4ccccc4)cc3)nc12]

To the solution of 2-biphenyl-4-yl-1H-benzoimidazole-4-carboxylic acid (0.35 g, 1.1 mmol) in THF (20 mL) was added N-methyl morpholine (0.2 mL, 1.6 mmol) and the mixture was cooled to −50° C. Isobutyl chloroformate (0.22 mL, 1.6 mmol) was then added drop wise, the reaction mixture was warmed to −10° C. and stirred for 2 h. The reaction mixture was again cooled to −50° C. and purged with ammonia gas for 10 minutes. Reaction mixture warmed to room temperature and stirred for 1 hour. TLC showed completion of the reaction. The crude mixture was filtered and the filtrate concentrated. The resulting residue was stirred with hexane and the free solid formed filtered and dried to obtain title compound (0.24 g, 70%).

Step 2:
2-Biphenyl-4-yl-1H-benzoimidazole-4-carbonitrile

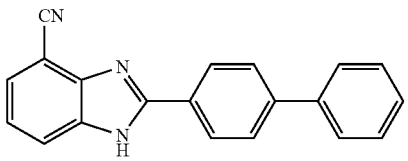 [SMILES: N#Cc1cccc2[nH]c(-c3ccc(-c4ccccc4)cc3)nc12]

To the solution of 2-biphenyl-4-yl-1H-benzoimidazole-4-carboxylic acid amide (0.24 g, 0.76 mmol) in pyridine (10 mL) was added imidazole (0.11 g, 1.53 mmol). The reaction mixture was cooled to −30° C. and phosphorous oxy chloride (0.3 mL, 3.1 mmol) was added drop wise. The reaction mixture was then stirred at −10° C. for 4 h. Progress of the reaction was monitored by TLC. The reaction mixture was concentrated to dryness and water was added. This mixture was extracted with ethyl acetate and the combined organic layers were concentrated. The resulting residue was purified by column chromatography using 30% ethyl acetate in hexane to get the title compound.

$^1$H NMR (300 MHz, DMSO-d$_6$): δ (ppm)=13.57 (br.s, 1H), 8.34-8.31 (m, 2H), 7.94-7.88 (m, 3H), 7.81-7.79 (m, 2H), 7.72-7.70 (m, 1H), 7.55-7.36 (m, 4H). HPLC purity: 95.63%.

Example 39

2-Naphthalen-1-yl-3H-benzoimidazole-4-carboxylic acid

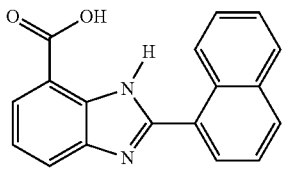 [SMILES: O=C(O)c1cccc2nc(-c3cccc4ccccc34)[nH]c12]

Example 39 is obtained as described in example 1 but starting from 1-naphthoic acid (commercially procured from Aldrich).

$^1$H NMR (300 MHz, DMSO-d$_6$): δ (ppm)=13.80 (br.s, 1H), 8.27-8.24 (m, 3H), 8.06 (dd, 3H, J$_1$=9 Hz, J$_2$=6.9 Hz), 7.77-7.58 (m, 5H). HPLC purity: 96.71%.

Example 40

2-(1H-Indol-2-yl)-6-methyl-3H-benzoimidazole-4-carboxylic acid

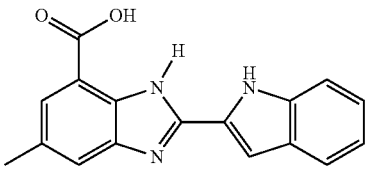 [SMILES: Cc1cc(C(=O)O)c2[nH]c(-c3cc4ccccc4[nH]3)nc2c1]

Example 40 is obtained as described in example 14 but starting from 1H-indole-2-carboxylic acid (commercially procured from Aldrich).

$^1$H NMR (300 MHz, DMSO-d$_6$): δ (ppm)=13.4 (br.s, 1H), 12.4 (br.s, 1H), 12.0 (br.s, 1H), 8.33 (s, 1H), 7.91-7.89 (m, 4H), 7.71-7.65 (m, 2H), 2.50 (s, 3H). HPLC purity: 90.26%.

Example 41

6-Methyl-2-(2,3,5,6-tetrafluoro-biphenyl-4-yl)-3H-benzoimidazole-4-carboxylic acid

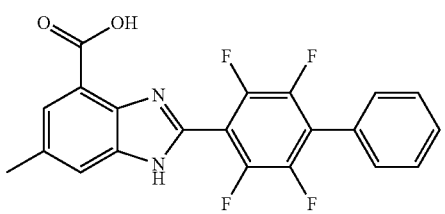 [SMILES: Cc1cc(C(=O)O)c2nc(-c3c(F)c(F)c(-c4ccccc4)c(F)c3F)[nH]c2c1]

Example 41 is obtained as described in example 14 but starting from 2,3,5,6-tetrafluorobiphenyl-4-carboxylic acid.

$^1$H NMR (300 MHz, CD$_3$OD): δ (ppm)=7.07 (s, 1H), 6.99 (s, 1H), 6.76 (m, 5H), 2.53 (s, 3H). HPLC purity: 97.64%.

Example 42

2-(1H-Indol-3-yl)-6-methyl-3H-benzoimidazole-4-carboxylic acid

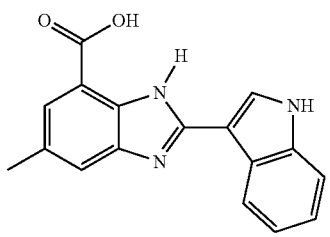 [SMILES: Cc1cc(C(=O)O)c2[nH]c(-c3c[nH]c4ccccc34)nc2c1]

Example 42 is obtained as described in example 14 but starting from 1H-indole-3-carboxylic acid (commercially procured from Aldrich).

$^1$H NMR (300 MHz, DMSO-d$_6$): δ (ppm)=12.0 (br.s, 1H), 11.80 (s, 2H), 8.01-7.98 (m, 3H), 7.47-7.44 (m, 2H), 7.20-7.11 (m, 4H) HPLC purity: 86.94%.

Example 43

2-Biphenyl-4-yl-4-trifluoromethyl-1H-benzoimidazole

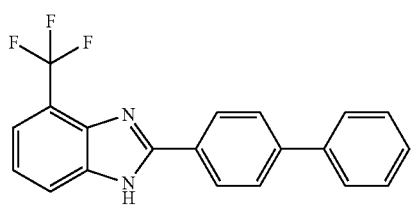 [SMILES: FC(F)(F)c1cccc2[nH]c(-c3ccc(-c4ccccc4)cc3)nc12]

Example 43 is obtained as described in example 1 but starting from 3-(trifluoromethyl)benzene-1,2-diamine Step 1: N-(3-Trifluoromethyl-phenyl)-acetamide

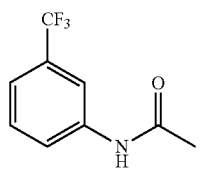

A mixture of 3-trifluoromethyl-phenylamine (4 g, 24.8 mmol), acetic anhydride (10.1 g, 99.3 mmol), DMAP (0.9 g, 7.4 mmol) and triethyl amine (2.5 g, 24.8 mmol) was heated to reflux 2 h. After completion of the reaction, the reaction mixture was cooled to room temperature, diluted with water, extracted with ethyl acetate, and the combined organic layers were dried over sodium sulphate and concentrated to dryness. The obtained residue was purified by column chromatography using 30% ethylacetate in hexane to get the title compound as off-white solid.

Step 2: N-(2-Nitro-3-trifluoromethyl-phenyl)-acetamide

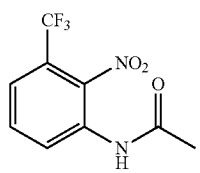 [SMILES: CC(=O)Nc1cccc(C(F)(F)F)c1[N+](=O)[O-]]

N-(3-trifluoromethyl-phenyl)-acetamide (2.8 g, 13.7 mmol) was added in small portions to the cold fuming nitric acid (10 mL) taken in a dry round bottom flask at −10° C. The reaction mixture was stirred for another 10 minutes at the same temperature then quenched with water (50 mL) and extracted with ethyl acetate. The combined organic layers were dried over sodium sulphate and concentrated to dryness. The obtained residue was purified by column chromatography using 20% ethylacetate in hexane to get the title compound as yellow solid (0.9 g, 27.74%).

Step 3: 2-Nitro-3-trifluoromethyl-phenylamine

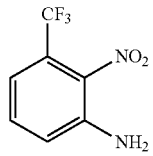

To a solution of N-(2-nitro-3-trifluoromethyl-phenyl)-acetamide (0.9 g, 3.6 mmol) in ethanol (23 mL) was added an aq. solution of 20% aq. sodium hydroxide (4.5 mL) and the mixture was heated to reflux for one hour. After completion of the reaction, the reaction mixture was cooled to room temperature and the solvents were evaporated. The reaction mixture was then diluted with water (50 mL), extracted with ethyl acetate (2×25 mL). The combined organic layers were dried over sodium sulphate and concentrated to dryness to get the title compound as yellow solid (0.67 g, 95.54%).

¹H NMR (300 MHz, DMSO-d₆): δ (ppm)=7.4-7.3 (m, 1H) 7.3 (d, J=12 Hz, 1H) 7.4-6.8 (m, 1H) 5.00 (bs, 2H)

Step 4: 3-Trifluoromethyl-benzene-1,2-diamine

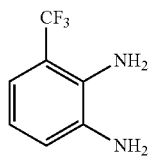

A slurry of 2-nitro-3-trifluoromethyl-phenylamine (0.678 g, 3.2 mmol) and 10% palladium on carbon (0.067 g) in methanol (20 mL) was hydrogenated with a hydrogen balloon for 2 h. After completion of the reaction, the reaction mixture was filtered and the solvent was evaporated under vacuum to obtain the title compound as off white solid (0.420 g, 73.17%).

Step 5: 2-Biphenyl-4-yl-4-trifluoromethyl-1H-benzoimidazole

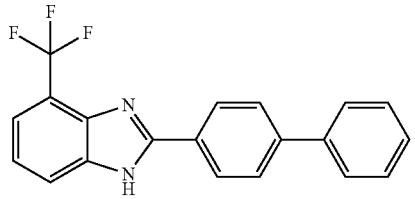 [SMILES: FC(F)(F)c1cccc2[nH]c(-c3ccc(-c4ccccc4)cc3)nc12]

¹H NMR (300 MHz, CDCl₃): δ (ppm)=9.8 (br.s, 1H), 8.15 (d, 2H, J=8.4 Hz), 7.95 (br.s, 1H), 7.77 (d, 2H, J=8.7 Hz), 7.71-7.63 (m, 2H), 7.56-7.46 (m, 3H), 7.43-7.35 (m, 2H). HPLC purity: 92.46%.

Example 44

6-Chloro-2-(3-fluoro-biphenyl-4-yl)-1H-benzoimidazole-4-carboxylic acid

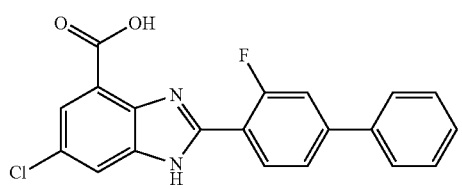 [SMILES: O=C(O)c1cc(Cl)cc2[nH]c(-c3ccc(-c4ccccc4)cc3F)nc12]

Example 44 is obtained as described in example 35 but starting from 3-fluorobiphenyl-4-carboxylic acid ¹H NMR (300 MHz, DMSO-d₆): δ (ppm)=12.20 (br.s, 2H), 8.25 (br.s, 1H), 8.05 (br.s, 1H), 7.90-7.65 (m, 5H), 7.60-7.40 (m, 3H). HPLC purity: 89.68%.

Example 45

6-Chloro-2-(2'-fluoro-biphenyl-4-yl)-1H-benzoimidazole-4-carboxylic acid

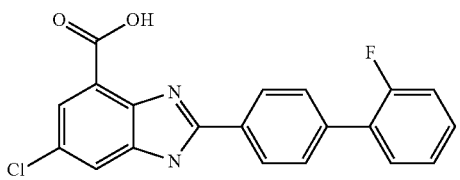 [SMILES: O=C(O)c1cc(Cl)cc2[nH]c(-c3ccc(-c4ccccc4F)cc3)nc12]

Example 45 is obtained as described in example 35 but starting from 2'-fluorobiphenyl-4-carboxylic acid.

¹H NMR (300 MHz, DMSO-d₆): δ (ppm)=8.43 (d, 2H, J=7.8 Hz), 8.02 (br.s, 1H), 7.75-7.62 (m, 4H), 7.49-7.33 (m, 4H). HPLC purity: 92.60%.

Example 46

2-(3-Methoxy-biphenyl-4-yl)-6-methyl-1H-benzoimidazole-4-carboxylic acid

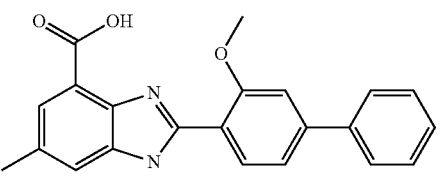 [SMILES: COc1cc(-c2ccccc2)ccc1-c1nc2c(C(=O)O)cc(C)cc2[nH]1]

Example 46 is obtained as described in example 14 but starting from 3-methoxybiphenyl-4-carboxylic acid.

Step 1: 3-Methoxy-biphenyl-4-carboxaldehyde

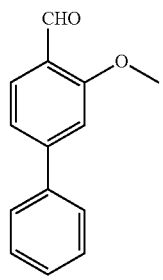 [SMILES: COc1cc(-c2ccccc2)ccc1C=O]

A mixture of toluene (30 mL) and water (5 mL) was degassed with nitrogen for 30 min. A mixture of sodium carbonate (2.26 g, 6.9 mmol) was added followed by 2-methoxy-4-bromobenzaldehyde (0.5 g, 2.3 mmol), phenylboronic acid (0.337 g, 2.7 mmol) and tetrakis triphenyl phosphene palladium(0) (0.261 g, 0.022 mmol) to the above degassed water/toluene mixture. The reaction mixture was then refluxed overnight. After the reaction is completed, it was cooled to room temperature and extracted with ethyl acetate.

The combined organic layers were dried over sodium sulphate and concentrated. The obtained residue was purified by column chromatography using 3% ethyl acetate in hexane to obtain the title compound.

$^1$H NMR (300 MHz, CDCl$_3$): δ (ppm)=4.0 (s, 3H), 7.2-7.9 (m, 8H), 10.5 (s, 1H).

Step 2: 3-Methoxy-biphenyl-4-carboxylic acid

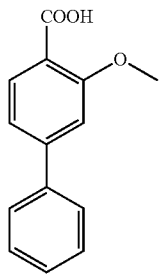 [SMILES: COc1cc(-c2ccccc2)ccc1C(=O)O]

To a cold solution of 3-methoxy-biphenyl-4-carboxaldehyde (0.32 g, 1.5 mmol) in acetone (10 mL), the Jone's reagent was added slowly drop wise at 0° C. until the reaction completes. Acetone was removed completely and the resulting residue was diluted with water, extracted with ethyl acetate. The combined organic layers were washed with water and brine, dried over sodium sulphate and concentrated to obtain the title compound (0.25 g, 73.5%)

Step 3: 2-(3-Methoxy-biphenyl-4-yl)-6-methyl-1H-benzoimidazole-4-carboxylic acid

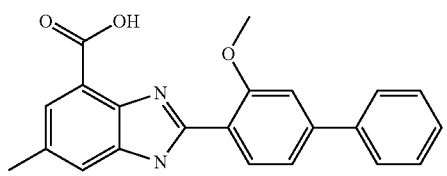

$^1$H NMR (300 MHz, DMSO-d$_6$): δ (ppm)=8.33 (d, 1H, J=8.1 Hz), 7.87-7.81 (m, 4H), 7.59-7.46 (m, 5H), 4.17 (s, 3H), 2.4 (s, 3H). HPLC purity: 91.20%.

Example 47

2-(4-Benzothiazol-2-yl-phenyl)-6-methyl-1H-benzoimidazole-4-carboxylic acid

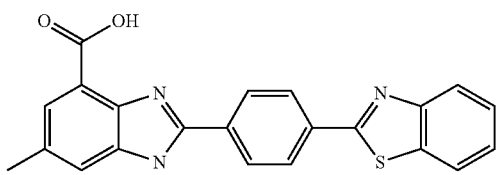 [SMILES: Cc1cc(C(=O)O)c2nc(-c3ccc(-c4nc5ccccc5s4)cc3)[nH]c2c1]

Example 47 is obtained as described in example 14 but starting from 4-(1,3-benzothiazol-2-yl)benzoic acid (synthesized using protocol described in U.S., 6251689, 26 Jun. 2001).

$^1$H NMR (300 MHz, DMSO-d$_6$): δ (ppm)=8.5 (d, 2H, J=7.5 Hz), 8.27 (d, 2H, J=8.1 Hz), 8.21 (d, 2H, J=7.8 Hz), 8.12 (d, 2H, J=7.8 Hz), 7.76 (s, 1H), 7.69 (s, 1H), 7.59 (t, 1H, J=7.5 Hz), 7.6 (t, 1H, J=6.9 Hz), 2.4 (s, 3H). HPLC purity: 92.66%.

Example 48

2-(3,5-Difluoro-biphenyl-4-yl)-6-methyl-1H-benzoimidazole-4-carboxylic acid

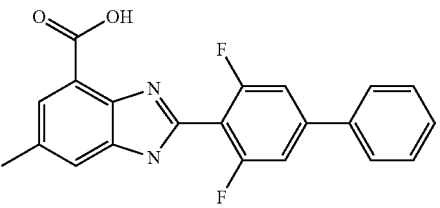 [SMILES: Cc1cc(C(=O)O)c2nc(-c3c(F)cc(-c4ccccc4)cc3F)[nH]c2c1]

Example 48 is obtained as described in example 14 but starting from 3,5-difluorobiphenyl-4-carboxylic acid (prepared according to the literature method PCT Int. Appl., 2005009941, 3 Feb. 2005).

$^1$H NMR (300 MHz, DMSO-d$_6$): δ (ppm)=7.84 (d, 2H, J=5.7 Hz), 7.79-7.48 (m, 7H), 2.4 (s, 3H). HPLC purity: 98.64%.

Example 49

6-Methyl-2-(4-phenyl-thiophen-2-yl)-1H-benzoimidazole-4-carboxylic acid

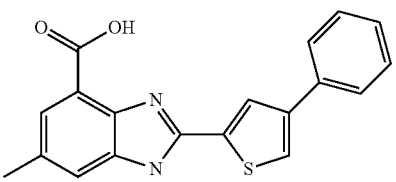 [SMILES: Cc1cc(C(=O)O)c2nc(-c3cc(-c4ccccc4)cs3)[nH]c2c1]

Example 49 is obtained as described in example 14 but starting from 4-phenylthiophene-2-carboxylic acid (commercially procured from Aldrich).

$^1$H NMR (300 MHz, DMSO-d$_6$): δ (ppm)=8.8 (s, 1H), 8.14 (s, 1H), 7.79 (d, 2H, J=9 Hz), 7.72 (d, 2H, J=3 Hz), 7.49 (t, 2H, J=7.8 Hz), 7.37 (t, 1H, J=7.2 Hz), 2.4 (s, 3H). HPLC purity: 99.44%.

Example 50

2-(6-Phenyl-pyridin-3-yl)-1H-benzoimidazole-4-carboxylic acid

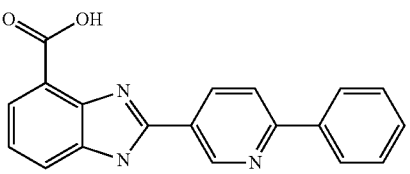

Example 50 is obtained as described in example 1 but starting from 6-phenylnicotinic acid (Prepared according to the literature method Tetrahedron letter 45(29), 5661-5663; 2004).

$^1$H NMR (300 MHz, DMSO-d$_6$): δ (ppm)=9.5 (s, 1H), 9.5 (m, 1H), 8.8-8.7 (m, 1H), 8.28-8.22 (m, 2H), 8.07 (d, 2H, J=8.1 Hz), 7.98 (d, 2H, J=7.5 Hz), 7.59-7.49 (m, 3H). HPLC purity: 94.90%.

Example 51

2-Biphenyl-4-yl-5-chloro-1H-indole-7-carboxylic acid

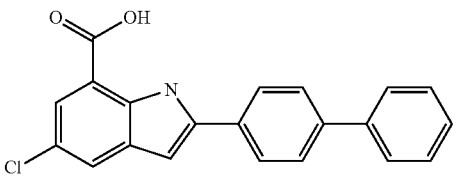 [SMILES: O=C(O)c1cc(Cl)cc2cc(-c3ccc(-c4ccccc4)cc3)[nH]c12]

Example 51 is obtained as described in example 61 but starting from a-Amino-5-chloro-3-iodo-benzoic acid methyl ester (commercially procured from aldrich).

$^1$H NMR (300 MHz, DMSO-d$_6$): δ (ppm)=9.5 (s, 1H), 9.5 (m, 1H), 8.8-8.7 (m, 1H), 8.28-8.22 (m, 2H), 8.07 (d, 2H, J=8.1 Hz), 7.98 (d, 2H, J=7.5 Hz), 7.59-7.49 (m, 3H). HPLC purity: 94.90%.

Example 52

2-(2',3'-Difluoro-biphenyl-4-yl)-6-methyl-1H-benzoimidazole-4-carboxylic acid

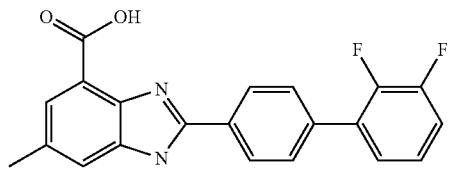 [SMILES: Cc1cc(C(=O)O)c2nc(-c3ccc(-c4cccc(F)c4F)cc3)[nH]c2c1]

Example 52 is obtained as described in example 14 but starting from 2',3'-difluorobiphenyl-4-carboxylic acid.

Step 1: 2,3'-Difluoro-biphenyl-4-carboxylic acid methyl ester

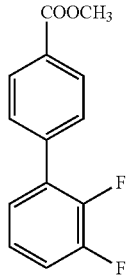

A mixture of toluene (16 mL) and water (4 mL) was degassed with nitrogen for 30 minutes. A mixture of sodium carbonate (1.4 g, 13.9 mmol), 4-bromomethylbenzoate (1 g, 4.6 mmol), 2,3-difluoro phenylboronic acid (0.726 g, 4.6 mmol) and dichloro bis(diphenylphosphine)ferrocene palladium (II) (0.18 g, 0.22 mmol) was added to the above degassed water/toluene mixture. The reaction mixture was then refluxed overnight. After the reaction is completed it was cooled to room temperature and extracted with ethyl acetate. The combined organic layers were dried over sodium sulphate and concentrated. The resulting residue was purified by column chromatography using 5% ethyl acetate in hexane to obtain the title compound.

$^1$H NMR (300 MHz, CDCl$_3$): δ (ppm)=4.0 (s, 3H), 7.2-7.9 (m, 3H), 7.6 (d, 2H), 8.1 (d, 2H).

Step 2: 2,3'-Difluoro-biphenyl-4-carboxylic acid

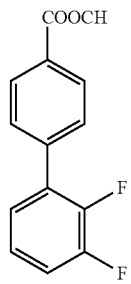

To a solution of 2',3'-difluoro-biphenyl-4-carboxylic acid methyl ester (0.4 g, 1.6 mmol) dissolved in 10% aq. THF, an aq. solution of 5 N NaOH (5 mL) was added and the reaction mixture refluxed for 5 h. THF was removed completely. The residue was cooled and acidified with an aq. solution of 50% aq. HCl solution. The resulting precipitate was filtered, washed thoroughly with water and dried to obtain the title compound (0.3 g, 79%).

Step 3: 2-(2',3'-Difluoro-biphenyl-4-yl)-6-methyl-1H-benzoimidazole-4-carboxylic acid

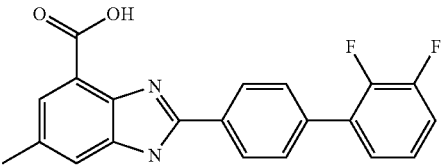 [SMILES: Cc1cc(C(=O)O)c2nc(-c3ccc(-c4cccc(F)c4F)cc3)[nH]c2c1]

$^1$H NMR (300 MHz, DMSO-d$_6$): δ (ppm)=8.42 (d, 2H, J=8.4 Hz), 7.83-7.77 (m, 4H), 7.54-7.36 (m, 3H), 2.43 (s, 3H). HPLC purity: 96.10%.

Example 53

6-Methyl-2-(5-phenyl-pyridin-2-yl)-1H-benzoimidazole-4-carboxylic acid

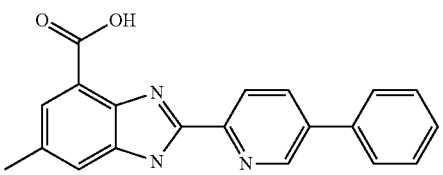 [SMILES: Cc1cc(C(=O)O)c2nc(-c3ccc(-c4ccccc4)cn3)[nH]c2c1]

Example 53 is obtained as described in example 14 but starting from 5-phenylpyridine-2-carboxylic acid (prepared according to the literature method PCT Int. Appl., 2005020899, 10 Mar. 2005).

¹H NMR (300 MHz, DMSO-d₆): δ (ppm)=9.16 (s, 1H), 8.6 (d, 1H, J=6 Hz), 8.4 (d, 1H, J=9 Hz), 7.9-7.81 (m, 4H), 7.61-7.51 (t, 3H, J=7.8 Hz), 2.42 (s, 3H). HPLC purity: 95.23%.

Example 54

2-(4-Benzenesulfonyl-phenyl)-1H-benzoimidazole-4-carboxylic acid

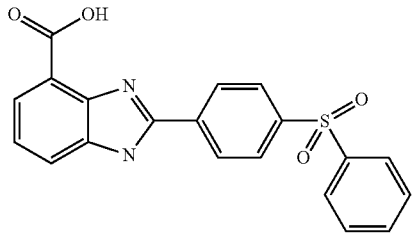 [SMILES: O=C(O)c1cccc2[nH]c(-c3ccc(S(=O)(=O)c4ccccc4)cc3)nc12]

Example 54 is obtained as described in example 1 but starting from 4-(phenylsulfonyl)benzoic acid.

Step 1: 4-Phenylsulfanyl-benzaldehyde

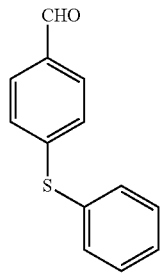 [SMILES: O=Cc1ccc(Sc2ccccc2)cc1]

To the solution of thiophenol (0.5 g, 0.463 mL, 4.5 mmol) in DMF (6 mL) was added potassium carbonate (0.94 g, 6.8 mmol) and the mixture was stirred at room temperature for 15 minutes. 4-fluoro benzaldehyde (0.675 g, 0.574 mL, 5.4 mmol) was added and the reaction mixture stirred at 80° C. for 6 h. The progress of the reaction was monitored by TLC. The reaction mixture quenched with water (20 mL) and extracted with ethyl acetate (50 mL×2). The combined organic layers were washed with water (25 mL×2) then with brine (25 mL), dried over anhydrous sodium sulphate and concentrated. The obtained residue was purified by column chromatography using 5% ethyl acetate in hexane to obtain title compound (0.94 g, 96%).

¹H NMR (300 MHz, DMSO-d₆): δ (ppm)=7.3 (d, 2H), 7.6 (m, 5H), 7.8 (d, 2H), 9.9 (s, 1H).

Step 2: 4-Benzenesulfinyl-benzoic acid

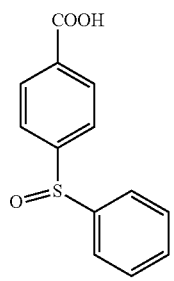 [SMILES: O=C(O)c1ccc(S(=O)c2ccccc2)cc1]

The solution of 4-phenylsulfanyl-benzaldehyde (0.2 g, 0.93 mmol) in acetone (10 mL) was cooled to 0° C. in an ice bath. A solution of sulfamic acid (0.272 g, 2.8 mmol) in water (1 mL) was added and allowed to stir for 5 minutes at same temperature. An aq. solution of sodium chlorite (0.338 g, 3.7 mmol in 1 mL) was added and thew reaction mixture was allowed to stir for 30 minutes. The progress of the reaction was monitored by TLC. The reaction mixture was diluted with water and the resulting precipitate was filtered, washed with water and dried to get the title compound.

¹H NMR (300 MHz, DMSO-D6): δ (ppm)=7.5 (m, 3H), 7.8 (m, 2H), 7.9 (d, 2H), 8.1 (d, 2H), 13.3 (s, 1H).

Step 3: 4-Benzenesulfonyl-benzoic acid

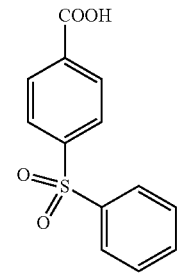 [SMILES: O=C(O)c1ccc(S(=O)(=O)c2ccccc2)cc1]

4-Benzenesulfinyl-benzoic acid (0.14 g, 0.5 mmol) was suspended in sodium hypochlorite solution (10 mL) and the reaction mixture stirred for 24 h at room temperature. The progress of the reaction was monitored by TLC. The reaction mixture was acidified with an aq. solution of 10% HCl solution. The resulting precipitate was filtered and washed with water. The residue was then redissolved in methanol and concentrated to get the title compound (0.105 g, 70%).

Step 4: 2-(4-Benzenesulfonyl-phenyl)-1H-benzoimidazole-4-carboxylic acid

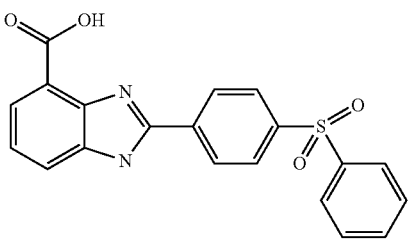 [SMILES: O=C(O)c1cccc2[nH]c(-c3ccc(S(=O)(=O)c4ccccc4)cc3)nc12]

¹H NMR (300 MHz, DMSO-d₆): δ (ppm)=8.3 (d, 2H), 7.86-7.73 (m, 6H), 7.65-7.52 (m, 3H), 7.23 (t, 2H). HPLC purity: 87.60%.

Example 55

2-(4-Phenylamino-phenyl)-1H-benzoimidazole-4-carboxylic acid

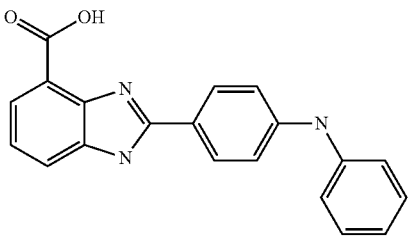

Example 55 is obtained as described in example 1 but starting from 4-anilinobenzoic acid (prepared according to the literature method Zhurnal Obshchei Khimii, 30, 2693-8; 1960).

¹H NMR (300 MHz, DMSO-d₆): δ (ppm)=8.86 (s, 1H), 8.17 (d, 2H), 7.89 (m, 2H), 7.43 (t, 1H), 7.34 (t, 2H), 7.2 (t, 4H), 6.99 (t, 1H). HPLC purity: 89.90%.

Example 56

2-[4-(2,6-Difluoro-phenoxy)-phenyl]-1H-benzoimidazole-4-carboxylic acid

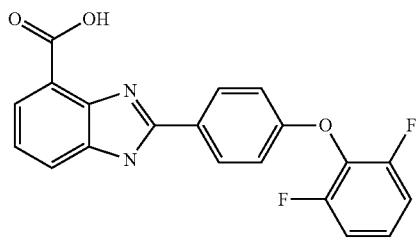 [SMILES: O=C(O)c1cccc2[nH]c(-c3ccc(Oc4c(F)cccc4F)cc3)nc12]

Example 56 is obtained as described in example 1 but starting from 4-(2,6-difluorophenoxy)benzoic acid.

Step 1: 4-(2,6-Difluoro-phenoxy)-benzaldehyde

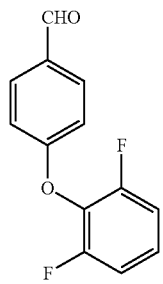

A slurry of 2,6-difluorophenol (1.0 g, 8 mmol), potassium carbonate (3.29 g, 24.2 mmol) and 4-fluoro benzaldehyde (1.36 g 10.4 mmol) in dry DMF (50 mL) was stirred at 100° C. overnight under nitrogen atmosphere. After the reaction is completed it was cooled to room temperature and poured in to ice cold water. The mixture was extracted with ethyl acetate (100 mL×2). The combined organic layers were washed with water (50 mL×2), brine, then dried over anhydrous sodium sulphate and concentrated. The resulting residue was purified by column chromatography using 3% ethyl acetate in hexane to obtain the title compound.

Step 2: 4-(2,6-Difluoro-phenoxy)-benzoic acid

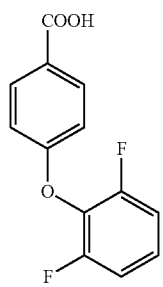

To a cold solution of 4-(2,6-difluoro-phenoxy)-benzaldehyde (1 g, 4.2 mmol) in acetone (10 mL) was added the Jone's reagent slowly drop wise at 0° C. until the reaction completes. The acetone was removed completely and the residue was diluted with water, extracted with ethyl acetate and the combined organic layers were washed with water and brine, then dried over sodium sulphate and concentrated to obtain the title compound (0.75 g, 70%)

¹H NMR (300 MHz, DMSO-d₆): δ (ppm)=7.0 (d, 2H), 7.4 (m, 3H), 8.0 (d, 2H), 19.9 (bs, 1H).

Step 3: 2-[4-(2,6-Difluoro-phenoxy)-phenyl]-1H-benzoimidazole-4-carboxylic acid

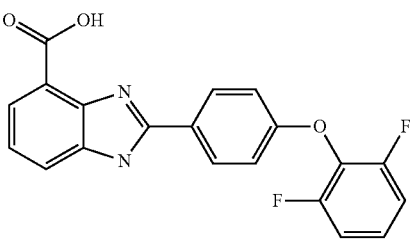 [SMILES: O=C(O)c1cccc2[nH]c(-c3ccc(Oc4c(F)cccc4F)cc3)nc12]

¹H NMR (300 MHz, DMSO-d₆): δ (ppm)=8.32 (d, 2H, J=9 Hz), 7.95 (dd, 2H, J₁=17.7 Hz, J₂=16.8 Hz), 7.49-7.36 (m, 4H), 7.2 (d, 2H, J=8.7 Hz). HPLC purity: 98.20%.

Example 57

2-(4-Pyridin-4-yl-phenyl)-1H-benzoimidazole-4-carboxylic acid

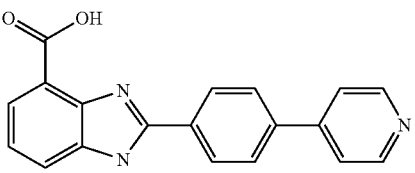 [SMILES: O=C(O)c1cccc2[nH]c(-c3ccc(-c4ccncc4)cc3)nc12]

Example 57 is obtained as described in example 1 but starting from 4-pyridin-4-ylbenzoic acid (prepared according to the literature method Synlett, (6), 829-831; 2000).

¹H NMR (300 MHz, DMSO-d₆): δ (ppm)=8.85 (d, 2H, J=5.1 Hz), 8.54 (d, 2H, J=8.4 Hz), 8.19-8.13 (m, 4H), 7.98 (d, 1H, J=7.8 Hz), 7.87 (d, 1H, J=6.9 Hz), 7.39 (t, 1H, J=7.8 Hz). HPLC purity: 93.93%.

Example 58

6-Fluoro-2-(4-pyridin-3-yl-phenyl)-1H-benzoimidazole-4-carboxylic acid

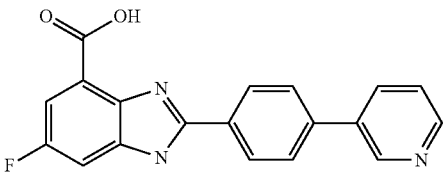

Example 58 is obtained as described in example 5 but starting from 4-pyridin-3-ylbenzoic acid (prepared according to the literature method Synlett, (6), 829-831; 2000).

¹H NMR (300 MHz, DMSO-d₆): δ (ppm)=8.41 (d, 2H, J=8.4 Hz), 7.88 (d, 2H, J=8.4 Hz), 7.83-7.78 (m, 3H), 7.62-7.58 (m, 1H), 7.54-7.49 (m, 2H), 7.45-7.40 (m, 1H). HPLC purity: 93.73%.

Example 59

6-Methyl-2-(4-pyridin-3-yl-phenyl)-1H-benzoimidazole-4-carboxylic acid

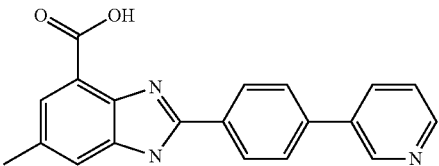

Example 59 is obtained as described in example 14 but starting from 4-pyridin-3-ylbenzoic acid.

$^1$H NMR (300 MHz, DMSO-$d_6$): δ (ppm)=8.29 (d, 2H, J=8.4 Hz), 7.97 (d, 2H, J=8.7), 7.87-7.8 (m, 4H), 7.59-7.54 (m, 2H), 2.45 (s, 3H). HPLC purity: 98.93%.

Example 60

2-(2',3'-Difluoro-biphenyl-4-yl)-1H-benzoimidazole-4-carboxylic acid

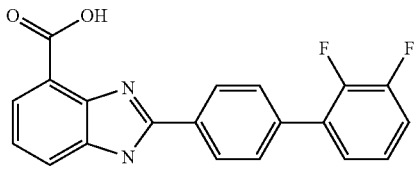 [SMILES: O=C(O)c1cccc2[nH]c(-c3ccc(-c4cccc(F)c4F)cc3)nc12]

Example 60 is obtained as described in example 1 but starting from 2',3'-difluorobiphenyl-4-carboxylic acid.

$^1$H NMR (300 MHz, DMSO-$d_6$): δ (ppm)=8.44 (d, 2H, J=8.4 Hz), 7.99 (d, 1H, J=8.1 Hz), 7.91 (d, 1H, J=7.2 Hz), 7.81 (d, 2H, J=6.9 Hz), 7.53-7.35 (m, 4H). HPLC purity: 86.73%.

Example 61

2-Biphenyl-4-yl-1H-indole-7-carboxylic acid

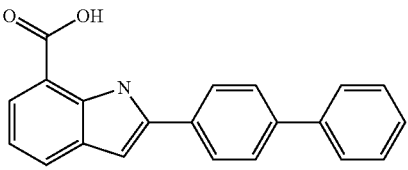

Step 1: 2-(hydroxyimino)-N-(2-iodophenyl)acetamide

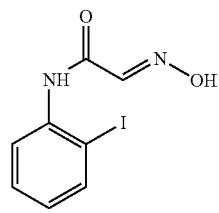 [SMILES: O=C(/C=N/O)Nc1ccccc1I]

A mixture of 2-iodobenzenamine (4 g, 0.018 mol), chloral hydrate (3.1 g, 0.021 mol) hydroxylamine hydrochloride (4 g, 0.057 mol), sodium sulphate (20 g, 0.14 mol) and conc. HCl (5 mL) was dissolved in water (150 mL). This mixture was heated at 80° C. for 3 h. The progress of the reaction was monitored by TLC. After the completion of the reaction, the reaction mixture was cooled to room temperature and the precipitated product was collected by filtration. It was then washed with water and dried in a vacuum oven to get the 3.2 g of the required product as a yellow coloured solid.

Step 2: 7-iodoindoline-2,3-dione

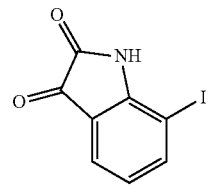 [SMILES: O=C1Nc2c(I)cccc2C1=O]

2-(hydroxyimino)-N-(2-iodophenyl)acetamide (3.2 g, 0.011 mmol) was added to conc. $H_2SO_4$ (15 mL) in small portions at 60° C. The reaction mixture was further heated at 85° C. for 5 h. After the reaction completion, the reaction mixture was cooled to room temperature and poured into crushed ice. A brown color solid product precipitated. It was then filtered and washed with chilled water several times, then dried in a vacuum oven to get 2.9 g of the required product as a red coloured solid (87%).

Step 3: 2-Amino-3-iodo-benzoic acid

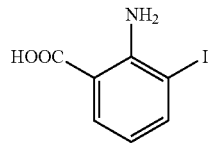 [SMILES: Nc1c(I)cccc1C(=O)O]

To a ice cold solution of 7-iodoindoline-2,3-dione (2.9 g, 0.0106 mol) in an aq. solution of 2 N NaOH (15 mL) was added drop wise an aq. solution of 35% $H_2O_2$ (3 mL) and then allowed to stir at room temperature over night. After the reaction is completed, the reaction mixture was diluted with water (50 mL), adjusted the pH to 2 with conc. HCl.

The precipitated solid was filtered, washed with water (10 mL) and dried in a vacuum oven to get 2.5 g (89%) of the required product as a yellow coloured solid.

Step 4: 2-Amino-3-iodo-benzoic acid methyl ester

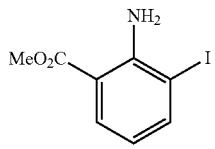 [SMILES: COC(=O)c1cccc(I)c1N]

A solution of 2-amino-3-iodo-benzoic acid (2.5 g, 9.5 mmol) in methanol and diethyl ether mixture (15 mL, 8:2) was added a freshly prepared solution of diazomethane gas in diethyl ether until all the starting material is consumed. Reaction mixture was then evaporated under reduced pressure to obtain a yellow solid which was purified by flash column using. 5% ethylacetate in hexane as an eluent. 1.5 g of the required product was isolated as a yellow viscous liquid.

$^1$H NMR (300 MHz, CDCl$_3$): δ (ppm)=7.81 (dd, 2H, J$_1$=8.1 Hz. J$_2$=8.1 Hz), 6.32-6.31 (m, 3H), 3.8 (s, 3H).

Step 5: 2-Biphenyl-4-yl-1H-indole-7-carboxylic acid

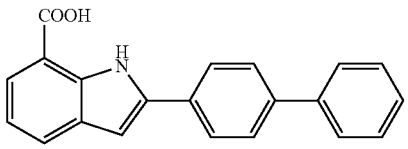 [SMILES: O=C(O)c1cccc2cc(-c3ccc(-c4ccccc4)cc3)[nH]c12]

To a solution of 2-amino-3-iodo-benzoic acid methyl ester (500 mg, 1.8 mmol), 4-ethynyl-biphenyl (416 mg, 2.3 mmol) in THF (20 mL), CuI (17 mg, 0.09 mmol), bis-(triphenylphosphine)-palladium (II)-chloride (64 mg, 0.09 mmol) and TEA (0.75 mL, 5.4 mmol) were added. This mixture was stirred at room temperature for 12 h. The progress of the reaction was monitored by TLC. After completion, the reaction mass was filtered through celite, and the collected filtrate was diluted with ethyl acetate (30 mL), washed with water (2×20 mL) and the combined organic layer was separated and dried over sodium sulphate and concentrated under reduced pressure to obtain brown mass which was purified by column chromatography using 5% ethyl acetate in hexane as an eluent to obtain 450 mg of 2-amino-3-biphenyl-4-ylethynyl-benzoic acid methyl ester as a pale yellow coloured solid (76%).

$^1$H NMR (300 MHz, CDCl$_3$): δ (ppm)=7.81 (dd, 1H, J$_1$=8.1 Hz, J$_2$=8.1 Hz), 7.57-7.18 (m, 10H), 6.56 (t, 1H, J=7.5 Hz), 6.44 (br.s, 2H), 3.81 (s, 3H).

To a cold solution of 2-amino-3-biphenyl-4-ylethynyl-benzoic acid methyl ester (300 mg, 0.91 mmol) in NMP (5 mL) was added dropwise a solution of potassium t-butoxide (205 mg, 1.83 mmol) in NMP (5 mL). This reaction mixture was allowed to stir at room temperature for 5 h. After the reaction is completed it was poured into water and pH was adjusted to 2. The resulting precipitate was collected by filtration and was washed with water. Finally it was dried in a vacuum oven to get the 145 mg of 2-biphenyl-4-yl-1H-indole-7-carboxylic acid as a pale yellow coloured solid.

$^1$H NMR (300 MHz, DMSO-d$_6$): δ (ppm)=13.05 (s, 1H) 10.75 (s, 1H) 8.00 (d, 2H, J=8.4 Hz), 7.86-7.73 (m, 5H) 7.50 (t, 2H, J=7.28 Hz), 7.41-7.36 (m, 1H), 7.15 (t, 1H, J=7.8 Hz), 7.09 (d, 1H, J=2.4 Hz). HPLC purity: 84.78%

Example 62

2-(4-Morpholin-4-yl-phenyl)-3H-benzoimidazole-4-carboxylic acid

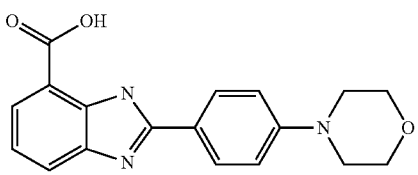 [SMILES: O=C(O)c1cccc2nc(-c3ccc(N4CCOCC4)cc3)[nH]c12]

Example 62 is obtained as described in example 1 but starting from 4-morpholin-4-ylbenzoic (prepared according to the literature method: Bioorganic and medicinal chemistry letters 15(5), 1529-1534; 2005).

$^1$H NMR (300 MHz, DMSO-d$_6$): δ (ppm)=8.22 (d, 2H, J=9 Hz), 7.93 (t, 2H, J=7.5 Hz), 7.48 (t, 1H, J=7.8 Hz), 7.15 (d, 2H, J=9 Hz), 3.76 (m, 4H); 3.34 (m, 4H). HPLC purity: 95.92%.

Example 63

2-[4-(2-oxo-2H-pyridin-1-yl)-phenyl]-3H-benzoimidazole-4-carboxylic acid

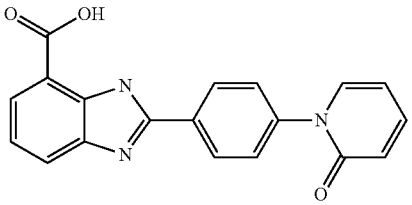 [SMILES: O=C(O)c1cccc2nc(-c3ccc(-n4ccccc4=O)cc3)[nH]c12]

Example 63 is obtained as described in example 1 but starting from 4-(2-oxopyridin-1(2H)-yl)benzoic acid (prepared according to the literature method: Bioorganic and medicinal chemistry letters 17(16), 4419-4427; 2007).

$^1$H NMR (300 MHz, DMSO-d$_6$): δ (ppm)=8.44 (d, 2H), 8.07-7.98 (m, 2H), 7.76-7.69 (m, 3H), 7.59-7.51 (m, 2H), 6.53 (d, 1H, J=9.3 Hz), 6.39 (t, 1H, J=6.6 Hz). HPLC purity: 97.48%.

Example 64

6-Methyl-2-[4-(2-oxo-2H-pyridin-1-yl)-phenyl]-1H-benzoimidazole-4-carboxylic acid

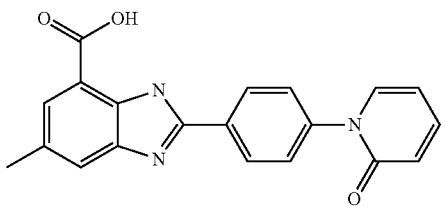 [SMILES: Cc1cc(C(=O)O)c2[nH]c(-c3ccc(-n4ccccc4=O)cc3)nc2c1]

Example 64 is obtained as described in example 14 but starting from 4-(2-oxopyridin-1(2H)-yl)benzoic acid. $^1$H NMR (300 MHz, DMSO-d$_6$): δ (ppm)=8.41 (d, 2H, J=8.7 Hz), 7.81-7.72 (m, 3H), 7.66 (d, 2H, J=8.4 Hz), 7.55 (t, 1H, J=6.9 Hz), 6.52 (d, 1H, J=9.3 Hz). 6.37 (t, 1H, J=6.6 Hz), 2.4 (s, 3H). HPLC purity: 87.39%.

Example 65

2-(2',6'-Difluoro-biphenyl-4-yl)-3H-benzoimidazole-4-carboxylic acid

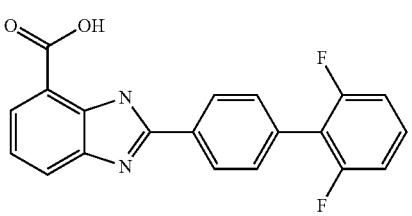 [SMILES: O=C(O)c1cccc2nc(-c3ccc(-c4c(F)cccc4F)cc3)[nH]c12]

Example 65 is obtained as described in example 1 but starting from 2',6'-difluorobiphenyl-4-carboxylic acid (prepared according to the literature method: J Med. Chem. 47(2), 355-374; 2004).

$^1$H NMR (300 MHz, DMSO-d$_6$): δ (ppm)=8.45 (d, 2H, J=8.4 Hz), 8.04 (d, 1H, J=8.1 Hz), 7.96 (d, 1H, J=7.5 Hz), 7.72 (d, 2H, J=8.1 Hz), 7.57-7.47 (m, 2H), 7.29 (d, 2H, J=8.1 Hz). HPLC purity: 96.80%.

Example 66

2-[4-(4,5-Dimethyl-oxazol-2-yl)-phenyl]-3H-benzoimidazole-4-carboxylic acid

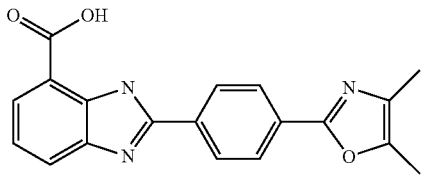 [SMILES: Cc1nc(-c2ccc(-c3nc4cccc(C(=O)O)c4[nH]3)cc2)oc1C]

Example 66 is obtained as described in example 1 but starting from 4-(4,5-dimethyl-1,3-oxazol-2-yl)benzoic acid.

Step 1: Terephthalic acid 1-methyl ester 4-(1-methyl-2-oxo-propyl) ester

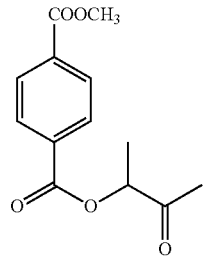 [SMILES: COC(=O)c1ccc(C(=O)OC(C)C(C)=O)cc1]

A mixture of terphthalic acid monomethyl ester (1.0 g, 5 mmol), 3-hydroxy-butane-2-one (0.531 g, 6.8 mmol), 4-dimethylamino pyridine (1.27 g, 10 mmol), pyridine (0.79 g, 10 mmol) and EDCl.HCl (1.6 g, 8 mmol) was stirred in dry DMF (10 mL) over night under nitrogen atmosphere. The reaction mixture was poured into ice cold water and extracted with ethyl acetate (100 mL×2). The combined organic layers were washed with water (50 mL×2) and with brine, then dried over anhydrous sodium sulphate and concentrated. the obtained residue was purified by column chromatography using 3% ethyl acetate in hexane to obtain the title compound.

$^1$H NMR (300 MHz, CDCl$_3$): δ (ppm)=2.2 (s, 3H), 3.9 (s, 3H), 5.1 (s, 2H), 8.1 (s, 4H).

Step 2: 4-(4,5-Dimethyl-oxazol-2-yl)-benzoic acid methyl ester

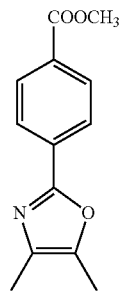

To a solution of terephthalic acid 1-methyl ester 4-(1-methyl-2-oxo-propyl) ester (0.5 g, 2 mmol) in acetic acid (20 mL) was added ammonium acetate (0.308 g 4 mmol) and the mixture was stirred at 90° C. over night. Acetic acid was removed under reduced pressure and ice cold water (10 mL) was added to the residue. The resulting mixture was extracted with ethyl acetate (50 mL×2), the combined organic layers were washed with water (25 mL×2) and with brine, dried over anhydrous sodium sulphate and concentrated to obtain the title compound.

$^1$H NMR (300 MHz, CDCl3): δ (ppm)=2.2 (s, 3H), 2.4 (s, 3H), 4.0 (s, 3H), 8.0 (m, 4H). LCMS– M+H 232, 56.34%

Step 3: 4-(4,5-Dimethyl-oxazol-2-yl)-benzoic acid.

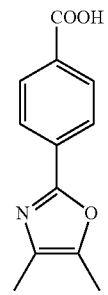

To a solution of 4-(4,5-dimethyl-oxazol-2-yl)-benzoic acid methyl ester (0.5 g, 2.1 mmol) in THF (20 mL), an aq. solution of 5 N sodium hydroxide (10 mL) was added. The reaction mixture refluxed at 90° C. over night. THF was removed completely under reduced pressure and the residue was acidified with conc. HCl, then E extracted with ethyl acetate (50 mL×2). The combined organic layers were washed with water (25 mL×2) and with brine, then dried over anhydrous sodium sulphate and concentrated to get the title compound (0.3 g, 63.8%).

HPLC purity: 97.19%.

Step 4: 2-[4-(4,5-Dimethyl-oxazol-2-yl)-phenyl]-3H-benzoimidazole-4-carboxylic acid

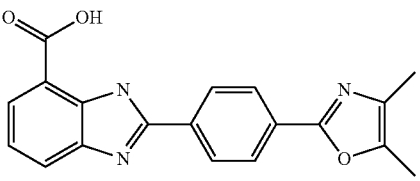 [SMILES: Cc1nc(-c2ccc(-c3nc4cccc(C(=O)O)c4[nH]3)cc2)oc1C]

$^1$H NMR (300 MHz, DMSO-d$_6$): δ (ppm)=8.39 (d, 2H, J=8.7 Hz), 8.07 (d, 2H, J=8.1 Hz), 7.92 (d, 1H, J=7.8 Hz), 7.85 (d, 1H, J=7.5 Hz), 7.37 (t, 1H, J=7.5 Hz), 2.35 (s, 3H), 2.13 (s, 3H). HPLC purity: 83.58%.

Example 67

6-Methyl-2-(4-phenoxy-phenyl)-3H-benzoimidazole-4-carboxylic acid

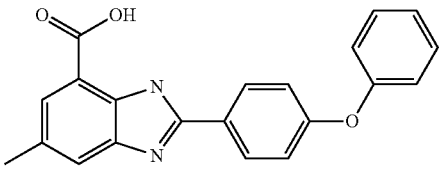 [SMILES: Cc1cc(C(=O)O)c2[nH]c(-c3ccc(Oc4ccccc4)cc3)nc2c1]

Example 67 is obtained as described in example 14 but starting from 4-phenoxybenzoic acid (commercially procured from aldrich).

$^1$H NMR (300 MHz, DMSO-d$_6$): δ (ppm)=8.3 (d, 2H, J=8.4 Hz), 7.71 (d, 2H, J=9.3 Hz), 7.47 (t, 2H, J=7.8 Hz); 7.23 (t, 1H, J=7.5 Hz); 7.16-7.12 (m, 4H), 2.48 (s, 3H). HPLC purity: 91.91%.

Example 68

2-(3,5-Difluoro-biphenyl-4-yl)-6-fluoro-1H-benzoimidazole-4-carboxylic acid

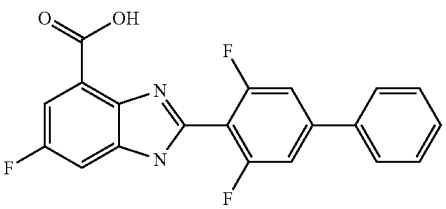 [SMILES: O=C(O)c1cc(F)cc2[nH]c(-c3c(F)cc(-c4ccccc4)cc3F)nc12]

Example 68 is obtained as described in example 5 but starting from 3,5-difluorobiphenyl-4-carboxylic acid (prepared according to the literature method: PCT Int. Appl., 2005009941, 3 Feb. 2005).

$^1$H NMR (300 MHz, DMSO-d$_6$): δ (ppm)=12.95 (br.s, 1H), 7.87-7.85 (m, 3H), 7.72-7.63 (m, 3H), 7.56-7.48 (m, 3H). HPLC purity: 89.25%.

Example 69

1-(2-Biphenyl-4-yl-1H-benzoimidazol-4-yl)-ethanone

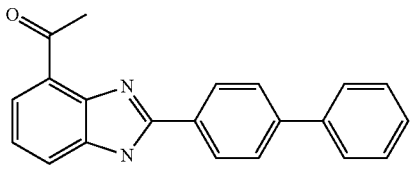

Example 69 is obtained as described in example 1, but from 1-(2,3-diaminophenyl)ethanone.

Step 1: N-(2-Acetyl-phenyl)-acetamide

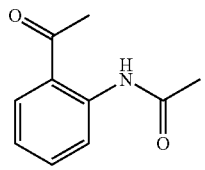

To an ice cold slurry of the 1-(2-amino-phenyl)-ethanone (2 g, 14.79 mmol) in dichloroethane (10 mL), acetyl chloride (1.22 g, 16.2 mmol) was added slowly. The reaction mixture was warmed to room temperature and stirred for 2 h. After completion of the reaction, the reaction mixture was quenched with water (10 mL) and extracted with dichloromethane (2×25 mL). The combined organic layers were washed with an aq. solution of 5% NaHCO$_3$ followed by water and brine, then dried over anhydrous sodium sulphate and concentrated to dryness. The obtained residue was purified by column chromatography using 2% ethyl acetate in hexane to obtain the title compound as off-white solid which directly used for the next reaction.

Step 2: N-(2-Acetyl-6-nitro-phenyl)-acetamide

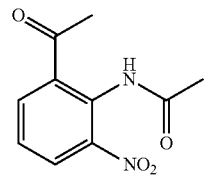 [SMILES: CC(=O)Nc1c(C(C)=O)cccc1[N+](=O)[O-]]

A solution of N-(2-acetyl-phenyl)-acetamide (1 g, 5.65 mmol) in conc. H$_2$SO$_4$ (2.8 mL, 45.2 mmol) was cooled to −20° C. and fuming nitric acid (2 mL, 33 mmol) was slowly added. The reaction mixture was warmed to 0° C. and stirred for 7 h. After completion of the starting material, the reaction mixture was quenched with water and extracted with dichloromethane (2×25 mL). The combined organic layers were washed with brine and water, then dried over anhydrous sodium sulphate and concentrated to dryness. The resulting residue was purified by column chromatography using 1% methanol in chloroform to get the title compound as yellow solid Step 3: 1-(2-Amino-3-nitro-phenyl)-ethanone

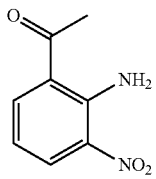

To a solution N-(2-acetyl-6-nitro-phenyl)-acetamide (0.3 g, 13.5 mmol) in ethanol (5 mL), was added an aq. solution of 5 N HCl (4.5 mL) and the reaction mixture was heated to reflux for one hour. After completion of the reaction, the reaction mixture was cooled to room temperature and evaporated under reduced pressure. The residue was diluted with water (25 mL) and extracted with ethyl acetate (2×25 mL). The combined organic layers were washed with a 10% aq. solution of sodium bicarbonate followed by water and dried over anhydrous sodium sulphate, then concentrated to dryness and purified by column chromatography using 15% ethyl acetate in hexane to get the title compound as yellow solid (0.20 g, 82.30%)

Step 4: 1-(2,3-Diamino-phenyl)-ethanone

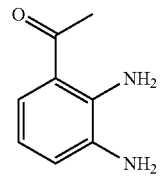

A slurry of 1-(2-amino-3-nitro-phenyl)-ethanone (0.2 g, 1.11 mmol) and 10% palladium on carbon (0.020 g) in methanol (10 mL) was hydrogenated with a hydrogen balloon for 2 h. After completion of the reaction, the reaction mixture was filtered and evaporated under vacuum to obtain the title compound as off white solid (0.120 g, 72.28%)

¹H NMR (300 MHz, DMSO-d6): δ (ppm)=7.12 (d, J=12 Hz, 1H) 6.80 (bs, 2H) 6.70 (d, J=12 Hz, 1H) 6.44-6.36 (m, 1H) 4.80 (s, 2H) 2.45 (s, 3H).

Step 5: 1-(2-Biphenyl-4-yl-1H-benzoimidazol-4-yl)-ethanone

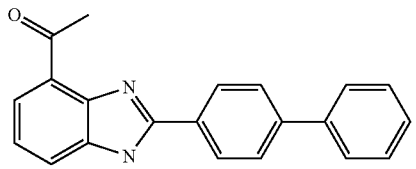

¹H NMR (300 MHz, CDCl₃): δ (ppm)=11.2 (br.s, 1H), 8.2 (d, 2H), 8.1 (d, 1H), 7.92-7.6 (m, 3H), 7.7 (d, 2H), 7.5 (t, 2H), 7.44 (m, 2H), 2.9 (s, 3H). HPLC purity: 96.25%.

Example 70

2-[4-(Pyridin-2-yloxy)-phenyl]-1H-benzoimidazole-4-carboxylic acid

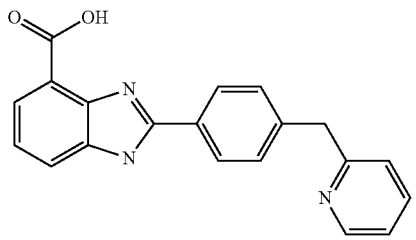 [SMILES: O=C(O)c1cccc2[nH]c(-c3ccc(Cc4ccccn4)cc3)nc12]

Example 70 is obtained as described in example 1 but starting from 4-(pyridin-2-yloxy)benzoic acid (prepared according to the literature method: Synlett, (2), 221-224; 2008).

¹H NMR (300 MHz, DMSO-d₆): δ (ppm)=8.27-7.90 (m, 4H), 7.66-7.60 (m, 2H), 7.23-7.09 (m, 5H). HPLC purity: 96.62%.

Example 71

6-Methyl-2-[4-(pyridin-2-yloxy)-phenyl]-1H-benzoimidazole-4-carboxylic acid

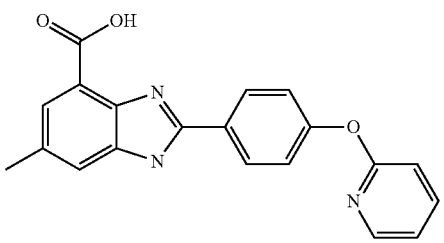 [SMILES: Cc1cc(C(=O)O)c2nc(-c3ccc(Oc4ccccn4)cc3)[nH]c2c1]

Example 71 is obtained as described in example 14 but starting from 4-(pyridin-2-yloxy)benzoic acid.

¹H NMR (300 MHz, DMSO-d₆): δ (ppm)=8.4 (d, 2H, J=9 Hz), 8.22 (d, 1H, J=4.8 Hz), 7.97-7.87 (m, 3H), 7.41 (d, 2H, J=8.7 Hz), 7.25-7.18 (m, 2H), 2.54 (s, 3H). HPLC purity: 92.02%.

Example 72

6-Methyl-2-(4-pentafluorophenyloxy-phenyl)-1H-benzoimidazole-4-carboxylic acid

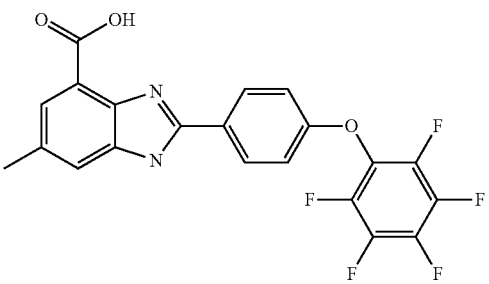 [SMILES: Cc1cc(C(=O)O)c2nc(-c3ccc(Oc4c(F)c(F)c(F)c(F)c4F)cc3)[nH]c2c1]

Example 72 is obtained as described in example 14 but starting from 4-(pentafluorophenoxy)benzoic acid.

Step 1: 4-Pentafluorophenyloxy-benzaldehyde

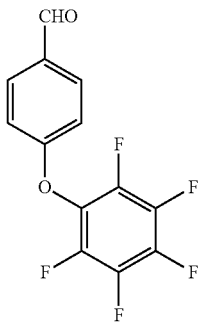 [SMILES: O=Cc1ccc(Oc2c(F)c(F)c(F)c(F)c2F)cc1]

A slurry of 2,3,4,5,6-pentafluorophenol (1.92 g, 10.4 mmol), potassium carbonate (3.3 g, 23.9 mmol) and 4-fluoro benzaldehyde (1.0 g, 8.0 mmol) in dry DMF (50 mL) was stirred at 100° C. overnight under nitrogen atmosphere. After the reaction is completed it was cooled to room temperature and poured in to ice cold water. The mixture was extracted with ethyl acetate (100 mL×2), the combined organic layers were washed with water (50 mL×2), brine, then dried over anhydrous sodium sulphate and concentrated. The residue was purified by column chromatography using 3% ethyl acetate in hexane to obtain the title compound.

¹H NMR (300 MHz, CDCl₃): δ (ppm)=7.2 (dd, 2H), 7.9 (dd, 2H), 10.0 (s, 1H).

Step 2: 4-Pentafluorophenyloxy-benzoic acid

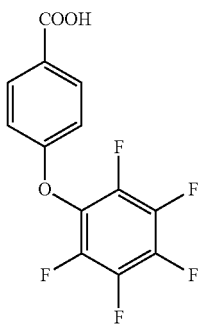 [SMILES: O=C(O)c1ccc(Oc2c(F)c(F)c(F)c(F)c2F)cc1]

To an ice cold solution of 4-pentafluorophenyloxy-benzaldehyde (0.6 g, 2.0 mmol) in acetone (10 mL), the Jone's reagent was added slowly drop wise until reaction the completed. Acetone was removed completely and diluted with water. The mixture was extracted with ethyl acetate, the combined organic layers were dried over anhydrous sodium sulphate and concentrated to get the title compound (0.45 g, 71%).

$^1$H NMR (300 MHz, CDCl$_3$): δ (ppm)=7.1 (m, 2H), 8.1 (m, 2H).

Step 3: 6-Methyl-2-(4-pentafluorophenyloxy-phenyl)-1H-benzoimidazole-4-carboxylic acid

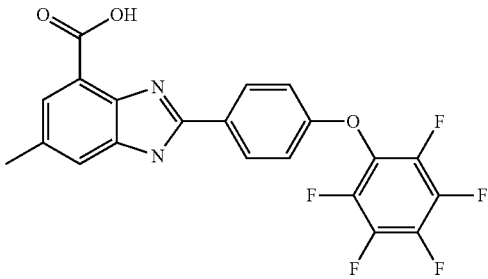 [SMILES: Cc1cc(C(=O)O)c2nc(-c3ccc(Oc4c(F)c(F)c(F)c(F)c4F)cc3)[nH]c2c1]

$^1$H NMR (300 MHz, DMSO-d$_6$): δ (ppm)=8.38-8.33 (m, 2H), 7.72 (d, 2H, J=12.6 Hz), 7.44-7.39 (m, 2H), 2.49 (s, 3H). HPLC purity: 94.98%.

Example 73

2-(4-Pyridin-2-yl-phenyl)-3H-benzoimidazole-4-carboxylic acid

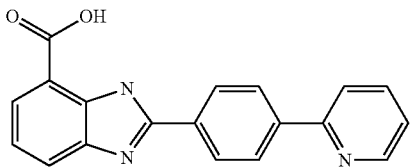 [SMILES: O=C(O)c1cccc2nc(-c3ccc(-c4ccccn4)cc3)[nH]c12]

Example 73 is obtained as described in example 1 but starting from 4-pyridin-2-ylbenzoic acid (Prepared according to the literature method: Bioorganic and medicinal chemistry letters 15(3), 631-634; 2005).

$^1$H NMR (300 MHz, DMSO-d$_6$): δ (ppm)=8.74 (d, 1H, J=4.2 Hz), 8.46 (d, 2H, J=8.4 Hz), 8.33 (s, 1H), 8.3 (d, 1H, J=3 Hz), 8.14 (d, 1H, J=7.8 Hz), 8.01-7.90 (m, 4H), 7.48-7.41 (m, 2H). HPLC purity: 95.53%.

Example 74

6-Methyl-2-(4-pyridin-2-yl-phenyl)-3H-benzoimidazole-4-carboxylic acid

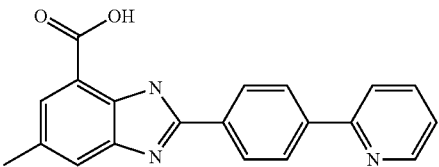

Example 74 is obtained as described in example 14 but starting from 4-pyridin-2-ylbenzoic acid.

$^1$H NMR (300 MHz, CD$_3$OD): δ (ppm)=7.87 (d, 1H, J=4.2 Hz), 7.48 (d, 2H, J=8.4 Hz), 7.39 (d, 2H, J=8.4 Hz), 7.18 (t, 2H, J=7.5 Hz), 7.05 (s, 1H), 6.95 (s, 1H), 6.64 (d, 1H, J=4.8 Hz), 2.48 (s, 3H). HPLC purity: 88.93%.

Example 75

6-Methyl-2-(6-phenyl-pyridin-3-yl)-3H-benzoimidazole-4-carboxylic acid

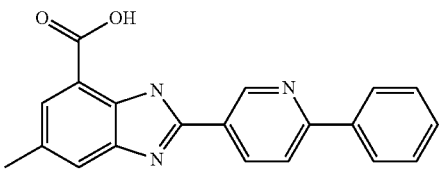 [SMILES: Cc1cc(C(=O)O)c2[nH]c(-c3ccc(-c4ccccc4)nc3)nc2c1]

Example 75 is obtained as described in example 14 but starting from 6-phenylnicotinic acid (prepared according to the literature method: Tetrahedron letter 45(29), 5661-5663; 2004).

$^1$H NMR (300 MHz, DMSO-d$_6$): δ (ppm)=9.52 (d, 1H, J=2.1 Hz), 8.79 (dd, 1H, J$_1$=8.4 Hz, J$_2$=8.7 Hz), 8.31-8.22 (m, 3H,), 7.89 (d, 2H, J=6.3 Hz), 7.6-7.54 (m, 3H,), 2.55 (s, 3H,). HPLC purity: 96.55%.

Example 76

2-(2',6'-Difluoro-biphenyl-4-yl)-6-methyl-3H-benzoimidazole-4-carboxylic acid

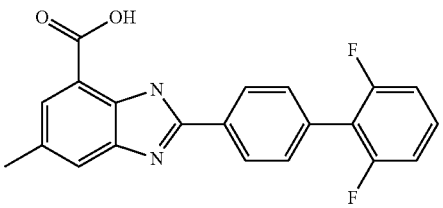 [SMILES: Cc1cc(C(=O)O)c2[nH]c(-c3ccc(-c4c(F)cccc4F)cc3)nc2c1]

Example 76 is obtained as described in example 14 but from 2',6'-difluorobiphenyl-4-carboxylic acid (prepared according to the literature method: J Med. Chem. 47(2), 355-374; 2004).

$^1$H NMR (300 MHz, DMSO-d$_6$): δ (ppm)=8.43 (d, 2H, J=8.1 Hz), 7.87 (d, 2H, J=4.5 Hz), 7.75 (d, 2H, J=8.4 Hz), 7.59-7.51 (m, 1H), 7.32-7.27 (m, 2H), 2.55 (s, 3H). HPLC purity: 96.71%.

Example 77

2-[4-(4-Cyano-phenoxy)-phenyl]-3H-benzoimidazole-4-carboxylic acid

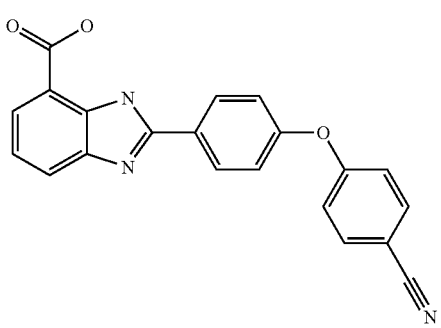 [SMILES: N#Cc1ccc(Oc2ccc(-c3nc4cccc(C(=O)O)c4[nH]3)cc2)cc1]

Example 77 is obtained as described in example 1 but starting from 4-(4-cyanophenoxy)benzoic acid.

Step 1: 4-(4-Cyano-phenoxy)-benzaldehyde

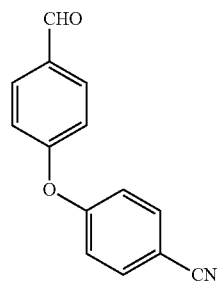 [SMILES: N#Cc1ccc(Oc2ccc(C=O)cc2)cc1]

A slurry of 4-cyanophenol (1.24 g, 10.4 mmol), potassium carbonate (3.3 g, 23.9 mmol), and 4-fluoro benzaldehyde (1.0 g, 8 mmol) in dry DMF (50 mL) was stirred at 100° C. overnight under nitrogen atmosphere. After the reaction is completed it was cooled to room temperature and poured in to ice cold water. The mixture was extracted with ethyl acetate (100 mL×2), the combined organic layers were washed with water (50 mL×2), and brine, then dried over anhydrous sodium sulphate and concentrated. The residue was purified by column chromatography using 3% ethyl acetate in hexane to obtain the title compound (2 g, 86%)

$^1$H NMR (300 MHz, CDCl$_3$): δ (ppm)=7.0-8.0 (m, 8H), 10.0 (s, 1H).

Step 2: 4-(4-Cyano-phenoxy)-benzoic acid

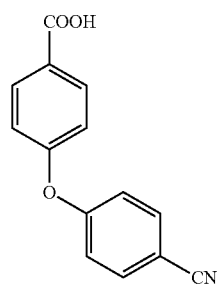 [SMILES: N#Cc1ccc(Oc2ccc(C(=O)O)cc2)cc1]

To an ice cold solution of 4-(4-cyano-phenoxy)-benzaldehyde (2.0 g, 8.9 mmol) in acetone (10 mL), the Jone's reagent (7 mL) was added slowly drop wise until reaction completes. Acetone was removed completely and diluted with water. The mixture was extracted with ethyl acetate. the combined organic layers were dried over anhydrous sodium sulphate and concentrated to get the title compound (1.5 g, 70%)

1H NMR (300 MHz, DMSO-d6): δ (ppm)=7.2 (m, 4H), 7.8 (d, 2H), 8.0 (d, 2H).

Step 3: 2-[4-(4-Cyano-phenoxy)-phenyl]-3H-benzoimidazole-4-carboxylic acid

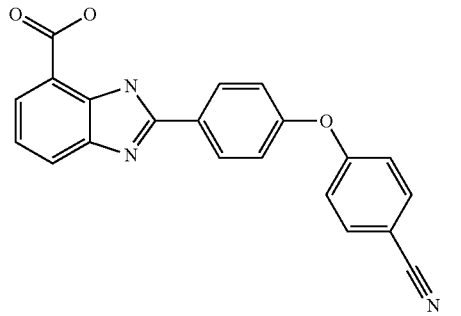 [SMILES: N#Cc1ccc(Oc2ccc(-c3nc4cccc(C(=O)O)c4[nH]3)cc2)cc1]

$^1$H NMR (300 MHz, DMSO-d$_6$): δ (ppm)=8.39-8.32 (m, 2H), 8.2-7.9 (m, 4H), 7.60-7.45 (m, 1H), 7.40-7.15 (m, 4H). HPLC purity: 72.20%.

Example 78

2-[4-(4-Cyano-phenoxy)-phenyl]-6-methyl-3H-benzoimidazole-4-carboxylic acid

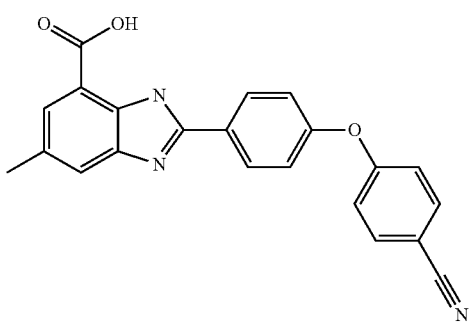 [SMILES: Cc1cc(C(=O)O)c2[nH]c(-c3ccc(Oc4ccc(C#N)cc4)cc3)nc2c1]

Example 78 is obtained as described in example 14 but starting from 4-(4-cyanophenoxy)benzoic acid.

$^1$H NMR (300 MHz, DMSO-d$_6$): δ (ppm)=8.39-8.32 (m, 2H), 7.97-7.88 (m, 2H), 7.646 (d, 2H, J=12 Hz), 7.29-7.12 (m, 5H); 2.50 (s, 3H). HPLC purity: 78.7%.

Example 79

2-Biphenyl-4-yl-1H-benzoimidazole-4-carboxylic acid methyl ester

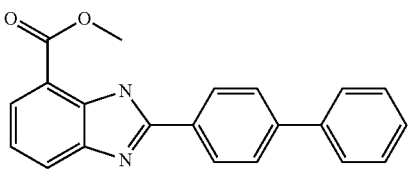 [SMILES: COC(=O)c1cccc2nc(-c3ccc(-c4ccccc4)cc3)[nH]c12]

Step 1: 2-Hydroxyimino-N-(2-nitro-phenyl)-acetamide

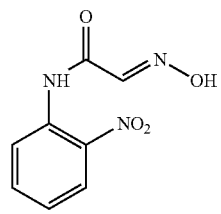 [SMILES: O=C(/C=N/O)Nc1ccccc1[N+](=O)[O-]]

A solution of chloral hydrate (29 g, 175 mmol), hydroxylamine hydrochloride (69.4 g, 1000 mmol) and anhydrous sodium sulphate (21 g, 149 mmol) in water (800 mL) was heated to 65° C. To this a suspension was added 2-nitroaniline (20 g, 150 mmol) in 2 M aqueous HCl (20 mL). This mixture was stirred overnight at the same temperature then was cooled to room temperature. The precipitated product was collected by filtration, washed with water dried in a vacuum oven to give 25 g of the required product as a yellow coloured solid (83%).

1H NMR (300 MHz, DMSO-d6): δ (ppm)=12.62 (s, 1H), 10.94 (s, 1H), 8.29 (d, 1H, J=8.4 Hz), 8.13 (dd, 1H, J=8.4 & 1.2 Hz), 7.77 (m, 1H), 7.62 (s, 1H), 7.36 (m, 1H). HPLC purity: 85%.

Step 2: 7-Nitro-1H-indole-2,3-dione

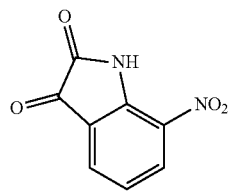 [SMILES: O=C1Nc2c(cccc2[N+](=O)[O-])C1=O]

2-Hydroxyimino-N-(2-nitro-phenyl)-acetamide (15 g, 72 mmol) was carefully added in small portions over a period of 30 min to a stirred solution of conc. sulphuric acid (45 mL) which was preheated to 90° C. The reaction mixture was stirred for another 2 h at the same temperature then cooled to room temperature, poured into crushed ice. The precipitated products were collected by filtrations, washed with water and dried in a vacuum oven to get 9 g (65%) of brick red colour powder.

$^1$H NMR (300 MHz, DMSO-$d_6$): δ (ppm)=11.68 (s, 1H), 8.31 (dd, 1H, J=8.4 & 0.9 Hz), 7.92 (dd, 1H, J=8.4 & 0.9 Hz), 7.25 (m, 1H). HPLC purity: 93%

Step 3: 2-Amino-3-nitro-benzoic acid

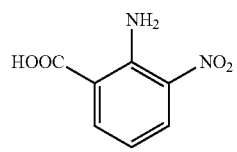

To a ice cold solution of 7-nitro-1H-indole-2,3-dione (9 g, 47 mmol) in 2 M aqueous sodium hydroxide (50 mL), an aq. solution of 30% hydrogen peroxide (9 mL) was added drop wise. The mixture was warmed to room temperature and stirred overnight. The resulting mixture was carefully acidified by the addition of an aq. saturated citric acid solution. The solid precipitate was collected by filtration, washed with water and dried in a vacuum oven to get 6 g of the required product as a yellow coloured solid (70%).

$^1$H NMR (300 MHz, DMSO-$d_6$): δ (ppm)=8.9 (br.s, 1H), 8.19 (m, 2H), 6.63 (m, 1H). HPLC purity: 98%. LCMC (–ive mode): 93% and m/z: 181.9

Step 4: 2-Amino-3-nitro-benzoic acid methyl ester

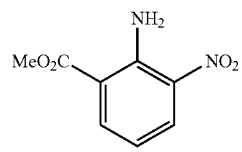 [SMILES: COC(=O)c1cccc([N+](=O)[O-])c1N]

To a solution of 2-amino-3-nitro-benzoic acid (6 g, 33 mmol) in methanol (20 mL), an ethereal solution of diazomethane gas was added until the staring material is completely consumed. The reaction mixture was then evaporated under reduced pressure and the crude resulting solid was purified by flash column chromatography using 5% ethylacetate & hexane as an eluent, to obtain 2 g of the required product as a yellow coloured solid.

$^1$H NMR (300 MHz, DMSO-$d_6$): δ (ppm)=8.35 (m, 3H), 8.22 (m, 1H), 6.75 (m, 1H), 3.86 (s, 3H). HPLC purity: 99%

Step 5: 2,3-Diamino-benzoic acid methyl ester

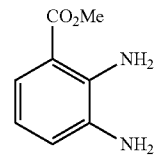

To a solution of 2-amino-3-nitro-benzoic acid methyl ester (2 g, 10 mmol) in methanol, a suspension of 10% Pd/C (300 mg) in methanol 5 mL was added and hydrogenated with a hydrogen balloon over a period of 8 h. The reaction mass was filtered and the filtrate was concentrated under reduced pressure to obtain 1.5 g of the required compound as a brown coloured solid (88%).

$^1$H NMR (300 MHz, DMSO-$d_6$): δ (ppm)=7.09 (dd, 1H, J=8.1 & 1.2 Hz), 6.70 (dd, 1H, J=8.1 & 1.2 Hz), 6.3.8 (m, 1H), 6.199 (s, 2H), 4.77 (s, 2H), 3.76 (s, 3H).

Step 6: 2-Amino-3-[(biphenyl-4-carbonyl)-amino]-benzoic acid methyl ester

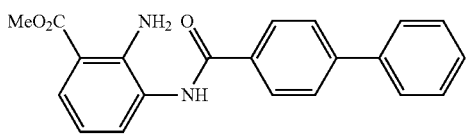 [SMILES: COC(=O)c1cccc(NC(=O)c2ccc(-c3ccccc3)cc2)c1N]

To a stirred solution of 2,3-diamino-benzoic acid methyl ester (200 mg, 1.2 mmol), biphenyl benzoic acid (238 mg, 1.2 mmol), HATU (1.14 g, 3 mmol) in dry DMF (5 mL) was added diisopropylethyl amine (0.6 mL, 3.6 mmol). The mixture was stirred at ambient temperature overnight then poured into water (50 mL). The precipitated solid was filtered and dried in a vacuum oven to afford the required compound, which was used directly for the next step without any purification (300 mg, 72%).

Step 7:
2-Biphenyl-4-yl-1H-benzoimidazole-4-carboxylic acid methyl ester

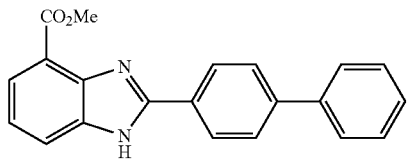

2-Amino-3-[(biphenyl-4-carbonyl)-amino]-benzoic acid methyl ester (300 mg, 0.86 mmol) was dissolved in glacial acetic acid (20 mL) and heated to 130° C. until the reaction was completed which was monitored by TLC (2 to 3 h). After the reaction is completed the solvent was removed and solid residue was purified over silica gel using chloroform and methanol as an eluent to get the required example 79.

$^1$H NMR (300 MHz, DMSO-$d_6$): δ (ppm)=12.43 (br.s, 1H), 8.42 (d, 2H, J=8.7 Hz), 7.99 (d, 1H, J=7.8 Hz), 7.89-7.78 (m, 5H), 7.54-7.33 (m, 4H), 4.00 (s, 3H). HPLC purity: 95.04%.

Example 80

6-Methyl-2-[4-(2-oxo-azepan-1-yl)-phenyl]-1H-benzoimidazole-4-carboxylic acid

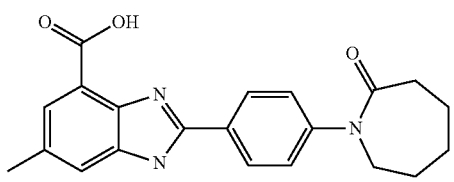 [SMILES: Cc1cc(C(=O)O)c2nc(-c3ccc(N4CCCCCC4=O)cc3)[nH]c2c1]

Example 80 is obtained as described in example 14 but starting from 4-(2-oxoazepan-1-yl)benzoic acid (prepared according to the literature method: Bioorganic and medicinal chemistry letters 17(16), 4419-4427, 2007).

$^1$H NMR (300 MHz, DMSO-$d_6$): δ (ppm)=8.27 (d, 2H, J=8.1 Hz), 7.69 (s, 1H), 7.643 (s, 1H), 7.38 (d, 2H, J=8.4 Hz), 3.81 (m, 2H), 2.63-1.76 (m, 8H), 2.55 (s, 3H). HPLC purity: 88.20%.

Example 81

2-[4-(2-Oxo-azepan-1-yl)-phenyl]-1H-benzoimidazole-4-carboxylic acid

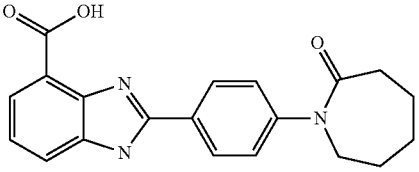 [SMILES: O=C(O)c1cccc2[nH]c(-c3ccc(N4CCCCCC4=O)cc3)nc12]

Example 81 is obtained as described in example 1 but starting from 4-(2-oxoazepan-1-yl)benzoic acid.

$^1$H NMR (300 MHz, DMSO-$d_6$): δ (ppm)=8.25 (d, 2H, J=7.2 Hz), 7.79-7.72 (m, 2H), 7.37 (d, 2H, J=8.4 Hz), 7.24 (s, 1H), 3.80 (m, 2H), 2.65-1.75 (m, 8H). HPLC purity: 90.10%.

Example 82

2-[4-(2,5-Dimethyl-pyrrol-1-yl)-2,3,5,6-tetrafluoro-phenyl]-6-methyl-1H-benzoimidazole-4-carboxylic acid

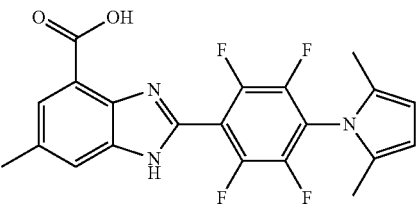 [SMILES: Cc1cc(C(=O)O)c2nc(-c3c(F)c(F)c(-n4c(C)ccc4C)c(F)c3F)[nH]c2c1]

Example 82 is obtained as described in example 1 but starting from 4-(2,5-Dimethyl-pyrrol-1-yl)-2,3,5,6-tetrafluoro-benzoic acid.

Step 1: 4-Amino-2,3,5,6-tetrafluoro-benzoic acid methyl ester

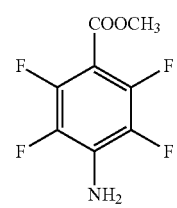

To a solution of 4-amino-2,3,5,6-tetrafluoro-benzoic acid (1.0 g, 4.78 mmol) in ether (75 mL), an ethereal solution of diazomethane gas was added until the starting material is completely consumed. The reaction mixture was then evaporated under reduced pressure. The crude solid obtained was purified by flash column chromatography using 0.5% ethyl acetate in hexane to obtain title compound (0.8 g, 75%).

Step 2: 4-(2,5-Dimethyl-pyrrol-1-yl)-2,3,5,6-tetrafluoro-benzoic acid methyl ester

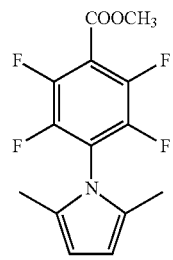 [SMILES: COC(=O)c1c(F)c(F)c(-n2c(C)ccc2C)c(F)c1F]

To the solution of 4-amino-2,3,5,6-tetrafluoro-benzoic acid methyl ester (0.5 g, 2.24 mmol) in absolute ethyl alcohol (20 mL) containing 2 drops of conc. HCl was added followed by acetonyl acetone (0.233 g, 2.041 mmol). The reaction mixture was then refluxed at 95° C. for 18 hours. The progress of the reaction was monitored by TLC. The reaction mixture was concentrated and the obtained residue was purified by column chromatography using 0.5% ethyl acetate in hexane to obtain the title compound.

$^1$H NMR (300 MHz, CDCl$_3$): δ (ppm)=2.0 (s, 6H), 4.0 (s, 3H), 6.0 (s, 2H).
LCMS– m/z 302, 96%

Step 3: 4-(2,5-Dimethyl-pyrrol-1-yl)-2,3,5,6-tetrafluoro-benzoic acid

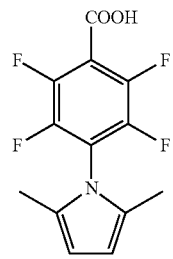 [SMILES: Cc1ccc(C)n1-c1c(F)c(F)c(C(=O)O)c(F)c1F]

To the solution of 4-(2,5-dimethyl-pyrrol-1-yl)-2,3,5,6-tetrafluoro-benzoic acid methyl ester (0.6 g, 1.99 mmol) in THF (20 mL) was added an aq. solution of 5 N NaOH (5 mL). The reaction mixture was stirred under refluxed at 90° C. for 3 hours. TLC shows completion of the reaction. The reaction mixture was concentrated and the resulting residue was cooled, acidified with aq. solution of 2 N HCl, extracted with ethyl acetate. The combined organic layers were washed with water, brine and dried over anhydrous sodium sulphate then concentrated. The resulting residue was purified by washing with hot hexane to get the title compound (0.43 g, 75%).
LCMS– m/z 288, 91%

Step 4: 2-[4-(2,5-Dimethyl-pyrrol-1-yl)-2,3,5,6-tetrafluoro-phenyl]-6-methyl-1H-benzoimidazole-4-carboxylic acid

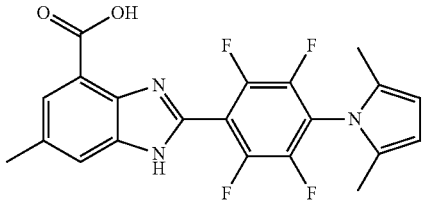 [SMILES: Cc1cc(C(=O)O)c2nc(-c3c(F)c(F)c(-n4c(C)ccc4C)c(F)c3F)[nH]c2c1]

$^1$H NMR (300 MHz, DMSO-d$_6$): δ (ppm)=2.10 (s, 6H), 2.45 (s, 3H), 5.97 (s, 2H), 7.60 (s, 2H). HPLC purity: 87.59%; LCMS m/e (M−1): 85.56%

Example 83

6-Methyl-2-(2,3,5,6-tetrafluoro-4'-piperidin-1-ylmethyl-biphenyl-4-yl)-1H-benzoimidazole-4-carboxylic acid

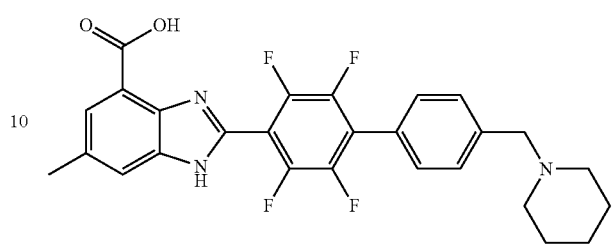

Step 1: 2,3,5,6-Tetrafluoro-4'-formyl-biphenyl-4-carboxylic acid methyl ester

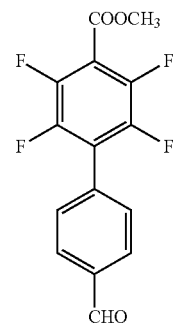 [SMILES: COC(=O)c1c(F)c(F)c(-c2ccc(C=O)cc2)c(F)c1F]

A toluene/Water (175 mL+25 mL) mixture was degassed with nitrogen for 30 minutes. Cesium carbonate (14.9 g, 43.55 mmol) was added followed by 4-bromo-2,3,5,6-tetrafluoro-benzoic acid methyl ester (5.0 g, 17.42 mmol), 4-formyl boronic acid (3.4 g, 22.64 mmol) and dichlorobis(triphenylphosphine)-palladium(II) catalyst (0.611 g, 0.87 mmol). The reaction mixture was refluxed for 15 h. TLC shows completion of the reaction. The reaction mixture was cooled to room temperature and was extracted with ethyl acetate. The combined organic layers were dried over sodium sulphate and concentrated. The obtained residue was purified by column chromatography using 5% ethyl acetate in hexane to get colorless solid (3.0 g, 55.24%).

$^1$H NMR (300 MHz, CDCl$_3$): δ (ppm) 4.0 (s, 3H), 7.6 (d, 2H), 8.0 (d, 2H), 10.0 (2, 1H).

Step 2: 2,3,5,6-Tetrafluoro-4'-hydroxymethyl-biphenyl-4-carboxylic acid methyl ester

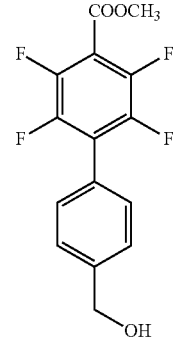 [SMILES: COC(=O)c1c(F)c(F)c(-c2ccc(CO)cc2)c(F)c1F]

2,3,5,6-Tetrafluoro-4'-formyl-biphenyl-4-carboxylic acid methyl ester (1.26 g, 4.03 mmol) was dissolved in methanol (30 mL) and cooled to −10° C. Sodium borohydride (0.76 g, 20.19 mmol) was added portion wise and reaction mixture stirred by maintaining the same temperature. The progress of the reaction was monitored by TLC. After completion, the reaction mixture was concentrated to dryness. The obtained residue was redissolved in ethyl acetate (50 mL) and washed with water (20 mL×2) followed by brine, dried over anhydrous sodium sulphate and concentrated to get colorless solid (1.1 g, 86.75%).

$^1$H NMR (300 MHz, CDCl$_3$): δ(ppm) 4.0 (s, 3H), 5.0 (s, 2H), 7.5 (m, 4H).

Step 3: 4'-(tert-Butyl-dimethyl-silanyloxymethyl)-2,3,5,6-tetrafluoro-biphenyl-4-carboxylic acid methyl ester

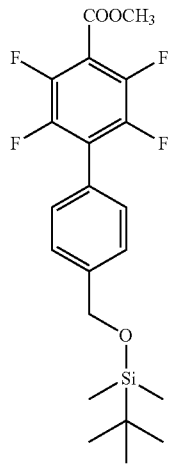 [SMILES: COC(=O)c1c(F)c(F)c(-c2ccc(CO[Si](C)(C)C(C)(C)C)cc2)c(F)c1F]

To a solution of 2,3,5,6-tetrafluoro-4'-hydroxymethyl-biphenyl-4-carboxylic acid methyl ester (1.6 g, 5.09 mmol) in dry dichloromethane (100 mL) was added imidazole (0.7 g, 10.19 mmol) and TBDMS chloride (0.92 g, 6.11 mmol). The reaction mixture was stirred under nitrogen at room temperature for 15 h. The progression of the reaction was monitored by TLC. The reaction mixture was dissolved in ethyl acetate, washed with water (50 mL×2) and with brine then dried over anhydrous sodium sulphate and concentrated to give colorless solid (2.0 g, 91.745).

$^1$H NMR (300 MHz, CDCl$_3$): δ (ppm) 0.2 (s, 6H), 1.0 (s, 9H), 4.0 (s, 3H), 4.8 (s, 2H), 7.4 (m, 4H).

Step 4: 4'-(tert-Butyl-dimethyl-silanyloxymethyl)-2,3,5,6-tetrafluoro-biphenyl-4-carboxylic acid

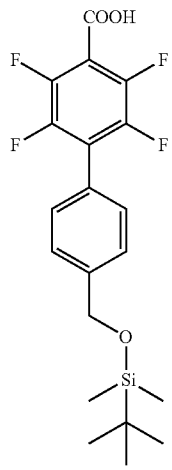 [SMILES: CC(C)(C)[Si](C)(C)OCc1ccc(-c2c(F)c(F)c(C(=O)O)c(F)c2F)cc1]

To a solution of 4'-(tert-butyl-dimethyl-silanyloxymethyl)-2,3,5,6-tetrafluoro-biphenyl-4-carboxylic acid methyl ester (2.6 g, 6.0 mmol) in tetrahydrofuran (50 mL) was added an aq. solution of 5 N sodium hydroxide (20 mL). The reaction mixture was stirred and refluxed for 5 hours. The progress of the reaction was monitored by TLC. The reaction mixture was concentrated. The resulting residue was cooled to 10° C. and acidified with an aq. solution of 50% HCl. The formed precipitate was filtered, washed thoroughly with water and dried to get colorless solid (2.2 g, 88.0%).

$^1$H NMR (300 MHz, CDCl$_3$): δ (ppm) 0.2 (s, 6H), 1.0 (s, 9H), 4.8 (s, 2H), 7.5 (m, 4H).

Step 5: 2-Amino-3-{[4'-(tert-butyl-dimethyl-silanyloxymethyl)-2,3,5,6-tetrafluoro-biphenyl-4-carbonyl]-amino}-5-methyl-benzoic acid methyl ester

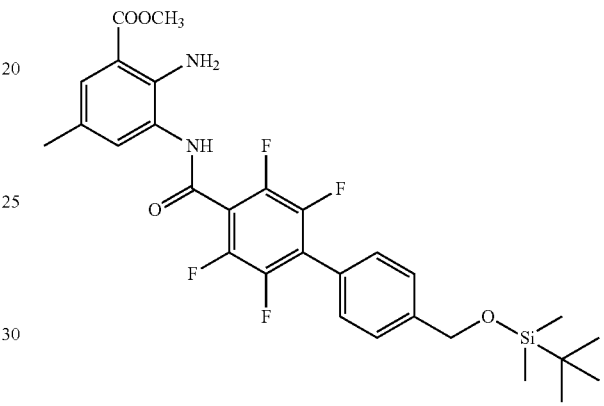

To a solution of 4'-(tert-butyl-dimethyl-silanyloxymethyl)-2,3,5,6-tetrafluoro-biphenyl-4-carboxylic acid (2.2 g, 5.3 mmol) in dry DMF (50 mL) was added 2,3-diamino-5-methyl-benzoic acid methyl ester (0.95 g, 5.3 mmol) and HATU (3.03 g, 7.9 mmol) followed by N,N-diisopropylethylamine (1 mL). The reaction mixture was stirred for 14 h at room temperature under nitrogen atmosphere. TLC shows completion of the reaction. The reaction mixture was quenched to crushed ice and the precipitate was filtered, washed with water and dried to get an off white solid (2.4 g, 80.80%) which was directly taken to the next step.

Step 6: 2-[4'-(tert-Butyl-dimethyl-silanyloxymethyl)-2,3,5,6-tetrafluoro-biphenyl-4-yl]-6-methyl-1H-benzoimidazole-4-carboxylic acid methyl ester

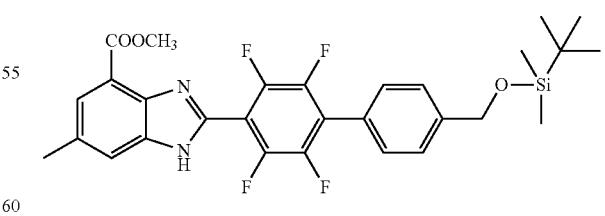

2-Amino-3-{[4'-(tert-butyl-dimethyl-silanyloxymethyl)-2,3,5,6-tetrafluoro-biphenyl-4-carbonyl]-amino}-5-methyl-benzoic acid methyl ester (2.4 g, 4.16 mmol) was dissolved in glacial acetic acid (75 mL) and stirred and refluxed for 4 hours. Progress of the reaction was monitored by TLC. Acetic acid was distilled under vacuum and the resulting residue was quenched with ice cold water. The precipitate was washed with water and dried (2.0 g, 84.03%) which was directly taken to the next step.

Step 7: 6-Methyl-2-(2,3,5,6-tetrafluoro-4'-hydroxymethyl-biphenyl-4-yl)-1H-benzoimidazole-4-carboxylic acid methyl ester

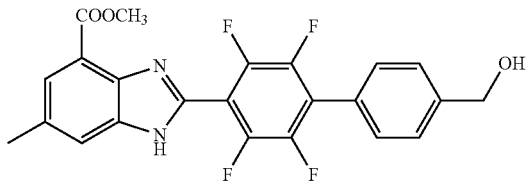 [SMILES: COC(=O)c1cc(C)cc2[nH]c(-c3c(F)c(F)c(-c4ccc(CO)cc4)c(F)c3F)nc12]

2-[4'-(tert-butyl-dimethyl-silanyloxymethyl)-2,3,5,6-tetrafluoro-biphenyl-4-yl]-6-methyl-1H-benzoimidazole-4-carboxylic acid methyl ester (2.0 g, 3.58 mmol) was suspended in an q. solution of 4 N HCl (100 mL) and stirred at room temperature for 4 h. TLC shows completion of the reaction. The reaction mixture was diluted with water and extracted with ethyl acetate (100 mL×3). Ethyl acetate layer washed with water (50 mL×2) and brine. Dried over anhydrous sodium sulphate and concentrated to get off white solid (1.2 g, 75.9%) which was directly taken to next step.

Step 8: 6-Methyl-2-(2,3,5,6-tetrafluoro-4'-formyl-biphenyl-4-yl)-1H-benzoimidazole-4-carboxylic acid methyl ester

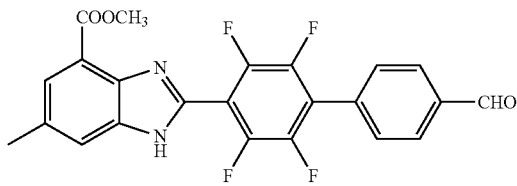 [SMILES: COC(=O)c1cc(C)cc2[nH]c(-c3c(F)c(F)c(-c4ccc(C=O)cc4)c(F)c3F)nc12]

To a solution of 6-methyl-2-(2,3,5,6-tetrafluoro-4'-hydroxymethyl-biphenyl-4-yl)-1H-benzoimidazole-4-carboxylic acid methyl ester (0.55 g, 1.22 mmol) in dry tetrahydrofuran (50 mL) was added pyridinium dichromate (0.2 g) portion wise. The reaction mixture was stirred at room temperature in nitrogen atmosphere for 14 hours. TLC shows completion of the reaction. The reaction mixture was filtered over celite bed and the filtrate was concentrated to dryness. The resulting residue was purified by column chromatography using 20% ethyl acetate in hexane to get to get the title compound as colorless solid (0.4 g, 74.07%).

$^1$H NMR (300 MHz, DMSO-$d_6$): δ (ppm) 2.6 (s, 3H), 4.0 (s, 3H), 7.6-8.2 (m, 6H), 10.1 (s, 1H), 13.0 (bs, 1H).

Step 9: 6-Methyl-2-(2,3,5,6-tetrafluoro-4'-piperidin-1-ylmethyl-biphenyl-4-yl)-1H-benzoimidazole-4-carboxylic acid methyl ester

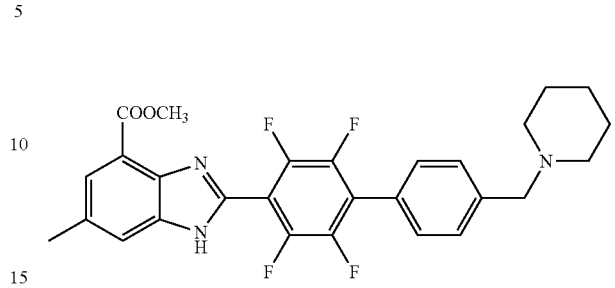

To a solution of 6-methyl-2-(2,3,5,6-tetrafluoro-4'-formyl-biphenyl-4-yl)-1H-benzoimidazole-4-carboxylic acid methyl ester (0.13 g, 0.29 mmol) in tetrahydrofuran (100 mL) was added piperidine (0.03 g, 0.35 mmol). The reaction mixture was stirred at room temperature for 30 minutes. Sodium triacetoxyborohydride (0.374 g, 1.76 mmol) was added and stirring continued for another 1 hour. The progression of the reaction was monitored by TLC. The reaction mixture quenched with sodium bicarbonate solution (3 mL) and concentrated. The residue was then extracted with ethyl acetate and the combined organic layered were washed with water and brine, dried over anhydrous sodium sulphate and concentrated to get the title compound (0.145 g, 96.66%) which was directly taken to next step.

Step 10: 6-Methyl-2-(2,3,5,6-tetrafluoro-4'-piperidin-1-ylmethyl-biphenyl-4-yl)-1H-benzoimidazole-4-carboxylic acid

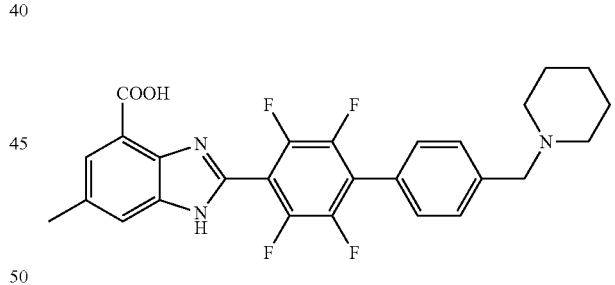

To the solution of 6-methyl-2-(2,3,5,6-tetrafluoro-4'-piperidin-1-ylmethyl-biphenyl-4-yl)-1H-benzoimidazole-4-carboxylic acid methyl ester (0.145 g, 0.283 mmol) in tetrahydrofuran (50 mL) was added an aq. solution of 5 N sodium hydroxide (10 mL). The reaction mixture was stirred at 60° C. for 4 hours. TLC shows completion of the reaction. The reaction mixture was cooled to room temperature, then concentrated and the obtained residue was acidified with an aq. solution of 50% HCl. The resulting precipitate was filtered and purified by preparative HPLC.

$^1$H NMR (300 MHz, DMSO-$d_6$): δ (ppm)=1.8 (m, 8H), 2.3 (s, 3H), 3.0 (s, 2H), 4.4 (s, 2H), 7.8 (s, 5H), 7.9 (s, 1H), 12.8 (br.s, 1H), 13.4 (br.s, 1H)

HPLC: 96.83%

Example 84
6-Methyl-2-phenylethynyl-1H-benzoimidazole-4-carboxylic acid
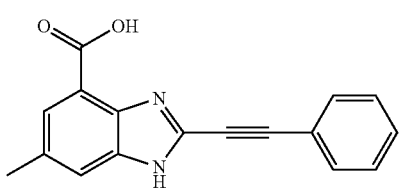
Example 84 is obtained as described in example 14 but starting from phenyl-propynoic acid (procured commercially from aldrich).
$^1$H NMR (300 MHz, DMSO-d$_6$): δ (ppm)=2.44 (s, 3H), 7.51 (m, 3H), 7.66-7.61 (m, 4H). HPLC purity: 84.3%
The following examples 185 to 1192 have been prepared following similar procedures as described above.
I85
I86
I87
I88
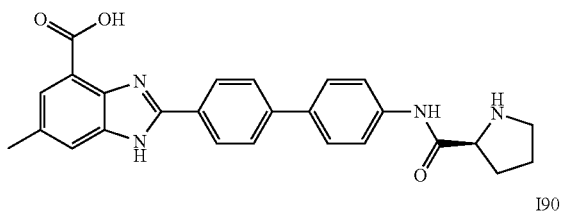
I89
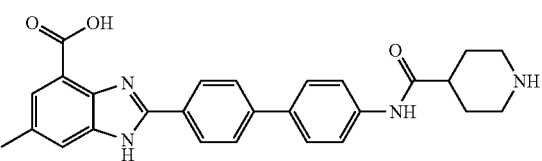
I90
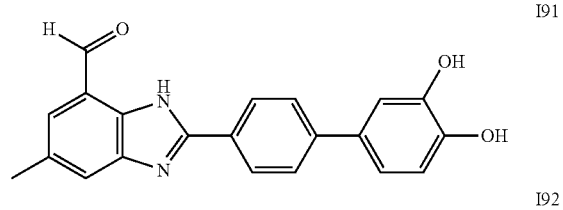
I91
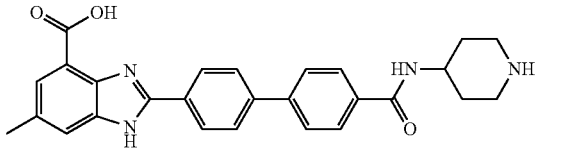
I92
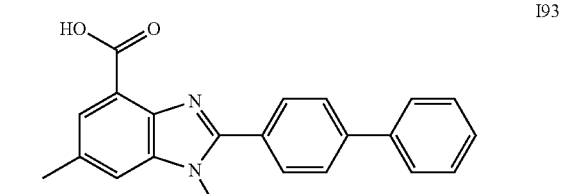
I93
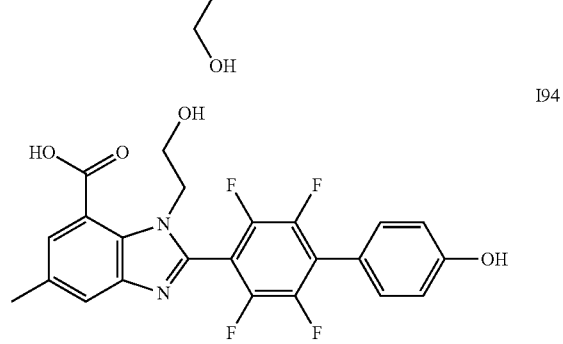
I94
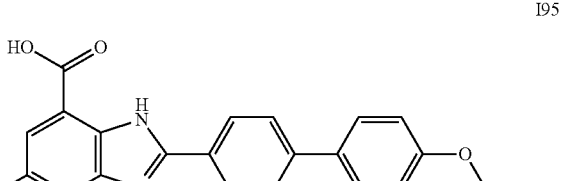
I95
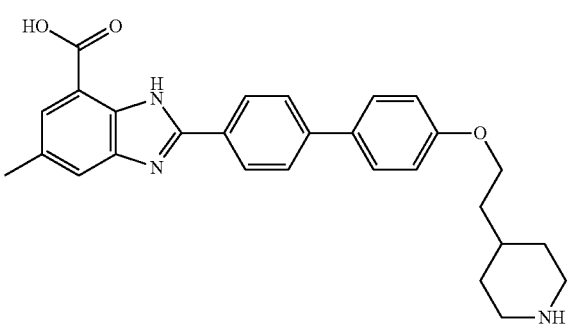

-continued
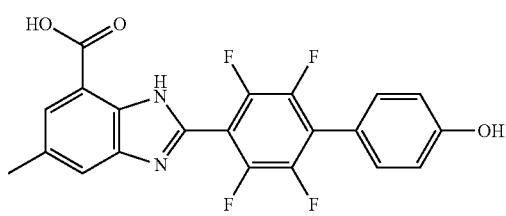
I96
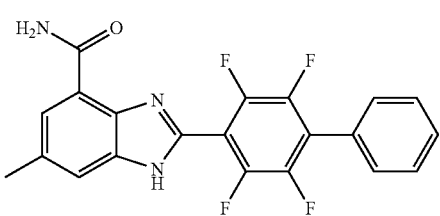
I102
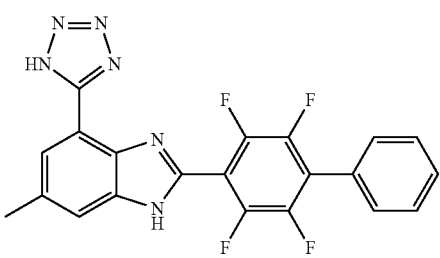
I103
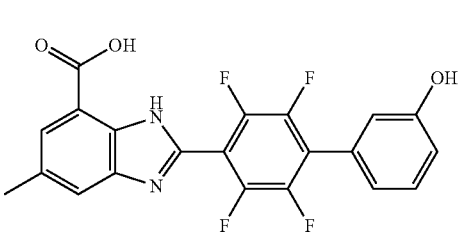
I104
I97
I98
I99
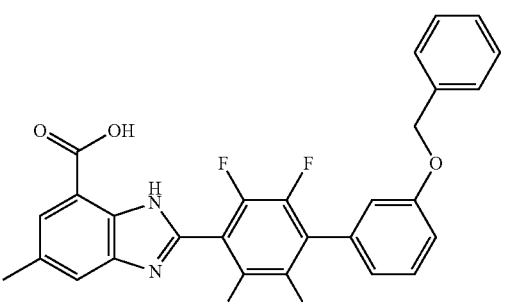
I105
I100
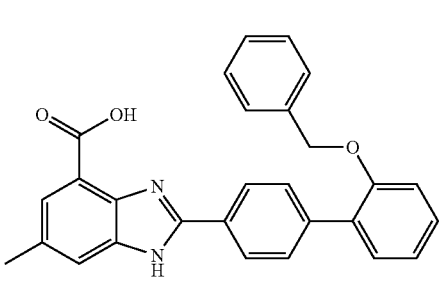
I106
I101
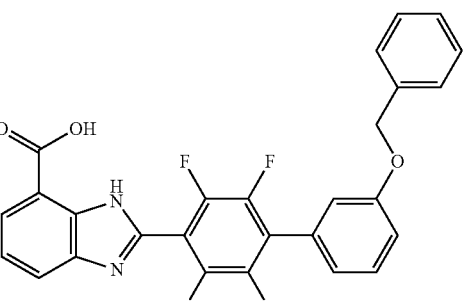
I107

I108 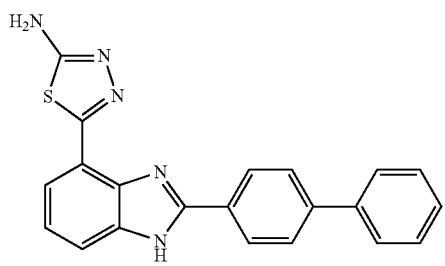
I109 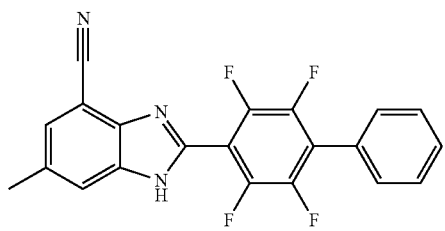
I110 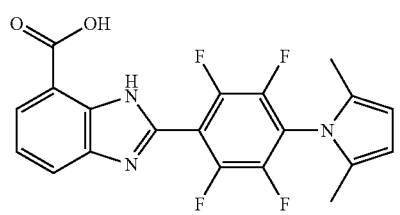
I111 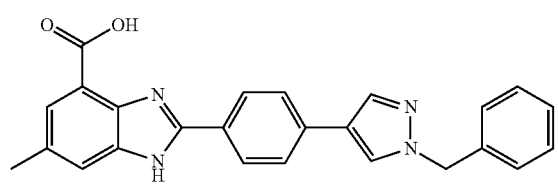
I112 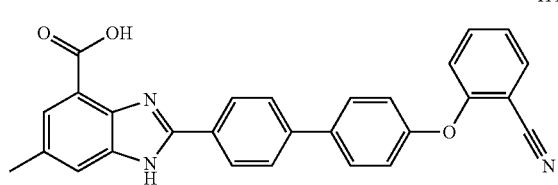
I113 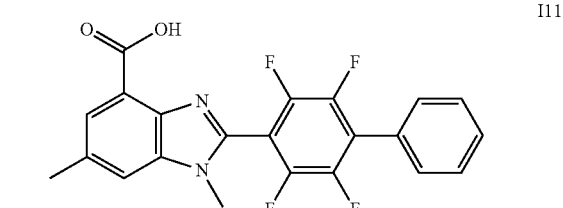
I114 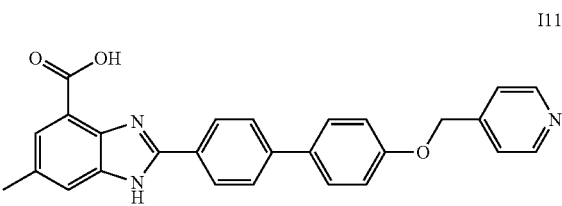
I115 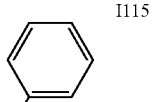 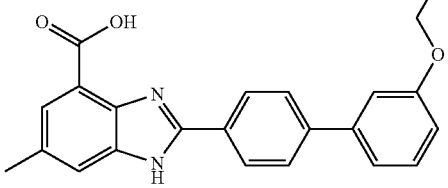
I116 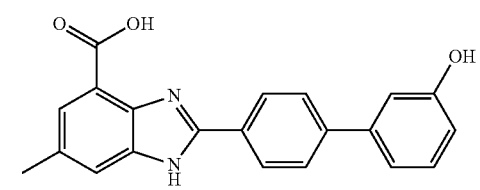
I117 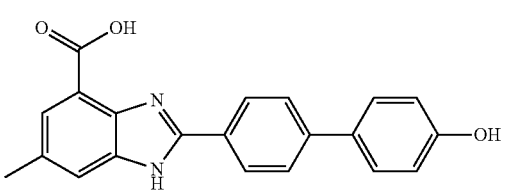
I118 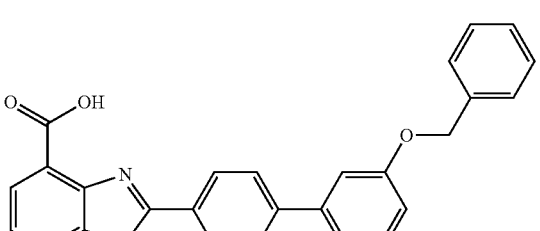
I119 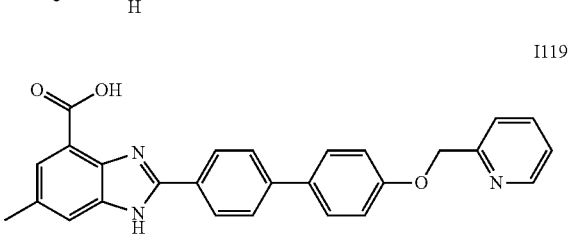
I120 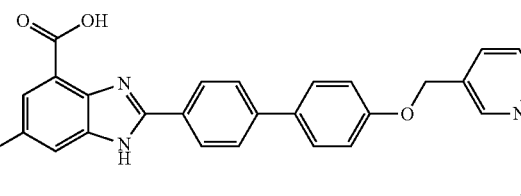
I121 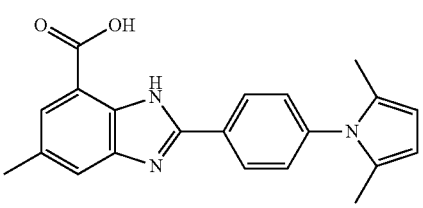

I122 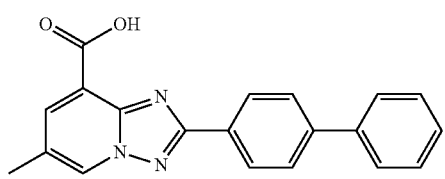
I123 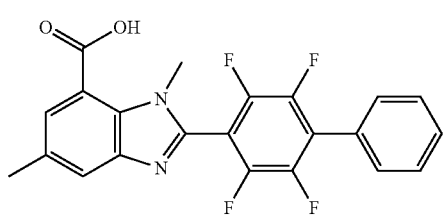
I124 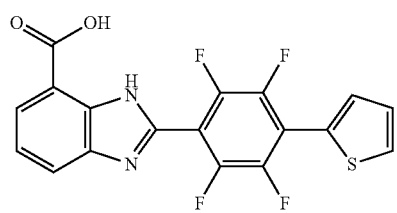
I125 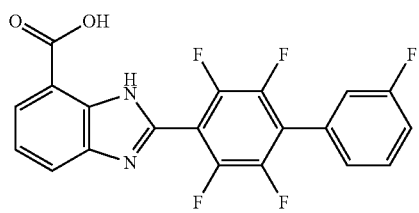
I126 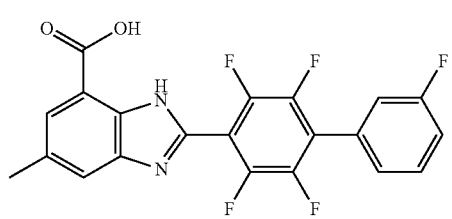
I127 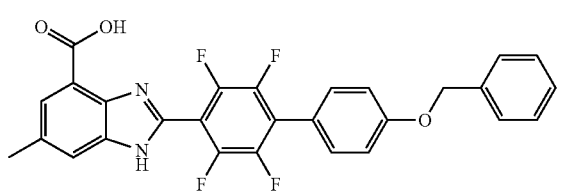
I128 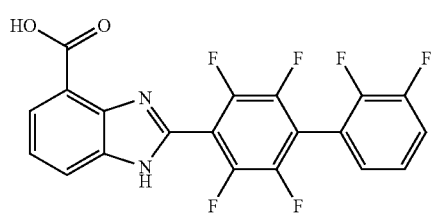
I129 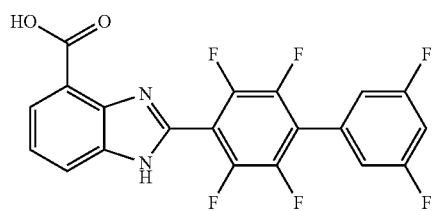
I130 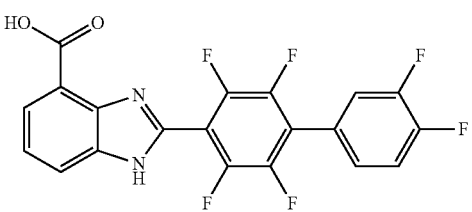
I131 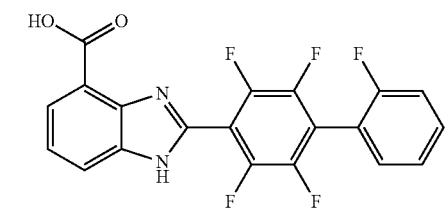
I132 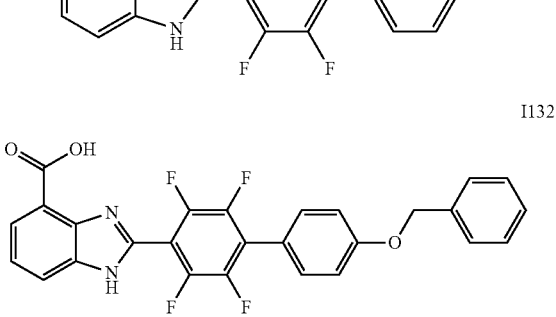
I133 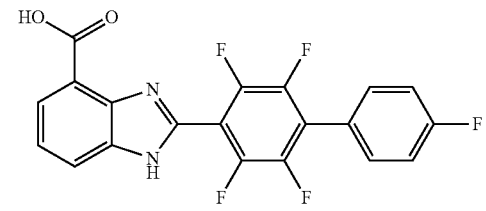
I134 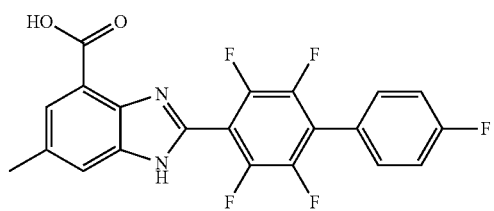
I135 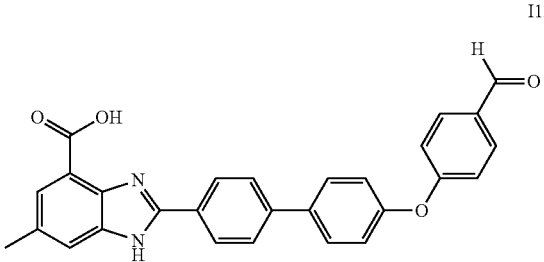

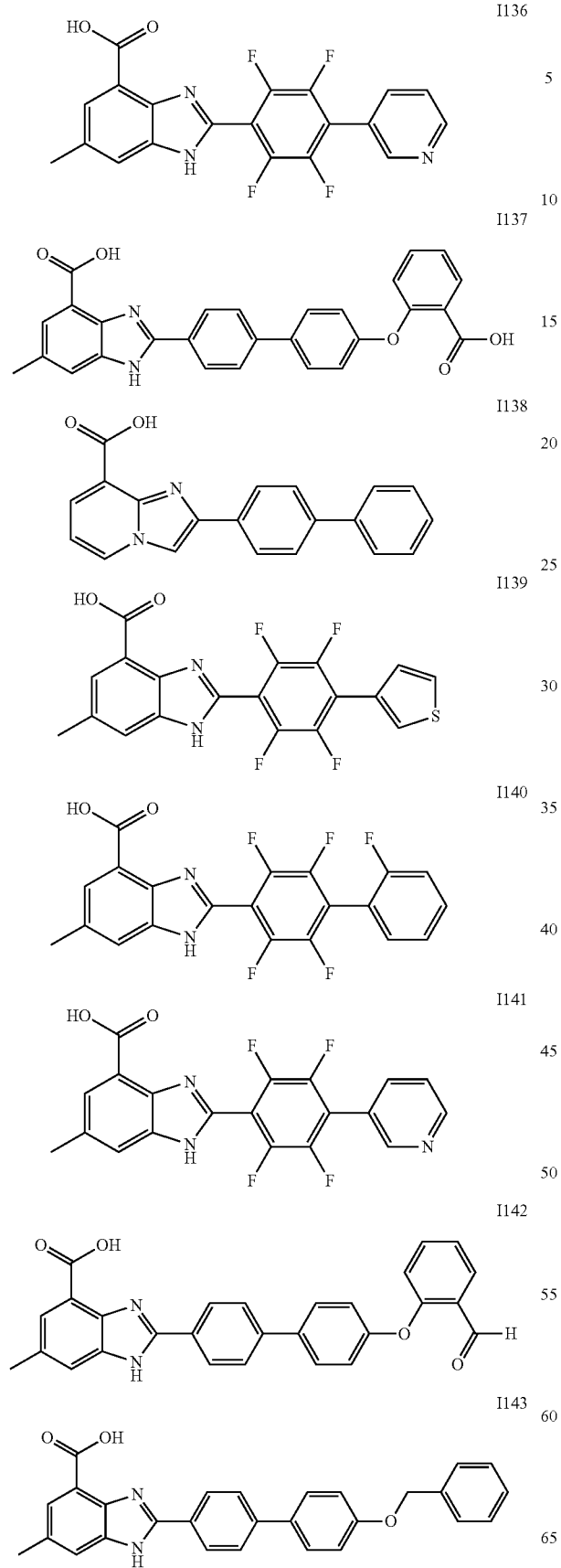

I151 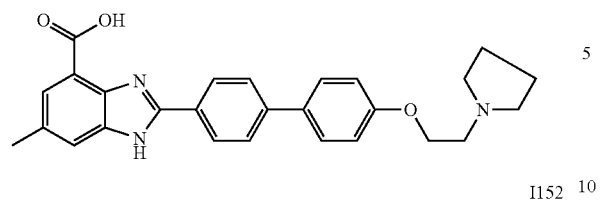
I152 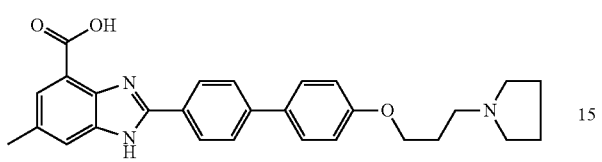
I153 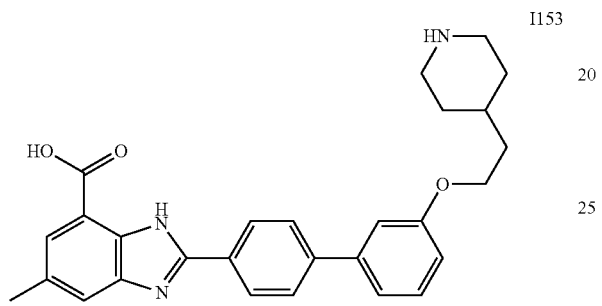
I154 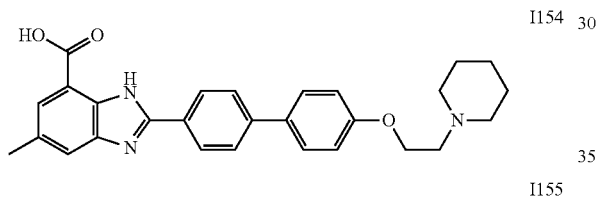
I155 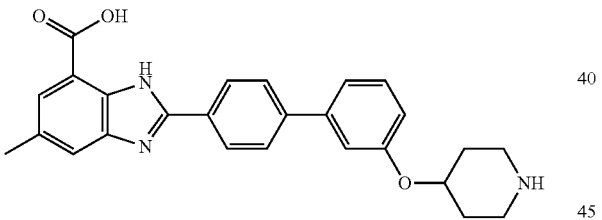
I156 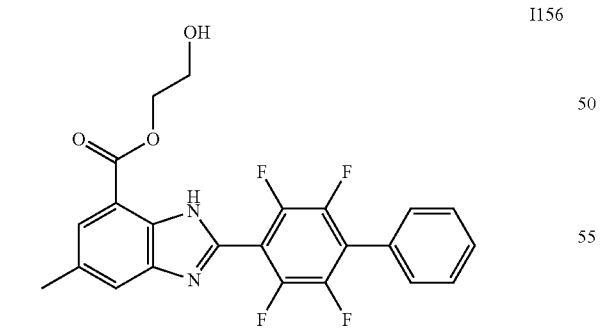
I157 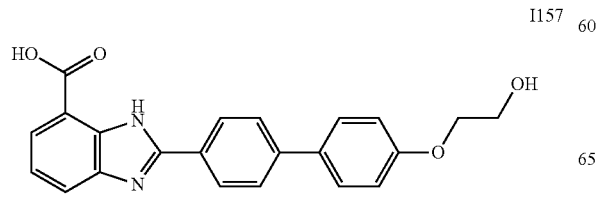
I158 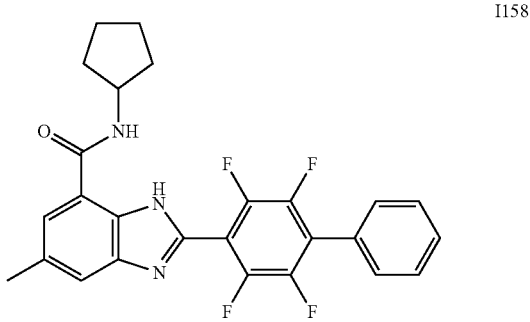
I159 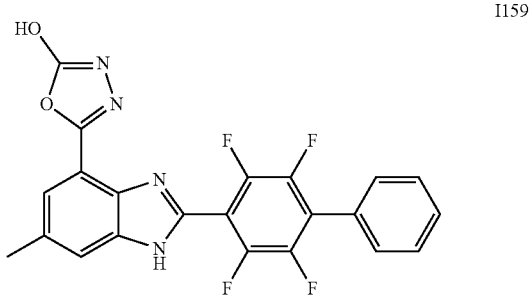
I160 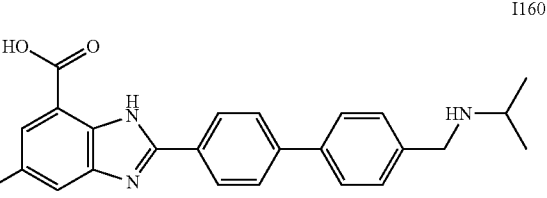
I161 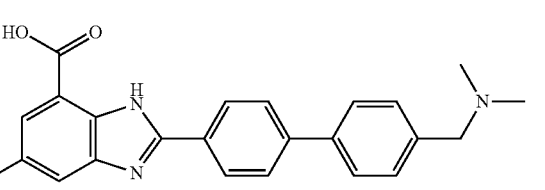
I162 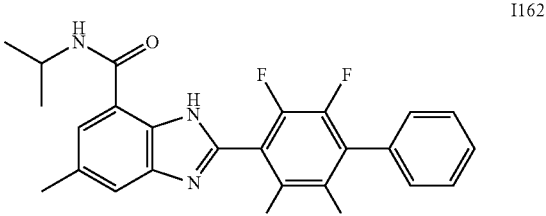
I163 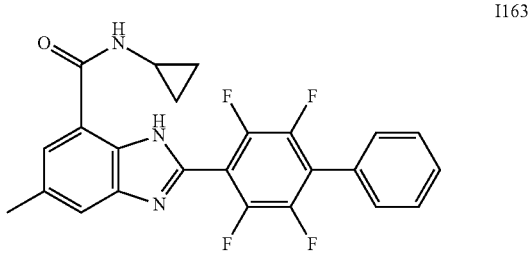

I164
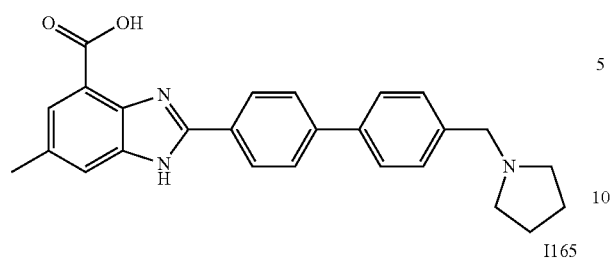
I165
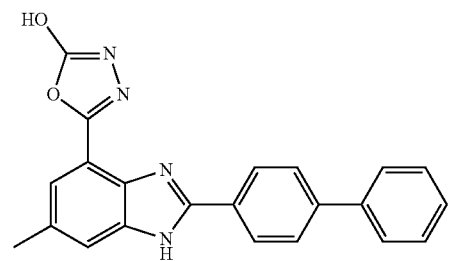
I166
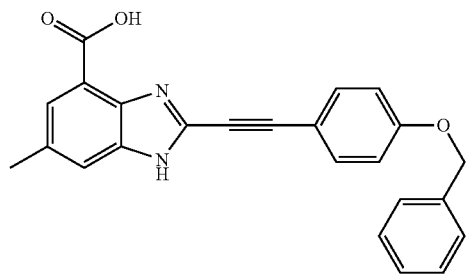
I167
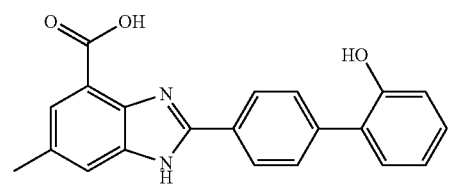
I168
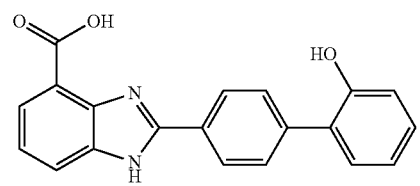
I169
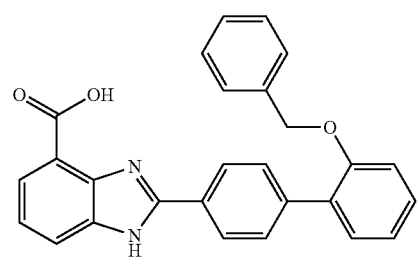
I170
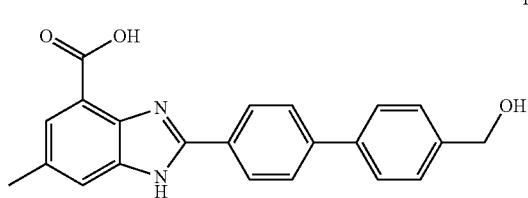
I171
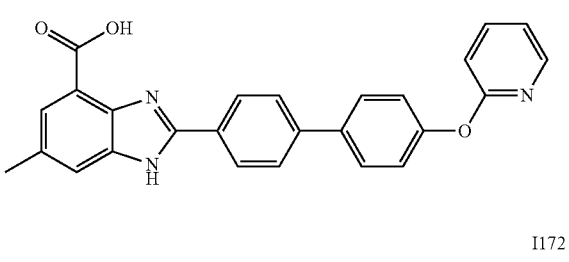
I172
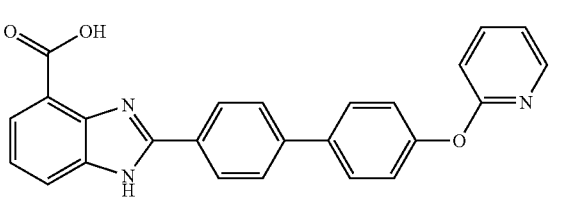
I173
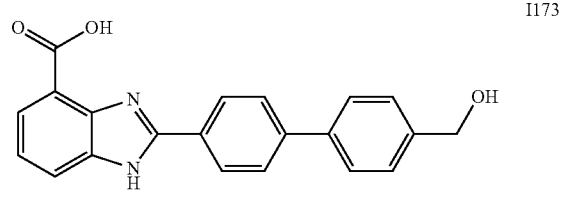
I174
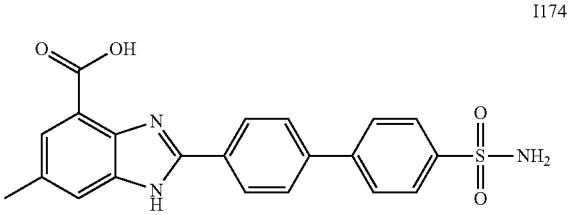
I175
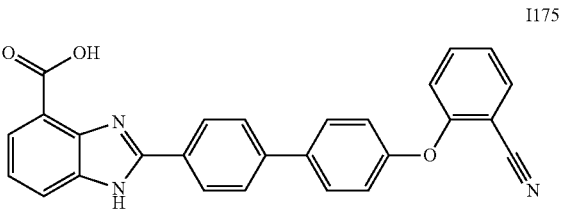
I176
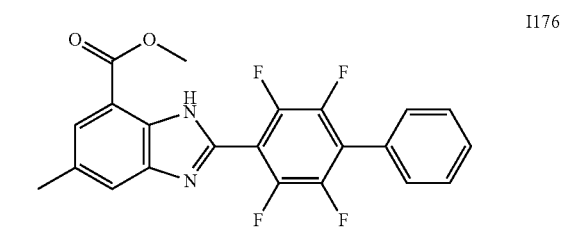
I177
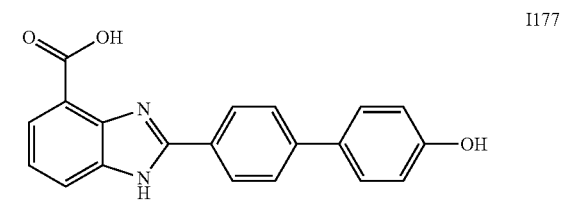

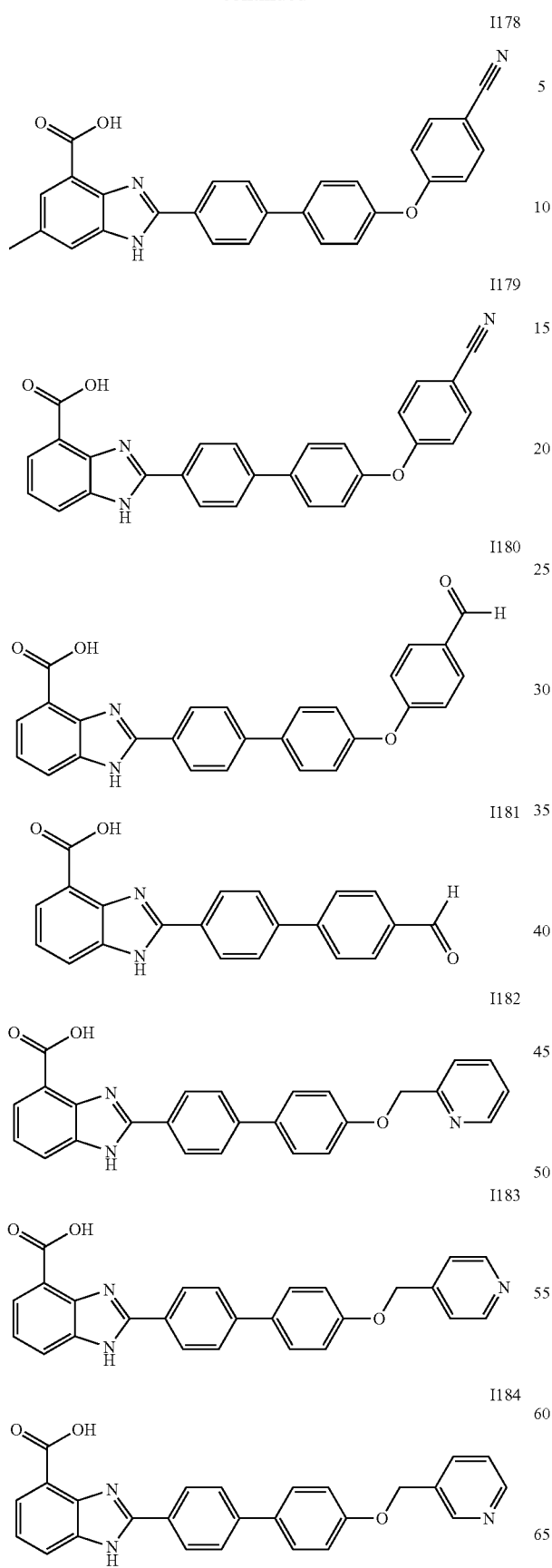
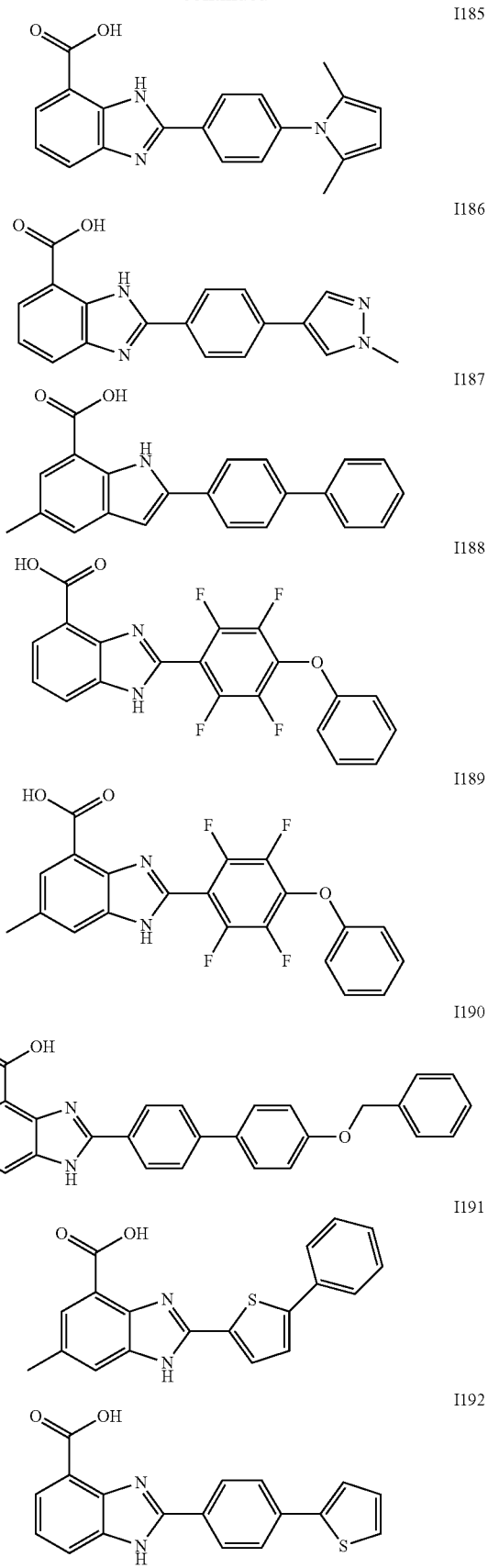

Example 193

Measurement of Enzyme Activity (In Vitro Assays)

The DHODH activity assay is a coupled enzyme assay in which oxidation of DHO and subsequent reduction of ubiquinone are stoichiometrically equivalent to the reduction of DCIP (2,6-dichlorophenol). The reduction of DCIP is accompanied by a loss of absorbance at 610 nm.

Reagents Used:

L-Dihydroorotic acid, Sigma, D7128, 2,6-Dichloroindophenol sodium salt hydrate, sigma, D1878 Dimethyl sulfoxide (DMSO), spectroscopic grade purchased from Spectrochem, cat no. 0704209, B. no.—3183650 Decylubiquinone, Sigma, D7911

Preparation of Solutions/Reagents:

Buffer Preparation: 50 mM tris HCl, 150 mM KCl, and pH 8.0, 0.8% triton.

L-Dihydroorotic acid stock solution of 20 mM in buffer 2,6-Dichloroindophenol Sodium salt hydrate stock solution of 20 mM in buffer Decylubiquinone stock solution of 20 mM in buffer DMSO used as vehicle Procedure:

5 µL of Dimethyl sulfoxide or a compound of formula I in DMSO solution was added to the wells of a 96 well plate. Compounds of formula I were measured at 10 µM.

Protein along with buffer was added, so that the total volume including the DMSO was 87 µL. Compound and protein were incubated for half an hour at room temperature after mixing. 5 µL of 20 mM solution of L-Dihydroorotic acid, 5 µL of 2 mM solution of Decylubiquinone and 3 µL of 2 mM solution of 2,6-Dichloroindophenol sodium salt hydrate were added to the above solution (total assay volume 100 µL). The mixture was stirred for 2 min and absorbance was recorded at every 10 min at 610 nanometers.

Percent Inhibition is Calculated as Follows $$100 * \frac{\{(Abs_{610} \text{ for reaction containing compound}) - (Abs_{610} \text{ for positive control})\}}{(Abs_{610} \text{ for no enzyme reaction}) - (Abs_{610} \text{ for positive control})}$$

Reaction containing compound has compound, buffer, enzyme and substrates

Positive control contains DMSO, buffer, enzyme and substrates

No Enzyme reaction contains DMSO, buffer and substrates

IC50 determination: • A 2 mM DMSO stock of the compound of formula I to be examined was prepared. ⅓rd dilutions were made as follows:

| S. No. | Stock Concentration of Compound in DMSO (mM) | Assay Concentration for Compound (µM) | Composition of compound solution used for assay |
|---|---|---|---|
| 1 | 2 | 100 | 60 µL 2 mM |
| 2 | 0.66667 | 33 | 20 µL 2 mM + 40 µL DMSO |
| 3 | 0.22222 | 11 | 20 µL 0.66667 mM + 40 µL DMSO |
| 4 | 0.07407 | 3.7 | 20 µL 0.22222 mM + 40 µL DMSO |
| 5 | 0.02469 | 1.2 | 20 µL 0.07407 mM + 40 µL DMSO |
| 6 | 0.00823 | 0.4 | 20 µL 0.02469 mM + 40 µL DMSO |
| 7 | 0.00274 | 0.13 | 20 µL 0.00823 mM + 40 µL DMSO |
| 8 | 0.00091 | 0.0457 | 20 µL 0.00274 mM + 40 µL DMSO |
| 9 | 0.00031 | 0.0152 | 20 µL 0.00091 mM + 40 µL DMSO |
| 10 | 0.0001 | 0.0051 | 20 µL 0.00031 mM + 40 µL DMSO |
| 11 | 0.00003 | 0.00017 | 20 µL 0.00010 mM + 40 µL DMSO |

5 µL of each stock of compound of formula I (solution indicated in column 4 of table) was used for each 100 µL assay. Therefore, 5 µL of the 2 mM stock provided 100 µL of 100 µM solution of compound of formula I, when made up with buffer, protein and substrate. See also: Ulrich et al. (2001) Eur. J. Biochem. 268, 1861-1868.

Example 194

Measurement of Cell Proliferation (Jurkat Cell)

See also Roehm, N et al [1991] An improved colorimetric assay for cell proliferation and viability utilizing the tetrazolium salt XTT. J. Immunol. Methods 142:257-265.

Reagents

Roswells park memorial institute's medium, (RPMI-1640 complete media) pH-7.4±0.2 (Sigma R6504).

Dimethyl sulfoxide (DMSO), spectroscopic grade purchased from Spectrochem, (cat no. 0704209, B. no.—3183650 MEM Cat. No. M0268, Sigma).

Fetal Bovine Serum (Cat. No. F9665, Sigma Aldrich).

XTT sodium salt (Sigma Cat. No. X4251).

PMS (Sigma Cat. No. 68600).

Preparation of Solutions/Reagents

RPMI media supplemented with antibiotics, 10% FBS, Sodium Pyruvate and NEA (non essential amino acids).

XTT—A freshly prepared solution of XTT is made in the growth medium, with a final concentration of 1 mg/ml.

PMS—Stock is prepared with 1×PBS at 0.383 mg/ml and stored in aliquots at −20° C.

The XTT solution at 20 µl/ml was added just before use.

Test solution—Serially diluted DMSO solutions are further diluted with media to 2× the required concentration in well.

Procedure

Culture Jurkat cells in T-25 flasks at a density of 0.2×106/ml 2-3 days before the day of experiment set up.

Centrifuge Jurkat T-cell suspension at 1200 rpm for 10 minutes and resuspend cells again in fresh RPMI medium with 10% FBS.

Count the cells and dilute suspension to a density of $2 \times 10^6$ cells/ml. Seed 50 µL of this suspension in each well of a 96 well plate (100,000 cells per well). Keep the edges of the plate empty to avoid evaporation.

Serially dilute DMSO stocks of compounds to get different concentrations for an EC50 curve. 50 µL of compound diluted in media (2× concentration required in well) is added to each well. DMSO concentration should be kept constant at 0.25-0.5% for all wells.

Typically, for all compounds with IC50<1 μM, compound concentration can start at 10 μM followed by half log dilutions for a total of 8-10 concentrations. Each concentration has to be tested in triplicate.

Include controls such as cells without compound (with same DMSO concentration as compound wells), and media control Incubate the 96 well plate in a $CO_2$ incubator at 37° C. for 72 hrs before determining cell viability using XTT assay XTT assay: to each well, add 50 μL of 1 mg/ml XTT solution with 20 μl of PMS/mL. Read the plates after 2 hours at 465 nm using the spectrophotometer. XTT reading for media without cells is used as background reading.

Calculate % cell viability assuming that the cells without compound are 100% viable.

Plot % cell viability as a function of concentration and determine EC50 by using software such as Graph Pad Prism to fit the curve.

The following results have been obtained:

| Structure | | inh @ 10 uM hDHODH (%) | hDHODH IC50 (uM) | % inh Jurkat_cells @ 1 uM (%) | EC50 Jurkat cells (uM) |
|---|---|---|---|---|---|
| 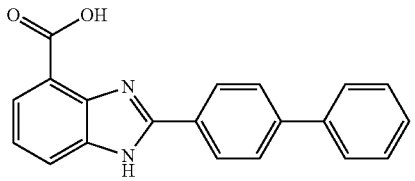 [SMILES: O=C(O)c1cccc2[nH]c(-c3ccc(-c4ccccc4)cc3)nc12] | I1 | 93.9 | 0.795 | — | 0.645 |
| 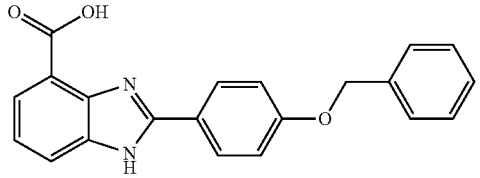 [SMILES: O=C(O)c1cccc2[nH]c(-c3ccc(OCc4ccccc4)cc3)nc12] | I2 | 66.1 | 4.95 | — | — |
| 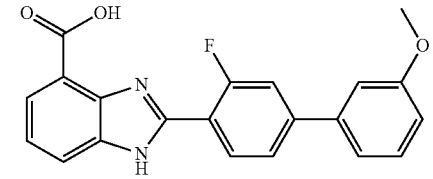 | I3 | 92.6 | 0.616 | — | 0.753 |
| 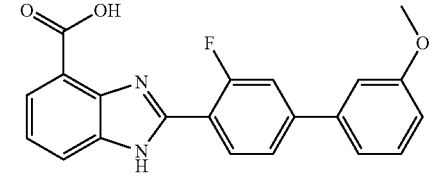 [SMILES: COc1cccc(-c2ccc(-c3nc4c(C(=O)O)cccc4[nH]3)c(F)c2)c1] | I4 | 2.1 | — | — | — |
| 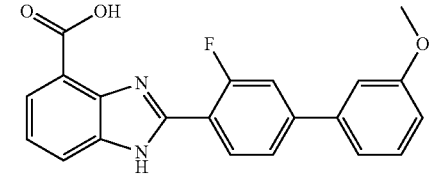 | I5 | 94.3 | 0.368 | — | 0.356 |
| 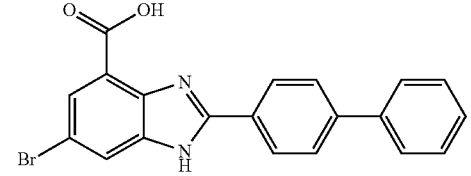 [SMILES: O=C(O)c1cc(Br)cc2[nH]c(-c3ccc(-c4ccccc4)cc3)nc12] | I6 | 96.7 | 0.574 | — | 0.388 |

| | | inh @ 10 uM hDHODH (%) | hDHODH IC50 (uM) | % inh Jurkat_cells @ 1 uM (%) | EC50 Jurkat cells (uM) |
|---|---|---|---|---|---|
| (structure) | I7 | 30.2 | — | — | — |
| (structure) | I8 | 90.5 | 1.6 | — | — |
| (structure) | I9 | 64 | 7.2 | 20 | — |
| (structure) | I10 | 80.3 | 2.87 | 35.1 | — |
| (structure) | I11 | 13.7 | — | 9.4 | — |
| (structure) | I12 | 9 | — | — | — |
| (structure) | I13 | 10.6 | — | — | — |
| (structure) | I14 | 102 | 0.304 | 76.9 | 0.263 |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 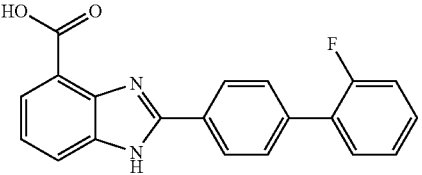 [SMILES: O=C(O)c1cccc2[nH]c(-c3ccc(-c4ccccc4F)cc3)nc12] | I15 | 96.4 | 0.49 | 64.4 | — |
| 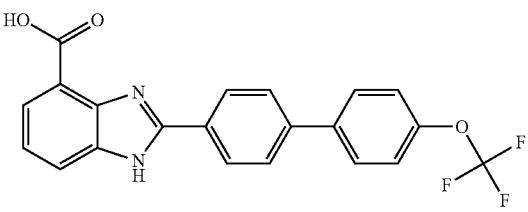 [SMILES: O=C(O)c1cccc2[nH]c(-c3ccc(-c4ccc(OC(F)(F)F)cc4)cc3)nc12] | I16 | 39.9 | — | 18 | — |
| 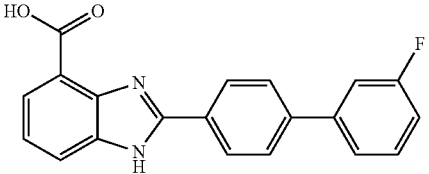 [SMILES: O=C(O)c1cccc2[nH]c(-c3ccc(-c4cccc(F)c4)cc3)nc12] | I17 | 65.2 | 3.79 | 23.5 | — |
| 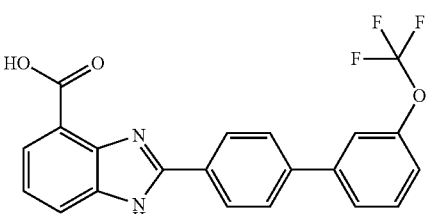 | I18 | 89 | 1.26 | 43.1 | — |
| 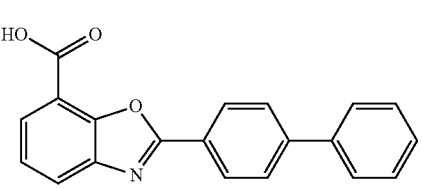 [SMILES: O=C(O)c1cccc2nc(-c3ccc(-c4ccccc4)cc3)oc12] | I19 | 80.1 | 3.03 | 34.3 | — |
| 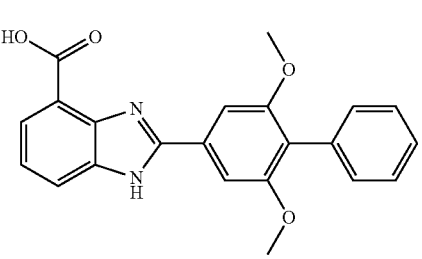 [SMILES: COc1cc(-c2nc3c(C(=O)O)cccc3[nH]2)cc(OC)c1-c1ccccc1] | I20 | 93.2 | 0.975 | 67.1 | 1 |
| 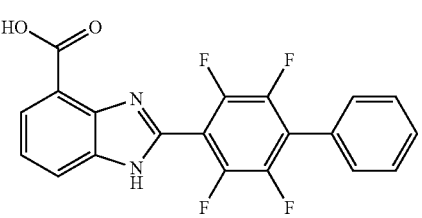 [SMILES: O=C(O)c1cccc2[nH]c(-c3c(F)c(F)c(-c4ccccc4)c(F)c3F)nc12] | I21 | 97.3 | 0.038 | 92.4 | 0.238 |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 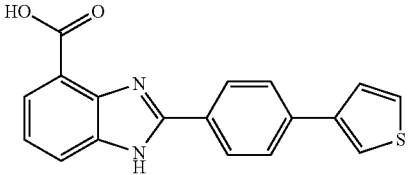 [SMILES: O=C(O)c1cccc2[nH]c(-c3ccc(-c4ccsc4)cc3)nc12] | I22 | 57.3 | — | 15.3 | — |
| 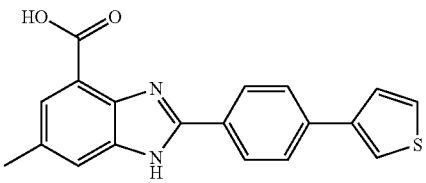 [SMILES: Cc1cc(C(=O)O)c2nc(-c3ccc(-c4ccsc4)cc3)[nH]c2c1] | I23 | 77.8 | — | 33.9 | — |
| 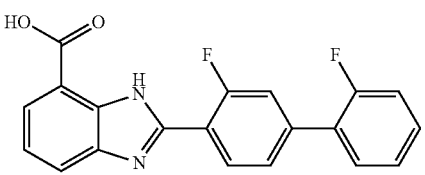 [SMILES: O=C(O)c1cccc2nc(-c3ccc(-c4ccccc4F)cc3F)[nH]c12] | I24 | 86.7 | 0.965 | 53.2 | — |
| 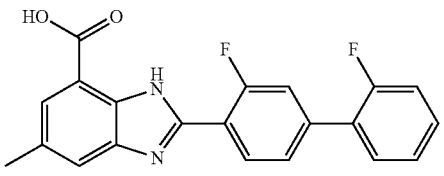 [SMILES: Cc1cc(C(=O)O)c2[nH]c(-c3ccc(-c4ccccc4F)cc3F)nc2c1] | I25 | 94 | 0.172 | 82 | 0.098 |
| 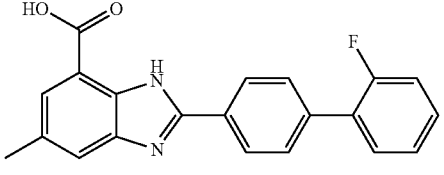 [SMILES: Cc1cc(C(=O)O)c2[nH]c(-c3ccc(-c4ccccc4F)cc3)nc2c1] | I26 | 93.9 | 0.373 | 75.9 | 0.105 |
| 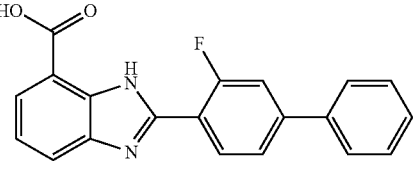 | I27 | 86.2 | 0.922 | 57.1 | — |
| 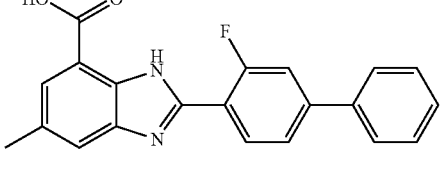 | I28 | 96.3 | 0.403 | 75.4 | 0.206 |
| 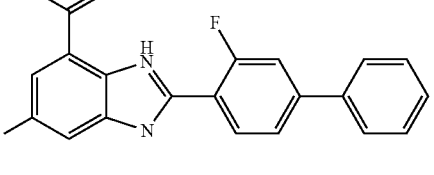 | I28 | 93.4 | 0.623 | 71.6 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 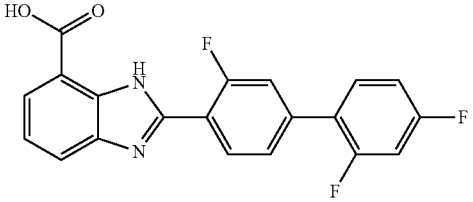 [SMILES: O=C(O)c1cccc2nc(-c3ccc(-c4ccc(F)cc4F)cc3F)[nH]c12] | I30 | 68.1 | — | 31.5 | — |
| 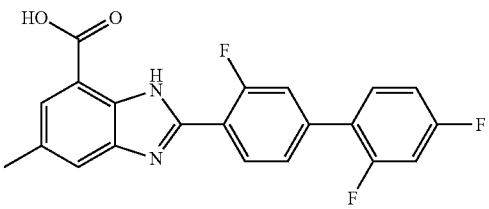 [SMILES: Cc1cc(C(=O)O)c2[nH]c(-c3ccc(-c4ccc(F)cc4F)cc3F)nc2c1] | I31 | 92.7 | 1.01 | 55.5 | — |
| 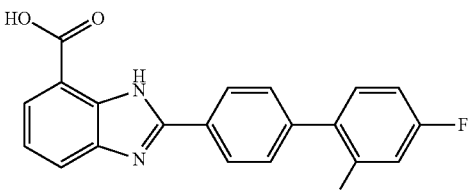 | I32 | 69.6 | — | 21.1 | — |
| 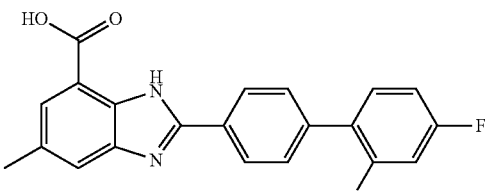 | I33 | 91.3 | 1.42 | 50.5 | — |
| 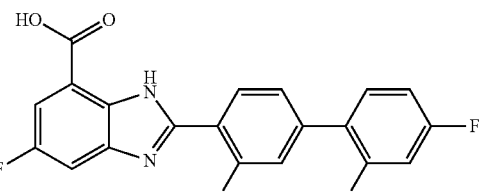 | I34 | 82 | — | 41.8 | — |
| 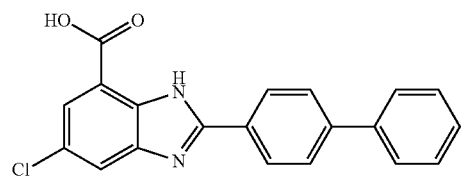 [SMILES: O=C(O)c1cc(Cl)cc2nc(-c3ccc(-c4ccccc4)cc3)[nH]c12] | I35 | 92.9 | 0.994 | 56.4 | 0.746 |
| 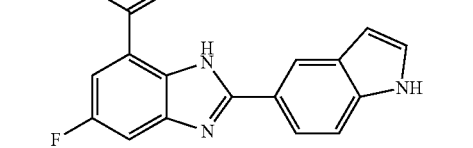 | I36 | 16.1 | — | 7.7 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 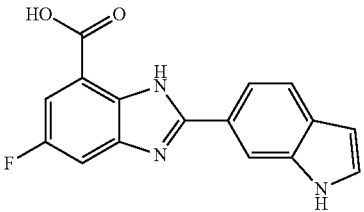 [SMILES: O=C(O)c1cc(F)cc2nc(-c3ccc4cc[nH]c4c3)[nH]c12] | I37 | 13.7 | — | 6.9 | — |
| 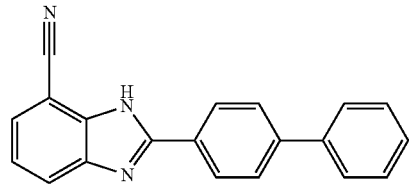 [SMILES: N#Cc1cccc2nc(-c3ccc(-c4ccccc4)cc3)[nH]c12] | I38 | 16.8 | — | 8 | — |
| 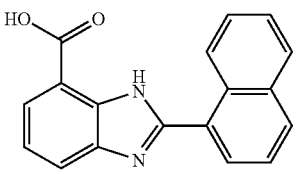 [SMILES: O=C(O)c1cccc2nc(-c3cccc4ccccc34)[nH]c12] | I39 | 19.9 | — | 12.3 | — |
| 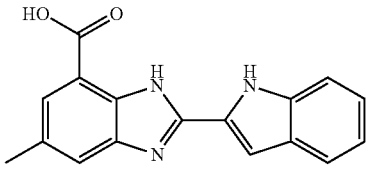 [SMILES: Cc1cc(C(=O)O)c2[nH]c(-c3cc4ccccc4[nH]3)nc2c1] | I40 | 23.3 | — | 3.7 | — |
| 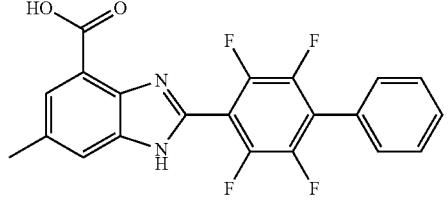 | I41 | 102.9 | 0.0068 | 103.1 | 0.018 |
| 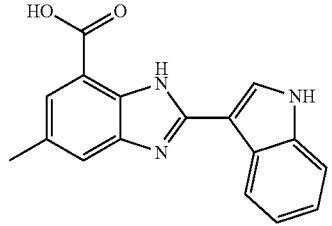 [SMILES: Cc1cc(C(=O)O)c2[nH]c(-c3c[nH]c4ccccc34)nc2c1] | I42 | 7.1 | — | — | — |
| 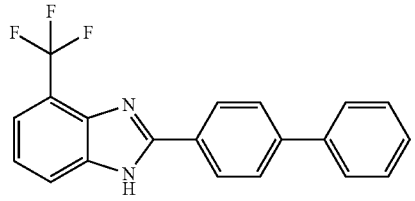 | I43 | 5.6 | — | — | — |

-continued

| Structure | | inh @ 10 uM hDHODH (%) | hDHODH IC50 (uM) | % inh Jurkat_cells @ 1 uM (%) | EC50 Jurkat cells (uM) |
|---|---|---|---|---|---|
| (2-fluoro-4-phenylphenyl benzimidazole with Cl, COOH) | I44 | 97.3 | 0.659 | 64.9 | — |
| (2'-fluorobiphenyl benzimidazole with Cl, COOH) | I45 | 92.2 | 0.949 | 49.5 | — |
| (2-methoxy-4-phenylphenyl benzimidazole with Me, COOH) | I46 | 97.7 | 1.18 | 57.1 | — |
| (4-(benzothiazol-2-yl)phenyl benzimidazole with Me, COOH) | I47 | 40.3 | — | 17.3 | — |
| (2,6-difluoro-4-phenylphenyl benzimidazole with Me, COOH) | I48 | 100 | 0.177 | 88.1 | 0.393 |
| (4-phenylthiophen-2-yl benzimidazole with Me, COOH) | I49 | 32.4 | — | 11 | — |
| (6-phenylpyridin-3-yl benzimidazole with COOH) | I50 | 64.7 | — | 21 | — |
| (4-phenylphenyl indoline with Cl, COOH) | I51 | 86.4 | 2.32 | 39.5 | — |

-continued

| | | inh @ 10 uM hDHODH (%) | hDHODH IC50 (uM) | % inh Jurkat_cells @ 1 uM (%) | EC50 Jurkat cells (uM) |
|---|---|---|---|---|---|
| | I52 | 84.4 | 0.898 | 56.7 | — |
| | I53 | 59.8 | 7.07 | 22.7 | — |
| | I54 | 26.6 | — | 8 | — |
| | I55 | 33.2 | 27.1 | 6.8 | — |
| | I56 | 83.2 | 1.57 | 38.8 | — |
| | I57 | 58 | | 12.6 | — |
| | I58 | 99.7 | 0.437 | 69.8 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 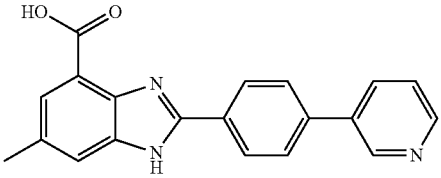 [SMILES: Cc1cc(C(=O)O)c2nc(-c3ccc(-c4cccnc4)cc3)[nH]c2c1] | I59 | 99.2 | 0.407 | 73.5 | 0.45 |
| 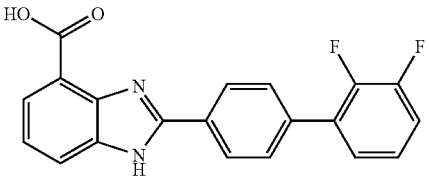 [SMILES: O=C(O)c1cccc2[nH]c(-c3ccc(-c4cccc(F)c4F)cc3)nc12] | I60 | 80.4 | — | 33.4 | — |
| 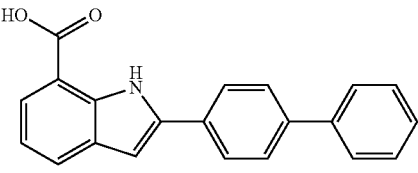 [SMILES: O=C(O)c1cccc2cc(-c3ccc(-c4ccccc4)cc3)[nH]c12] | I61 | 94.8 | 0.595 | 67.2 | 0.202 |
| 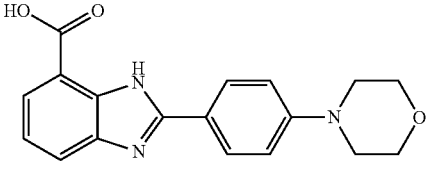 [SMILES: O=C(O)c1cccc2nc(-c3ccc(N4CCOCC4)cc3)[nH]c12] | I62 | 8.4 | — | — | — |
| 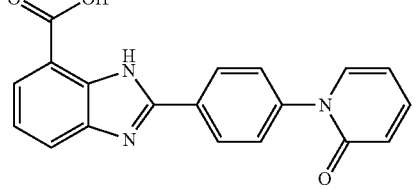 | I63 | 5.3 | — | 1.4 | — |
| 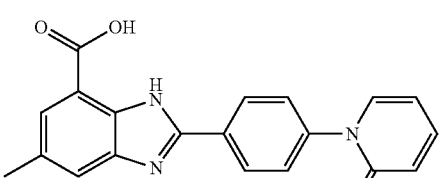 | I64 | 5.7 | — | 1.5 | — |
| 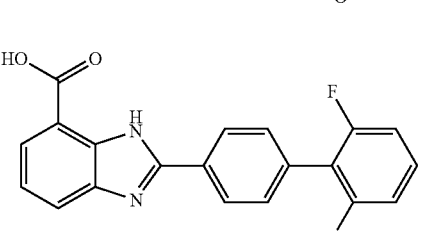 | I65 | 82 | 1.84 | 43 | — |

-continued

| | | inh @ 10 uM hDHODH (%) | hDHODH IC50 (uM) | % inh Jurkat_cells @ 1 uM (%) | EC50 Jurkat cells (uM) |
|---|---|---|---|---|---|
| | I66 | 8.4 | — | — | — |
| | I67 | 74.2 | 3.41 | 29.3 | — |
| | I68 | 97.8 | 0.276 | 78.4 | — |
| | I69 | 12.5 | — | 9.2 | — |
| | I70 | 58.6 | — | 14.6 | — |
| | I71 | 75.5 | 4.38 | 28.3 | — |
| | I72 | 38 | — | 9 | — |

-continued

| | | inh @ 10 uM hDHODH (%) | hDHODH IC50 (uM) | % inh Jurkat_cells @ 1 uM (%) | EC50 Jurkat cells (uM) |
|---|---|---|---|---|---|
| [structure] | I73 | 29.6 | — | 13.6 | — |
| [structure] | I74 | 56.6 | — | 18.4 | — |
| [structure] | I75 | 82.4 | 3.82 | 39.3 | — |
| [structure] | I76 | 100 | 0.344 | 83.5 | — |
| [structure] | I77 | 34.6 | — | 11.5 | — |
| [structure] | I78 | 58.5 | — | 22.2 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 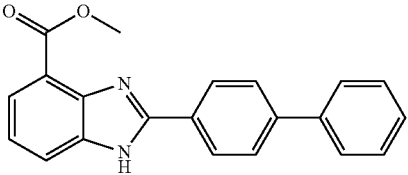 [SMILES: COC(=O)c1cccc2[nH]c(-c3ccc(-c4ccccc4)cc3)nc12] | I79 | 5.3 | — | — | — |
| 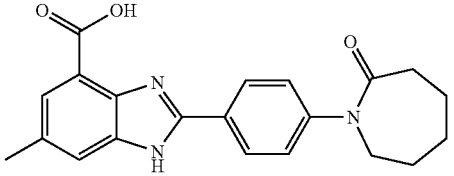 [SMILES: Cc1cc(C(=O)O)c2nc(-c3ccc(N4CCCCCC4=O)cc3)[nH]c2c1] | I80 | 9.4 | — | — | — |
| 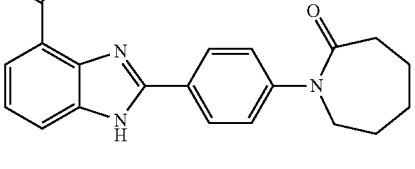 | I81 | 17.9 | — | 6.7 | — |
| 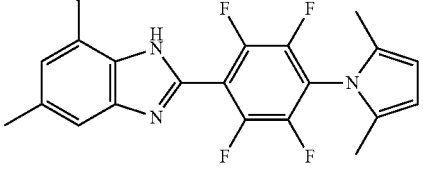 | I82 | 111 | 0.0056 | 106 | — |
| 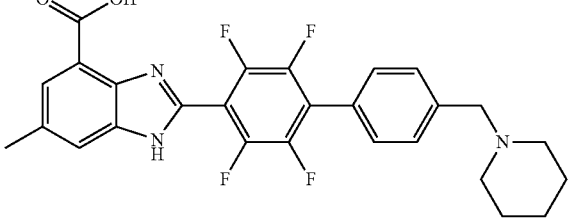 | I83 | 111 | 0.078 | 93 | — |
| 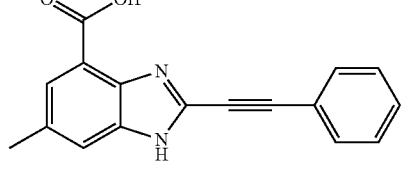 | I84 | 59.5 | 11.41 | — | — |
| 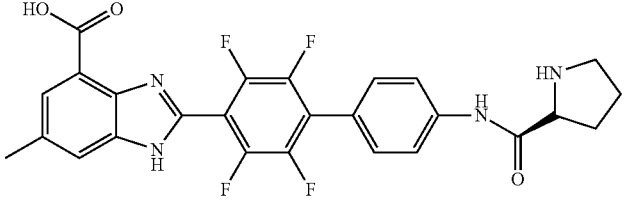 | I85 | 103.7 | 0.056 | 93.4 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 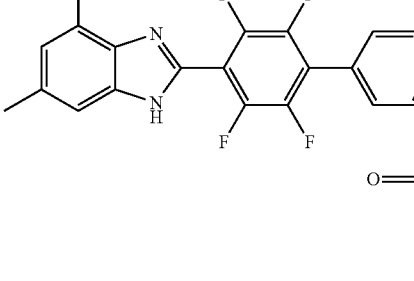 | I86 | 93.1 | 0.815 | 70.8 | — |
| 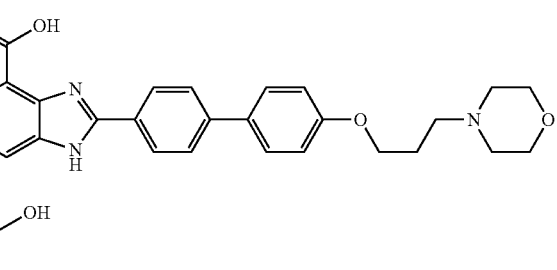 | I87 | 74.1 | 3.023 | 35.7 | — |
| 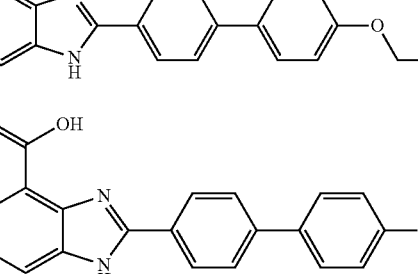 | I88 | 82.9 | 1.632 | 40.3 | — |
| 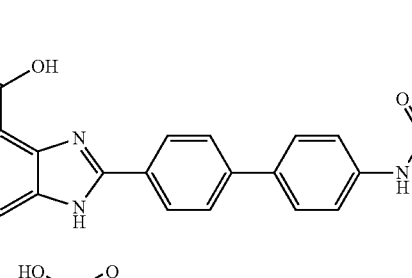 | I89 | 94.1 | 0.692 | 52 | — |
| 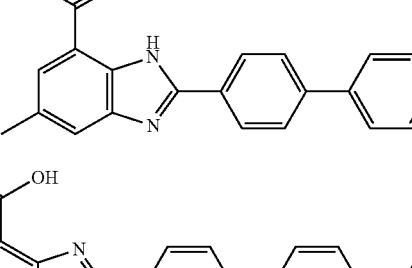 | I90 | 78.8 | 3.691 | 44.5 | — |
| 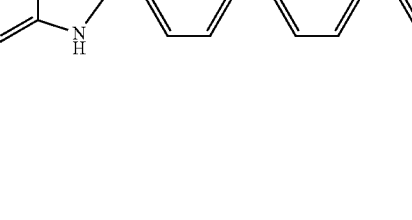 | I91 | 94.2 | 0.645 | 62.3 | — |
|  | I92 | 59.7 | 6.637 | 16.3 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 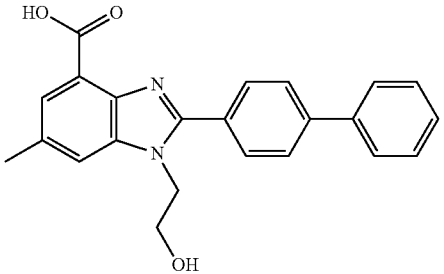 [SMILES: Cc1cc(C(=O)O)c2nc(-c3ccc(-c4ccccc4)cc3)n(CCO)c2c1] | I93 | 78.8 | 4.789 | 29 | — |
| 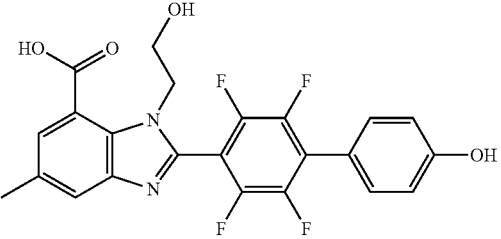 [SMILES: Cc1cc(C(=O)O)c2c(c1)nc(-c1c(F)c(F)c(-c3ccc(O)cc3)c(F)c1F)n2CCO] | I94 | 89.7 | 0.078 | 82.5 | — |
| 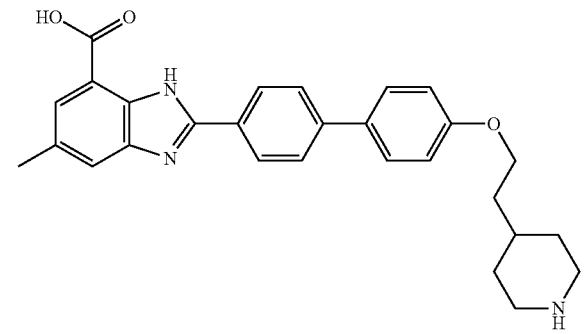 [SMILES: Cc1cc(C(=O)O)c2[nH]c(-c3ccc(-c4ccc(OCCC5CCNCC5)cc4)cc3)nc2c1] | I95 | 58.7 | 6.014 | 14.3 | — |
| 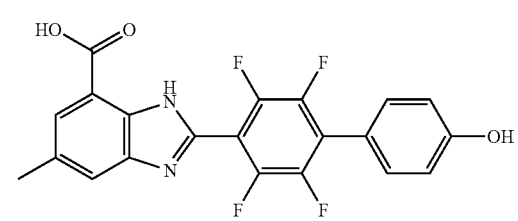 [SMILES: Cc1cc(C(=O)O)c2[nH]c(-c3c(F)c(F)c(-c4ccc(O)cc4)c(F)c3F)nc2c1] | I96 | 98.4 | 0.016 | 101.9 | — |
| 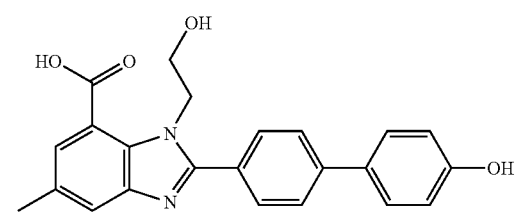 [SMILES: Cc1cc(C(=O)O)c2c(c1)nc(-c1ccc(-c3ccc(O)cc3)cc1)n2CCO] | I97 | 80 | 2.145 | 37.6 | — |
| 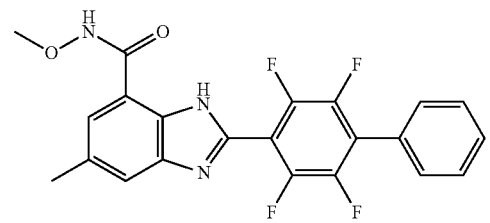 [SMILES: CONC(=O)c1cc(C)cc2nc(-c3c(F)c(F)c(-c4ccccc4)c(F)c3F)[nH]c12] | I98 | 66.2 | 2.2 | 30.1 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 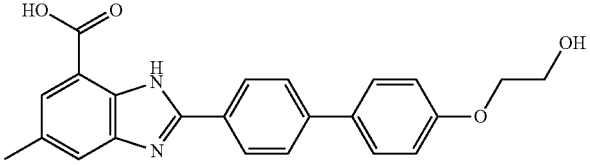 [SMILES: Cc1cc(C(=O)O)c2[nH]c(-c3ccc(-c4ccc(OCCO)cc4)cc3)nc2c1] | I99 | 71 | 3.1 | 27.7 | — |
| 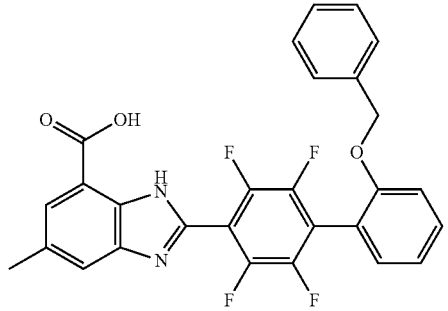 [SMILES: Cc1cc(C(=O)O)c2[nH]c(-c3c(F)c(F)c(-c4ccccc4OCc4ccccc4)c(F)c3F)nc2c1] | I100 | 104.4 | 0.06 | 96.2 | — |
| 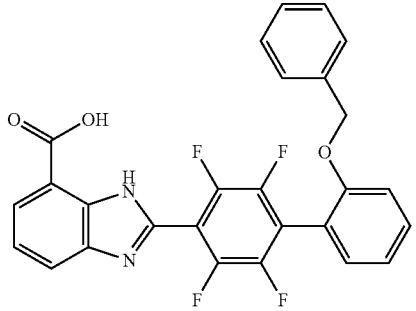 [SMILES: O=C(O)c1cccc2nc(-c3c(F)c(F)c(-c4ccccc4OCc4ccccc4)c(F)c3F)[nH]c12] | I101 | 82.2 | 0.707 | 60.1 | — |
| 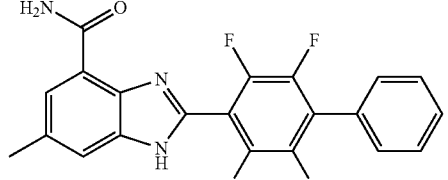 | I102 | 87.9 | 0.446 | 64.2 | — |
| 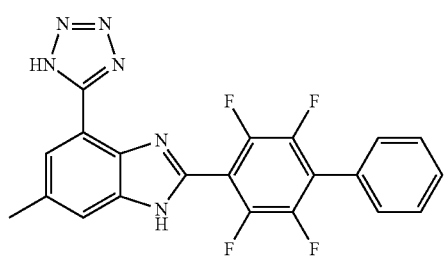 [SMILES: Cc1cc(-c2nnn[nH]2)c2nc(-c3c(F)c(F)c(-c4ccccc4)c(F)c3F)[nH]c2c1] | I103 | 107 | 1.2 | 64.2 | — |
| 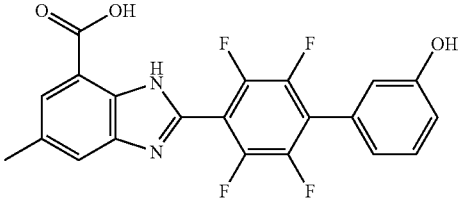 [SMILES: Cc1cc(C(=O)O)c2[nH]c(-c3c(F)c(F)c(-c4cccc(O)c4)c(F)c3F)nc2c1] | I104 | 104.3 | 0.0135 | 109.8 | — |

| | | inh @ 10 uM hDHODH (%) | hDHODH IC50 (uM) | % inh Jurkat_cells @ 1 uM (%) | EC50 Jurkat cells (uM) |
|---|---|---|---|---|---|
| | I105 | 95.8 | 0.0136 | 91.9 | — |
| | I106 | 91 | 1.5 | 48 | — |
| | I107 | 108 | 0.026 | 99 | — |
| | I108 | 53 | 15.9 | 11 | — |
| | I109 | 87 | 1.65 | 49 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 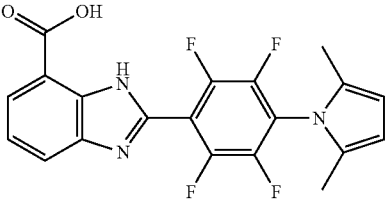 [SMILES: Cc1ccc(C)n1-c1c(F)c(F)c(-c2nc3cccc(C(=O)O)c3[nH]2)c(F)c1F] | I110 | 106 | 0.11 | 97 | — |
| 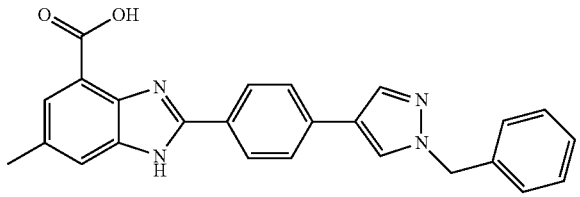 [SMILES: Cc1cc(C(=O)O)c2nc(-c3ccc(-c4cnn(Cc5ccccc5)c4)cc3)[nH]c2c1] | I111 | 91 | 0.155 | 62 | — |
| 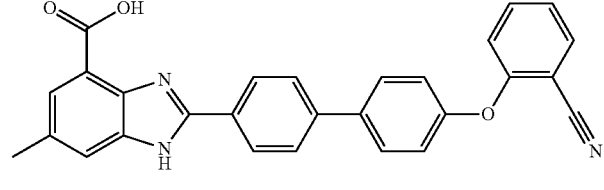 [SMILES: Cc1cc(C(=O)O)c2nc(-c3ccc(-c4ccc(Oc5ccccc5C#N)cc4)cc3)[nH]c2c1] | I112 | 85 | 2.03 | 49 | — |
| 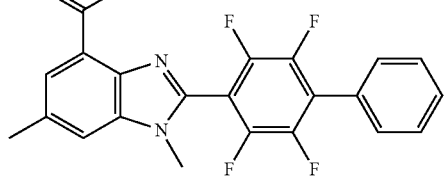 | I113 | 95 | 0.116 | — | — |
| 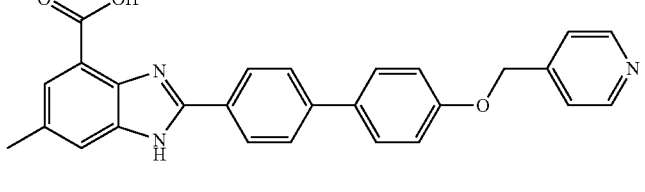 | I114 | 65 | 1.73 | 49 | — |
| 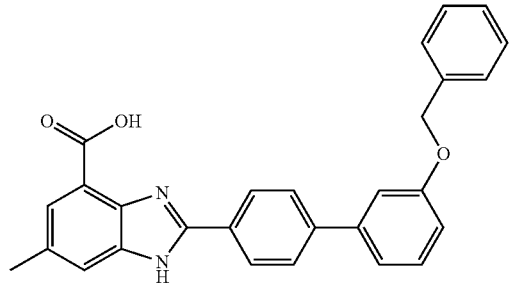 [SMILES: Cc1cc(C(=O)O)c2nc(-c3ccc(-c4cccc(OCc5ccccc5)c4)cc3)[nH]c2c1] | I115 | 88 | 1.2 | 52 | — |
| 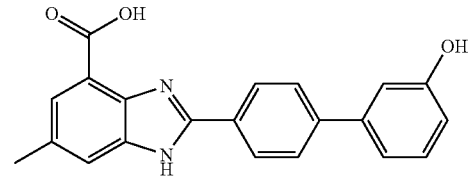 [SMILES: Cc1cc(C(=O)O)c2nc(-c3ccc(-c4cccc(O)c4)cc3)[nH]c2c1] | I116 | 78 | 0.862 | 59 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 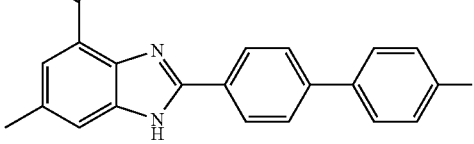 | I117 | 102 | 0.35 | 76 | — |
|  | I118 | 84 | 1.3 | 41.4 | — |
| 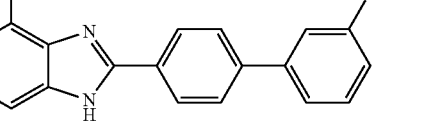 | I119 | 88.1 | 2.23 | 40.3 | — |
| 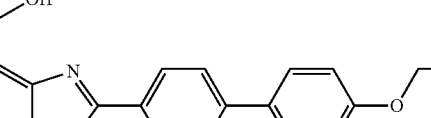 | I120 | 89.9 | 0.755 | 66.1 | — |
|  | I121 | 108.3 | 0.401 | 70.7 | — |
| 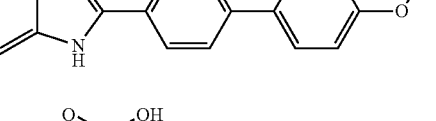 | I122 | 88 | 1.2 | 55.4 | — |
| 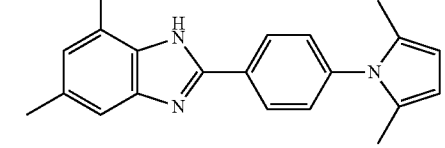 | I123 | 105 | 0.003 | 111.1 | 0.041 |

-continued

| | | inh @ 10 uM hDHODH (%) | hDHODH IC50 (uM) | % inh Jurkat_cells @ 1 uM (%) | EC50 Jurkat cells (uM) |
|---|---|---|---|---|---|
| | I124 | 103.7 | 0.5 | 80.1 | — |
| | I125 | 97 | 0.0282 | 92 | — |
| | I126 | 97 | 0.00886 | 94 | — |
| | I127 | 101 | 0.048 | 96 | — |
| | I128 | 73.1 | 0.209 | 64.9 | — |
| | I129 | 90.8 | 0.02 | 70.5 | — |
| | I130 | 66.9 | 1.22 | 23.2 | — |

-continued

| | | inh @ 10 uM hDHODH (%) | hDHODH IC50 (uM) | % inh Jurkat_cells @ 1 uM (%) | EC50 Jurkat cells (uM) |
|---|---|---|---|---|---|
| | I131 | 79.3 | 0.018 | 78.8 | — |
| | I132 | 91.5 | 0.378 | 67.8 | — |
| | I133 | 100.8 | 0.808 | 54.7 | — |
| | I134 | 88.1 | 0.118 | 77.9 | — |
| | I135 | 65.1 | 1.59 | 21.8 | — |
| | I136 | 89.5 | 0.282 | 68.4 | — |
| | I137 | 65.1 | 2.24 | 31 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 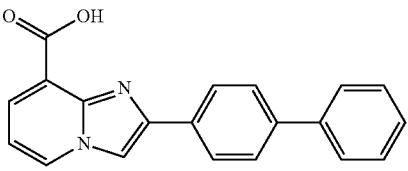 [SMILES: O=C(O)c1cccn2cc(-c3ccc(-c4ccccc4)cc3)nc12] | I138 | 76.1 | 3.8 | 44.8 | — |
| 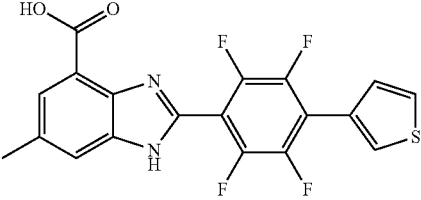 [SMILES: Cc1cc(C(=O)O)c2nc(-c3c(F)c(F)c(-c4ccsc4)c(F)c3F)[nH]c2c1] | I139 | 105.0 | 0.05 | 94.9 | — |
| 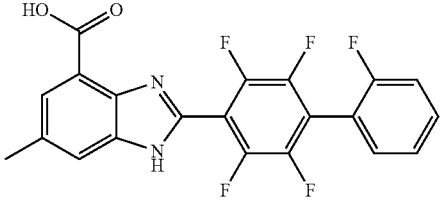 [SMILES: Cc1cc(C(=O)O)c2nc(-c3c(F)c(F)c(-c4ccccc4F)c(F)c3F)[nH]c2c1] | I140 | 100.3 | 0.0035 | 101.2 | 0.033 |
| 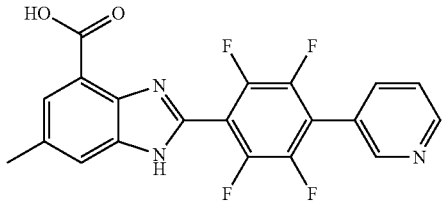 [SMILES: Cc1cc(C(=O)O)c2nc(-c3c(F)c(F)c(-c4cccnc4)c(F)c3F)[nH]c2c1] | I141 | 92.5 | 0.032 | 86.9 | 2.6 |
| 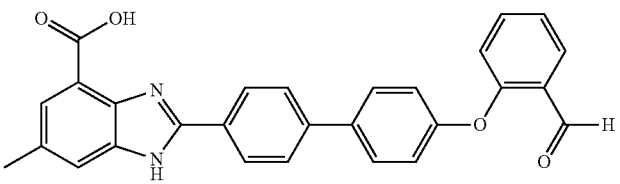 [SMILES: Cc1cc(C(=O)O)c2nc(-c3ccc(-c4ccc(Oc5ccccc5C=O)cc4)cc3)[nH]c2c1] | I142 | 84.7 | 1.05 | 54.5 | — |
| 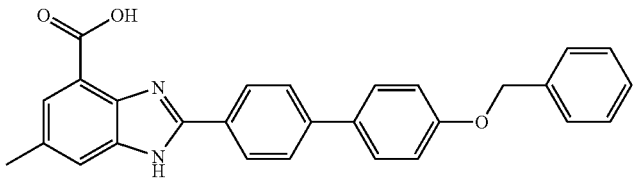 | I143 | 87 | 1.23 | 42.2 | — |
| 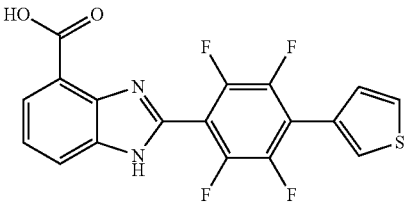 [SMILES: O=C(O)c1cccc2[nH]c(-c3c(F)c(F)c(-c4ccsc4)c(F)c3F)nc12] | I144 | 89.8 | 0.441 | 68.2 | — |

| | | inh @ 10 uM hDHODH (%) | hDHODH IC50 (uM) | % inh Jurkat_cells @ 1 uM (%) | EC50 Jurkat cells (uM) |
|---|---|---|---|---|---|
| [structure] | I145 | 95.6 | 0.314 | 75.8 | — |
| [structure] | I146 | 96.4 | 0.021 | 89.9 | 0.013 |
| [structure] | I147 | 44.3 | 8.45 | — | — |
| [structure] | I148 | 102.8 | 0.218 | 88.6 | — |
| [structure] | I149 | 88.4 | 1.68 | 47.5 | — |
| [structure] | I150 | 30.5 | — | 15.4 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 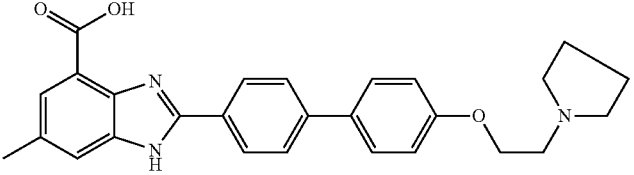 [SMILES: Cc1cc(C(=O)O)c2nc(-c3ccc(-c4ccc(OCCN5CCCC5)cc4)cc3)[nH]c2c1] | I151 | 67.9 | — | 16 | — |
| 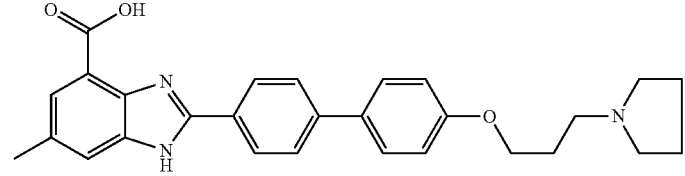 [SMILES: Cc1cc(C(=O)O)c2nc(-c3ccc(-c4ccc(OCCCN5CCCC5)cc4)cc3)[nH]c2c1] | I152 | 47.2 | — | 23.8 | — |
| 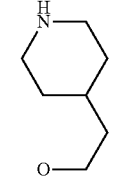 | I153 | 53.4 | — | 15.1 | — |
| 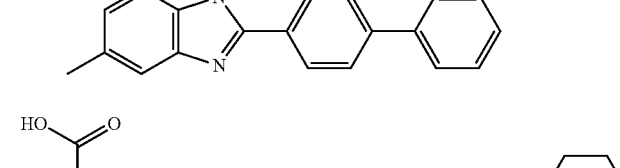 | I154 | 49.1 | — | 8.7 | — |
| 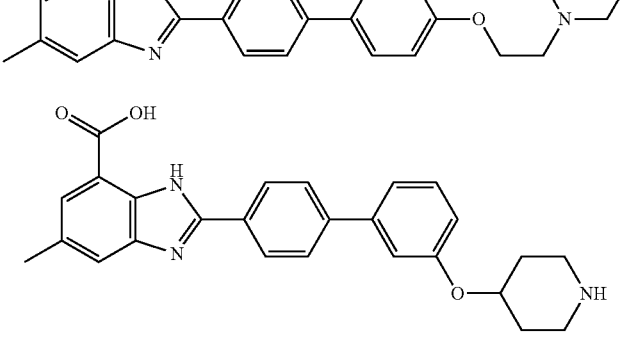 | I155 | 48.5 | — | 14.2 | — |
| 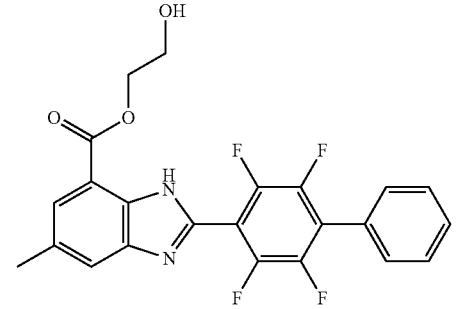 [SMILES: Cc1cc(C(=O)OCCO)c2[nH]c(-c3c(F)c(F)c(-c4ccccc4)c(F)c3F)nc2c1] | I156 | 69.1 | — | 31.4 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 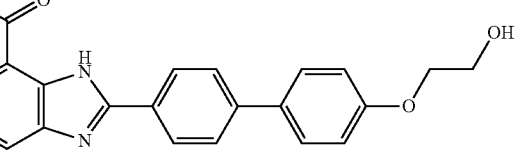 | I157 | 51.8 | — | 15.5 | — |
| 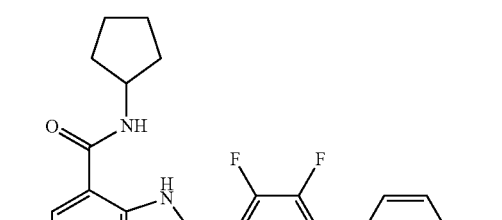 | I158 | 48.5 | — | 6.5 | — |
| 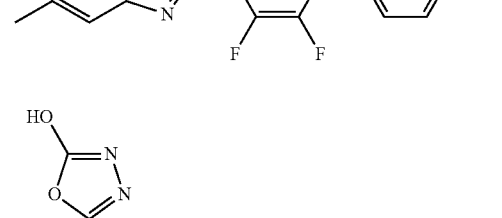 | I159 | 32.3 | — | 13.4 | — |
| 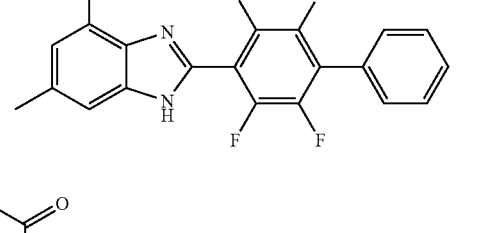 | I160 | 57.4 | — | 19.6 | — |
| 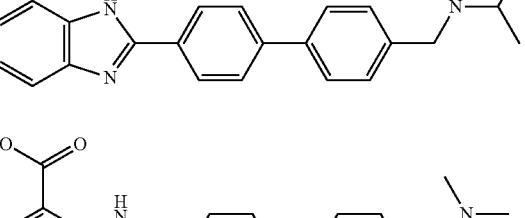 | I161 | 43.3 | — | 9.7 | — |
| 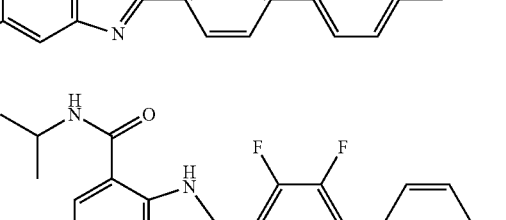 | I162 | 71.3 | — | 28.5 | — |

-continued
| | | inh @ 10 uM hDHODH (%) | hDHODH IC50 (uM) | % inh Jurkat_cells @ 1 uM (%) | EC50 Jurkat cells (uM) |
|---|---|---|---|---|---|
| 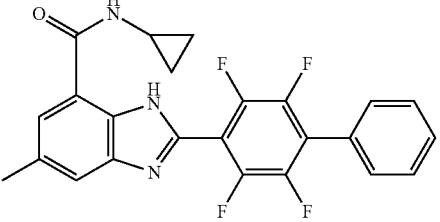 | I163 | 75.6 | — | 37.7 | — |
| 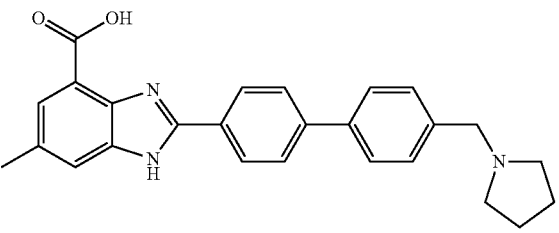 [SMILES: Cc1cc(C(=O)O)c2nc(-c3ccc(-c4ccc(CN5CCCC5)cc4)cc3)[nH]c2c1] | I164 | 59.3 | — | 12.1 | — |
| 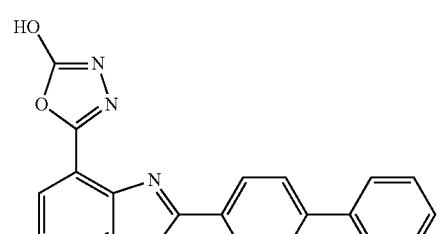 | I165 | 46 | — | 29.7 | — |
| 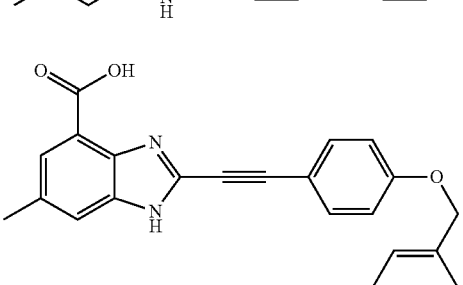 | I166 | 53.2 | — | 13.4 | — |
| 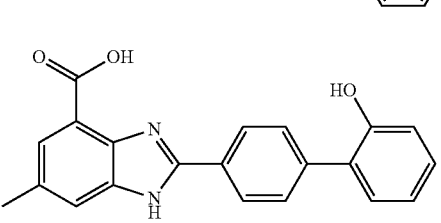 | I167 | 82.7 | — | 34.5 | — |
| 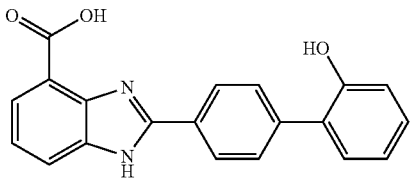 [SMILES: O=C(O)c1cccc2[nH]c(-c3ccc(-c4ccccc4O)cc3)nc12] | I168 | 85 | — | 34 | — |

-continued

| | | inh @ 10 uM hDHODH (%) | hDHODH IC50 (uM) | % inh Jurkat_cells @ 1 uM (%) | EC50 Jurkat cells (uM) |
|---|---|---|---|---|---|
| | I169 | 72 | — | 22 | — |
| | I170 | 84 | — | 57 | — |
| | I171 | 86 | — | 35 | — |
| | I172 | 60 | — | 21 | — |
| | I173 | 80 | — | 44 | — |
| | I174 | 43 | — | 9 | — |
| | I175 | 30 | — | 15 | — |

-continued

| | | inh @ 10 uM hDHODH (%) | hDHODH IC50 (uM) | % inh Jurkat_cells @ 1 uM (%) | EC50 Jurkat cells (uM) |
|---|---|---|---|---|---|
| | I176 | 45 | — | 7 | — |
| | I177 | 51.3 | — | 40.5 | — |
| | I178 | 53.3 | — | 37.6 | — |
| | I179 | 45.8 | — | 10.1 | — |
| | I180 | 30.5 | — | 9.8 | — |
| | I181 | 40.4 | — | 9.4 | — |

| Structure | | inh @ 10 uM hDHODH (%) | hDHODH IC50 (uM) | % inh Jurkat_cells @ 1 uM (%) | EC50 Jurkat cells (uM) |
|---|---|---|---|---|---|
| [2-(4'-(pyridin-2-ylmethoxy)-[1,1'-biphenyl]-4-yl)-1H-benzimidazole-4-carboxylic acid] | I182 | 57.7 | — | 26.9 | — |
| [2-(4'-(pyridin-4-ylmethoxy)-[1,1'-biphenyl]-4-yl)-1H-benzimidazole-4-carboxylic acid] | I183 | 63.9 | — | 23.5 | — |
| [2-(4'-(pyridin-3-ylmethoxy)-[1,1'-biphenyl]-4-yl)-1H-benzimidazole-4-carboxylic acid] | I184 | 53.3 | — | 25.4 | — |
| [2-(4-(2,5-dimethyl-1H-pyrrol-1-yl)phenyl)-1H-benzimidazole-4-carboxylic acid] | I185 | 59.4 | — | 21.5 | — |
| [2-(4-(1-methyl-1H-pyrazol-4-yl)phenyl)-1H-benzimidazole-4-carboxylic acid] | I186 | 31.9 | — | 13.5 | — |
| [2-([1,1'-biphenyl]-4-yl)-5-methyl-1H-indole-7-carboxylic acid] | I187 | 32.1 | — | 15.3 | — |
| [2-(2,3,5,6-tetrafluoro-4-phenoxyphenyl)-1H-benzimidazole-4-carboxylic acid] | I188 | 41.5 | — | 17 | — |

| | inh @ 10 uM hDHODH (%) | hDHODH IC50 (uM) | % inh Jurkat_cells @ 1 uM (%) | EC50 Jurkat cells (uM) |
|---|---|---|---|---|
| I189 | 39.8 | — | 3 | — |
| I190 | 47.5 | — | 16.5 | — |
| I191 | 40.7 | — | 17.6 | — |
| I192 | 74.7 | — | 26.1 | — |

Example 195

Preparation of a Pharmaceutical Formulation

Formulation 1—Tablets

A compound of formula I and related formulae is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula I and related formulae is admixed as a dry powder with a starch diluent in an approximate 1:1 weight ratio. The mixture is filled into 250 mg capsules (125 mg of active compound according to the invention per capsule).

Formulation 3—Liquid

A compound of formula I and related formulae (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula I and related formulae is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula I and related formulae is dissolved in a buffered sterile saline injectable aqueous medium to a concentration of approximately 5 mg/mL.

The invention claimed is:

1. A compound of formula II:

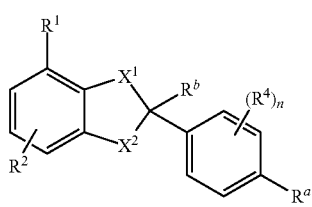

II wherein, $R^1$ denotes COOH, COOA, cyano, tetrazolyl, $CON(R^3)_2$ or CONHA;

R² denotes H, Hal or A;

Rᵃ is selected from the group consisting of:

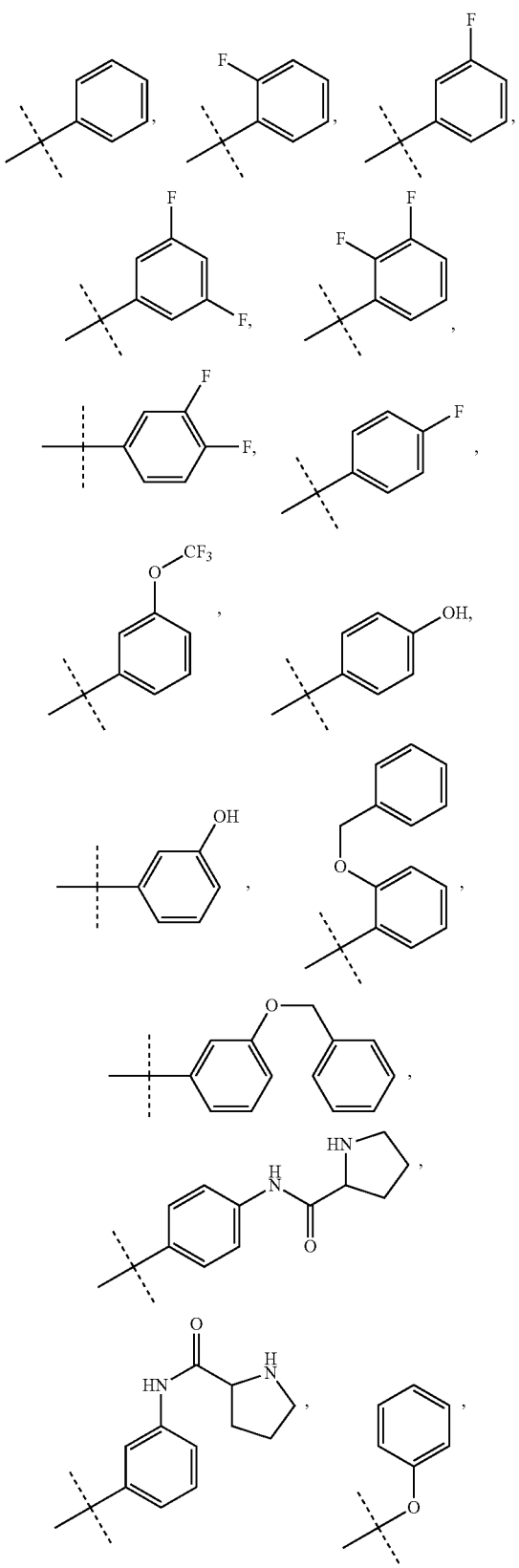

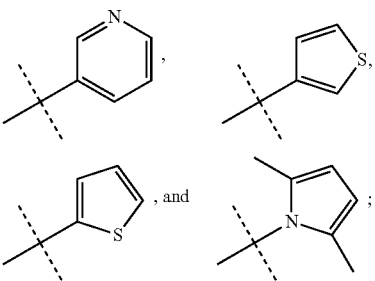

X¹, X² denote each independently of one another NR$^c$ or NR$^d$, and provided that one of X¹ and X² is NR$^d$ and the other is NR$^c$;

R$^b$ and R$^c$ together represent a chemical bond;

R$^d$ denotes H or A;

R³ is H;

R⁴ is Hal;

Hal denotes F, Cl, Br or I;

A is a branched or linear alkyl having 1 to 12 C-atoms, wherein 1 to 7 H-atoms may be replaced by Hal, OR³, CN or N(R³)₂ and wherein 1 to 7 non-adjacent CH₂-groups may be replaced by O, or S and/or by —CH=CH— or —C≡C— groups, or denote cycloalkyl having 3-7 ring C atoms;

n is 4;

and pharmaceutically acceptable solvates, tautomers, salts and stereoisomers thereof, including mixtures thereof in all ratios.

2. The compound of claim 1, wherein R⁴ is F.

3. The compound of claim 1, selected from the group consisting of:

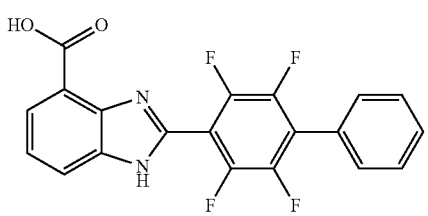

I21

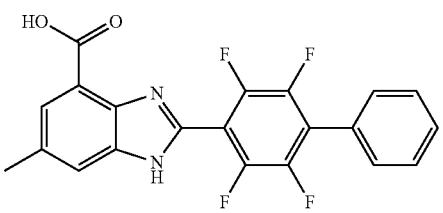

I41

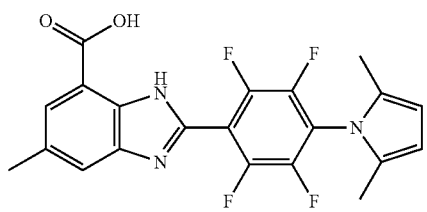

I82

-continued
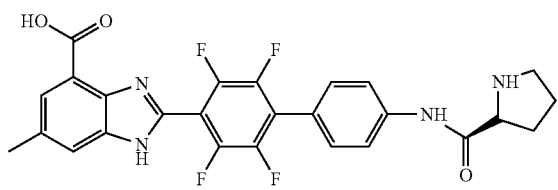
I85
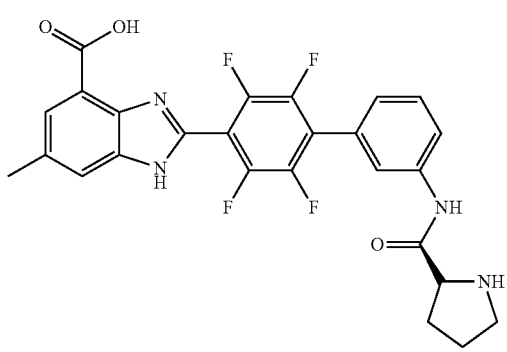
I86
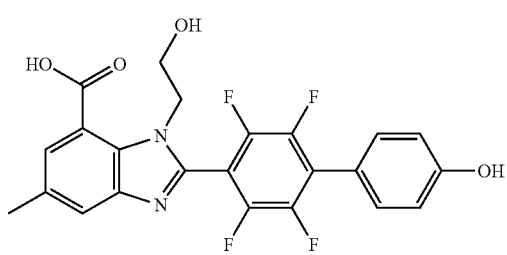
I94
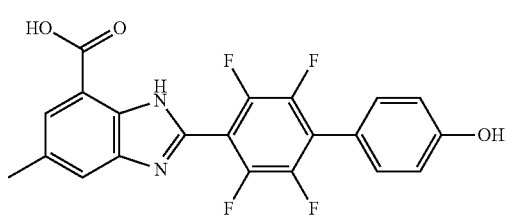
I96
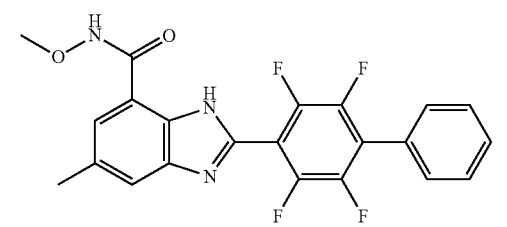
I98
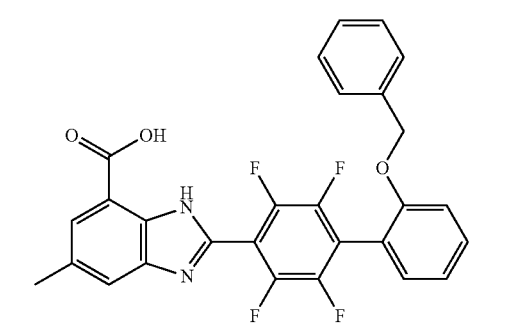
I100
-continued
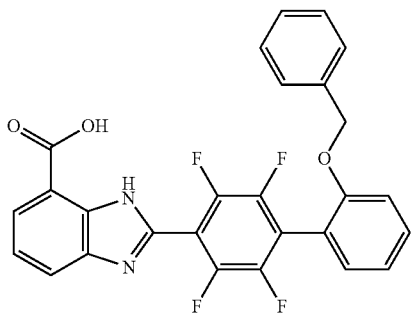
I101
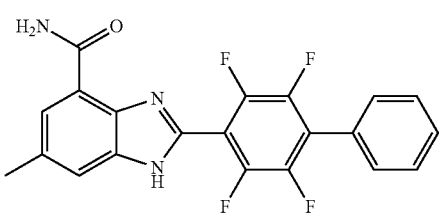
I102
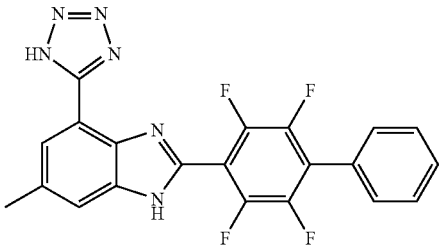
I103
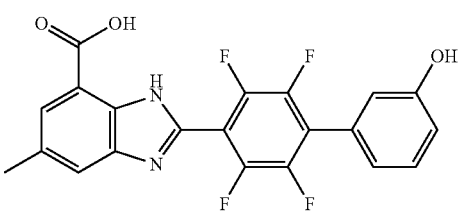
I104
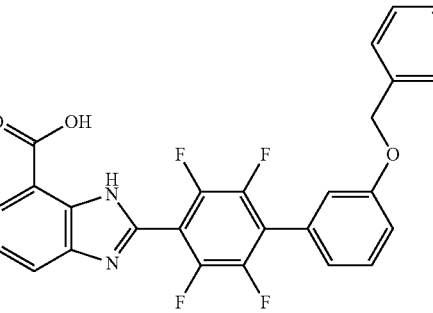
I105
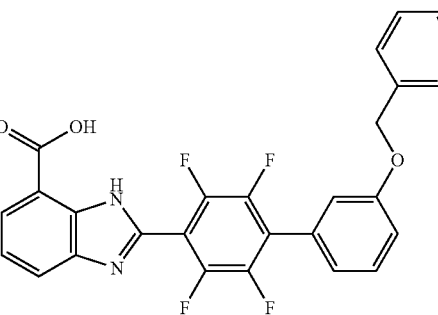
I107

221
-continued
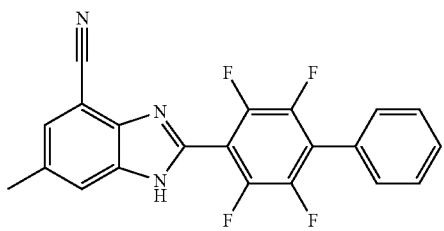
I109
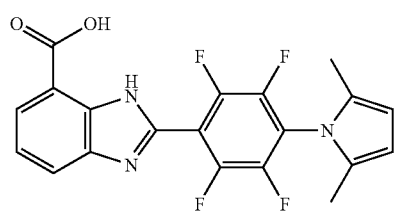
I110
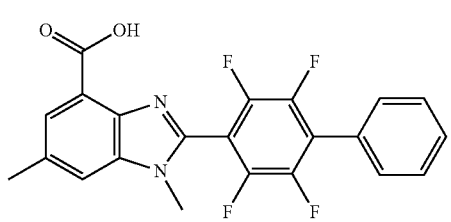
I113
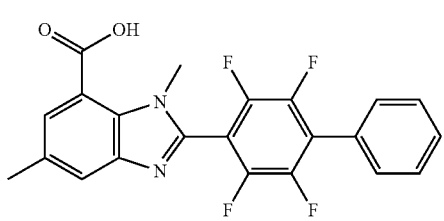
I123
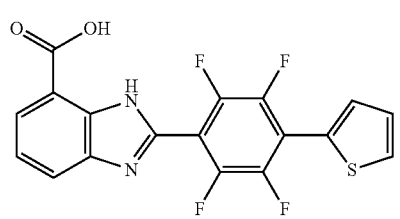
I124
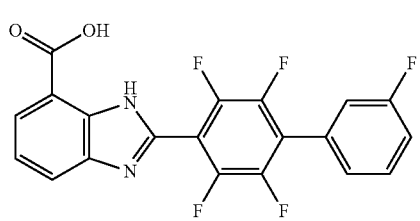
I125
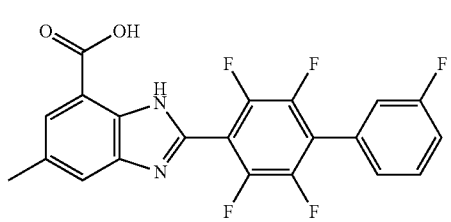
I126
222
-continued
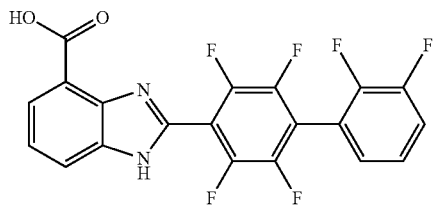
I128
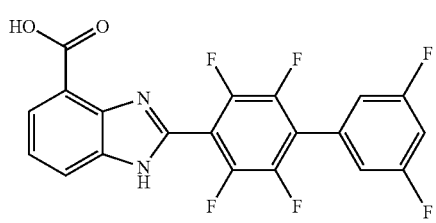
I129
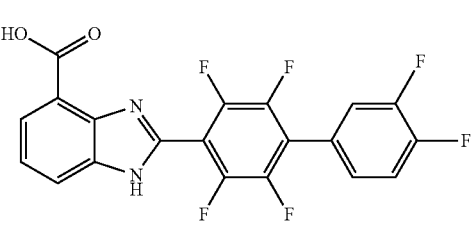
I130
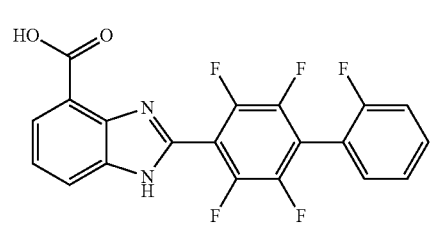
I131
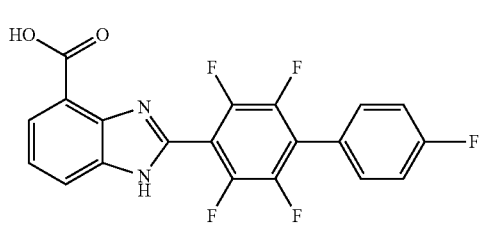
I133
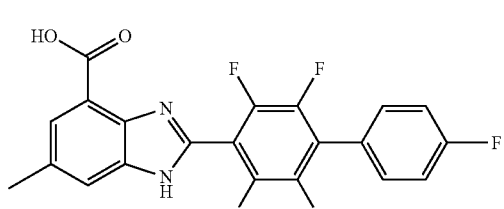
I134
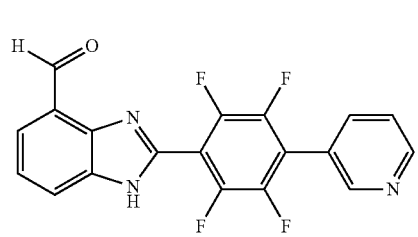
I136

-continued
I139
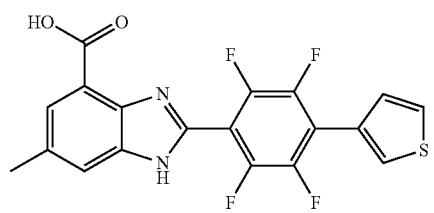
I140
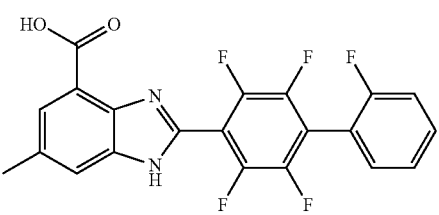
I141
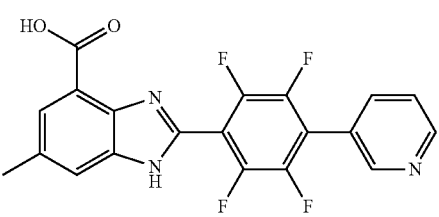
I144
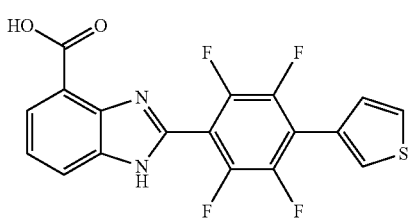
I145
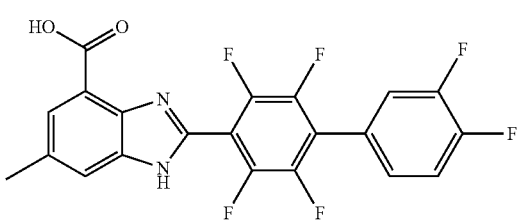
I146
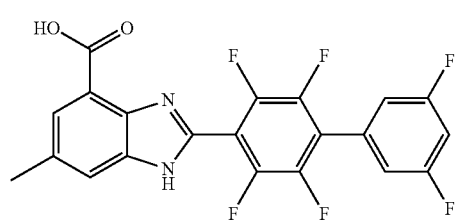
I148
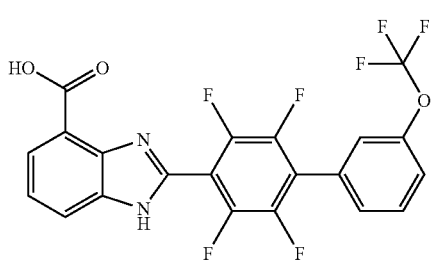
-continued
I156
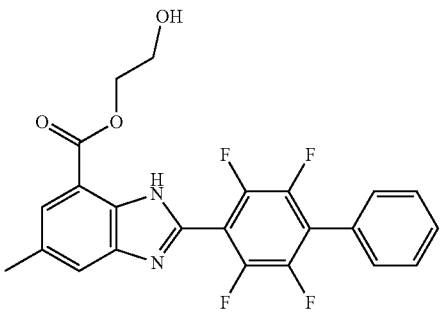
I158
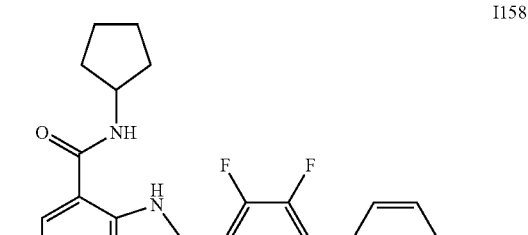
I162
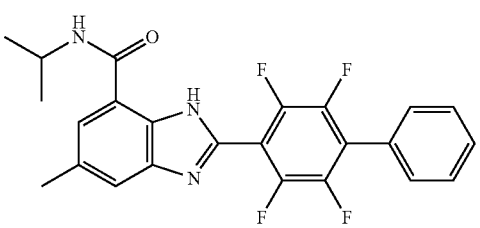
I163
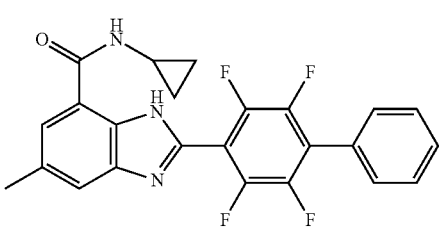
I176
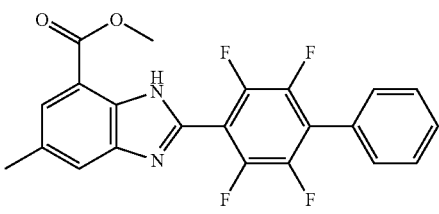 [SMILES: COC(=O)c1cc(C)cc2[nH]c(-c3c(F)c(F)c(-c4ccccc4)c(F)c3F)nc12]
I188
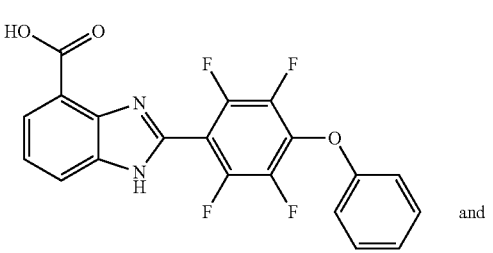
and

I189

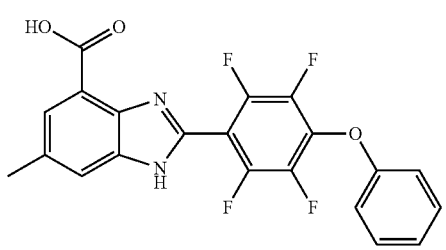 [SMILES: Cc1cc(C(=O)O)c2nc(-c3c(F)c(F)c(Oc4ccccc4)c(F)c3F)[nH]c2c1]

and pharmaceutically acceptable solvates, tautomers, salts and stereoisomers thereof, including mixtures thereof in all ratios.

4. A pharmaceutical composition comprising at least one compound according to claim 1 and/or pharmaceutically usable tautomers, salts, solvates and stereoisomers thereof, including mixtures thereof in all ratios, and optionally excipients and/or adjuvants.

5. A pharmaceutical composition comprising at least one compound according to claim 1 and/or pharmaceutically usable tautomers, salts, solvates and stereo-isomers thereof, including mixtures thereof in all ratios, and at least one further active ingredient.

* * * * *

UNITED STATES PATENT AND TRADEMARK OFFICE
CERTIFICATE OF CORRECTION

Page 1 of 1

PATENT NO.         : 9,006,454 B2
APPLICATION NO.    : 13/262640
DATED              : April 14, 2015
INVENTOR(S)        : Siva Sanjeeva Rao Thunuguntla et al.

It is certified that error appears in the above-identified patent and that said Letters Patent is hereby corrected as shown below:

IN THE SPECIFICATION

In Example I129, column no. 196, --0.02-- should be replaced with --0.2--.

Signed and Sealed this
Eighth Day of December, 2015

Michelle K. Lee
*Director of the United States Patent and Trademark Office*